(12) United States Patent
Williams et al.

(10) Patent No.: US 10,654,926 B2
(45) Date of Patent: May 19, 2020

(54) P2X4 ANTIBODIES AND USES THEREOF

(71) Applicant: MedImmune Limited, Cambridge (GB)

(72) Inventors: Wendy A Williams, Cambridge (GB); Clare Jones, Cambridge (GB); James Button, Cambridge (GB); John Linley, Cambridge (GB); Harm Jan Snijder, Mölndal (SE); Ling Huang, Cambridge (GB); Yoko Shibata, Cambridge (GB); Sudharsan Sridharan, Cambridge (GB); Maria Groves, Cambridge (GB); Claire Dobson, Cambridge (GB)

(73) Assignee: MedImmune Limited, Cambridge (GB)

(*) Notice: Subject to any disclaimer, the term of this patent is extended or adjusted under 35 U.S.C. 154(b) by 0 days.

(21) Appl. No.: 15/308,294

(22) PCT Filed: May 2, 2015

(86) PCT No.: PCT/EP2015/059633
§ 371 (c)(1),
(2) Date: Nov. 1, 2016

(87) PCT Pub. No.: WO2015/166105
PCT Pub. Date: Nov. 5, 2015

(65) Prior Publication Data
US 2017/0166634 A1    Jun. 15, 2017

Related U.S. Application Data

(60) Provisional application No. 61/987,929, filed on May 2, 2014.

(51) Int. Cl.
*A61K 39/395* (2006.01)
*C07K 16/28* (2006.01)
*A61K 39/00* (2006.01)

(52) U.S. Cl.
CPC ........ *C07K 16/28* (2013.01); *A61K 2039/505* (2013.01); *C07K 2317/21* (2013.01); *C07K 2317/24* (2013.01); *C07K 2317/34* (2013.01); *C07K 2317/56* (2013.01); *C07K 2317/565* (2013.01); *C07K 2317/622* (2013.01); *C07K 2317/75* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 6,242,216 B1 | 6/2001 | Lynch et al. |
| 2005/0074819 A1 | 4/2005 | Inoue et al. |
| 2008/0287467 A1 | 11/2008 | Tamura et al. |

FOREIGN PATENT DOCUMENTS

WO    WO 02/48395 A1    6/2002

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
Young et al, "Molecular shape, architecture, and size of P2X4 receptors determined using fluorescence . . . ," Journal of Biological Chemistry, 2008, vol. 283(38), p. 26241-26251.
Valente et al, "Expression, purification, electron microscopy, N-glycosylation mutagenesis and molecular . . . ," Biochimica et Biophysica Acta, 2011, vol. 1808(12), p. 2859-2866.
Tsuda et al, "P2X4 receptors induced in spinal microglia gate tactile allodynia after nerve injury," Nature, 2003, vol. 424(6950), p. 778-783.
Garcia-Guzman et al, "Characterization of recombinant human P2X4 receptor reveals pharmacological differences to the . . . ," Molecular Pharmacology, 1997, vol. 51(1), p. 109-118.
Gum et al, "P2X receptor antagonists for pain management: examination of binding and physicochemical properties," Purinergic Signalling, 2012, vol. 8(supp 1), p. 41-56.
Toulme et al, "P2X4 receptors in activated C8-B4 cells of cerebellar microglial origin," The Journal of General Physiology, 2010, vol. 135(4), p. 333-353.
International Search Report and Written Opinion for International Application No. PCT/EP2015/059633, dated Nov. 18, 2015, p. 1-21.

* cited by examiner

*Primary Examiner* — Christine J Saoud
*Assistant Examiner* — Jon M Lockard

(57) ABSTRACT

The invention provides antibodies that specifically bind a P2X4 polypeptide and modulate P2X4 channel activity, recombinant P2X4 polypeptides and methods for generating such polypeptides, as well as compositions and methods for generating anti-P2X4 antibodies, and methods of using P2X4 antibodies for the treatment of neuropathic pain and other indications.

11 Claims, 50 Drawing Sheets
Specification includes a Sequence Listing.

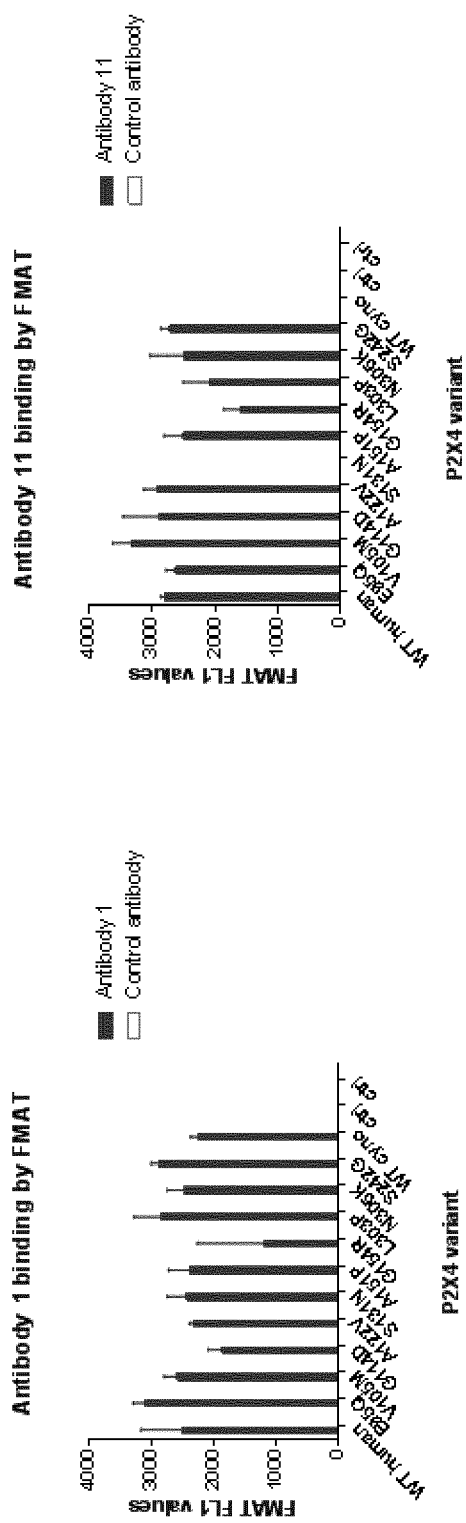
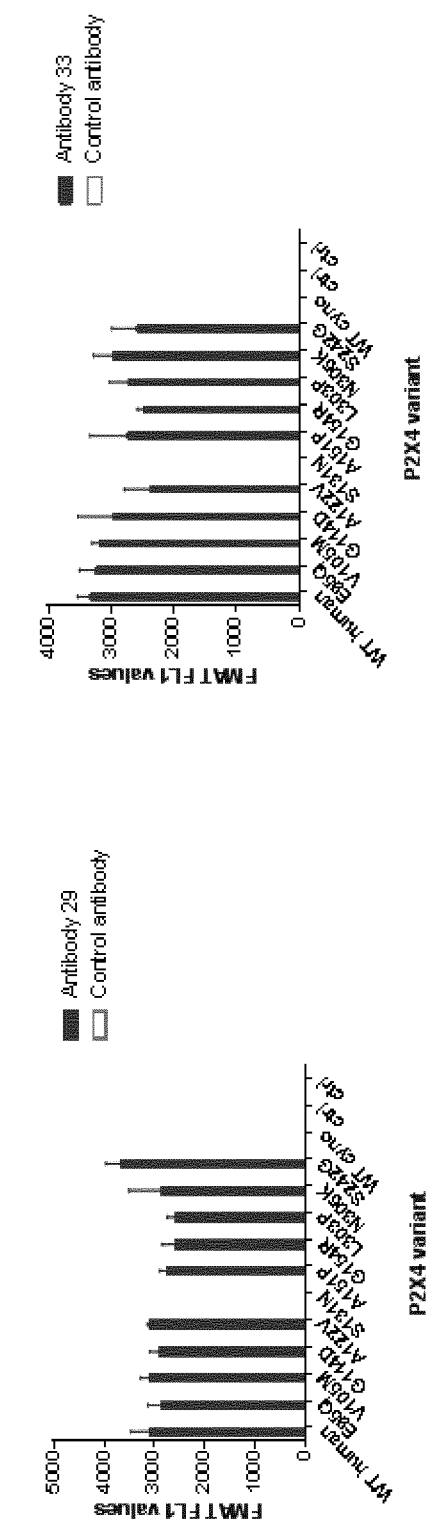
Figure 1A
Figure 1B
Figure 1C
Figure 1D

Figure 2:
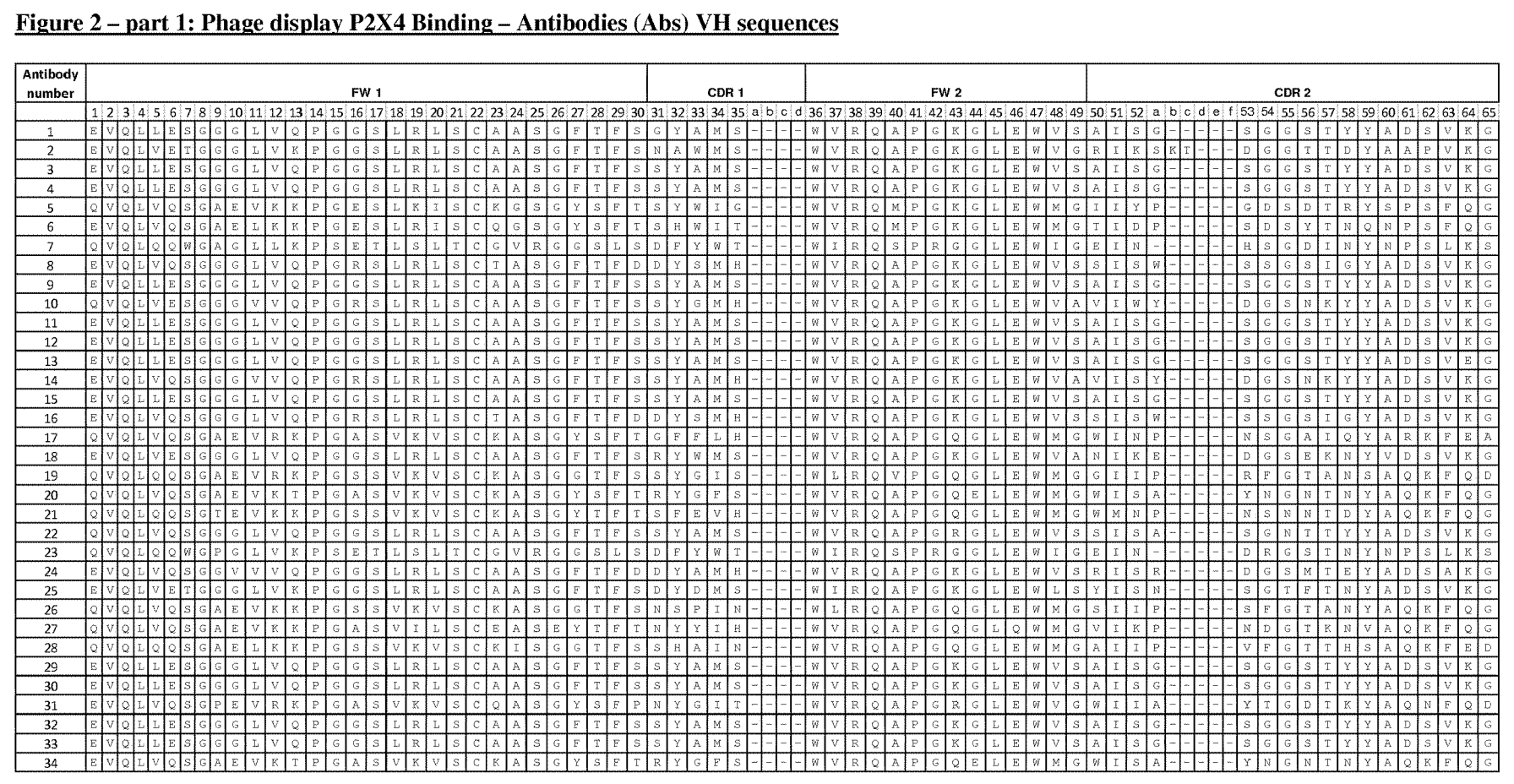
Figure 2:
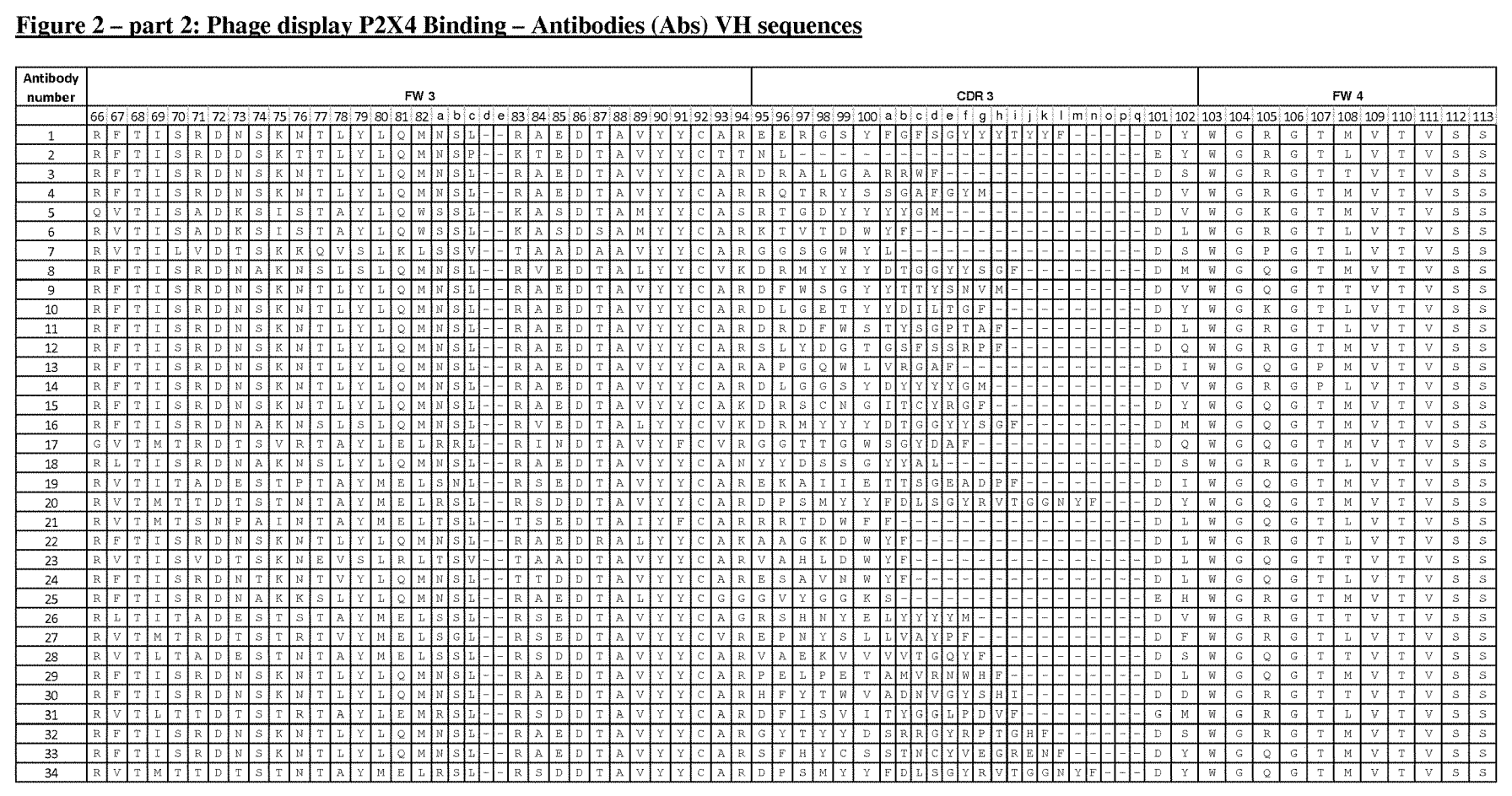
Figure 2:
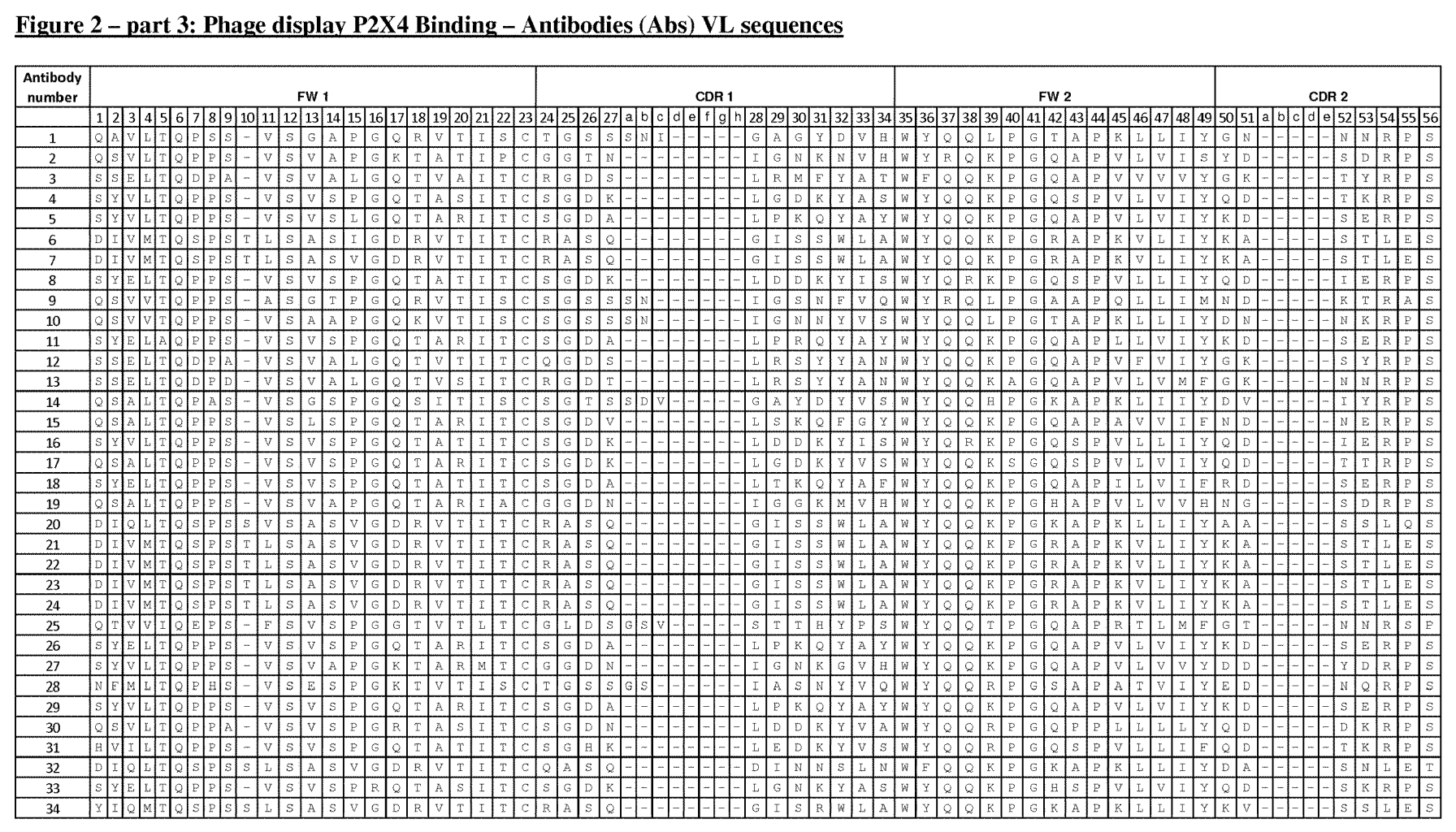
Figure 2:
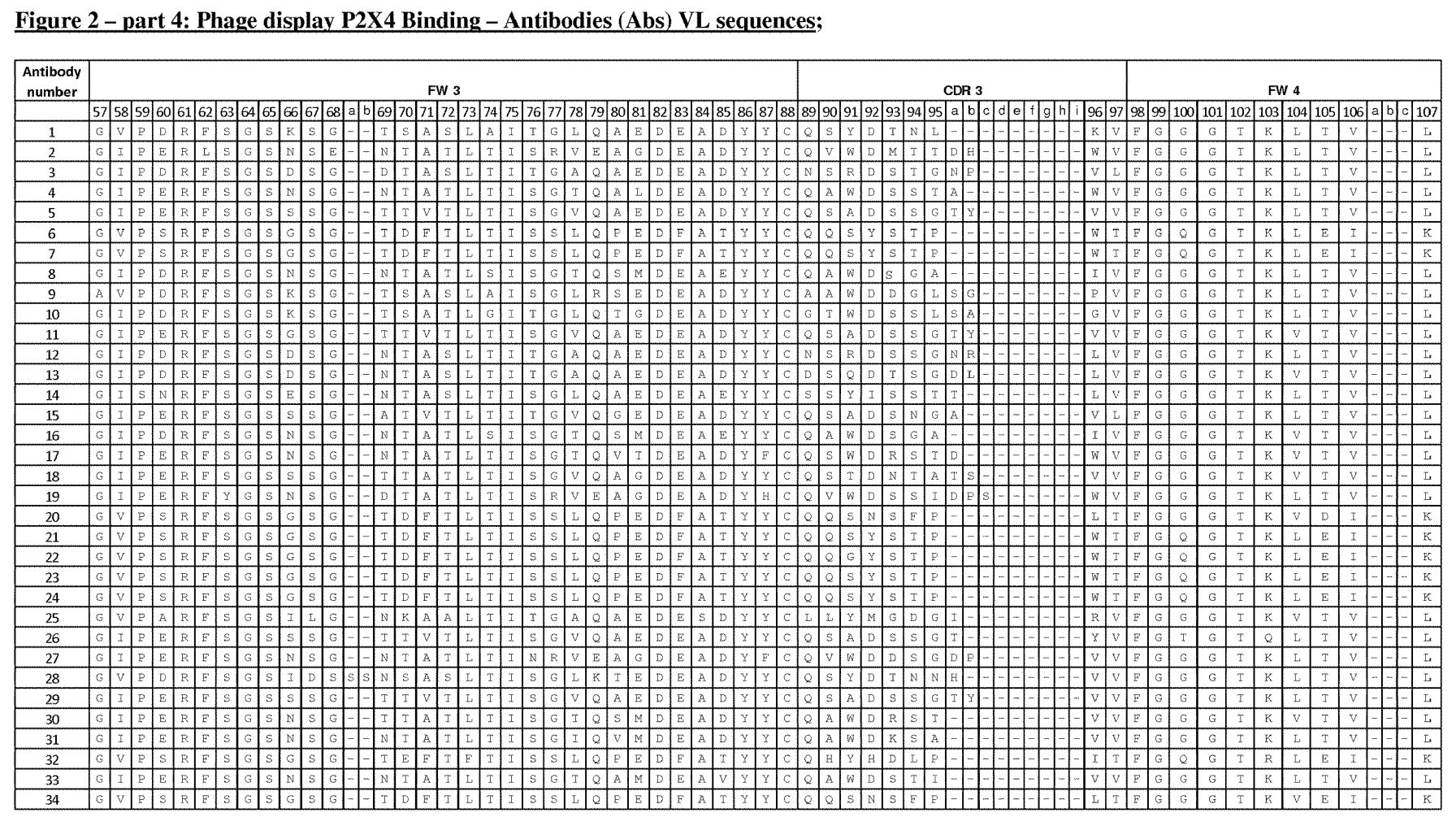

Figure 2 – part 1: Phage display P2X4 Binding – Antibodies (Abs) VH sequences

Figure 2 – part 2: Phage display P2X4 Binding – Antibodies (Abs) VH sequences

Figure 2 – part 3: Phage display P2X4 Binding – Antibodies (Abs) VL sequences

Figure 2 – part 4: Phage display P2X4 Binding – Antibodies (Abs) VL sequences;

Figure 3 – part 1: Antibodies (Abs) Binding and Function: Phage display P2X4 binding antibodies

| Antibody number | Human P2X4 binding | Cynomolgus P2X4 binding | Mouse P2X4 binding | Fraction of control at Human P2X4 | Fraction of control at Cyno P2X4 | Fraction of control at Mouse P2X4 | Concentration in Human ephys assay (mg/ml) | Concentration in Cyno ephys assay (mg/ml) | Concentration in Mouse ephys assay (mg/ml) |
|---|---|---|---|---|---|---|---|---|---|
| 1 | + | + |  | 4.01 | 5.80 | NT | 2.1 | 2.1 |  |
| 2 | + |  |  | 1.27 | NT | NT | 1 |  |  |
| 3 | + |  |  | 2.08 | NT | 1.39 | 1 |  | 1.0 |
| 4 | + |  |  | 1.17 | NT | NT | 1.6 |  |  |
| 5 | + | - |  | 0.80 | 0.89 | NT | 1.3 | 1.3 |  |
| 6 | + |  |  | 1.35 | NT | NT | 1 |  |  |
| 7 | + |  |  | 1.20 | 1.11 | NT | 3.3 |  |  |
| 8 | + | - |  | 0.52 | 1.03 | NT | 1.46 |  |  |
| 9 | + |  | + | 1.52 | NT | 1.12 | 1.75 | 1.5 | 1.0 |
| 10 | + |  |  | 1.21 | NT | NT | 1 |  |  |
| 11 | + | - |  | 0.01 | 1.06 | 1.11 | 1.23 | 2.1 | 1.0 |
| 12 | + |  |  | 2.06 | NT | NT | 0.11 |  |  |
| 13 | + |  |  | 1.18 | NT | NT | 0.05 |  |  |
| 14 | + |  |  | 0.84 | NT | NT | 0.25 |  |  |
| 15 | + |  |  | 2.89 | NT | NT | 0.18 |  |  |
| 16 | + |  |  | 1.00 | NT | NT | 0.1 |  |  |
| 17 | + |  |  | 1.09 | NT | NT | 0.27 |  |  |
| 18 | + | + |  | 0.57 | 0.62 | NT | 3.3 | 3.3 |  |
| 19 | + |  |  | 1.20 | NT | NT | 0.13 |  |  |
| 20 | + |  |  | 1.38 | NT | NT | 0.1 |  |  |
| 21 | + |  |  | 2.04 | NT | NT | 0.49 |  |  |
| 22 | + |  |  | 1.31 | NT | NT | 0.5 |  |  |
| 23 | + |  |  | 1.63 | NT | NT | 0.54 |  |  |
| 24 | + | + | + | 1.69 | NT | 1.76 | 0.53 |  | 0.53 |
| 25 | - |  | + | NT | NT | 0.96 |  |  | 0.59 |
| 26 | + |  |  | 1.31 | NT | NT | 0.61 |  |  |
| 27 | + |  |  | 1.02 | NT | NT | 0.39 |  |  |

Figure 3 – part 2: Antibodies (Abs) Binding and Function: Phage display P2X4 binding antibodies

| Antibody number | Human P2X4 binding | Cynomolgus P2X4 binding | Mouse P2X4 binding | Fraction of control at Human P2X4 | Fraction of control at Cyno P2X4 | Fraction of control at Mouse P2X4 | Concentration in Human ephys assay (mg/ml) | Concentration in Cyno ephys assay (mg/ml) | Concentration in Mouse ephys assay (mg/ml) |
|---|---|---|---|---|---|---|---|---|---|
| 28 | + | + | | 1.41 | NT | NT | 0.56 | | |
| 29 | + | - | | 0.27 | 1.11 | NT | 4.2 | 1.1 | |
| 30 | + | | | 1.28 | NT | NT | 0.63 | | 0.33 |
| 31 | + | | | 2.41 | NT | 1.37 | 0.35 | | |
| 32 | + | | | 0.84 | NT | 1.04 | 0.61 | | 0.61 |
| 33 | + | - | | 0.62 | 0.95 | NT | 3.8 | 3.8 | |
| 34 | + | + | + | 1.10 | NT | NT | 1.16 | | |

| Key | |
|---|---|
| + | Binding observed in FMAT assay |
| - | No binding observed in FMAT assay |
| NT | Not tested in assay |
| blank | Data not disclosed |

Figure 4: Lead Panel Ephys

| Antibody number | Conc (mg/ml) | Fraction of control at human P2X4 | | | Fraction of control at cyno P2X4 | | |
|---|---|---|---|---|---|---|---|
| | | Mean | SEM | n | Mean | SEM | n |
| 5 | 1.3 | 0.74 | 0.037 | 7 | | | |
| 8 | 1.5 | 0.53 | 0.011 | 8 | | | |
| 11 | 2 | 0.03 | 0.031 | 7 | | | |
| 18 | 3.3 | 0.56 | 0.010 | 6 | 0.62 | 0.009 | 11 |
| 29 | 4.2 | 0.27 | 0.013 | 18 | | | |
| 33 | 3.8 | 0.62 | 0.024 | 4 | | | |

Figure 5: Summary of human cross reactive hybridoma antibodies (Abs)

| Antibody number | Human P2X4 binding | Cynomologus P2X4 binding | Mouse P2X4 binding | Concentration (μM) | Fraction of control at Mouse P2X4 | Fraction of control at Mouse P2X4 (repeat) | N | SD | Concentration (μM) | Fraction of control at Human P2X4 | N | SD |
|---|---|---|---|---|---|---|---|---|---|---|---|---|
| 35 | + | | + | 0.80 | 0.461 | 0.194 | 3 | 0.157 | 0.689 | 0.648 | 3 | 0.120 |
| 36 | + | | + | 2.18 | 0.051 | 0.045 | 3 | 0.018 | 2.067 | 0.604 | 2 | 0.207 |
| 37 | + | | + | 1.38 | 0.270 | 0.242 | 4 | 0.068 | 2.200 | 1.056 | 3 | 0.139 |
| 38 | + | | + | 0.269 | 0.178 | 0.157 | 3 | 0.021 | 0.733 | 0.486 | 2 | 0.085 |
| 39 | + | | + | 0.941 | -0.067 | 0.068 | 3 | 0.074 | | NT | | |
| 40 | + | | + | 1.17 | 0.231 | 0.191 | 2 | 0.018 | 1.711 | 0.815 | 3 | 0.178 |
| 41 | + | | + | 0.49 | 0.072 | 0.195 | 4 | 0.033 | 0.378 | 0.633 | 4 | 0.103 |
| 42 | + | | + | 0.724 | 0.333 | 0.193 | 3 | 0.075 | 1.089 | 0.414 | 3 | 0.071 |
| 43 | + | + | + | 0.571 | 0.307 | 0.342 | 3 | 0.060 | 2.044 | 0.395 | 3 | 0.058 |
| 44 | + | | + | 0.23 | 0.253 | 0.364 | 4 | 0.107 | | NT | | |
| 45 | + | | + | 1.05 | 0.281 | 0.298 | 1 | | 1.844 | 0.620 | 3 | 0.140 |
| 46 | + | | + | 2.64 | -0.079 | -0.053 | 4 | 0.095 | 1.622 | 0.383 | 2 | 0.036 |
| 47 | + | | + | 1.07 | 0.196 | 0.174 | 3 | 0.089 | 0.311 | 0.912 | 3 | 0.112 |
| 48 | + | | + | 1.51 | 0.041 | 0.019 | 3 | 0.076 | 1.956 | 0.560 | 3 | 0.096 |

| Key | Description |
|---|---|
| + | Binding observed in FMAT assay |
| - | No binding observed in FMAT assay |
| Blank or NT | Data not disclosed / not tested |

Figure 6 part 1: Hybridoma derived P2X4 Antibodies (Abs) VH sequences

| Antibody number | | | | | | | | | FW 1 | | | | | | | | | | | | | | | | | | | | | | | | CDR 1 | | | | | | |
|---|---|---|---|---|---|---|---|---|---|---|---|---|---|---|---|---|---|---|---|---|---|---|---|---|---|---|---|---|---|---|---|---|---|---|---|---|---|---|---|
| Kabat numbering | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | a | b | c | d |
| 35 | E | I | Q | L | Q | E | S | G | P | G | L | V | K | P | S | Q | S | L | S | L | T | C | S | V | T | G | Y | T | I | T | S | G | Y | D | - | - | - | - | - |
| 36 | Q | V | Q | L | K | E | S | G | P | G | L | V | K | P | S | Q | T | L | S | L | T | C | T | V | S | G | F | S | L | T | S | Y | H | V | N | - | - | - | - |
| 37 | Q | V | N | L | L | Q | S | G | A | A | L | V | K | P | G | A | S | V | K | L | S | C | K | A | S | G | Y | T | F | T | D | Y | Y | I | H | - | - | - | - |
| 38 | E | I | Q | L | Q | E | S | G | P | G | L | V | K | P | S | Q | S | L | S | L | T | C | S | V | T | G | Y | T | I | T | S | G | Y | D | - | - | - | - | - |
| 39 | E | I | Q | L | Q | E | S | G | P | G | L | V | K | P | S | Q | S | L | S | L | T | C | S | V | T | G | Y | T | I | T | S | G | S | D | - | - | - | - | - |
| 40 | Q | V | T | L | K | E | S | G | P | G | I | L | Q | P | S | Q | T | L | S | L | T | C | S | F | S | G | F | S | L | S | T | F | G | I | C | V | S | - | - |
| 41 | Q | V | Q | L | K | E | S | G | P | G | L | V | K | P | S | Q | T | L | S | L | T | C | T | V | S | G | F | S | L | T | S | Y | H | V | R | - | - | - | - |
| 42 | E | I | Q | L | Q | E | S | G | P | G | L | V | K | P | S | Q | S | L | S | L | T | C | S | V | T | G | Y | T | I | T | S | G | Y | D | - | - | - | - | - |
| 43 | Q | V | Q | L | K | E | S | G | P | G | L | V | K | P | S | Q | T | L | S | L | T | C | T | V | S | G | F | S | L | T | S | Y | D | V | H | - | - | - | - |
| 44 | Q | V | T | L | K | E | S | G | P | G | I | L | Q | P | S | Q | S | L | S | L | T | C | S | F | T | G | F | T | L | N | R | Y | G | I | C | V | S | - | - |
| 45 | E | I | Q | L | Q | E | S | G | P | G | L | V | K | P | S | Q | S | L | S | L | T | C | S | V | S | G | Y | S | I | T | T | Y | F | D | - | - | - | - | - |
| 46 | Q | V | Q | L | K | E | S | G | P | G | L | V | K | P | S | Q | T | L | S | L | T | C | T | V | T | G | F | T | L | T | S | Y | H | V | S | - | - | - | - |
| 47 | E | I | Q | L | Q | E | S | G | P | G | L | V | K | P | S | Q | S | L | S | L | T | C | S | V | S | G | Y | S | I | T | S | G | F | D | - | - | - | - | - |
| 48 | Q | V | Q | L | K | E | S | G | P | G | L | V | K | P | S | Q | T | L | S | L | T | C | T | V | S | G | F | S | L | T | S | Y | H | V | S | - | - | - | - |

Figure 6 part 2: Hybridoma derived P2X4 Antibodies (Abs) VH sequences

| Antibody number | FW 2 | | | | | | | | | | | | | | | | CDR 2 | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|
| Kabat numbering | 36 | 37 | 38 | 39 | 40 | 41 | 42 | 43 | 44 | 45 | 46 | 47 | 48 | 49 | 50 | 51 | 52 | a | b | c | d | e | f | 53 | 54 | 55 | 56 | 57 | 58 | 59 | 60 | 61 | 62 | 63 | 64 | 65 |
| 35 | W | S | W | - | R | K | F | P | G | N | K | M | E | W | M | G | Y | I | S | - | - | - | - | Y | S | G | S | T | N | Y | N | P | S | L | K | S |
| 36 | W | V | R | Q | P | P | G | K | G | L | E | W | M | G | V | I | W | - | - | - | - | - | - | G | D | G | S | T | A | Y | N | S | A | L | K | S |
| 37 | W | V | K | Q | S | H | G | M | S | L | E | W | I | G | L | I | N | - | - | - | - | - | - | D | S | G | Y | P | N | Y | N | E | N | F | K | G |
| 38 | W | S | W | - | R | K | F | P | G | N | K | M | E | W | M | G | Y | I | S | - | - | - | - | Y | S | G | S | T | N | Y | N | P | S | L | K | S |
| 39 | W | T | W | - | R | K | F | P | G | N | K | M | E | W | M | G | Y | I | S | - | - | - | - | Y | S | G | S | T | N | Y | N | P | S | L | K | S |
| 40 | W | I | R | Q | P | S | G | K | G | L | E | W | L | A | A | I | C | - | - | - | - | - | - | W | E | D | S | K | G | Y | N | S | A | L | K | S |
| 41 | W | V | R | Q | P | P | G | K | G | L | E | W | M | G | A | I | W | - | - | - | - | - | - | G | D | G | S | T | A | Y | N | S | A | L | K | S |
| 42 | W | S | W | - | R | K | F | P | G | N | K | M | E | W | M | G | Y | I | S | - | - | - | - | Y | S | G | S | T | N | Y | N | P | S | L | K | S |
| 43 | W | V | R | Q | P | P | G | K | G | L | E | W | M | G | G | I | W | - | - | - | - | - | - | G | D | G | S | T | D | Y | N | P | S | L | K | S |
| 44 | W | I | R | - | R | K | F | P | G | N | K | M | E | W | T | I | C | - | - | - | - | - | - | W | E | D | S | K | V | Y | N | P | S | L | K | S |
| 45 | W | S | W | F | R | K | F | P | G | N | K | M | E | W | M | G | Y | I | S | - | - | - | - | Y | S | G | S | T | N | Y | N | P | S | L | K | S |
| 46 | W | V | R | Q | P | P | G | K | G | L | E | W | M | G | I | I | W | - | - | - | - | - | - | G | D | G | S | T | A | Y | N | S | A | L | K | S |
| 47 | W | V | W | F | R | K | F | P | G | N | K | M | E | W | M | G | Y | I | S | - | - | - | - | Y | S | G | S | T | N | Y | N | P | S | L | K | S |
| 48 | W | V | R | Q | P | P | G | K | G | L | E | W | M | G | V | I | W | - | - | - | - | - | - | G | D | G | S | T | A | F | N | S | A | L | K | S |

Figure 6 part 3: Hybridoma derived P2X4 Antibodies (Abs) VH sequences

| Antibody number | Kabat numbering | | | | | | | | | | | | FW 3 | | | | | | | | | | | | | | | | | | | | | | | CDR 3 | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | 66 | 67 | 68 | 69 | 70 | 71 | 72 | 73 | 74 | 75 | 76 | 77 | 78 | 79 | 80 | 81 | 82 | a | b | c | d | e | 83 | 84 | 85 | 86 | 87 | 88 | 89 | 90 | 91 | 92 | 93 | 94 | 95 | 96 | 97 | 98 | 99 | 100 | a | b | c | d | e | f | g | h | i | j | k | l | m | n | o | p | q | 101 | 102 |
| 35 | | R | I | S | I | T | R | D | T | S | K | N | Q | F | F | L | Q | L | N | S | V | - | - | T | T | E | D | T | A | T | Y | Y | C | A | R | G | M | M | V | L | - | - | - | - | - | - | - | - | - | - | - | - | - | - | - | - | - | P | N |
| 36 | | R | L | S | L | S | R | D | T | S | K | S | Q | V | F | L | K | M | N | S | L | - | - | Q | T | E | D | S | A | T | Y | Y | C | A | R | G | G | D | Y | Y | D | G | S | Y | Y | E | - | - | - | - | - | - | - | - | - | - | - | G | Y |
| 37 | | K | A | T | L | T | V | D | K | S | T | N | T | A | Y | M | E | L | R | R | L | - | - | T | S | E | D | S | A | T | Y | Y | C | T | R | S | R | I | Y | Y | D | G | S | V | F | - | - | - | - | - | - | - | - | - | - | - | D | Y |
| 38 | | R | I | S | I | T | R | D | T | S | K | N | Q | F | F | L | Q | L | N | S | V | - | - | T | T | E | D | T | A | T | Y | Y | C | A | R | G | M | V | V | L | V | - | - | - | - | - | - | - | - | - | - | - | - | - | - | - | - | S | T |
| 39 | | R | L | S | I | S | R | D | T | S | K | S | Q | A | F | L | K | M | I | S | S | - | - | D | T | A | D | - | A | - | Y | Y | C | G | S | G | G | Y | I | Y | - | - | - | - | - | - | - | - | - | - | - | - | - | - | - | - | - | D | Y |
| 40 | | R | L | S | I | S | R | D | T | S | K | N | Q | V | F | L | K | M | N | S | L | - | - | Q | T | E | D | T | A | T | Y | Y | C | A | R | R | S | V | M | Y | T | T | A | P | Y | Y | F | - | - | - | - | - | - | - | - | - | D | Y |
| 41 | | R | L | S | I | T | K | D | T | S | R | S | Q | A | F | L | K | I | S | S | V | - | - | D | T | A | A | - | A | - | Y | Y | C | A | R | R | R | V | H | Y | S | D | G | S | Y | Y | V | G | - | - | - | - | - | - | - | - | - | D | Y |
| 42 | | R | I | S | I | T | R | D | T | S | K | N | Q | V | F | L | Q | L | N | S | V | - | - | T | T | E | D | T | A | T | Y | Y | C | A | R | G | M | M | V | L | - | - | - | - | - | - | - | - | - | - | - | - | - | - | - | - | - | G | N |
| 43 | | R | L | T | I | S | K | D | T | S | N | S | Q | V | F | L | K | I | T | S | V | - | - | D | T | A | D | - | A | - | Y | F | C | T | R | S | L | D | Y | S | - | G | D | G | F | - | - | - | - | - | - | - | - | - | - | - | - | A | Y |
| 44 | | R | I | S | I | S | R | D | T | S | K | N | Q | V | F | L | Q | M | N | S | L | - | - | Q | T | E | D | T | A | T | Y | Y | C | A | R | R | R | R | W | S | S | - | Y | F | - | - | - | - | - | - | - | - | - | - | - | - | - | A | Y |
| 45 | | R | L | S | I | S | R | D | T | S | K | N | Q | V | F | L | Q | L | N | S | L | - | - | D | T | A | D | T | A | T | Y | Y | C | A | R | G | V | S | S | L | - | - | - | - | - | - | - | - | - | - | - | - | - | - | - | - | - | D | Y |
| 46 | | R | L | T | L | S | K | D | T | S | K | S | Q | V | F | L | K | M | N | S | L | - | - | Q | T | E | D | T | A | T | Y | Y | C | A | R | A | G | H | Y | S | D | G | S | Y | Y | V | G | - | - | - | - | - | - | - | - | - | A | Y |
| 47 | | R | L | S | I | T | R | D | T | S | K | N | Q | V | F | L | Q | L | N | S | L | - | - | T | T | E | D | T | A | T | Y | Y | C | A | R | G | V | Y | S | L | - | - | - | - | - | - | - | - | - | - | - | - | - | - | - | - | - | A | Y |
| 48 | | R | L | S | I | S | R | D | T | S | K | S | Q | V | F | L | K | M | N | S | L | - | - | Q | T | E | D | T | A | T | Y | Y | C | A | R | A | G | V | Y | Y | D | G | S | Y | Y | F | - | - | - | - | - | - | - | - | - | A | Y |

Figure 6 part 4: Hybridoma derived P2X4 Antibodies (Abs) VH sequences

| Antibody number | | | | | | FW 4 | | | | | |
|---|---|---|---|---|---|---|---|---|---|---|---|
| Kabat numbering | 103 | 104 | 105 | 106 | 107 | 108 | 109 | 110 | 111 | 112 | 113 |
| 35 | W | G | Q | G | V | M | V | T | V | S | S |
| 36 | W | G | Q | G | V | M | V | T | V | S | S |
| 37 | W | G | Q | G | V | M | V | T | V | S | S |
| 38 | W | G | Q | G | V | M | V | T | V | S | S |
| 39 | W | G | R | G | V | M | V | T | V | S | S |
| 40 | W | G | Q | G | V | M | V | T | V | S | S |
| 41 | W | G | Q | G | T | L | V | T | V | S | S |
| 42 | W | G | Q | G | V | M | V | T | V | S | S |
| 43 | W | G | Q | G | T | L | V | T | V | S | S |
| 44 | W | G | Q | G | V | M | V | T | V | S | S |
| 45 | W | G | Q | G | T | L | V | T | V | S | S |
| 46 | W | G | Q | G | T | L | V | T | V | S | S |
| 47 | W | G | Q | G | T | L | V | T | V | S | S |
| 48 | W | G | Q | G | T | L | V | T | V | S | S |

Figure 6 part 5: Hybridoma derived P2X4 Antibodies (Abs) VL sequences

| Antibody number | FW 1 | | | | | | | | | | | | | | | | | | | | | | | CDR 1 | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|
| Kabat numbering | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | a | b | c | d | e | f | g | h | 28 | 29 | 30 | 31 | 32 | 33 | 34 |
| 35 | D | V | Q | M | T | Q | S | P | S | Y | L | T | A | S | P | G | E | S | V | S | I | S | C | K | A | S | K | - | - | - | - | - | - | - | - | S | - | T | N | Y | L | A |
| 36 | D | I | Q | M | T | Q | S | P | A | S | L | S | A | S | L | E | E | S | V | T | I | T | C | Q | A | S | Q | - | - | - | - | - | - | - | - | D | - | G | N | Y | L | S |
| 37 | E | I | V | L | T | Q | S | P | P | T | M | A | V | S | P | G | E | K | V | T | I | T | C | R | A | R | S | - | - | - | - | - | - | - | - | D | S | V | S | W | M | Y |
| 38 | D | V | Q | M | T | Q | S | P | S | Y | L | A | A | S | P | G | E | S | V | S | I | S | C | K | A | S | K | - | - | - | - | - | - | - | - | S | - | T | H | Y | L | A |
| 39 | D | V | Q | M | T | Q | S | P | S | Y | L | S | A | S | P | G | E | S | V | S | I | S | C | K | A | N | K | - | - | - | - | - | - | - | - | R | - | T | N | Y | L | A |
| 40 | D | I | Q | M | T | Q | S | P | A | S | L | S | A | S | L | E | E | - | V | T | I | T | C | Q | A | S | Q | - | - | - | - | - | - | - | - | D | - | G | N | W | L | A |
| 41 | D | I | Q | M | T | Q | S | P | A | S | L | S | A | S | L | E | E | - | V | T | I | T | C | Q | A | S | Q | - | - | - | - | - | - | - | - | D | - | G | N | W | L | A |
| 42 | D | V | Q | M | T | Q | S | P | S | Y | L | A | A | S | P | G | E | S | V | S | I | S | C | K | A | S | K | - | - | - | - | - | - | - | - | S | - | T | H | Y | L | A |
| 43 | D | I | Q | M | T | Q | S | P | P | A | L | S | A | S | L | G | D | K | V | T | I | T | C | Q | A | S | Q | - | - | - | - | - | - | - | - | N | - | N | K | Y | I | A |
| 44 | D | I | Q | M | T | Q | S | P | A | S | L | S | A | S | L | E | E | - | V | T | I | T | C | Q | A | S | Q | - | - | - | - | - | - | - | - | D | - | G | N | W | L | A |
| 45 | D | V | Q | M | T | Q | S | P | S | Y | L | A | A | S | P | G | E | S | V | S | I | S | C | K | A | S | K | - | - | - | - | - | - | - | - | S | - | T | N | Y | L | A |
| 46 | D | I | Q | M | T | Q | S | P | A | S | L | S | A | S | L | E | E | - | V | T | I | T | C | Q | A | S | Q | - | - | - | - | - | - | - | - | L | - | G | N | W | L | A |
| 47 | D | V | Q | M | T | Q | S | P | S | Y | L | A | A | S | P | G | E | S | V | S | I | S | C | K | A | S | K | - | - | - | - | - | - | - | - | D | - | T | N | Y | L | A |
| 48 | D | I | Q | M | T | Q | S | P | A | S | L | S | A | S | L | G | E | - | V | T | I | T | C | Q | A | S | Q | - | - | - | - | - | - | - | - | D | - | G | N | W | L | A |

Figure 6 part 6: Hybridoma derived P2X4 Antibodies (Abs) VL sequences

| Antibody number | | | | FW 2 | | | | | | | | | | | | CDR 2 | | | | | | | | |
|---|---|---|---|---|---|---|---|---|---|---|---|---|---|---|---|---|---|---|---|---|---|---|---|---|
| Kabat numbering | 35 | 36 | 37 | 38 | 39 | 40 | 41 | 42 | 43 | 44 | 45 | 46 | 47 | 48 | 49 | 50 | 51 | a | b | c | d | e | 52 | 53 | 54 | 55 | 56 |
| 35 | W | Y | H | Q | K | P | G | E | P | Y | N | L | L | - | Y | S | G | - | - | - | - | - | S | T | L | Q | S |
| 36 | W | Y | Q | Q | K | P | G | K | S | P | Q | L | L | - | Y | D | A | - | - | - | - | - | T | S | L | A | D |
| 37 | W | Y | Q | Q | K | S | G | A | S | P | K | P | W | - | Y | E | T | - | - | - | - | - | S | K | L | A | S |
| 38 | W | Y | Q | Q | K | P | G | E | A | F | K | L | L | - | Y | S | G | - | - | - | - | - | S | T | L | A | S |
| 39 | W | Y | Q | Q | K | P | G | E | A | N | K | L | L | - | Y | S | G | - | - | - | - | - | S | T | L | Q | S |
| 40 | W | F | Q | Q | K | P | G | K | S | P | Q | L | L | - | Y | D | A | - | - | - | - | - | T | S | L | A | D |
| 41 | W | Y | Q | Q | K | P | G | K | A | Y | Q | L | L | L | Y | D | A | - | - | - | - | - | T | T | L | A | D |
| 42 | W | Y | Q | Q | K | P | G | E | A | P | K | L | L | - | Y | S | G | - | - | - | - | - | S | S | L | Q | S |
| 43 | W | Y | Q | Q | K | P | G | K | A | P | R | Q | L | - | R | Y | T | - | - | - | - | - | S | A | L | V | S |
| 44 | W | Y | Q | Q | K | P | G | K | S | P | Q | L | L | - | Y | D | A | - | - | - | - | - | T | S | L | A | D |
| 45 | W | Y | Q | Q | K | P | G | E | P | Y | N | L | L | - | Y | S | G | - | - | - | - | - | S | T | L | Q | S |
| 46 | W | Y | Q | Q | K | P | G | K | S | P | Q | L | L | - | Y | D | A | - | - | - | - | - | T | T | L | A | D |
| 47 | W | Y | Q | Q | K | P | G | E | P | Y | N | L | L | - | H | S | G | - | - | - | - | - | S | T | L | Q | S |
| 48 | W | Y | Q | Q | K | P | G | K | S | P | H | L | L | - | Y | D | A | - | - | - | - | - | T | T | L | A | D |

Figure 6 part 7: Hybridoma derived P2X4 Antibodies (Abs) VL sequences

| Antibody number | | | | | | | | | | | | | | FW 3 | | | | | | | | | | | | | | | | | | | | CDR 3 | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Kabat numbering | 57 | 58 | 59 | 60 | 61 | 62 | 63 | 64 | 65 | 66 | 67 | 68 | a | b | 69 | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | a b c d e f g h i | 96 | 97 |
| 35 | G | T | P | S | R | F | S | G | S | R | S | G | - | - | T | D | F | T | L | T | I | R | S | L | E | P | E | D | F | G | L | Y | Y | C | Q | Q | Y | Y | E | K | P | - - - - - - - - - | Y | T |
| 36 | G | V | P | S | R | F | S | G | S | R | S | G | - | - | T | Q | Y | S | L | K | I | S | R | M | Q | V | E | D | - | G | I | Y | S | C | L | Q | A | H | S | N | P | - - - - - - - - - | W | T |
| 37 | G | V | P | D | R | F | S | G | S | G | S | G | - | - | T | S | Y | S | F | T | I | S | S | L | E | T | E | D | A | A | T | Y | Y | C | H | Q | W | S | R | T | P | - - - - - - - - - | P | T |
| 38 | G | T | P | S | R | F | S | G | S | G | S | V | - | - | T | D | F | T | L | T | I | R | N | L | E | P | E | D | F | G | L | Y | Y | C | Q | Q | Y | Y | E | N | P | - - - - - - - - - | Y | T |
| 39 | G | T | P | S | R | F | S | G | S | G | S | G | - | - | T | D | F | T | L | T | I | S | R | L | E | P | E | D | F | A | V | Y | Y | C | Q | Q | Y | Y | E | K | P | - - - - - - - - - | L | T |
| 40 | G | V | P | S | R | F | S | G | S | R | S | G | - | - | T | Q | F | S | L | K | I | S | R | L | Q | V | E | D | F | G | S | Y | Y | C | Q | Q | Y | Y | N | N | P | - - - - - - - - - | N | T |
| 41 | G | V | P | S | R | F | S | G | S | G | S | G | - | - | T | Q | Y | S | L | K | I | S | R | L | Q | V | E | D | - | G | S | Y | Y | C | Q | Q | A | H | S | N | P | - - - - - - - - - | R | T |
| 42 | G | T | P | S | R | F | S | G | S | G | S | A | - | - | R | D | F | T | F | S | I | S | R | L | E | P | E | D | - | A | L | Y | Y | C | Q | Q | A | Y | E | K | P | - - - - - - - - - | Y | T |
| 43 | G | V | P | S | R | F | S | G | S | G | S | G | - | - | T | Q | Y | S | L | K | I | S | R | V | Q | S | E | D | - | G | S | Y | Y | C | L | Q | A | Y | N | L | P | - - - - - - - - - | Y | T |
| 44 | G | T | P | S | R | F | S | G | S | G | S | G | - | - | T | D | F | T | L | T | I | S | R | L | Q | V | E | D | F | A | L | Y | Y | C | Q | Q | Y | D | T | N | P | - - - - - - - - - | L | T |
| 45 | G | V | P | S | R | F | S | G | S | G | S | G | - | - | T | D | F | T | L | T | I | S | S | L | Q | P | E | D | - | G | S | Y | Y | C | Q | Q | A | H | E | K | P | - - - - - - - - - | Y | T |
| 46 | G | T | P | S | R | F | S | G | S | G | S | G | - | - | T | D | F | T | L | T | I | S | R | L | Q | V | E | D | F | G | L | Y | Y | C | Q | Q | Y | Y | S | H | P | - - - - - - - - - | R | T |
| 47 | G | V | P | S | R | F | S | G | S | G | S | G | - | - | T | D | F | T | L | T | I | S | R | L | E | Q | P | E | D | F | L | Y | Y | C | Q | Q | T | Y | E | N | P | - - - - - - - - - | Y | T |
| 48 | G | V | P | S | R | F | S | G | S | G | S | G | - | - | T | Q | Y | S | L | K | I | S | R | L | Q | V | E | D | - | G | S | Y | Y | C | Q | K | A | H | S | N | P | - - - - - - - - - | W | T |

Figure 6 part 8: Hybridoma derived P2X4 Antibodies (Abs) VL sequences

| Antibody number | | | | | | | FW 4 | | | | | |
|---|---|---|---|---|---|---|---|---|---|---|---|---|
| Kabat numbering | 98 | 99 | 100 | 101 | 102 | 103 | 104 | 105 | 106a | b | c | 107 |
| 35 | F | G | A | G | T | K | L | E | L | - | - | K |
| 36 | F | G | G | G | S | K | L | E | L | - | - | K |
| 37 | F | G | G | G | T | K | L | E | M | - | - | R |
| 38 | F | G | A | G | T | K | L | E | L | - | - | K |
| 39 | F | G | S | G | T | K | L | E | I | - | - | K |
| 40 | F | G | P | G | T | K | L | E | L | - | - | K |
| 41 | F | G | G | G | T | K | L | E | L | - | - | K |
| 42 | F | G | A | G | T | K | L | E | L | - | - | K |
| 43 | F | G | A | G | T | K | L | E | L | - | - | K |
| 44 | F | G | S | G | T | K | L | E | I | - | - | K |
| 45 | F | G | A | G | T | K | L | E | L | - | - | K |
| 46 | F | G | G | G | T | N | L | E | L | - | - | K |
| 47 | F | G | A | G | T | K | L | E | L | - | - | K |
| 48 | F | G | G | G | T | K | L | E | L | - | - | K |

Figure 7: Part 1a - Antibodies (Abs) Binding and Function: Hybridoma P2X4 binding antibodies (all clones)

| Antibody number | Human P2X4 binding | Cynomolgus P2X4 binding | Mouse P2X4 binding | Fraction of control current at Human P2X4 (ephys) | Fraction of control current at Mouse P2X4 (ephys) | Concentration in ephys assay (µg/ml) |
|---|---|---|---|---|---|---|
| 35 | + |   | + | 0.648 | 0.461 | 119 |
| 36 | + | - | + | 0.604 | 0.051 | 327 |
| 37 | + |   | + | 1.056 | 0.270 | 207 |
| 38 | + | - | + | 0.486 | 0.178 | 40 |
| 39 | + | - | + |   | -0.067 | 141 |
| 40 | + |   | + | 0.815 | 0.231 | 176 |
| 41 | + |   | + | 0.633 | 0.072 | 73 |
| 42 | + |   | + | 0.414 | 0.333 | 109 |
| 43 | + | + | + | 0.395 | 0.307 | 86 |
| 44 | + |   | + |   | 0.253 | 35 |
| 45 | + |   | + | 0.620 | 0.281 | 158 |
| 46 | + | - | + | 0.383 | -0.079 | 396 |
| 47 | + | - | + | 0.912 | 0.196 | 161 |
| 48 | + | - | + | 0.560 | 0.041 | 227 |
| 49 |   |   | + |   | 0.940 | 53 |
| 50 |   |   | + |   | 0.584 | 246 |
| 51 |   |   | + |   | 0.516 | 57 |
| 52 |   |   | + |   | 0.569 | 81 |
| 53 |   |   | + |   | 3.187 | 113 |
| 54 |   |   | + |   | 0.570 | 104 |
| 55 |   |   | + |   | 0.607 | 86 |
| 56 |   |   | + |   | 1.080 | 113 |
| 57 |   |   | + |   | 0.651 | <LOD |
| 58 |   |   | + |   | 0.486 | 179 |
| 59 |   |   | + |   | 1.093 | 83 |
| 60 |   |   | + |   | 1.733 | <LOD |
| 61 | + |   | + |   | 0.115 | 24 |
| 62 |   |   | + |   | 1.177 | 20 |

| Key | | |
|---|---|---|
|   | + | Binding observed in FMAT assay |
|   | - | No binding observed in FMAT assay |
|   | NT or Blank | Not tested in assay |
|   | < LOD | [IgG] below limit of detection |

Figure 7: Part 1b

| Antibody number | Human P2X4 binding | Cynomolgus P2X4 binding | Mouse P2X4 binding | Fraction of control current at Human P2X4 (ephys) | Fraction of control current at Mouse P2X4 (ephys) | Concentration in ephys assay (µg/ml) |
|---|---|---|---|---|---|---|
| 63 | | | + | | 0.976 | <LOD |
| 64 | | | + | | 1.893 | 67 |
| 65 | - | - | + | | 0.394 | 364 |
| 66 | | | + | | 1.574 | 85 |
| 67 | | | + | | 0.714 | 107 |
| 68 | | | + | | 1.767 | 107 |
| 69 | | | + | | 0.887 | 89 |
| 70 | | | + | | 0.794 | 161 |
| 71 | | | + | | 3.280 | 76 |
| 72 | | | + | | 0.662 | 337 |
| 73 | | | + | | 0.467 | 71 |
| 74 | | | + | | 3.767 | 95 |
| 75 | | | + | | 0.713 | 61 |
| 76 | | | + | | 0.793 | 91 |
| 77 | | | + | | 1.118 | 37 |
| 78 | | | + | | 0.763 | 54 |
| 79 | | | + | | 0.686 | 38 |
| 80 | | | + | | 0.650 | <LOD |
| 81 | | | + | | 0.832 | 199 |
| 82 | | | + | | 1.240 | 181 |
| 83 | | | + | | 1.091 | 372 |
| 84 | | | + | | 0.381 | 31 |
| 85 | | | + | | 1.821 | <LOD |
| 86 | | | + | | 1.153 | <LOD |
| 87 | | | + | | 0.760 | 212 |
| 88 | | | + | | 1.003 | 219 |

Figure 7: Part 1c

| Antibody number | Human P2X4 binding | Cynomolgus P2X4 binding | Mouse P2X4 binding | Fraction of control current at Human P2X4 (ephys) | Fraction of control current at Mouse P2X4 (ephys) | Concentration in ephys assay (mg/ml) |
|---|---|---|---|---|---|---|
| 89 | | | + | | 1.710 | 381 |
| 90 | | | + | | 0.533 | 210 |
| 91 | | | + | | 1.338 | 116 |
| 92 | | | + | | 2.653 | 80 |
| 93 | | | + | | 1.743 | 171 |
| 94 | | | + | | 2.033 | 136 |
| 95 | | | + | | 1.221 | 48 |
| 96 | | | + | | 0.539 | 89 |
| 97 | | | + | | 0.976 | 94 |
| 98 | | | + | | 0.564 | 69 |
| 99 | | | + | | 0.821 | 181 |
| 100 | | | + | | 0.907 | 30 |
| 101 | | | + | | 4.969 | 318 |
| 102 | | | + | | 0.778 | 321 |
| 103 | | | + | | 0.860 | 94 |
| 104 | | | + | | 0.720 | 311 |
| 105 | | | + | | 0.398 | 233 |
| 106 | | | + | | 0.703 | 233 |
| 107 | - | | + | 0.540 | 0.151 | 84 |
| 108 | | | + | | 1.007 | 258 |
| 109 | | | + | | 0.805 | 52 |
| 110 | | | + | | 0.780 | 89 |
| 111 | | | + | | 0.025 | 216 |
| 112 | | | + | | 0.650 | 86 |
| 113 | | | + | | 1.136 | 238 |
| 114 | | | + | | 1.567 | 398 |
| 115 | | | + | | 1.635 | 183 |

Figure 7: Part 1d

| Antibody number | Human P2X4 binding | Cynomolgus P2X4 binding | Mouse P2X4 binding | Fraction of control current at Human P2X4 (ephys) | Fraction of control current at Mouse P2X4 (ephys) | Concentration in ephys assay (mg/ml) |
|---|---|---|---|---|---|---|
| 115 | | | + | | 1.635 | 183 |
| 116 | | | + | | 1.287 | 141 |
| 117 | | | + | | 0.749 | 315 |
| 118 | - | - | + | | 0.398 | 103 |
| 119 | | | + | | 2.211 | 49 |
| 120 | | | + | | 0.845 | 317 |
| 121 | | | + | | 0.952 | 73 |
| 122 | | | + | | 0.982 | 103 |
| 123 | | | + | | 0.933 | 235 |
| 124 | | | + | | 0.711 | 120 |
| 125 | | | + | | 1.738 | 360 |
| 126 | | | + | | 1.792 | 106 |
| 127 | | | + | | 0.467 | 75 |
| 128 | | | + | | 0.542 | 76 |
| 129 | | | + | | 0.716 | 57 |
| 130 | | | + | | 0.595 | 138 |
| 131 | | | + | | 1.233 | 351 |
| 132 | | | + | | 0.560 | 118 |
| 133 | | | + | | 0.608 | 195 |
| 134 | | | + | | 1.455 | 97 |
| 135 | | | + | | 1.157 | 81 |
| 136 | | | + | | 0.679 | 70 |
| 137 | | | + | | 0.903 | 118 |
| 138 | | | + | | 1.521 | 295 |
| 139 | | | + | | 1.458 | 150 |
| 140 | | | + | | 0.573 | 118 |

Figure 7: Part 1e

| Antibody number | Human P2X4 binding | Cynomolgus P2X4 binding | Mouse P2X4 binding | Fraction of control current at Human P2X4 (ephys) | Fraction of control current at Mouse P2X4 (ephys) | Concentration in ephys assay (mg/ml) |
|---|---|---|---|---|---|---|
| 141 | | | + | | 0.892 | 231 |
| 142 | | | + | | 1.505 | 367 |
| 143 | | | + | | 0.770 | 269 |
| 144 | | | + | | 0.656 | 174 |
| 145 | | + | + | | 0.150 | 69 |
| 146 | | | + | | 1.480 | 141 |
| 147 | | | + | | 0.727 | 60 |
| 148 | | | + | | 2.619 | 391 |
| 149 | | | + | | 1.602 | 379 |
| 150 | | | + | | 0.450 | 203 |
| 151 | | | + | | 1.011 | 293 |
| 152 | | | + | | 0.538 | 400 |
| 153 | | | + | | 1.928 | 282 |
| 154 | | | + | | 0.704 | 444 |
| 155 | | | + | | 0.928 | 279 |
| 156 | | | + | | 1.078 | <LOD |
| 157 | | | + | | 1.035 | 247 |
| 158 | | | + | | 1.306 | 298 |
| 159 | | | + | | 5.781 | 118 |
| 160 | | | + | | 0.918 | 180 |
| 161 | | | + | | 0.956 | 205 |
| 162 | | | + | | 1.388 | 155 |
| 163 | - | ' | + | | 0.375 | 59 |
| 164 | | | + | | 0.546 | 268 |
| 165 | | | + | | 0.615 | <LOD |

Figure 7: Part 1f

| Antibody number | Human P2X4 binding | Cynomolgus P2X4 binding | Mouse P2X4 binding | Fraction of control current at Human P2X4 (ephys) | Fraction of control current at Mouse P2X4 (ephys) | Concentration in ephys assay (mg/ml) |
|---|---|---|---|---|---|---|
| 166 | | | + | | 0.810 | 182 |
| 167 | | | + | | 1.258 | 151 |
| 168 | | | + | | 1.808 | 88 |
| 169 | | | + | | 1.773 | 128 |
| 170 | | | + | | 0.690 | 93 |
| 171 | | | + | | 0.524 | 396 |
| 172 | | | + | 1.078 | 0.307 | 364 |
| 173 | | | + | | 0.702 | 154 |
| 174 | | | + | | 0.656 | 225 |
| 175 | | | + | | 1.223 | 286 |
| 176 | | | + | | 1.444 | 148 |
| 177 | | | + | | 0.728 | 251 |
| 178 | | | + | | 1.356 | 297 |
| 179 | | | + | | 0.988 | 332 |
| 180 | | | + | | 0.679 | 351 |
| 181 | | | + | | 1.392 | 89 |
| 182 | | | + | | 0.572 | <LOD |
| 183 | | | + | 0.593 | 0.627 | 193 |
| 184 | | | + | | 0.373 | 84 |
| 185 | | | + | | 0.484 | 310 |
| 186 | | | + | | 1.320 | 257 |
| 187 | | | + | | 0.846 | 315 |
| 188 | | | + | | 0.645 | 114 |
| 189 | + | | + | | 0.082 | 208 |
| 190 | | - | + | | 0.505 | 127 |
| 191 | | | + | | 0.932 | 97 |
| 192 | | | + | | 1.855 | 29 |
| 193 | | | + | | 0.660 | <LOD |
| 194 | | | + | | 0.940 | 225 |

Figure 7: Part 1g

| Antibody number | Human P2X4 binding | Cynomolgus P2X4 binding | Mouse P2X4 binding | Fraction of control current at Human P2X4 (ephys) | Fraction of control current at Mouse P2X4 (ephys) | Concentration in ephys assay (mg/ml) |
|---|---|---|---|---|---|---|
| 195 | | | + | | 0.896 | 110 |
| 196 | | | + | | 0.860 | 100 |
| 197 | | | + | | 0.666 | 155 |
| 198 | | | + | | 0.801 | 57 |
| 199 | | | + | | 0.650 | 413 |
| 200 | | | + | | 0.503 | 110 |
| 201 | | | + | | 0.584 | 124 |
| 202 | | | + | | 0.998 | 317 |
| 203 | | | + | | 0.690 | 283 |
| 204 | | | + | | 1.202 | 104 |
| 205 | | | + | | 0.707 | 279 |
| 206 | | | + | | 0.911 | 104 |
| 207 | | - | + | | 0.629 | 324 |
| 208 | | | + | 0.937 | 0.072 | 296 |
| 209 | | | + | | 0.709 | 126 |
| 210 | | | + | | 1.506 | 411 |
| 211 | | | + | | 1.108 | 74 |
| 212 | | | + | | 1.031 | 91 |
| 213 | | | + | | 1.346 | 223 |
| 214 | | | + | | 0.873 | 85 |
| 215 | | | + | | 0.512 | 373 |
| 216 | | | + | | 1.177 | 124 |
| 217 | | | + | | 0.826 | 66 |
| 218 | | | + | | 0.711 | 73 |
| 219 | | | + | | 0.746 | 100 |
| 220 | - | | + | | 0.645 | 139 |
| 221 | - | - | + | 1.009 | 0.163 | 363 |

Figure 7: Part 1h

| Antibody number | Human P2X4 binding | Cynomolgus P2X4 binding | Mouse P2X4 binding | Fraction of control current at Human P2X4 (ephys) | Fraction of control current at Mouse P2X4 (ephys) | Concentration in ephys assay (mg/ml) |
|---|---|---|---|---|---|---|
| 222 | | | + | | 1.317 | <LOD |
| 223 | | | + | | 1.071 | 102 |
| 224 | | | + | | 1.047 | 337 |
| 225 | | | + | | 0.539 | 81 |
| 226 | | | + | | 0.914 | 207 |
| 227 | | | + | | 0.781 | 111 |
| 228 | | | + | | 0.946 | 92 |
| 229 | | | + | | 0.760 | 135 |
| 230 | | | + | | 1.131 | 117 |
| 231 | | | + | | 1.840 | 262 |
| 232 | | | + | | 0.652 | 281 |
| 233 | | | + | | 0.714 | 486 |
| 234 | - | | + | 0.807 | 0.156 | 452 |
| 235 | | | + | | 0.660 | 287 |
| 236 | | | + | | 0.530 | 58 |
| 237 | | | + | | 0.725 | 355 |
| 238 | - | | + | 0.968 | 0.238 | 157 |
| 239 | | | + | | 1.064 | <LOD |
| 240 | | | + | | 1.899 | <LOD |
| 241 | | | + | | 0.877 | <LOD |
| 242 | | | + | | 1.059 | 230 |
| 243 | | | + | | 1.143 | 18 |
| 244 | | | + | | 0.787 | 171 |
| 245 | | | + | | 0.625 | 357 |
| 246 | | | + | | 1.059 | 64 |
| 247 | | | + | | 0.967 | 268 |
| 248 | | | + | | 0.747 | 32 |

Figure 7: Part 1i

| Antibody number | Human P2X4 binding | Cynomolgus P2X4 binding | Mouse P2X4 binding | Fraction of control current at Human P2X4 (ephys) | Fraction of control current at Mouse P2X4 (ephys) | Concentration in ephys assay (mg/ml) |
|---|---|---|---|---|---|---|
| 249 | | | + | | 0.535 | 153 |
| 250 | | | + | | 0.800 | 53 |
| 251 | | | + | | 0.460 | 199 |
| 252 | | | + | | 1.979 | <LOD |
| 253 | | | + | | 1.036 | 252 |
| 254 | | | + | | 1.097 | 144 |
| 255 | | | + | | 0.926 | 273 |
| 256 | | | + | | 0.688 | 392 |
| 257 | | | + | | 1.316 | <LOD |
| 258 | | | + | | 0.606 | 67 |
| 259 | | | + | | 1.145 | 57 |
| 260 | | | + | | 0.585 | 244 |
| 261 | | | + | | 0.691 | 79 |
| 262 | | | + | | 0.557 | 220 |
| 263 | | | + | | 1.286 | 92 |
| 264 | | | + | | 0.161 | 66 |
| 265 | | | + | | 1.076 | <LOD |
| 266 | - | | + | | 0.463 | 61 |
| 267 | | | + | | 0.443 | 49 |
| 268 | | | + | | 4.067 | 73 |
| 269 | | | + | | 0.757 | <LOD |
| 270 | | | + | | 0.802 | 91 |
| 271 | | | + | | 0.696 | 112 |
| 272 | | | + | | 0.832 | 158 |
| 273 | | | + | | 0.814 | 403 |
| 274 | | | + | | 0.801 | 300 |
| 275 | | | + | | 0.982 | 141 |

Figure 7: Part 1j

| Antibody number | Human P2X4 binding | Cynomolgus P2X4 binding | Mouse P2X4 binding | Fraction of control current at Human P2X4 (ephys) | Fraction of control current at Mouse P2X4 (ephys) | Concentration in ephys assay (mg/ml) |
|---|---|---|---|---|---|---|
| 276 | | | + | | 1.172 | 90 |
| 277 | | | + | | 0.936 | 136 |
| 278 | | | + | | 1.142 | 101 |
| 279 | | | + | | 0.640 | 359 |
| 280 | | | + | | 1.134 | 91 |
| 281 | - | - | + | 0.800 | 0.098 | 306 |
| 282 | | | + | | 1.342 | 25 |
| 283 | | | + | | 0.730 | 78 |
| 284 | | | + | | 1.665 | 94 |
| 285 | | | + | | 0.436 | 55 |
| 286 | | | + | | 0.753 | <LOD |

Example of a potentiating IgG - activity against huP2X4

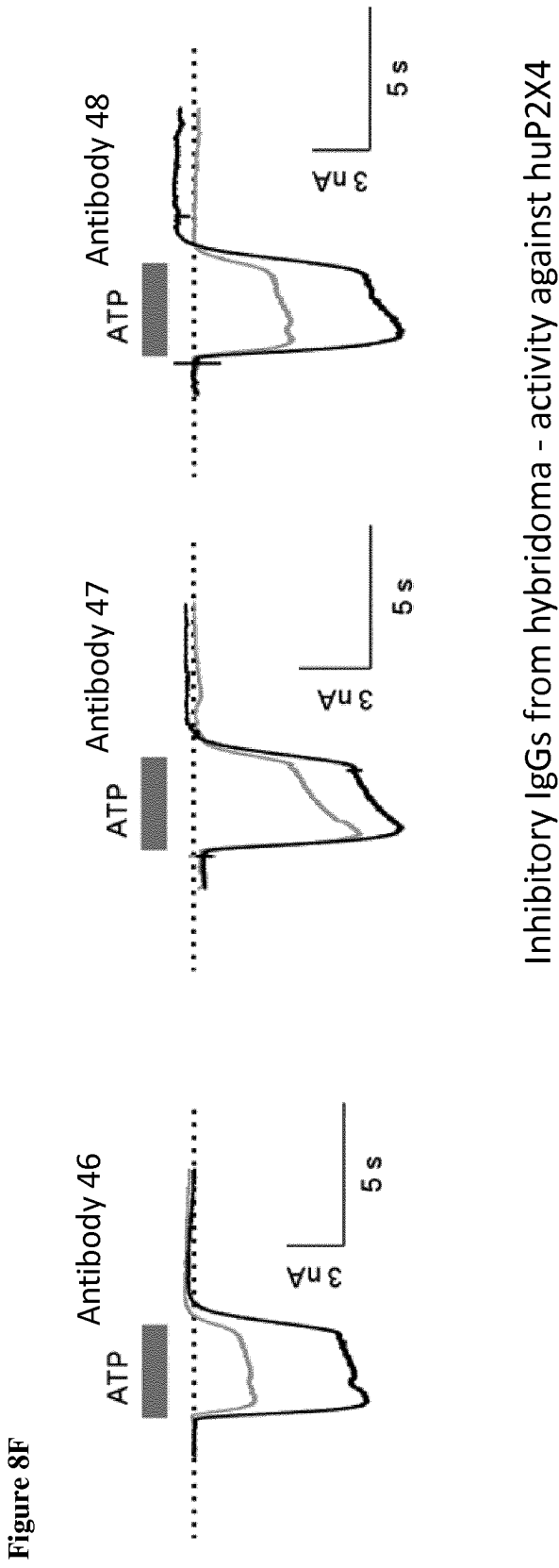

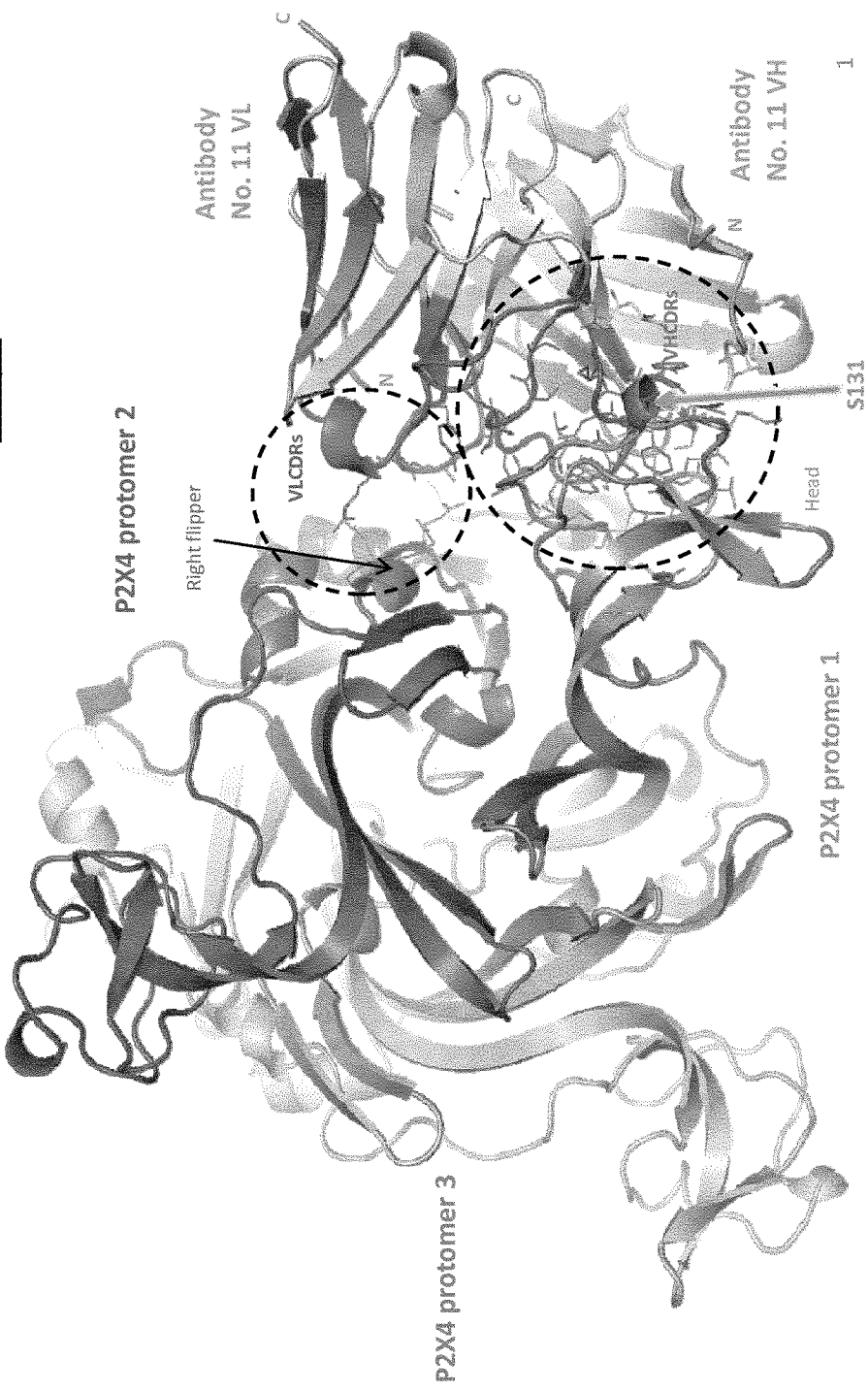

Figure 9

Bipartite epitope-paratope interface – Antibody No. 11 VHCDRs-P2X4 protomer 1 head (major interface); Antibody No. 11 VLCDRs-P2X4 protomer 2 right flipper (minor interface).

Three Antibody No. 11 molecules can potentially bind the same P2X4 trimer molecule.
The two Fab arms of Antibody No. 11 are not likely to engage the same P2X4 trimer molecule.
The ab is predicted to bind a P2X heteromer across the epitope formed by two P2X4 subunits.

Figure 10

Predicted epitope is only moderately identical in sequence between human and mouse P2X4.
All epitope differences in orthologs are restricted to the head region.

Comparison of predicted epitope sequence in orthologs against human P2X4

| Species | % identity | % similarity |
|---------|-----------|--------------|
| cyno    | 92.3      | 92.3         |
| mouse   | 65.4      | 76.9         |
| rat     | 65.4      | 80.8         |

Predicted epitope ▇  Head ☐

Figure 12: Part 1: Phage display derived P2X4 binding – antibodies (Abs) VH sequences

Figure 12: Part 2: Phage display derived P2X4 binding – antibodies (Abs) VH sequences Figure 12: Part 3: Phage display derived P2X4 binding – antibodies (Abs) VL sequences Figure 12: Part 4: Phage display derived P2X4 binding – antibodies (Abs) VL sequences FIGURE 13 Part 1: Hybridoma derived P2X4 binding – antibodies (Abs) VH sequences FIGURE 13 Part 2: Hybridoma derived P2X4 binding – antibodies (Abs) VH sequences FIGURE 13 Part 3: Hybridoma derived P2X4 binding – antibodies (Abs) VL sequences FIGURE 13 Part 4: Hybridoma derived P2X4 binding – antibodies (Abs) VL sequences

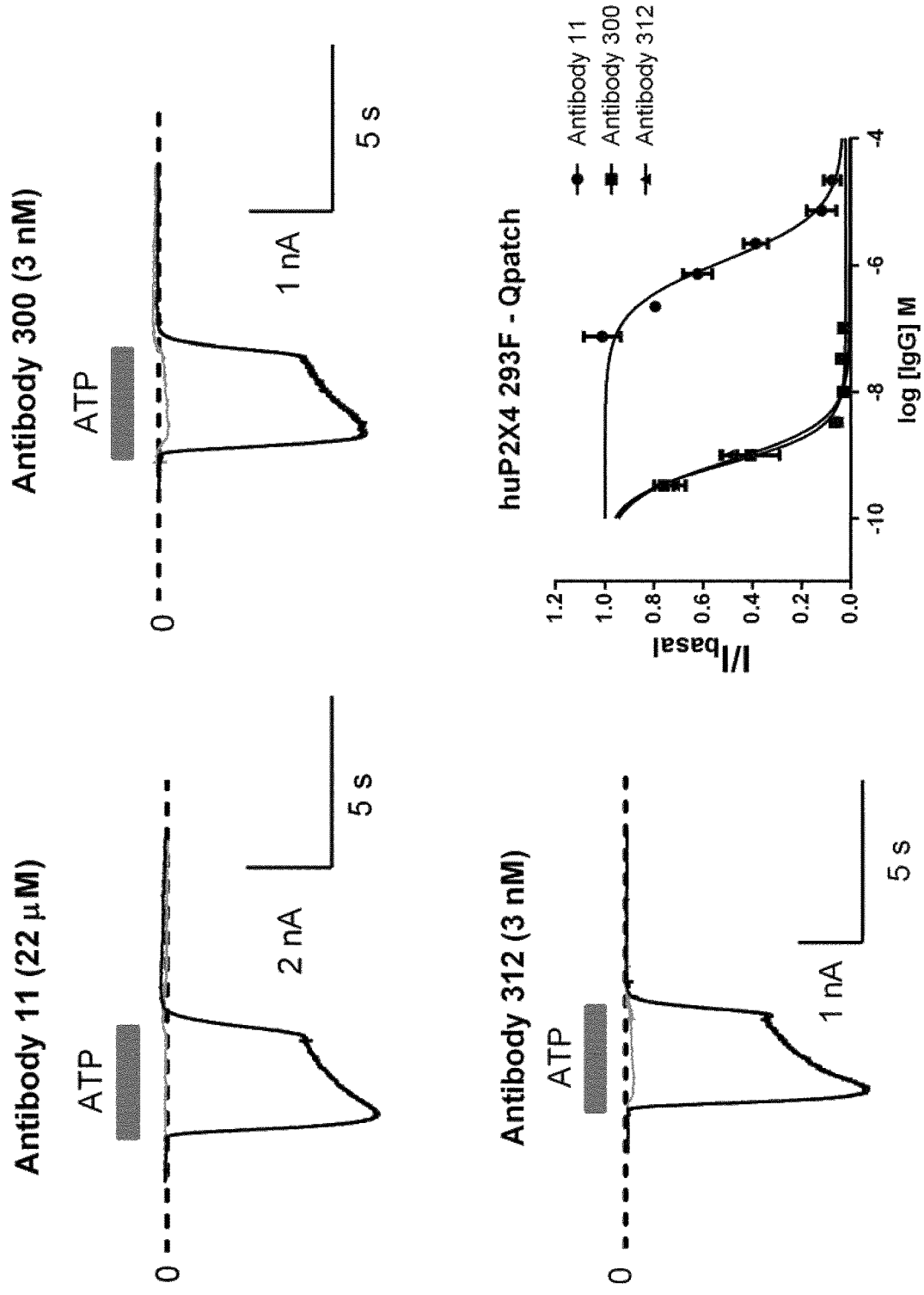
Figure 14: Activity of antibodies in a huP2X4 electrophysiology assay

Figure 15: Potency of Antibody 11 optimized antibodies at huP2X4

| Antibody number | Geometric mean IC$_{50}$ (Molar) huP2X4 FLIPR assay | IC$_{50}$ (Molar) huP2X4 Ephys (HEK293f) |
|---|---|---|
| 287 | 3.9E-08 | 3.5E-09 |
| 288 | | 4.7E-08 |
| 289 | | 4.5E-08 |
| 290 | 4.6E-07 | 2.6E-09 |
| 291 | 1.1E-07 | 4.9E-09 |
| 292 | 1.8E-07 | 7.4E-09 |
| 293 | 7.7E-08 | 4.9E-09 |
| 294 | 1.6E-07 | 1.5E-08 |
| 295 | 2.4E-07 | 1.2E-09 |
| 296 | 4.5E-08 | 1.3E-09 |
| 297 | 5.3E-08 | 1.8E-09 |
| 298 | 2.9E-08 | 1.1E-09 |
| 299 | | 2.2E-09 |
| 300 | 7.9E-09 | 7.1E-10 |
| 302 | 8.0E-10 | 5.6E-10 |
| 303 | 1.9E-07 | 2.4E-09 |
| 304 | 9.5E-08 | 2.4E-09 |
| 305 | | >1E-07 |
| 306 | | >1E-07 |
| 307 | | >1E-07 |
| 308 | 7.0E-10 | 6.1E-10 |
| 309 | 7.3E-08 | 1.2E-09 |
| 310 | | 6.2E-09 |
| 311 | 4.0E-10 | 5.0E-10 |
| 312 | 5.8E-10 | 5.3E-10 |
| 313 | 3.3E-10 | 5.4E-10 |
| 314 | 3.5E-08 | 1.1E-09 |
| 315 | 3.0E-10 | 6.9E-10 | blank = data not disclosed

Figure 16: Potency of hybridoma derived antibodies at mouse and human P2X4

| Antibody Number | IC$_{50}$ (Molar) huP2X4 Ephys (HEK293f) | n | IC$_{50}$ (Molar) moP2X4 Ephys (HEK293f) | n |
|---|---|---|---|---|
| 38 | 3.26E-07 | 3 | 4.89E-09 | 4 |
| 43 | NT | | 8.13E-09 | 4 |
| 46 | 1.79E-07 | 4 | 2.03E-08 | 8 |
| 208 | > 30E-06 | 4 | 2.57E-08 | 16 |

NT indicates not tested

Figure 17: Effect of P2X4 antibodies on mouse microglial P2X4 currents

| Antibody Number | huIgG1 | | | | rat IgG1 | | | |
|---|---|---|---|---|---|---|---|---|
| | Concentration (mg/ml) | Current (pA) | n | Significant difference from Control | Concentration (mg/ml) | Current (pA) | n | Significant difference from Control |
| Control IgG | 0.33 | -446.2 | 11 | - | 0.4 | -622.5 | 10 | - |
| 38 | 0.33 | -99.29 | 4 | N | 0.11 | -244.6 | 5 | N |
| 43 | 0.33 | -332.3 | 3 | N | - | NT | - | - |
| 46 | 0.33 | 9.06 | 3 | Y | 0.25 | 40.96 | 7 | Y |
| 208 | 0.33 | 12.12 | 4 | Y | 0.4 | 35.09 | 3 | Y |

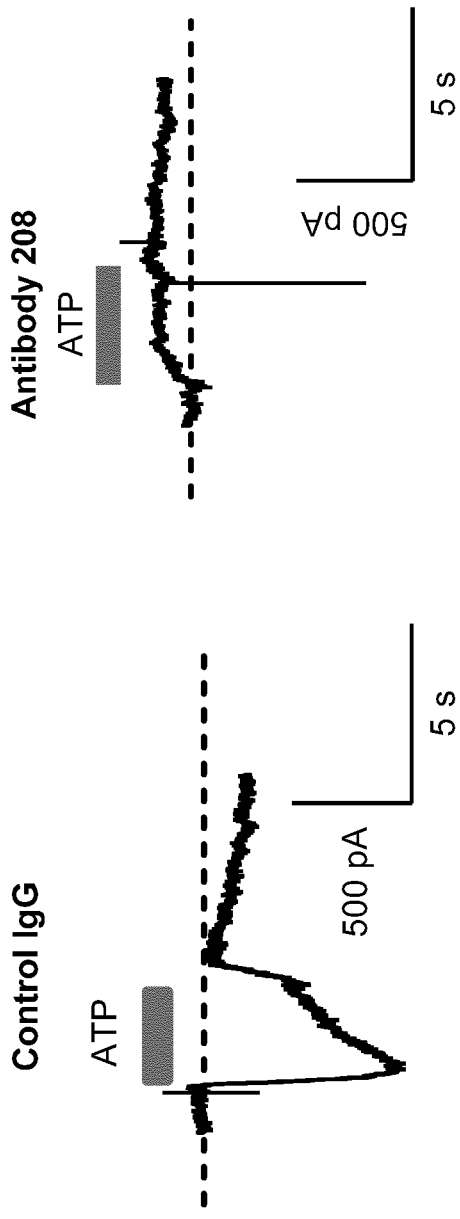
Figure 18: Exemplar effect of antibody 208 on native P2X4 currents in primary mouse microglia

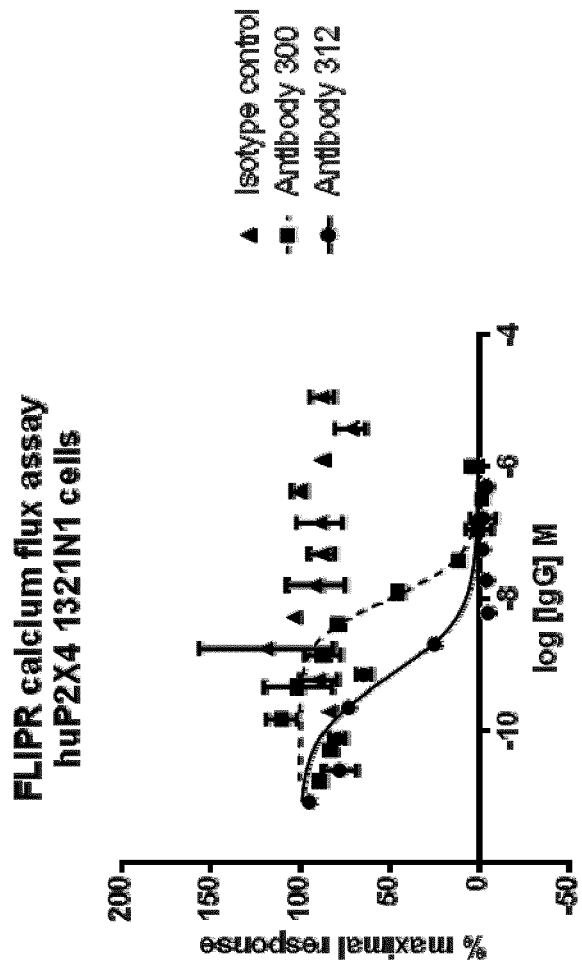
Figure 19. Example of activity of two anti-P2X4 antibodies in a calcium flux assay.

Figure 20: Effect of mouse reactive P2X4 antibodies on native mouse microglial P2X4 assayed on FLIPR
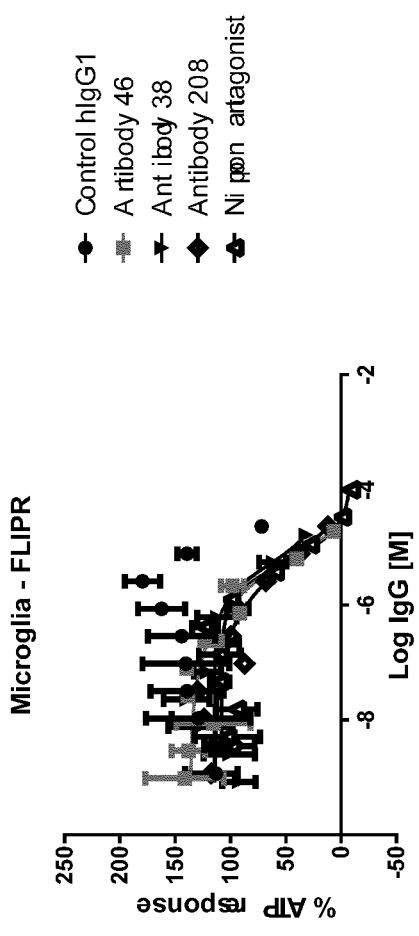

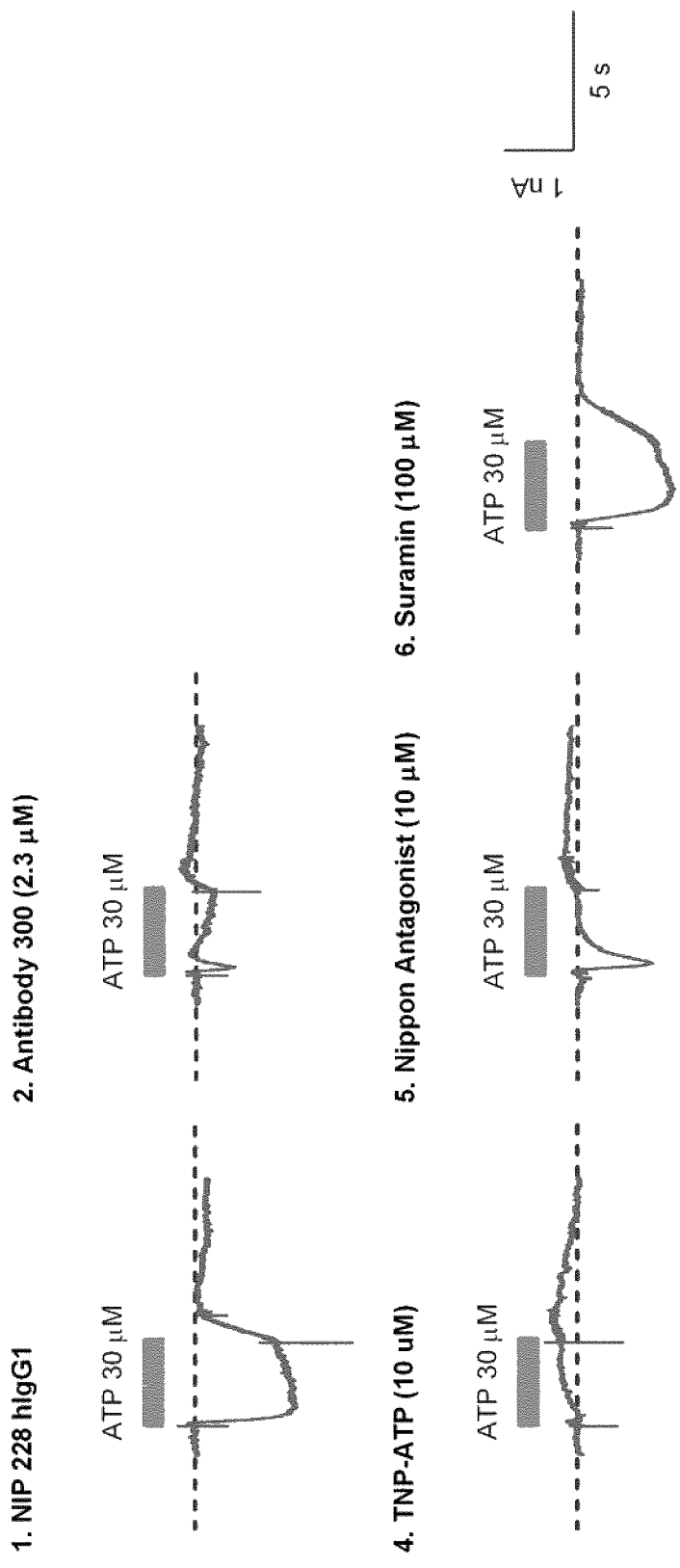
Figure 21: Exemplary electrophysiology current traces from human monocyte derived macrophages Figure 22: Summary of the effect of P2X4 antibodies on human monocyte derived macrophage, ATP induced currents.

| Nickname | Antibody number | Donor 1 | | | Donor 2 | | |
|---|---|---|---|---|---|---|---|
| | | Mean Current (A) | SD | n | Mean Current (A) | SD | n |
| NIP 228 | | -1.4E-09 | 1.3E-09 | 8 | -7.0E-10 | 1.3E-09 | 7 |
| | 300 | -2.5E-11 | 2.4E-10 | 5 | 1.4E-12 | 3.2E-10 | 7 |
| TNP ATP | | 3.6E-10 | 3.1E-10 | 7 | | | |
| Nippon Antagonist | | | | | 1.3E-10 | 7.4E-11 | 6 |

SEQUENCE LISTING

<160> NUMBER OF SEQ ID NOS: 1072

<210> SEQ ID NO 1
<211> LENGTH: 387
<212> TYPE: DNA
<213> ORGANISM: Homo sapiens

<400> SEQUENCE: 1
gaggtgcagc tgttggagtc tgggggaggc ttggtacagc ctggggggtc cctgagactc     60
tcctgtgcag cctctggatt cacctttagc ggctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gagagaagaa    300
cgagggagtt actttggttt tagtggttat tactacacat actactttga ctactggggc    360
cgagggacaa tggtcaccgt ctcgagt                                         387

<210> SEQ ID NO 2
<211> LENGTH: 129
<212> TYPE: PRT
<213> ORGANISM: Homo sapiens

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Arg Gly Ser Tyr Phe Gly Phe Ser Gly Tyr Tyr Tyr
            100                 105                 110

Thr Tyr Tyr Phe Asp Tyr Trp Gly Arg Gly Thr Met Val Thr Val Ser
        115                 120                 125

Ser

```
<210> SEQ ID NO 3
<211> LENGTH: 5
<212> TYPE: PRT
<213> ORGANISM: Homo sapiens

<400> SEQUENCE: 3

Gly Tyr Ala Met Ser
1               5

<210> SEQ ID NO 4
<211> LENGTH: 17
<212> TYPE: PRT
<213> ORGANISM: Homo sapiens

<400> SEQUENCE: 4

Ala Ile Ser Gly Ser Gly Gly Ser Thr Tyr Tyr Ala Asp Ser Val Lys
1               5                   10                  15

Gly

<210> SEQ ID NO 5
<211> LENGTH: 20
<212> TYPE: PRT
<213> ORGANISM: Homo sapiens

<400> SEQUENCE: 5

Glu Glu Arg Gly Ser Tyr Phe Gly Phe Ser Gly Tyr Tyr Tyr Thr Tyr
1               5                   10                  15

Tyr Phe Asp Tyr
            20

<210> SEQ ID NO 6
<211> LENGTH: 30
<212> TYPE: PRT
<213> ORGANISM: Homo sapiens

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 7
<211> LENGTH: 14
<212> TYPE: PRT
<213> ORGANISM: Homo sapiens

<400> SEQUENCE: 7

Trp Val Arg Gln Ala Pro Gly Lys Gly Leu Glu Trp Val Ser
1               5                   10

<210> SEQ ID NO 8
<211> LENGTH: 32
<212> TYPE: PRT
<213> ORGANISM: Homo sapiens

<400> SEQUENCE: 8

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 9
```

<211> LENGTH: 11
<212> TYPE: PRT
<213> ORGANISM: Homo sapiens

<400> SEQUENCE: 9

Trp Gly Arg Gly Thr Met Val Thr Val Ser Ser
1               5                   10

<210> SEQ ID NO 10
<211> LENGTH: 327
<212> TYPE: DNA
<213> ORGANISM: Homo sapiens

<400> SEQUENCE: 10
caggctgtgc tgactcagcc gtcctcagtg tctggggccc cagggcagag ggtcaccatc      60
tcctgcactg ggagcagctc caacatcggg gcaggttatg atgtacactg gtaccagcag     120
cttccaggaa cagcccccaa actcctcatc tacggtaaca acaatcggcc ctccggggtc     180
cctgaccgat tctctggctc caagtctggc acctcagcct ccctggccat cactgggctc     240
caggctgagg atgaagctga ttattactgc cagtcctatg acaccaacct gaaagttttt     300
ggcggaggga ccaagctgac cgtccta                                          327

<210> SEQ ID NO 11
<211> LENGTH: 109
<212> TYPE: PRT
<213> ORGANISM: Homo sapiens

<400> SEQUENCE: 11

Gln Ala Val Leu Thr Gln Pro Ser Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Asn
                85                  90                  95

Leu Lys Val Phe Gly Gly Gly Thr Lys Leu Thr Val Leu
            100                 105

<210> SEQ ID NO 12
<211> LENGTH: 14
<212> TYPE: PRT
<213> ORGANISM: Homo sapiens

<400> SEQUENCE: 12

Thr Gly Ser Ser Ser Asn Ile Gly Ala Gly Tyr Asp Val His
1               5                   10

<210> SEQ ID NO 13
<211> LENGTH: 7
<212> TYPE: PRT
<213> ORGANISM: Homo sapiens

<400> SEQUENCE: 13

Gly Asn Asn Asn Arg Pro Ser
1               5

<210> SEQ ID NO 14
<211> LENGTH: 9
<212> TYPE: PRT
<213> ORGANISM: Homo sapiens

<400> SEQUENCE: 14

Gln Ser Tyr Asp Thr Asn Leu Lys Val
1               5

<210> SEQ ID NO 15
<211> LENGTH: 22
<212> TYPE: PRT
<213> ORGANISM: Homo sapiens

<400> SEQUENCE: 15

Gln Ala Val Leu Thr Gln Pro Ser Ser Val Ser Gly Ala Pro Gly Gln
1               5                   10                  15

Arg Val Thr Ile Ser Cys
            20

<210> SEQ ID NO 16
<211> LENGTH: 15
<212> TYPE: PRT
<213> ORGANISM: Homo sapiens

<400> SEQUENCE: 16

Trp Tyr Gln Gln Leu Pro Gly Thr Ala Pro Lys Leu Leu Ile Tyr
1               5                   10                  15

<210> SEQ ID NO 17
<211> LENGTH: 32
<212> TYPE: PRT
<213> ORGANISM: Homo sapiens

<400> SEQUENCE: 17

Gly Val Pro Asp Arg Phe Ser Gly Ser Lys Ser Gly Thr Ser Ala Ser
1               5                   10                  15

Leu Ala Ile Thr Gly Leu Gln Ala Glu Asp Glu Ala Asp Tyr Tyr Cys
            20                  25                  30

<210> SEQ ID NO 18
<211> LENGTH: 10
<212> TYPE: PRT
<213> ORGANISM: Homo sapiens

<400> SEQUENCE: 18

Phe Gly Gly Gly Thr Lys Leu Thr Val Leu
1               5                   10

<210> SEQ ID NO 19
<211> LENGTH: 363
<212> TYPE: DNA
<213> ORGANISM: Homo sapiens

<400> SEQUENCE: 19
caggtgcagc tggtgcaatc tggagcagag gtgaaaaagc ccggggagtc tctgaagatc     60
tcctgtaagg gttctggata cagctttacc agctactgga tcggctgggt gcgccagatg    120
cccgggaaag gcctggagtg gatggggatc atctatcctg gtgactctga taccagatac    180
agcccgtcct tccaaggcca ggtcaccatc tcagccgaca gtccatcag caccgcctac    240 ctgcagtgga gcagcctgaa ggcctcggac accgccatgt attactgtgc gagccggact    300

```
gggattact actactacgg tatggacgtc tggggcaaag ggacaatggt caccgtctcg    360
agt                                                                 363
```

<210> SEQ ID NO 20
<211> LENGTH: 121
<212> TYPE: PRT
<213> ORGANISM: Homo sapiens

<400> SEQUENCE: 20

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Ser Arg Thr Gly Asp Tyr Tyr Tyr Tyr Gly Met Asp Val Trp Gly
            100                 105                 110

Lys Gly Thr Met Val Thr Val Ser Ser
        115                 120
```

<210> SEQ ID NO 21
<211> LENGTH: 5
<212> TYPE: PRT
<213> ORGANISM: Homo sapiens

<400> SEQUENCE: 21

```
Ser Tyr Trp Ile Gly
1               5
```

<210> SEQ ID NO 22
<211> LENGTH: 17
<212> TYPE: PRT
<213> ORGANISM: Homo sapiens

<400> SEQUENCE: 22

```
Ile Ile Tyr Pro Gly Asp Ser Asp Thr Arg Tyr Ser Pro Ser Phe Gln
1               5                   10                  15

Gly
```

<210> SEQ ID NO 23
<211> LENGTH: 12
<212> TYPE: PRT
<213> ORGANISM: Homo sapiens

<400> SEQUENCE: 23

```
Arg Thr Gly Asp Tyr Tyr Tyr Tyr Gly Met Asp Val
1               5                   10
```

<210> SEQ ID NO 24
<211> LENGTH: 30
<212> TYPE: PRT
<213> ORGANISM: Homo sapiens

<400> SEQUENCE: 24

Gln Val Gln Leu Val Gln Ser Gly Ala Glu Val Lys Pro Gly Glu
1               5                   10                  15

Ser Leu Lys Ile Ser Cys Lys Gly Ser Gly Tyr Ser Phe Thr
            20                  25                  30

<210> SEQ ID NO 25
<211> LENGTH: 14
<212> TYPE: PRT
<213> ORGANISM: Homo sapiens

<400> SEQUENCE: 25

Trp Val Arg Gln Met Pro Gly Lys Gly Leu Glu Trp Met Gly
1               5                   10

<210> SEQ ID NO 26
<211> LENGTH: 32
<212> TYPE: PRT
<213> ORGANISM: Homo sapiens

<400> SEQUENCE: 26

Gln Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Ser
            20                  25                  30

<210> SEQ ID NO 27
<211> LENGTH: 11
<212> TYPE: PRT
<213> ORGANISM: Homo sapiens

<400> SEQUENCE: 27

Trp Gly Lys Gly Thr Met Val Thr Val Ser Ser
1               5                   10

<210> SEQ ID NO 28
<211> LENGTH: 324
<212> TYPE: DNA
<213> ORGANISM: Homo sapiens

<400> SEQUENCE: 28

```
tcctatgtgc tgactcagcc accctcggtg tcagtgtccc taggacagac ggccaggatc     60
acctgctctg gagatgcatt gccaaagcaa tatgcttatt ggtaccagca gaagccaggc    120
caggcccctg tgctggtgat atataaagac agtgagaggc cctcagggat ccctgagcga    180
ttctctggct ccagctcagg gacaacagtc acgttgacca tcagtggagt ccaggcagaa    240
gacgaggctg actattactg tcaatcagca gacagcagtg gtacttatgt ggtattcggc    300
ggagggacca agctgaccgt ccta                                           324
```

<210> SEQ ID NO 29
<211> LENGTH: 108
<212> TYPE: PRT
<213> ORGANISM: Homo sapiens

<400> SEQUENCE: 29

Ser Tyr Val Leu Thr Gln Pro Pro Ser Val Ser Val Ser Leu Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
 50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gln Ser Ala Asp Ser Ser Gly Thr Tyr
                 85                  90                  95

Val Val Phe Gly Gly Gly Thr Lys Leu Thr Val Leu
            100                 105

<210> SEQ ID NO 30
<211> LENGTH: 11
<212> TYPE: PRT
<213> ORGANISM: Homo sapiens

<400> SEQUENCE: 30

Ser Gly Asp Ala Leu Pro Lys Gln Tyr Ala Tyr
1               5                   10

<210> SEQ ID NO 31
<211> LENGTH: 7
<212> TYPE: PRT
<213> ORGANISM: Homo sapiens

<400> SEQUENCE: 31

Lys Asp Ser Glu Arg Pro Ser
1               5

<210> SEQ ID NO 32
<211> LENGTH: 11
<212> TYPE: PRT
<213> ORGANISM: Homo sapiens

<400> SEQUENCE: 32

Gln Ser Ala Asp Ser Ser Gly Thr Tyr Val Val
1               5                   10

<210> SEQ ID NO 33
<211> LENGTH: 22
<212> TYPE: PRT
<213> ORGANISM: Homo sapiens

<400> SEQUENCE: 33

Ser Tyr Val Leu Thr Gln Pro Pro Ser Val Ser Val Ser Leu Gly Gln
1               5                   10                  15

Thr Ala Arg Ile Thr Cys
            20

<210> SEQ ID NO 34
<211> LENGTH: 15
<212> TYPE: PRT
<213> ORGANISM: Homo sapiens

<400> SEQUENCE: 34

Trp Tyr Gln Gln Lys Pro Gly Gln Ala Pro Val Leu Val Ile Tyr
1               5                   10                  15

<210> SEQ ID NO 35
<211> LENGTH: 32
<212> TYPE: PRT
<213> ORGANISM: Homo sapiens

<400> SEQUENCE: 35

```
Gly Ile Pro Glu Arg Phe Ser Gly Ser Ser Gly Thr Thr Val Thr
1               5                   10                  15

Leu Thr Ile Ser Gly Val Gln Ala Glu Asp Glu Ala Asp Tyr Tyr Cys
            20                  25                  30
```

<210> SEQ ID NO 36
<211> LENGTH: 10
<212> TYPE: PRT
<213> ORGANISM: Homo sapiens

<400> SEQUENCE: 36

```
Phe Gly Gly Gly Thr Lys Leu Thr Val Leu
1               5                   10
```

<210> SEQ ID NO 37
<211> LENGTH: 378
<212> TYPE: DNA
<213> ORGANISM: Homo sapiens

<400> SEQUENCE: 37

```
gaggtgcagc tggtgcagtc tgggggaggc ctggtacagc ctggcaggtc cctgagactc    60
tcctgtacag cctctggatt cacctttgat gattattcca tgcactgggt ccggcaagct   120
ccagggaagg gcctggagtg ggtctcaagt attagttgga gtagtggtag cataggctat   180
gcggactctg tgaagggccg attcaccatc tccagagaca acgccaagaa ctccttgtct   240
ctgcaaatga acagtctgag agttgaggac acggccttgt attactgtgt aaaggatcga   300
atgtattact atgatactgg tggatattat tctggttttg atatgtgggg ccaagggaca   360
atggtcaccg tctcgagt                                                 378
```

<210> SEQ ID NO 38
<211> LENGTH: 126
<212> TYPE: PRT
<213> ORGANISM: Homo sapiens

<400> SEQUENCE: 38

```
Glu Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Ser Ile Ser Trp Ser Ser Gly Ser Ile Gly Tyr Ala Asp Ser Val
    50                  55                  60

Lys Gly Arg Phe Thr Ile Ser Arg Asp Asn Ala Lys Asn Ser Leu Ser
65                  70                  75                  80

Leu Gln Met Asn Ser Leu Arg Val Glu Asp Thr Ala Leu Tyr Tyr Cys
                85                  90                  95

Val Lys Asp Arg Met Tyr Tyr Tyr Asp Thr Gly Gly Tyr Tyr Ser Gly
            100                 105                 110

Phe Asp Met Trp Gly Gln Gly Thr Met Val Thr Val Ser Ser
        115                 120                 125
```

<210> SEQ ID NO 39
<211> LENGTH: 5
<212> TYPE: PRT
<213> ORGANISM: Homo sapiens

<400> SEQUENCE: 39

Asp Tyr Ser Met His
1               5

<210> SEQ ID NO 40
<211> LENGTH: 17
<212> TYPE: PRT
<213> ORGANISM: Homo sapiens

<400> SEQUENCE: 40

Ser Ile Ser Trp Ser Ser Gly Ser Ile Gly Tyr Ala Asp Ser Val Lys
1               5                   10                  15

Gly

<210> SEQ ID NO 41
<211> LENGTH: 17
<212> TYPE: PRT
<213> ORGANISM: Homo sapiens

<400> SEQUENCE: 41

Asp Arg Met Tyr Tyr Tyr Asp Thr Gly Gly Tyr Tyr Ser Gly Phe Asp
1               5                   10                  15

Met

<210> SEQ ID NO 42
<211> LENGTH: 30
<212> TYPE: PRT
<213> ORGANISM: Homo sapiens

<400> SEQUENCE: 42

Glu Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Asp
            20                  25                  30

<210> SEQ ID NO 43
<211> LENGTH: 14
<212> TYPE: PRT
<213> ORGANISM: Homo sapiens

<400> SEQUENCE: 43

Trp Val Arg Gln Ala Pro Gly Lys Gly Leu Glu Trp Val Ser
1               5                   10

<210> SEQ ID NO 44
<211> LENGTH: 32
<212> TYPE: PRT
<213> ORGANISM: Homo sapiens

<400> SEQUENCE: 44

Arg Phe Thr Ile Ser Arg Asp Asn Ala Lys Asn Ser Leu Ser Leu Gln
1               5                   10                  15

Met Asn Ser Leu Arg Val Glu Asp Thr Ala Leu Tyr Tyr Cys Val Lys
            20                  25                  30

<210> SEQ ID NO 45
<211> LENGTH: 11
<212> TYPE: PRT
<213> ORGANISM: Homo sapiens

<400> SEQUENCE: 45

Trp Gly Gln Gly Thr Met Val Thr Val Ser Ser
1               5                   10

<210> SEQ ID NO 46
<211> LENGTH: 318
<212> TYPE: DNA
<213> ORGANISM: Homo sapiens

<400> SEQUENCE: 46

```
tcctatgagc tgactcagcc accctcagtg tccgtgtccc caggacagac agccaccatc      60
acctgctctg gagataaaat tggatgataaa tatatatctt ggtatcaaag gaagccaggc     120
cagtcccctg tcctgctcat ctatcaagat atagagcggc cctcagggat ccctgaccga     180
ttctctggct ctaattctgg gaacacagcc actctgtcca tcagcgggac ccagtctatg     240
gatgaggctg agtattactg tcaggcgtgg gacaacggtg ctattgtatt cggcggaggg     300
accaagctga ccgtccta                                                    318
```

<210> SEQ ID NO 47
<211> LENGTH: 106
<212> TYPE: PRT
<213> ORGANISM: Homo sapiens

<400> SEQUENCE: 47

```
Ser Tyr Glu Leu Thr Gln Pro Pro Ser Val Ser Val Ser Pro Gly Gln
 1               5                  10                  15

Thr Ala Thr Ile Thr Cys Ser Gly Asp Lys Leu Asp Asp Lys Tyr Ile
             20                  25                  30

Ser Trp Tyr Gln Arg Lys Pro Gly Gln Ser Pro Val Leu Leu Ile Tyr
         35                  40                  45

Gln Asp Ile Glu Arg Pro Ser Gly Ile Pro Asp Arg Phe Ser Gly Ser
     50                  55                  60

Asn Ser Gly Asn Thr Ala Thr Leu Ser Ile Ser Gly Thr Gln Ser Met
 65                  70                  75                  80

Asp Glu Ala Glu Tyr Tyr Cys Gln Ala Trp Asp Ser Gly Ala Ile Val
                 85                  90                  95

Phe Gly Gly Gly Thr Lys Leu Thr Val Leu
            100                 105
```

<210> SEQ ID NO 48
<211> LENGTH: 11
<212> TYPE: PRT
<213> ORGANISM: Homo sapiens

<400> SEQUENCE: 48

```
Ser Gly Asp Lys Leu Asp Asp Lys Tyr Ile Ser
 1               5                  10
```

<210> SEQ ID NO 49
<211> LENGTH: 7
<212> TYPE: PRT
<213> ORGANISM: Homo sapiens

<400> SEQUENCE: 49

```
Gln Asp Ile Glu Arg Pro Ser
 1               5
```

<210> SEQ ID NO 50
<211> LENGTH: 9
<212> TYPE: PRT
<213> ORGANISM: Homo sapiens

<400> SEQUENCE: 50

Gln Ala Trp Asp Ser Gly Ala Ile Val
1               5

<210> SEQ ID NO 51
<211> LENGTH: 22
<212> TYPE: PRT
<213> ORGANISM: Homo sapiens

<400> SEQUENCE: 51

Ser Tyr Glu Leu Thr Gln Pro Pro Ser Val Ser Val Ser Pro Gly Gln
1               5                   10                  15

Thr Ala Thr Ile Thr Cys
            20

<210> SEQ ID NO 52
<211> LENGTH: 15
<212> TYPE: PRT
<213> ORGANISM: Homo sapiens

<400> SEQUENCE: 52

Trp Tyr Gln Arg Lys Pro Gly Gln Ser Pro Val Leu Leu Ile Tyr
1               5                   10                  15

<210> SEQ ID NO 53
<211> LENGTH: 32
<212> TYPE: PRT
<213> ORGANISM: Homo sapiens

<400> SEQUENCE: 53

Gly Ile Pro Asp Arg Phe Ser Gly Ser Asn Ser Gly Asn Thr Ala Thr
1               5                   10                  15

Leu Ser Ile Ser Gly Thr Gln Ser Met Asp Glu Ala Glu Tyr Tyr Cys
            20                  25                  30

<210> SEQ ID NO 54
<211> LENGTH: 10
<212> TYPE: PRT
<213> ORGANISM: Homo sapiens

<400> SEQUENCE: 54

Phe Gly Gly Gly Thr Lys Leu Thr Val Leu
1               5                   10

<210> SEQ ID NO 55
<211> LENGTH: 375
<212> TYPE: DNA
<213> ORGANISM: Homo sapiens

<400> SEQUENCE: 55
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gagagatagg     300 gattttttgga gtacttattc gggtccaact gcttttgatc tctggggcag aggcaccctg     360
gtcaccgtct cgagt                                                     375

<210> SEQ ID NO 56
<211> LENGTH: 125
<212> TYPE: PRT

-continued

<213> ORGANISM: Homo sapiens

<400> SEQUENCE: 56

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Asp Phe Trp Ser Thr Tyr Ser Gly Pro Thr Ala Phe
            100                 105                 110

Asp Leu Trp Gly Arg Gly Thr Leu Val Thr Val Ser Ser
            115                 120             125
```

<210> SEQ ID NO 57
<211> LENGTH: 5
<212> TYPE: PRT
<213> ORGANISM: Homo sapiens

<400> SEQUENCE: 57

```
Ser Tyr Ala Met Ser
1               5
```

<210> SEQ ID NO 58
<211> LENGTH: 17
<212> TYPE: PRT
<213> ORGANISM: Homo sapiens

<400> SEQUENCE: 58

```
Ala Ile Ser Gly Ser Gly Gly Ser Thr Tyr Tyr Ala Asp Ser Val Lys
1               5                   10                  15

Gly
```

<210> SEQ ID NO 59
<211> LENGTH: 16
<212> TYPE: PRT
<213> ORGANISM: Homo sapiens

<400> SEQUENCE: 59

```
Asp Arg Asp Phe Trp Ser Thr Tyr Ser Gly Pro Thr Ala Phe Asp Leu
1               5                   10                  15
```

<210> SEQ ID NO 60
<211> LENGTH: 30
<212> TYPE: PRT
<213> ORGANISM: Homo sapiens

<400> SEQUENCE: 60

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30
```

<210> SEQ ID NO 61

<210> SEQ ID NO 61
<211> LENGTH: 14
<212> TYPE: PRT
<213> ORGANISM: Homo sapiens

<400> SEQUENCE: 61

Trp Val Arg Gln Ala Pro Gly Lys Gly Leu Glu Trp Val Ser
1               5                   10

<210> SEQ ID NO 62
<211> LENGTH: 32
<212> TYPE: PRT
<213> ORGANISM: Homo sapiens

<400> SEQUENCE: 62

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ala Arg
            20                  25                  30

<210> SEQ ID NO 63
<211> LENGTH: 11
<212> TYPE: PRT
<213> ORGANISM: Homo sapiens

<400> SEQUENCE: 63

Trp Gly Arg Gly Thr Leu Val Thr Val Ser Ser
1               5                   10

<210> SEQ ID NO 64
<211> LENGTH: 324
<212> TYPE: DNA
<213> ORGANISM: Homo sapiens

<400> SEQUENCE: 64
tcctatgagc tggctcagcc accctcggtg tcagtgtccc caggacagac ggccaggatc        60
acctgctctg gagatgcatt gccaaggcaa tatgcttact ggtaccagca gaagccaggc       120
caggccccte tactggtgat atataaagac agtgagaggc cctcagggat ccctgagcga       180
ttctctggct ccggctcagg acaacagtc acgttgacca tcagtggagt ccaggcagaa       240
gacgaggctg actattactg tcaatcagca gacagcagtg gtacctatgt ggtattcggc       300
ggagggacca aggtcaccgt ccta                                               324

<210> SEQ ID NO 65
<211> LENGTH: 108
<212> TYPE: PRT
<213> ORGANISM: Homo sapiens

<400> SEQUENCE: 65

Ser Tyr Glu Leu Ala Gln Pro Pro Ser Val Ser Val Ser Pro Gly Gln
1               5                   10                  15
Thr Ala Arg Ile Thr Cys Ser Gly Asp Ala Leu Pro Arg Gln Tyr Ala
            20                  25                  30
Tyr Trp Tyr Gln Gln Lys Pro Gly Gln Ala Pro Leu Leu Val Ile Tyr
        35                  40                  45
Lys Asp Ser Glu Arg Pro Ser Gly Ile Pro Glu Arg Phe Ser Gly Ser
    50                  55                  60
Gly Ser Gly Thr Thr Val Thr Leu Thr Ile Ser Gly Val Gln Ala Glu
65                  70                  75                  80
Asp Glu Ala Asp Tyr Tyr Cys Gln Ser Ala Asp Ser Ser Gly Thr Tyr
                85                  90                  95

Val Val Phe Gly Gly Gly Thr Lys Val Thr Val Leu
            100                 105

<210> SEQ ID NO 66
<211> LENGTH: 11
<212> TYPE: PRT
<213> ORGANISM: Homo sapiens

<400> SEQUENCE: 66

Ser Gly Asp Ala Leu Pro Arg Gln Tyr Ala Tyr
1               5                   10

<210> SEQ ID NO 67
<211> LENGTH: 7
<212> TYPE: PRT
<213> ORGANISM: Homo sapiens

<400> SEQUENCE: 67

Lys Asp Ser Glu Arg Pro Ser
1               5

<210> SEQ ID NO 68
<211> LENGTH: 11
<212> TYPE: PRT
<213> ORGANISM: Homo sapiens

<400> SEQUENCE: 68

Gln Ser Ala Asp Ser Ser Gly Thr Tyr Val Val
1               5                   10

<210> SEQ ID NO 69
<211> LENGTH: 22
<212> TYPE: PRT
<213> ORGANISM: Homo sapiens

<400> SEQUENCE: 69

Ser Tyr Glu Leu Ala Gln Pro Pro Ser Val Ser Val Ser Pro Gly Gln
1               5                   10                  15

Thr Ala Arg Ile Thr Cys
            20

<210> SEQ ID NO 70
<211> LENGTH: 15
<212> TYPE: PRT
<213> ORGANISM: Homo sapiens

<400> SEQUENCE: 70

Trp Tyr Gln Gln Lys Pro Gly Gln Ala Pro Leu Leu Val Ile Tyr
1               5                   10                  15

<210> SEQ ID NO 71
<211> LENGTH: 32
<212> TYPE: PRT
<213> ORGANISM: Homo sapiens

<400> SEQUENCE: 71

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
                20                  25                  30

<210> SEQ ID NO 72
<211> LENGTH: 10

```
<212> TYPE: PRT
<213> ORGANISM: Homo sapiens

<400> SEQUENCE: 72

Phe Gly Gly Gly Thr Lys Val Thr Val Leu
1               5                   10

<210> SEQ ID NO 73
<211> LENGTH: 363
<212> TYPE: DNA
<213> ORGANISM: Homo sapiens

<400> SEQUENCE: 73
gaggtgcagc tggtggagtc cgggggaggc ttggtccagc ctgggggggtc cctgagactc      60 tcctgtgcag cctctggatt tacctttagt aggtattgga tgagctgggt ccgccaggct     120
ccagggaagg ggctggagtg ggtggccaac ataaaggaag atggaagtga aaaaactat      180 gtggactctg tgaagggccg actcaccatc tccagagaca acgccaagaa ctcactgtat     240
ctgcaaatga acagcctgag agccgaggac acggccgtgt attactgtgc gaactactat     300
gatagtagtg gttattatgc ccttgatagc tggggccgag gcaccctggt cactgtctcc     360
tca                                                                  363

<210> SEQ ID NO 74
<211> LENGTH: 121
<212> TYPE: PRT
<213> ORGANISM: Homo sapiens

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Glu Asp Gly Ser Glu Lys Asn Tyr Val Asp Ser Val
    50                  55                  60

Lys Gly Arg Leu Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Asn Tyr Tyr Asp Ser Ser Gly Tyr Tyr Ala Leu Asp Ser Trp Gly
            100                 105                 110

Arg Gly Thr Leu Val Thr Val Ser Ser
        115                 120

<210> SEQ ID NO 75
<211> LENGTH: 5
<212> TYPE: PRT
<213> ORGANISM: Homo sapiens

<400> SEQUENCE: 75

Arg Tyr Trp Met Ser
1               5

<210> SEQ ID NO 76
<211> LENGTH: 17
<212> TYPE: PRT
<213> ORGANISM: Homo sapiens
```

<400> SEQUENCE: 76

Asn Ile Lys Glu Asp Gly Ser Glu Lys Asn Tyr Val Asp Ser Val Lys
1               5                   10                  15

Gly

<210> SEQ ID NO 77
<211> LENGTH: 12
<212> TYPE: PRT
<213> ORGANISM: Homo sapiens

<400> SEQUENCE: 77

Tyr Tyr Asp Ser Ser Gly Tyr Tyr Ala Leu Asp Ser
1               5                   10

<210> SEQ ID NO 78
<211> LENGTH: 30
<212> TYPE: PRT
<213> ORGANISM: Homo sapiens

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 79
<211> LENGTH: 14
<212> TYPE: PRT
<213> ORGANISM: Homo sapiens

<400> SEQUENCE: 79

Trp Val Arg Gln Ala Pro Gly Lys Gly Leu Glu Trp Val Ala
1               5                   10

<210> SEQ ID NO 80
<211> LENGTH: 32
<212> TYPE: PRT
<213> ORGANISM: Homo sapiens

<400> SEQUENCE: 80

Arg Leu Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Asn
            20                  25                  30

<210> SEQ ID NO 81
<211> LENGTH: 11
<212> TYPE: PRT
<213> ORGANISM: Homo sapiens

<400> SEQUENCE: 81

Trp Gly Arg Gly Thr Leu Val Thr Val Ser Ser
1               5                   10

<210> SEQ ID NO 82
<211> LENGTH: 324
<212> TYPE: DNA
<213> ORGANISM: Homo sapiens

<400> SEQUENCE: 82
tcctatgagc tgactcagcc accctcagtg tccgtgtccc caggacagac agccaccatc    60
acctgctctg gagatgcatt gacaaaacaa tatgcttttt ggtaccaaca gaagccaggc   120

```
caggcccota tattggtgat ctttagagac tctgagaggc cctcaggat ccctgagcga    180 ttctctggct ccagctcagg gacaacagcg acgttgacca tcagtggggt ccaggcagga   240
gacgaggctg actattactg tcaatctaca gacaatactg cgacctccgt cgtcttcggc   300
ggagggacca aggtcaccgt ccta                                          324
```

```
<210> SEQ ID NO 83
<211> LENGTH: 108
<212> TYPE: PRT
<213> ORGANISM: Homo sapiens

<400> SEQUENCE: 83

Ser Tyr Glu Leu Thr Gln Pro Pro Ser Val Ser Val Ser Pro Gly Gln
1               5                   10                  15

Thr Ala Thr Ile Thr Cys Ser Gly Asp Ala Leu Thr Lys Gln Tyr Ala
            20                  25                  30

Phe Trp Tyr Gln Gln Lys Pro Gly Gln Ala Pro Ile Leu Val Ile Phe
        35                  40                  45

Arg Asp Ser Glu Arg Pro Ser Gly Ile Pro Glu Arg Phe Ser Gly Ser
    50                  55                  60

Ser Ser Gly Thr Thr Ala Thr Leu Thr Ile Ser Gly Val Gln Ala Gly
65                  70                  75                  80

Asp Glu Ala Asp Tyr Tyr Cys Gln Ser Thr Asp Asn Thr Ala Thr Ser
                85                  90                  95

Val Val Phe Gly Gly Gly Thr Lys Val Thr Val Leu
            100                 105
```

```
<210> SEQ ID NO 84
<211> LENGTH: 11
<212> TYPE: PRT
<213> ORGANISM: Homo sapiens

<400> SEQUENCE: 84

Ser Gly Asp Ala Leu Thr Lys Gln Tyr Ala Phe
1               5                   10
```

```
<210> SEQ ID NO 85
<211> LENGTH: 7
<212> TYPE: PRT
<213> ORGANISM: Homo sapiens

<400> SEQUENCE: 85

Arg Asp Ser Glu Arg Pro Ser
1               5
```

```
<210> SEQ ID NO 86
<211> LENGTH: 11
<212> TYPE: PRT
<213> ORGANISM: Homo sapiens

<400> SEQUENCE: 86

Gln Ser Thr Asp Asn Thr Ala Thr Ser Val Val
1               5                   10
```

```
<210> SEQ ID NO 87
<211> LENGTH: 22
<212> TYPE: PRT
<213> ORGANISM: Homo sapiens

<400> SEQUENCE: 87
```

Ser Tyr Glu Leu Thr Gln Pro Pro Ser Val Ser Val Ser Pro Gly Gln
1               5                   10                  15

Thr Ala Thr Ile Thr Cys
            20

<210> SEQ ID NO 88
<211> LENGTH: 15
<212> TYPE: PRT
<213> ORGANISM: Homo sapiens

<400> SEQUENCE: 88

Trp Tyr Gln Gln Lys Pro Gly Gln Ala Pro Ile Leu Val Ile Phe
1               5                   10                  15

<210> SEQ ID NO 89
<211> LENGTH: 32
<212> TYPE: PRT
<213> ORGANISM: Homo sapiens

<400> SEQUENCE: 89

Gly Ile Pro Glu Arg Phe Ser Gly Ser Ser Ser Gly Thr Thr Ala Thr
1               5                   10                  15

Leu Thr Ile Ser Gly Val Gln Ala Gly Asp Glu Ala Asp Tyr Tyr Cys
            20                  25                  30

<210> SEQ ID NO 90
<211> LENGTH: 10
<212> TYPE: PRT
<213> ORGANISM: Homo sapiens

<400> SEQUENCE: 90

Phe Gly Gly Gly Thr Lys Val Thr Val Leu
1               5                   10

<210> SEQ ID NO 91
<211> LENGTH: 375
<212> TYPE: DNA
<213> ORGANISM: Homo sapiens

<400> SEQUENCE: 91
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gagacccgag     300
ctccctgaga cagctatggt tagaaactgg cacttcgatc tctggggcca ggggacaatg     360
gtcaccgtct cgagt                                                      375

<210> SEQ ID NO 92
<211> LENGTH: 125
<212> TYPE: PRT
<213> ORGANISM: Homo sapiens

<400> SEQUENCE: 92

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val

```
                35                  40                  45
Ser Ala Ile Ser Gly Ser Gly Gly Ser Thr Tyr Tyr Ala Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Pro Glu Leu Pro Glu Thr Ala Met Val Arg Asn Trp His Phe
            100                 105                 110
Asp Leu Trp Gly Gln Gly Thr Met Val Thr Val Ser Ser
            115                 120                 125

<210> SEQ ID NO 93
<211> LENGTH: 5
<212> TYPE: PRT
<213> ORGANISM: Homo sapiens

<400> SEQUENCE: 93

Ser Tyr Ala Met Ser
 1               5

<210> SEQ ID NO 94
<211> LENGTH: 17
<212> TYPE: PRT
<213> ORGANISM: Homo sapiens

<400> SEQUENCE: 94

Ala Ile Ser Gly Ser Gly Gly Ser Thr Tyr Tyr Ala Asp Ser Val Lys
 1               5                  10                  15

Gly

<210> SEQ ID NO 95
<211> LENGTH: 16
<212> TYPE: PRT
<213> ORGANISM: Homo sapiens

<400> SEQUENCE: 95

Pro Glu Leu Pro Glu Thr Ala Met Val Arg Asn Trp His Phe Asp Leu
 1               5                  10                  15

<210> SEQ ID NO 96
<211> LENGTH: 30
<212> TYPE: PRT
<213> ORGANISM: Homo sapiens

<400> SEQUENCE: 96

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser
             20                  25                  30

<210> SEQ ID NO 97
<211> LENGTH: 14
<212> TYPE: PRT
<213> ORGANISM: Homo sapiens

<400> SEQUENCE: 97

Trp Val Arg Gln Ala Pro Gly Lys Gly Leu Glu Trp Val Ser
 1               5                  10

<210> SEQ ID NO 98
```

<211> LENGTH: 32
<212> TYPE: PRT
<213> ORGANISM: Homo sapiens

<400> SEQUENCE: 98

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
                20                  25                  30

<210> SEQ ID NO 99
<211> LENGTH: 11
<212> TYPE: PRT
<213> ORGANISM: Homo sapiens

<400> SEQUENCE: 99

Trp Gly Gln Gly Thr Met Val Thr Val Ser Ser
1               5                   10

<210> SEQ ID NO 100
<211> LENGTH: 324
<212> TYPE: DNA
<213> ORGANISM: Homo sapiens

<400> SEQUENCE: 100
tcctatgtgc tgactcagcc accctcggtg tcagtgtccc caggacagac ggccaggatc      60
acctgctctg gagatgcatt gccaaagcaa tatgcttatt ggtaccagca gaagccaggc     120
caggcccctg tgctggtgat atataaagac agtgagaggc cctcagggat ccctgagcga     180
ttctctggct ccagctcagg gacaacagtc acgttgacca tcagtggagt ccaggcagaa     240
gatgaggctg actattactg tcaatcagca gacagcagtg gtacttatgt ggtattcggc     300
ggagggacca agctgaccgt ccta                                            324

<210> SEQ ID NO 101
<211> LENGTH: 108
<212> TYPE: PRT
<213> ORGANISM: Homo sapiens

<400> SEQUENCE: 101

Ser Tyr Val Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
                20                  25                  30

Tyr Trp Tyr Gln Gln Lys Pro Gly Gln Ala Pro Val Leu Val Ile Tyr
            35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Val Val Phe Gly Gly Gly Thr Lys Leu Thr Val Leu
                100                 105

<210> SEQ ID NO 102
<211> LENGTH: 11
<212> TYPE: PRT
<213> ORGANISM: Homo sapiens

<400> SEQUENCE: 102

-continued

Ser Gly Asp Ala Leu Pro Lys Gln Tyr Ala Tyr
1               5                   10

<210> SEQ ID NO 103
<211> LENGTH: 7
<212> TYPE: PRT
<213> ORGANISM: Homo sapiens

<400> SEQUENCE: 103

Lys Asp Ser Glu Arg Pro Ser
1               5

<210> SEQ ID NO 104
<211> LENGTH: 11
<212> TYPE: PRT
<213> ORGANISM: Homo sapiens

<400> SEQUENCE: 104

Gln Ser Ala Asp Ser Ser Gly Thr Tyr Val Val
1               5                   10

<210> SEQ ID NO 105
<211> LENGTH: 22
<212> TYPE: PRT
<213> ORGANISM: Homo sapiens

<400> SEQUENCE: 105

Ser Tyr Val Leu Thr Gln Pro Pro Ser Val Ser Val Ser Pro Gly Gln
1               5                   10                  15

Thr Ala Arg Ile Thr Cys
            20

<210> SEQ ID NO 106
<211> LENGTH: 15
<212> TYPE: PRT
<213> ORGANISM: Homo sapiens

<400> SEQUENCE: 106

Trp Tyr Gln Gln Lys Pro Gly Gln Ala Pro Val Leu Val Ile Tyr
1               5                   10                  15

<210> SEQ ID NO 107
<211> LENGTH: 32
<212> TYPE: PRT
<213> ORGANISM: Homo sapiens

<400> SEQUENCE: 107

Gly Ile Pro Glu Arg Phe Ser Gly Ser Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 108
<211> LENGTH: 10
<212> TYPE: PRT
<213> ORGANISM: Homo sapiens

<400> SEQUENCE: 108

Phe Gly Gly Gly Thr Lys Leu Thr Val Leu
1               5                   10

<210> SEQ ID NO 109
<211> LENGTH: 387

<212> TYPE: DNA
<213> ORGANISM: Homo sapiens

<400> SEQUENCE: 109

```
gaggtgcagc tgttggagtc tgggggaggc ttggtacagc ctgggggtc cctgagactc        60
tcctgtgcag cctctggatt cacctttagc agctatgcca tgagctgggt ccgccaggct      120
ccagggaagg ggctggagtg ggtctcagct attagtggta gtggtggtag cacatactac      180
gcagactccg tgaagggccg gttcaccatc tccagagaca attccaagaa cacgctgtat      240
ctgcaaatga acagcctgag agccgaggac acggccgtgt attactgtgc gagaagcttt      300
cattattgta gtagtaccaa ctgctatgtg gagggtcggg aaaactttga ctactggggc      360
caagggacaa tggtcaccgt ctcgagt                                           387
```

<210> SEQ ID NO 110
<211> LENGTH: 129
<212> TYPE: PRT
<213> ORGANISM: Homo sapiens

<400> SEQUENCE: 110

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Phe His Tyr Cys Ser Ser Thr Asn Cys Tyr Val Glu Gly
            100                 105                 110

Arg Glu Asn Phe Asp Tyr Trp Gly Gln Gly Thr Met Val Thr Val Ser
        115                 120                 125

Ser

<210> SEQ ID NO 111
<211> LENGTH: 5
<212> TYPE: PRT
<213> ORGANISM: Homo sapiens

<400> SEQUENCE: 111

Ser Tyr Ala Met Ser
1               5

<210> SEQ ID NO 112
<211> LENGTH: 17
<212> TYPE: PRT
<213> ORGANISM: Homo sapiens

<400> SEQUENCE: 112

Ala Ile Ser Gly Ser Gly Gly Ser Thr Tyr Tyr Ala Asp Ser Val Lys
1               5                   10                  15

Gly

<210> SEQ ID NO 113

```
<211> LENGTH: 20
<212> TYPE: PRT
<213> ORGANISM: Homo sapiens

<400> SEQUENCE: 113

Ser Phe His Tyr Cys Ser Ser Thr Asn Cys Tyr Val Glu Gly Arg Glu
1               5                   10                  15

Asn Phe Asp Tyr
            20

<210> SEQ ID NO 114
<211> LENGTH: 30
<212> TYPE: PRT
<213> ORGANISM: Homo sapiens

<400> SEQUENCE: 114

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 115
<211> LENGTH: 14
<212> TYPE: PRT
<213> ORGANISM: Homo sapiens

<400> SEQUENCE: 115

Trp Val Arg Gln Ala Pro Gly Lys Gly Leu Glu Trp Val Ser
1               5                   10

<210> SEQ ID NO 116
<211> LENGTH: 32
<212> TYPE: PRT
<213> ORGANISM: Homo sapiens

<400> SEQUENCE: 116

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 117
<211> LENGTH: 11
<212> TYPE: PRT
<213> ORGANISM: Homo sapiens

<400> SEQUENCE: 117

Trp Gly Gln Gly Thr Met Val Thr Val Ser Ser
1               5                   10

<210> SEQ ID NO 118
<211> LENGTH: 318
<212> TYPE: DNA
<213> ORGANISM: Homo sapiens

<400> SEQUENCE: 118
tcctatgagc tgactcagcc accctcagtg tccgtgtccc ccgacagac agccagcatc      60 acctgctctg gagataaaatt ggggaataaa tatgcttcgt ggtatcaaca gaagccaggc    120
cactcccctg tactggtcat ctatcaagat tccaagcggc cctcagggat ccctgagcga    180
ttctctggct ccaactctgg gaacacagcc actctgacca tcagcgggac ccaggctatg    240
gatgaggctg tctattactg tcaggcgtgg gacagcacca tcgtggtctt cggcggaggg    300
```
accaagctga ccgtccta                                                318

<210> SEQ ID NO 119
<211> LENGTH: 106
<212> TYPE: PRT
<213> ORGANISM: Homo sapiens

<400> SEQUENCE: 119

Ser Tyr Glu Leu Thr Gln Pro Pro Ser Val Ser Val Ser Pro Arg Gln
1               5                   10                  15

Thr Ala Ser Ile Thr Cys Ser Gly Asp Lys Leu Gly Asn Lys Tyr Ala
            20                  25                  30

Ser Trp Tyr Gln Gln Lys Pro Gly His Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Val Tyr Tyr Cys Gln Ala Trp Asp Ser Thr Ile Val Val
                85                  90                  95

Phe Gly Gly Gly Thr Lys Leu Thr Val Leu
            100                 105

<210> SEQ ID NO 120
<211> LENGTH: 11
<212> TYPE: PRT
<213> ORGANISM: Homo sapiens

<400> SEQUENCE: 120

Ser Gly Asp Lys Leu Gly Asn Lys Tyr Ala Ser
1               5                   10

<210> SEQ ID NO 121
<211> LENGTH: 7
<212> TYPE: PRT
<213> ORGANISM: Homo sapiens

<400> SEQUENCE: 121

Gln Asp Ser Lys Arg Pro Ser
1               5

<210> SEQ ID NO 122
<211> LENGTH: 9
<212> TYPE: PRT
<213> ORGANISM: Homo sapiens

<400> SEQUENCE: 122

Gln Ala Trp Asp Ser Thr Ile Val Val
1               5

<210> SEQ ID NO 123
<211> LENGTH: 22
<212> TYPE: PRT
<213> ORGANISM: Homo sapiens

<400> SEQUENCE: 123

Ser Tyr Glu Leu Thr Gln Pro Pro Ser Val Ser Val Ser Pro Arg Gln
1               5                   10                  15

Thr Ala Ser Ile Thr Cys
            20

<210> SEQ ID NO 124
<211> LENGTH: 15
<212> TYPE: PRT
<213> ORGANISM: Homo sapiens

<400> SEQUENCE: 124

Trp Tyr Gln Gln Lys Pro Gly His Ser Pro Val Leu Val Ile Tyr
1               5                   10                  15

<210> SEQ ID NO 125
<211> LENGTH: 32
<212> TYPE: PRT
<213> ORGANISM: Homo sapiens

<400> SEQUENCE: 125

Gly Ile Pro Glu Arg Phe Ser Gly Ser Asn Ser Gly Asn Thr Ala Thr
1               5                   10                  15

Leu Thr Ile Ser Gly Thr Gln Ala Met Asp Glu Ala Val Tyr Tyr Cys
            20                  25                  30

<210> SEQ ID NO 126
<211> LENGTH: 10
<212> TYPE: PRT
<213> ORGANISM: Homo sapiens

<400> SEQUENCE: 126

Phe Gly Gly Gly Thr Lys Leu Thr Val Leu
1               5                   10

<210> SEQ ID NO 127
<211> LENGTH: 351
<212> TYPE: DNA
<213> ORGANISM: Homo sapiens

<400> SEQUENCE: 127
gagatacagc tgcaggagtc aggacctggc cttgtgaaac cttcacagtc actctccctc      60
acctgttctg tcactggtta caccattacc agtggttatg attggagctg gatccggaag     120
ttcccaggaa ataaaatgga gtggatggga tacataagct acagtggtag cactaactac     180
aacccatcgc tcaaaagtcg aatctccatt accagagaca catccaagaa tcagttcttc     240
ctgcagttga actctgtaac tactgaggat acagccacat attactgtgc aagagggatg     300
atggtactta ttcctaactg gggccaggga gtcatggtca cagtctcctc a              351

<210> SEQ ID NO 128
<211> LENGTH: 117
<212> TYPE: PRT
<213> ORGANISM: Homo sapiens

<400> SEQUENCE: 128

Glu Ile Gln Leu Gln Glu Ser Gly Pro Gly Leu Val Lys Pro Ser Gln
1               5                   10                  15

Ser Leu Ser Leu Thr Cys Ser Val Thr Gly Tyr Thr Ile Thr Ser Gly
            20                  25                  30

Tyr Asp Trp Ser Trp Ile Arg Lys Phe Pro Gly Asn Lys Met Glu Trp
        35                  40                  45

Met Gly Tyr Ile Ser Tyr Ser Gly Ser Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

-continued

```
Leu Gln Leu Asn Ser Val Thr Thr Glu Asp Thr Ala Thr Tyr Tyr Cys
                 85                  90                  95

Ala Arg Gly Met Met Val Leu Ile Pro Asn Trp Gly Gln Gly Val Met
            100                 105                 110

Val Thr Val Ser Ser
        115

<210> SEQ ID NO 129
<211> LENGTH: 4
<212> TYPE: PRT
<213> ORGANISM: Homo sapiens

<400> SEQUENCE: 129

Ser Gly Tyr Asp
1

<210> SEQ ID NO 130
<211> LENGTH: 18
<212> TYPE: PRT
<213> ORGANISM: Homo sapiens

<400> SEQUENCE: 130

Met Gly Tyr Ile Ser Tyr Ser Gly Ser Thr Asn Tyr Asn Pro Ser Leu
1               5                   10                  15

Lys Ser

<210> SEQ ID NO 131
<211> LENGTH: 8
<212> TYPE: PRT
<213> ORGANISM: Homo sapiens

<400> SEQUENCE: 131

Gly Met Met Val Leu Ile Pro Asn
1               5

<210> SEQ ID NO 132
<211> LENGTH: 30
<212> TYPE: PRT
<213> ORGANISM: Homo sapiens

<400> SEQUENCE: 132

Glu Ile Gln Leu Gln Glu Ser Gly Pro Gly Leu Val Lys Pro Ser Gln
1               5                   10                  15

Ser Leu Ser Leu Thr Cys Ser Val Thr Gly Tyr Thr Ile Thr
            20                  25                  30

<210> SEQ ID NO 133
<211> LENGTH: 14
<212> TYPE: PRT
<213> ORGANISM: Homo sapiens

<400> SEQUENCE: 133

Trp Ser Trp Ile Arg Lys Phe Pro Gly Asn Lys Met Glu Trp
1               5                   10

<210> SEQ ID NO 134
<211> LENGTH: 32
<212> TYPE: PRT
<213> ORGANISM: Homo sapiens

<400> SEQUENCE: 134

Arg Ile Ser Ile Thr Arg Asp Thr Ser Lys Asn Gln Phe Phe Leu Gln
1               5                   10                  15
```

Leu Asn Ser Val Thr Thr Glu Asp Thr Ala Thr Tyr Tyr Cys Ala Arg
            20                  25                  30

<210> SEQ ID NO 135
<211> LENGTH: 11
<212> TYPE: PRT
<213> ORGANISM: Homo sapiens

<400> SEQUENCE: 135

Trp Gly Gln Gly Val Met Val Thr Val Ser Ser
1               5                   10

<210> SEQ ID NO 136
<211> LENGTH: 321
<212> TYPE: DNA
<213> ORGANISM: Homo sapiens

<400> SEQUENCE: 136
gatgtccaga tgacccagtc tccgtcttat cttactgcgt ctcctggaga aagtgtttcc      60
atcagttgca aggcaagtaa gagcattact aattatttag cctggtatca tcagaaacct     120
ggggaaccat ataaccttct tatctactct gggtcaactt tgcaatctgg aactccatca     180
aggttcagtg gcagtagatc tggtacagat ttcattctca ccatcagaag cctggagcct     240
gaagattttg gactctatta ctgtcaacag tattatgaaa aaccgtacac gtttggagct     300
gggaccaagc tggaactgaa a                                                321

<210> SEQ ID NO 137
<211> LENGTH: 107
<212> TYPE: PRT
<213> ORGANISM: Homo sapiens

<400> SEQUENCE: 137

Asp Val Gln Met Thr Gln Ser Pro Ser Tyr Leu Thr Ala Ser Pro Gly
1               5                   10                  15

Glu Ser Val Ser Ile Ser Cys Lys Ala Ser Lys Ser Ile Thr Asn Tyr
            20                  25                  30

Leu Ala Trp Tyr His Gln Lys Pro Gly Glu Pro Tyr Asn Leu Leu Ile
        35                  40                  45

Tyr Ser Gly Ser Thr Leu Gln Ser Gly Thr Pro Ser Arg Phe Ser Gly
    50                  55                  60

Ser Arg Ser Gly Thr Asp Phe Ile Leu Thr Ile Arg Ser Leu Glu Pro
65                  70                  75                  80

Glu Asp Phe Gly Leu Tyr Tyr Cys Gln Gln Tyr Tyr Glu Lys Pro Tyr
                85                  90                  95

Thr Phe Gly Ala Gly Thr Lys Leu Glu Leu Lys
            100                 105

<210> SEQ ID NO 138
<211> LENGTH: 11
<212> TYPE: PRT
<213> ORGANISM: Homo sapiens

<400> SEQUENCE: 138

Lys Ala Ser Lys Ser Ile Thr Asn Tyr Leu Ala
1               5                   10

<210> SEQ ID NO 139
<211> LENGTH: 7
<212> TYPE: PRT

<213> ORGANISM: Homo sapiens

<400> SEQUENCE: 139

Ser Gly Ser Thr Leu Gln Ser
1               5

<210> SEQ ID NO 140
<211> LENGTH: 9
<212> TYPE: PRT
<213> ORGANISM: Homo sapiens

<400> SEQUENCE: 140

Gln Gln Tyr Tyr Glu Lys Pro Tyr Thr
1               5

<210> SEQ ID NO 141
<211> LENGTH: 23
<212> TYPE: PRT
<213> ORGANISM: Homo sapiens

<400> SEQUENCE: 141

Asp Val Gln Met Thr Gln Ser Pro Ser Tyr Leu Thr Ala Ser Pro Gly
1               5                   10                  15

Glu Ser Val Ser Ile Ser Cys
            20

<210> SEQ ID NO 142
<211> LENGTH: 15
<212> TYPE: PRT
<213> ORGANISM: Homo sapiens

<400> SEQUENCE: 142

Trp Tyr His Gln Lys Pro Gly Glu Pro Tyr Asn Leu Leu Ile Tyr
1               5                   10                  15

<210> SEQ ID NO 143
<211> LENGTH: 32
<212> TYPE: PRT
<213> ORGANISM: Homo sapiens

<400> SEQUENCE: 143

Gly Thr Pro Ser Arg Phe Ser Gly Ser Arg Ser Gly Thr Asp Phe Ile
1               5                   10                  15

Leu Thr Ile Arg Ser Leu Glu Pro Glu Asp Phe Gly Leu Tyr Tyr Cys
                20                  25                  30

<210> SEQ ID NO 144
<211> LENGTH: 10
<212> TYPE: PRT
<213> ORGANISM: Homo sapiens

<400> SEQUENCE: 144

Phe Gly Ala Gly Thr Lys Leu Glu Leu Lys
1               5                   10

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163
<211> LENGTH: 363
<212> TYPE: DNA
<213> ORGANISM: Homo sapiens

<400> SEQUENCE: 163

```
caggtcaacc tactgcagtc tggggctgca ctggtgaagc ctggggcctc tgtgaagttg      60
tcttgcaaag cctctggtta tacattcact gactactata tacactgggt gaagcagagt     120
catggaatga gccttgagtg gattgggctt attaatcctg acagtggtta tcctaactac     180
aatgaaaatt tcaagggcaa ggccacattg actgttgaca atccaccaa tacagcctat     240 atggagcttc gcagattgac atctgaggac tctgcaacct attactgtac aagatcgagg     300
atttactatg atggttcggt ttttgattac tggggccaag gagtcatggt cacagtctcc     360
tca                                                                   363
```

<210> SEQ ID NO 164
<211> LENGTH: 121
<212> TYPE: PRT
<213> ORGANISM: Homo sapiens

<400> SEQUENCE: 164

Gln Val Asn Leu Leu Gln Ser Gly Ala Ala Leu Val Lys Pro Gly Ala
1               5                   10                  15

Ser Val Lys Leu Ser Cys Lys Ala Ser Gly Tyr Thr Phe Thr Asp Tyr
            20                  25                  30

Tyr Ile His Trp Val Lys Gln Ser His Gly Met Ser Leu Glu Trp Ile
        35                  40                  45

Gly Leu Ile Asn Pro Asp Ser Gly Tyr Pro Asn Tyr Asn Glu Asn Phe
    50                  55                  60

Lys Gly Lys Ala Thr Leu Thr Val Asp Lys Ser Thr Asn Thr Ala Tyr

```
                65                  70                  75                  80
Met Glu Leu Arg Arg Leu Thr Ser Glu Asp Ser Ala Thr Tyr Tyr Cys
                    85                  90                  95

Thr Arg Ser Arg Ile Tyr Tyr Asp Gly Ser Val Phe Asp Tyr Trp Gly
                100                 105                 110

Gln Gly Val Met Val Thr Val Ser Ser
            115                 120
```

<210> SEQ ID NO 165
<211> LENGTH: 5
<212> TYPE: PRT
<213> ORGANISM: Homo sapiens

<400> SEQUENCE: 165

```
Asp Tyr Tyr Ile His
1               5
```

<210> SEQ ID NO 166
<211> LENGTH: 17
<212> TYPE: PRT
<213> ORGANISM: Homo sapiens

<400> SEQUENCE: 166

```
Leu Ile Asn Pro Asp Ser Gly Tyr Pro Asn Tyr Asn Glu Asn Phe Lys
1               5                   10                  15

Gly
```

<210> SEQ ID NO 167
<211> LENGTH: 12
<212> TYPE: PRT
<213> ORGANISM: Homo sapiens

<400> SEQUENCE: 167

```
Ser Arg Ile Tyr Tyr Asp Gly Ser Val Phe Asp Tyr
1               5                   10
```

<210> SEQ ID NO 168
<211> LENGTH: 30
<212> TYPE: PRT
<213> ORGANISM: Homo sapiens

<400> SEQUENCE: 168

```
Gln Val Asn Leu Leu Gln Ser Gly Ala Ala Leu Val Lys Pro Gly Ala
1               5                   10                  15

Ser Val Lys Leu Ser Cys Lys Ala Ser Gly Tyr Thr Phe Thr
            20                  25                  30
```

<210> SEQ ID NO 169
<211> LENGTH: 14
<212> TYPE: PRT
<213> ORGANISM: Homo sapiens

<400> SEQUENCE: 169

```
Trp Val Lys Gln Ser His Gly Met Ser Leu Glu Trp Ile Gly
1               5                   10
```

<210> SEQ ID NO 170
<211> LENGTH: 32
<212> TYPE: PRT
<213> ORGANISM: Homo sapiens

<400> SEQUENCE: 170

```
Lys Ala Thr Leu Thr Val Asp Lys Ser Thr Asn Thr Ala Tyr Met Glu
1               5                   10                  15

Leu Arg Arg Leu Thr Ser Glu Asp Ser Ala Tyr Tyr Cys Thr Arg
            20                  25                  30
```

<210> SEQ ID NO 171
<211> LENGTH: 11
<212> TYPE: PRT
<213> ORGANISM: Homo sapiens

<400> SEQUENCE: 171

```
Trp Gly Gln Gly Val Met Val Thr Val Ser Ser
1               5                   10
```

<210> SEQ ID NO 172
<211> LENGTH: 318
<212> TYPE: DNA
<213> ORGANISM: Homo sapiens

<400> SEQUENCE: 172

```
gaaattgtgc taacccagtc tccaacaacc atggctgtat ctccggggga gaaggtcacc      60
atcacctgcc gtgccaggtc cagtgtaagc tacatgtact ggtaccagca gaagtcaggc     120
gcctccccta aaccctggat ttatgaaaca tccaaactgg cttctggagt cccagatcgc     180
ttcagtggca gtgggtctgg gacctcttat cgttcacaa tcagctccat ggagactgaa      240
gatgctgcca cttattattg tcaccagtgg agtaggaccc acccacgtt tggaggtggg      300
accaagctgg aaatgaga                                                   318
```

<210> SEQ ID NO 173
<211> LENGTH: 106
<212> TYPE: PRT
<213> ORGANISM: Homo sapiens

<400> SEQUENCE: 173

```
Glu Ile Val Leu Thr Gln Ser Pro Thr Thr Met Ala Val Ser Pro Gly
1               5                   10                  15

Glu Lys Val Thr Ile Thr Cys Arg Ala Arg Ser Ser Val Ser Tyr Met
            20                  25                  30

Tyr Trp Tyr Gln Gln Lys Ser Gly Ala Ser Pro Lys Pro Trp Ile Tyr
        35                  40                  45

Glu Thr Ser Lys Leu Ala Ser Gly Val Pro Asp Arg Phe Ser Gly Ser
    50                  55                  60

Gly Ser Gly Thr Ser Tyr Ser Phe Thr Ile Ser Ser Met Glu Thr Glu
65                  70                  75                  80

Asp Ala Ala Thr Tyr Tyr Cys His Gln Trp Ser Arg Thr Pro Pro Thr
                85                  90                  95

Phe Gly Gly Gly Thr Lys Leu Glu Met Arg
                100                 105
```

<210> SEQ ID NO 174
<211> LENGTH: 10
<212> TYPE: PRT
<213> ORGANISM: Homo sapiens

<400> SEQUENCE: 174

```
Arg Ala Arg Ser Ser Val Ser Tyr Met Tyr
1               5                   10
```

<210> SEQ ID NO 175

```
<211> LENGTH: 7
<212> TYPE: PRT
<213> ORGANISM: Homo sapiens

<400> SEQUENCE: 175

Glu Thr Ser Lys Leu Ala Ser
1               5

<210> SEQ ID NO 176
<211> LENGTH: 9
<212> TYPE: PRT
<213> ORGANISM: Homo sapiens

<400> SEQUENCE: 176

His Gln Trp Ser Arg Thr Pro Pro Thr
1               5

<210> SEQ ID NO 177
<211> LENGTH: 23
<212> TYPE: PRT
<213> ORGANISM: Homo sapiens

<400> SEQUENCE: 177

Glu Ile Val Leu Thr Gln Ser Pro Thr Thr Met Ala Val Ser Pro Gly
1               5                   10                  15

Glu Lys Val Thr Ile Thr Cys
            20

<210> SEQ ID NO 178
<211> LENGTH: 15
<212> TYPE: PRT
<213> ORGANISM: Homo sapiens

<400> SEQUENCE: 178

Trp Tyr Gln Gln Lys Ser Gly Ala Ser Pro Lys Pro Trp Ile Tyr
1               5                   10                  15

<210> SEQ ID NO 179
<211> LENGTH: 32
<212> TYPE: PRT
<213> ORGANISM: Homo sapiens

<400> SEQUENCE: 179

Gly Val Pro Asp Arg Phe Ser Gly Ser Gly Ser Gly Thr Ser Tyr Ser
1               5                   10                  15

Phe Thr Ile Ser Ser Met Glu Thr Glu Asp Ala Ala Thr Tyr Tyr Cys
            20                  25                  30

<210> SEQ ID NO 180
<211> LENGTH: 10
<212> TYPE: PRT
<213> ORGANISM: Homo sapiens

<400> SEQUENCE: 180

Phe Gly Gly Gly Thr Lys Leu Glu Met Arg
1               5                   10

<210> SEQ ID NO 181
<211> LENGTH: 351
<212> TYPE: DNA
<213> ORGANISM: Homo sapiens

<400> SEQUENCE: 181
gagatacagc tgcaggagtc aggacctggc cttgtgaaac cttcacagtc actctccctc    60
```

```
acctgttctg tcactggtta caccattacc agcggttatg attggagctg gatccggaag    120
ttcccaggaa ataaaatgga gtggatggga tacataagct acagtggtaa cactaactac    180
aacccatcgc tcaaaagtcg aatctccatt accagagaca catccaagaa tcagttcttc    240
ctgcagttga actctgttac tactgaggat atagccacat attactgtgg aagagggatg    300
gtggtacttg ttagtacctg gggccaagga gtcatggtca cagtctcctc a             351
```

<210> SEQ ID NO 182
<211> LENGTH: 117
<212> TYPE: PRT
<213> ORGANISM: Homo sapiens

<400> SEQUENCE: 182

```
Glu Ile Gln Leu Gln Glu Ser Gly Pro Gly Leu Val Lys Pro Ser Gln
1               5                   10                  15

Ser Leu Ser Leu Thr Cys Ser Val Thr Gly Tyr Thr Ile Thr Ser Gly
            20                  25                  30

Tyr Asp Trp Ser Trp Ile Arg Lys Phe Pro Gly Asn Lys Met Glu Trp
        35                  40                  45

Met Gly Tyr Ile Ser Tyr Ser Gly Asn Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Ile Ala Thr Tyr Tyr Cys
                85                  90                  95

Gly Arg Gly Met Val Val Leu Val Ser Thr Trp Gly Gln Gly Val Met
            100                 105                 110

Val Thr Val Ser Ser
        115
```

<210> SEQ ID NO 183
<211> LENGTH: 4
<212> TYPE: PRT
<213> ORGANISM: Homo sapiens

<400> SEQUENCE: 183

```
Ser Gly Tyr Asp
1
```

<210> SEQ ID NO 184
<211> LENGTH: 18
<212> TYPE: PRT
<213> ORGANISM: Homo sapiens

<400> SEQUENCE: 184

```
Met Gly Tyr Ile Ser Tyr Ser Gly Asn Thr Asn Tyr Asn Pro Ser Leu
1               5                   10                  15

Lys Ser
```

<210> SEQ ID NO 185
<211> LENGTH: 8
<212> TYPE: PRT
<213> ORGANISM: Homo sapiens

<400> SEQUENCE: 185

```
Gly Met Val Val Leu Val Ser Thr
1               5
```

<210> SEQ ID NO 186
<211> LENGTH: 30
<212> TYPE: PRT
<213> ORGANISM: Homo sapiens

<400> SEQUENCE: 186

Glu Ile Gln Leu Gln Glu Ser Gly Pro Gly Leu Val Lys Pro Ser Gln
1               5                   10                  15

Ser Leu Ser Leu Thr Cys Ser Val Thr Gly Tyr Thr Ile Thr
            20                  25                  30

<210> SEQ ID NO 187
<211> LENGTH: 14
<212> TYPE: PRT
<213> ORGANISM: Homo sapiens

<400> SEQUENCE: 187

Trp Ser Trp Ile Arg Lys Phe Pro Gly Asn Lys Met Glu Trp
1               5                   10

<210> SEQ ID NO 188
<211> LENGTH: 32
<212> TYPE: PRT
<213> ORGANISM: Homo sapiens

<400> SEQUENCE: 188

Arg Ile Ser Ile Thr Arg Asp Thr Ser Lys Asn Gln Phe Phe Leu Gln
1               5                   10                  15

Leu Asn Ser Val Thr Thr Glu Asp Ile Ala Thr Tyr Tyr Cys Gly Arg
            20                  25                  30

<210> SEQ ID NO 189
<211> LENGTH: 11
<212> TYPE: PRT
<213> ORGANISM: Homo sapiens

<400> SEQUENCE: 189

Trp Gly Gln Gly Val Met Val Thr Val Ser Ser
1               5                   10

<210> SEQ ID NO 190
<211> LENGTH: 321
<212> TYPE: DNA
<213> ORGANISM: Homo sapiens

<400> SEQUENCE: 190
gatgtccaga tgacccagtc tccgtcttat cttgctgcgt ctcctggaga aagtgtttcc      60
atcagttgca agacaagtaa gagcattacc cattatttag cctggtatca acagaagcct     120
ggggaagcat ttaaacttct tatctattct gggtcaactt tgcaatctgg aactccatca     180
aggttcattg gcagtggagc tgttacagat ttcactctca ccatcagaag cctggagcct     240
gaagattttg gactctatta ctgtcaacag tattatgaaa acccgtacac gtttggagct     300
gggaccaagc tggaactgaa a                                                321

<210> SEQ ID NO 191
<211> LENGTH: 107
<212> TYPE: PRT
<213> ORGANISM: Homo sapiens

<400> SEQUENCE: 191

Asp Val Gln Met Thr Gln Ser Pro Ser Tyr Leu Ala Ala Ser Pro Gly
1               5                   10                  15

```
Glu Ser Val Ser Ile Ser Cys Lys Thr Ser Lys Ser Ile Thr His Tyr
             20                  25                  30

Leu Ala Trp Tyr Gln Gln Lys Pro Gly Glu Ala Phe Lys Leu Leu Ile
         35                  40                  45

Tyr Ser Gly Ser Thr Leu Gln Ser Gly Thr Pro Ser Arg Phe Ile Gly
 50                  55                  60

Ser Gly Ala Val Thr Asp Phe Thr Leu Thr Ile Arg Ser Leu Glu Pro
 65                  70                  75                  80

Glu Asp Phe Gly Leu Tyr Tyr Cys Gln Gln Tyr Tyr Glu Asn Pro Tyr
                 85                  90                  95

Thr Phe Gly Ala Gly Thr Lys Leu Glu Leu Lys
            100                 105

<210> SEQ ID NO 192
<211> LENGTH: 11
<212> TYPE: PRT
<213> ORGANISM: Homo sapiens

<400> SEQUENCE: 192

Lys Thr Ser Lys Ser Ile Thr His Tyr Leu Ala
1               5                   10

<210> SEQ ID NO 193
<211> LENGTH: 7
<212> TYPE: PRT
<213> ORGANISM: Homo sapiens

<400> SEQUENCE: 193

Ser Gly Ser Thr Leu Gln Ser
1               5

<210> SEQ ID NO 194
<211> LENGTH: 9
<212> TYPE: PRT
<213> ORGANISM: Homo sapiens

<400> SEQUENCE: 194

Gln Gln Tyr Tyr Glu Asn Pro Tyr Thr
1               5

<210> SEQ ID NO 195
<211> LENGTH: 23
<212> TYPE: PRT
<213> ORGANISM: Homo sapiens

<400> SEQUENCE: 195

Asp Val Gln Met Thr Gln Ser Pro Ser Tyr Leu Ala Ala Ser Pro Gly
1               5                   10                  15

Glu Ser Val Ser Ile Ser Cys
            20

<210> SEQ ID NO 196
<211> LENGTH: 15
<212> TYPE: PRT
<213> ORGANISM: Homo sapiens

<400> SEQUENCE: 196

Trp Tyr Gln Gln Lys Pro Gly Glu Ala Phe Lys Leu Leu Ile Tyr
1               5                   10                  15

<210> SEQ ID NO 197
```

<211> LENGTH: 32
<212> TYPE: PRT
<213> ORGANISM: Homo sapiens

<400> SEQUENCE: 197

Gly Thr Pro Ser Arg Phe Ile Gly Ser Gly Ala Val Thr Asp Phe Thr
1               5                   10                  15

Leu Thr Ile Arg Ser Leu Glu Pro Glu Asp Phe Gly Leu Tyr Tyr Cys
            20                  25                  30

<210> SEQ ID NO 198
<211> LENGTH: 10
<212> TYPE: PRT
<213> ORGANISM: Homo sapiens

<400> SEQUENCE: 198

Phe Gly Ala Gly Thr Lys Leu Glu Leu Lys
1               5                   10

<210> SEQ ID NO 199

<400> SEQUENCE: 199

000

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203

<400> SEQUENCE: 203

000

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209

<400> SEQUENCE: 209

000

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217
<211> LENGTH: 372
<212> TYPE: DNA
<213> ORGANISM: Homo sapiens

<400> SEQUENCE: 217
caggttactc tgaaagagtc tggccctggg atattgcagc cttcccagac cctcagtctg    60

```
acttgctctt tctctgggtt ttcactgagc acttttggta tatgtgtgag ctggattcgt      120
cagccttcag ggaagggtct ggagtggctg gcaattattt gttgggagga tagtaagggc      180 tacaacccttt ctctgaagaa ccggctcaca atctccaagg acacctccaa caaccaagca     240
ttcctcaaga tctccagtgt ggacactgca gataccgcca tatactactg tgctcggagg     300
tccgttatgt atactacggc cccgtactac tttgattact ggggccaagg agtcatggtc     360
acagtctcct ca                                                         372
```

```
<210> SEQ ID NO 218
<211> LENGTH: 124
<212> TYPE: PRT
<213> ORGANISM: Homo sapiens

<400> SEQUENCE: 218

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Phe
            20                  25                  30

Gly Ile Cys Val Ser Trp Ile Arg Gln Pro Ser Gly Lys Gly Leu Glu
        35                  40                  45

Trp Leu Ala Ile Ile Cys Trp Glu Asp Ser Lys Gly Tyr Asn Pro Ser
    50                  55                  60

Leu Lys Asn Arg Leu Thr Ile Ser Lys Asp Thr Ser Asn Asn Gln Ala
65                  70                  75                  80

Phe Leu Lys Ile Ser Ser Val Asp Thr Ala Asp Thr Ala Ile Tyr Tyr
                85                  90                  95

Cys Ala Arg Arg Ser Val Met Tyr Thr Thr Ala Pro Tyr Tyr Phe Asp
            100                 105                 110

Tyr Trp Gly Gln Gly Val Met Val Thr Val Ser Ser
        115                 120

<210> SEQ ID NO 219
<211> LENGTH: 7
<212> TYPE: PRT
<213> ORGANISM: Homo sapiens

<400> SEQUENCE: 219

Thr Phe Gly Ile Cys Val Ser
1               5

<210> SEQ ID NO 220
<211> LENGTH: 16
<212> TYPE: PRT
<213> ORGANISM: Homo sapiens

<400> SEQUENCE: 220

Ile Ile Cys Trp Glu Asp Ser Lys Gly Tyr Asn Pro Ser Leu Lys Asn
1               5                   10                  15

<210> SEQ ID NO 221
<211> LENGTH: 14
<212> TYPE: PRT
<213> ORGANISM: Homo sapiens

<400> SEQUENCE: 221

Arg Ser Val Met Tyr Thr Thr Ala Pro Tyr Tyr Phe Asp Tyr
1               5                   10
```

-continued

<210> SEQ ID NO 222
<211> LENGTH: 30
<212> TYPE: PRT
<213> ORGANISM: Homo sapiens

<400> SEQUENCE: 222

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser
            20                  25                  30

<210> SEQ ID NO 223
<211> LENGTH: 14
<212> TYPE: PRT
<213> ORGANISM: Homo sapiens

<400> SEQUENCE: 223

Trp Ile Arg Gln Pro Ser Gly Lys Gly Leu Glu Trp Leu Ala
1               5                   10

<210> SEQ ID NO 224
<211> LENGTH: 32
<212> TYPE: PRT
<213> ORGANISM: Homo sapiens

<400> SEQUENCE: 224

Arg Leu Thr Ile Ser Lys Asp Thr Ser Asn Asn Gln Ala Phe Leu Lys
1               5                   10                  15

Ile Ser Ser Val Asp Thr Ala Asp Thr Ala Ile Tyr Tyr Cys Ala Arg
            20                  25                  30

<210> SEQ ID NO 225
<211> LENGTH: 11
<212> TYPE: PRT
<213> ORGANISM: Homo sapiens

<400> SEQUENCE: 225

Trp Gly Gln Gly Val Met Val Thr Val Ser Ser
1               5                   10

<210> SEQ ID NO 226
<211> LENGTH: 321
<212> TYPE: DNA
<213> ORGANISM: Homo sapiens

<400> SEQUENCE: 226
gacatccaga tgacacagtc tcctgcctcc ctgtctgcat ctctggaaga aattgtcacc      60
atcacatgcc aggcaagcca agacattggt aattggttgg catggtttca gcagaaaccg     120
gggaaatctc ctcagctcct gatttatgat gcaaccacct tggcagatgg ggtcccatca     180
cggttcagcg gcagtagatc tggcacacag ttttctctta agatcaacag attacaggtt     240
gaagatattg gaagctatta ctgtcaacag gctcataata tccgaacac gtttggacgg     300 gggaccaagc tggaaatgaa a                                               321

<210> SEQ ID NO 227
<211> LENGTH: 107
<212> TYPE: PRT
<213> ORGANISM: Homo sapiens

<400> SEQUENCE: 227

Asp Ile Gln Met Thr Gln Ser Pro Ala Ser Leu Ser Ala Ser Leu Glu
1               5                   10                  15

```
Glu Ile Val Thr Ile Thr Cys Gln Ala Ser Gln Asp Ile Gly Asn Trp
            20                  25                  30

Leu Ala Trp Phe Gln Gln Lys Pro Gly Lys Ser Pro Gln Leu Leu Ile
        35                  40                  45

Tyr Asp Ala Thr Thr Leu Ala Asp Gly Val Pro Ser Arg Phe Ser Gly
 50                  55                  60

Ser Arg Ser Gly Thr Gln Phe Ser Leu Lys Ile Asn Arg Leu Gln Val
 65                  70                  75                  80

Glu Asp Ile Gly Ser Tyr Tyr Cys Gln Gln Ala His Asn Asn Pro Asn
            85                  90                  95

Thr Phe Gly Arg Gly Thr Lys Leu Glu Met Lys
            100                 105

<210> SEQ ID NO 228
<211> LENGTH: 11
<212> TYPE: PRT
<213> ORGANISM: Homo sapiens

<400> SEQUENCE: 228

Gln Ala Ser Gln Asp Ile Gly Asn Trp Leu Ala
1               5                   10

<210> SEQ ID NO 229
<211> LENGTH: 7
<212> TYPE: PRT
<213> ORGANISM: Homo sapiens

<400> SEQUENCE: 229

Asp Ala Thr Thr Leu Ala Asp
1               5

<210> SEQ ID NO 230
<211> LENGTH: 9
<212> TYPE: PRT
<213> ORGANISM: Homo sapiens

<400> SEQUENCE: 230

Gln Gln Ala His Asn Asn Pro Asn Thr
1               5

<210> SEQ ID NO 231
<211> LENGTH: 23
<212> TYPE: PRT
<213> ORGANISM: Homo sapiens

<400> SEQUENCE: 231

Asp Ile Gln Met Thr Gln Ser Pro Ala Ser Leu Ser Ala Ser Leu Glu
1               5                   10                  15

Glu Ile Val Thr Ile Thr Cys
            20

<210> SEQ ID NO 232
<211> LENGTH: 15
<212> TYPE: PRT
<213> ORGANISM: Homo sapiens

<400> SEQUENCE: 232

Trp Phe Gln Gln Lys Pro Gly Lys Ser Pro Gln Leu Leu Ile Tyr
1               5                   10                  15

<210> SEQ ID NO 233
```

```
<211> LENGTH: 32
<212> TYPE: PRT
<213> ORGANISM: Homo sapiens

<400> SEQUENCE: 233

Gly Val Pro Ser Arg Phe Ser Gly Ser Arg Ser Gly Thr Gln Phe Ser
1               5                   10                  15

Leu Lys Ile Asn Arg Leu Gln Val Glu Asp Ile Gly Ser Tyr Tyr Cys
                20                  25                  30

<210> SEQ ID NO 234
<211> LENGTH: 10
<212> TYPE: PRT
<213> ORGANISM: Homo sapiens

<400> SEQUENCE: 234

Phe Gly Arg Gly Thr Lys Leu Glu Met Lys
1               5                   10

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000
```

<210> SEQ ID NO 243

<400> SEQUENCE: 243

000

<210> SEQ ID NO 244
<211> LENGTH: 321
<212> TYPE: DNA
<213> ORGANISM: Homo sapiens

<400> SEQUENCE: 244
gacatccaga tgacacagtc tcctgcctcc ctgtctgcat ctctggaaga aattgtcacc    60
atcacatgcc aggcaagcca agacattggt aattggttgg catggtatca gcagaaaccg   120
gggaaatctc ctcagctcct gctttatgat gcaaccagct tggcagatgg ggtcccatca   180
cggttcagcg gcagtagatc tggcacacag tattctctta agatcagcag actacaggtt   240
gaagatattg gaagctatta ctgtcaacag gctcatagta atccttggac gttcggtgga   300
ggcaccaagc tggaattgaa a                                             321

<210> SEQ ID NO 245
<211> LENGTH: 107
<212> TYPE: PRT
<213> ORGANISM: Homo sapiens

<400> SEQUENCE: 245

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ala Trp Tyr Gln Gln Lys Pro Gly Lys Ser Pro Gln Leu Leu Leu
        35                  40                  45

Tyr Asp Ala Thr Ser Leu Ala Asp Gly Val Pro Ser Arg Phe Ser Gly
    50                  55                  60

Ser Arg Ser Gly Thr Gln Tyr Ser Leu Lys Ile Ser Arg Leu Gln Val
65                  70                  75                  80

Glu Asp Ile Gly Ser Tyr Tyr Cys Gln Gln Ala His Ser Asn Pro Trp
                85                  90                  95

Thr Phe Gly Gly Gly Thr Lys Leu Glu Leu Lys
            100                 105

<210> SEQ ID NO 246
<211> LENGTH: 11
<212> TYPE: PRT
<213> ORGANISM: Homo sapiens

<400> SEQUENCE: 246

Gln Ala Ser Gln Asp Ile Gly Asn Trp Leu Ala
1               5                   10

<210> SEQ ID NO 247
<211> LENGTH: 7
<212> TYPE: PRT
<213> ORGANISM: Homo sapiens

<400> SEQUENCE: 247

Asp Ala Thr Ser Leu Ala Asp
1               5

```
<210> SEQ ID NO 248
<211> LENGTH: 9
<212> TYPE: PRT
<213> ORGANISM: Homo sapiens

<400> SEQUENCE: 248

Gln Gln Ala His Ser Asn Pro Trp Thr
1               5

<210> SEQ ID NO 249
<211> LENGTH: 23
<212> TYPE: PRT
<213> ORGANISM: Homo sapiens

<400> SEQUENCE: 249

Asp Ile Gln Met Thr Gln Ser Pro Ala Ser Leu Ser Ala Ser Leu Glu
1               5                   10                  15

Glu Ile Val Thr Ile Thr Cys
            20

<210> SEQ ID NO 250
<211> LENGTH: 15
<212> TYPE: PRT
<213> ORGANISM: Homo sapiens

<400> SEQUENCE: 250

Trp Tyr Gln Gln Lys Pro Gly Lys Ser Pro Gln Leu Leu Leu Tyr
1               5                   10                  15

<210> SEQ ID NO 251
<211> LENGTH: 32
<212> TYPE: PRT
<213> ORGANISM: Homo sapiens

<400> SEQUENCE: 251

Gly Val Pro Ser Arg Phe Ser Gly Ser Arg Ser Gly Thr Gln Tyr Ser
1               5                   10                  15

Leu Lys Ile Ser Arg Leu Gln Val Glu Asp Ile Gly Ser Tyr Tyr Cys
            20                  25                  30

<210> SEQ ID NO 252
<211> LENGTH: 10
<212> TYPE: PRT
<213> ORGANISM: Homo sapiens

<400> SEQUENCE: 252

Phe Gly Gly Gly Thr Lys Leu Glu Leu Lys
1               5                   10

<210> SEQ ID NO 253
<211> LENGTH: 351
<212> TYPE: DNA
<213> ORGANISM: Homo sapiens

<400> SEQUENCE: 253
gagatacagc tgcaggagtc aggacctggc cttgtgaaac cttcacagtc actctccctc      60
acctgttctg tcactggtta caccattacc agtggttatg attggagctg gatccggaag     120
ttcccaggaa ataaaatgga gtggatggga tacataagct acagtggtag cactaactac     180
aacccatcgc tcaaaagtcg aatctccatt accagagaca catccaagaa tcagttcttc     240
ctgcagttga actctgttac tactgaggat atagccacat attactgtgc aagagggatg     300
atggtactta ttagtaactg gggccaagga gtcatggtca cagtctcctc a              351
```

<210> SEQ ID NO 254
<211> LENGTH: 117
<212> TYPE: PRT
<213> ORGANISM: Homo sapiens

<400> SEQUENCE: 254

Glu Ile Gln Leu Gln Glu Ser Gly Pro Gly Leu Val Lys Pro Ser Gln
1               5                   10                  15

Ser Leu Ser Leu Thr Cys Ser Val Thr Gly Tyr Thr Ile Thr Ser Gly
            20                  25                  30

Tyr Asp Trp Ser Trp Ile Arg Lys Phe Pro Gly Asn Lys Met Glu Trp
        35                  40                  45

Met Gly Tyr Ile Ser Tyr Ser Gly Ser Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Ile Ala Thr Tyr Tyr Cys
                85                  90                  95

Ala Arg Gly Met Met Val Leu Ile Ser Asn Trp Gly Gln Gly Val Met
            100                 105                 110

Val Thr Val Ser Ser
        115

<210> SEQ ID NO 255
<211> LENGTH: 4
<212> TYPE: PRT
<213> ORGANISM: Homo sapiens

<400> SEQUENCE: 255

Ser Gly Tyr Asp
1

<210> SEQ ID NO 256
<211> LENGTH: 18
<212> TYPE: PRT
<213> ORGANISM: Homo sapiens

<400> SEQUENCE: 256

Met Gly Tyr Ile Ser Tyr Ser Gly Ser Thr Asn Tyr Asn Pro Ser Leu
1               5                   10                  15

Lys Ser

<210> SEQ ID NO 257
<211> LENGTH: 8
<212> TYPE: PRT
<213> ORGANISM: Homo sapiens

<400> SEQUENCE: 257

Gly Met Met Val Leu Ile Ser Asn
1               5

<210> SEQ ID NO 258
<211> LENGTH: 30
<212> TYPE: PRT
<213> ORGANISM: Homo sapiens

<400> SEQUENCE: 258

Glu Ile Gln Leu Gln Glu Ser Gly Pro Gly Leu Val Lys Pro Ser Gln
1               5                   10                  15

```
Ser Leu Ser Leu Thr Cys Ser Val Thr Gly Tyr Thr Ile Thr
            20                  25                  30
```

<210> SEQ ID NO 259
<211> LENGTH: 14
<212> TYPE: PRT
<213> ORGANISM: Homo sapiens

<400> SEQUENCE: 259

```
Trp Ser Trp Ile Arg Lys Phe Pro Gly Asn Lys Met Glu Trp
1               5                   10
```

<210> SEQ ID NO 260
<211> LENGTH: 32
<212> TYPE: PRT
<213> ORGANISM: Homo sapiens

<400> SEQUENCE: 260

```
Arg Ile Ser Ile Thr Arg Asp Thr Ser Lys Asn Gln Phe Phe Leu Gln
1               5                   10                  15

Leu Asn Ser Val Thr Thr Glu Asp Ile Ala Thr Tyr Tyr Cys Ala Arg
            20                  25                  30
```

<210> SEQ ID NO 261
<211> LENGTH: 11
<212> TYPE: PRT
<213> ORGANISM: Homo sapiens

<400> SEQUENCE: 261

```
Trp Gly Gln Gly Val Met Val Thr Val Ser Ser
1               5                   10
```

<210> SEQ ID NO 262
<211> LENGTH: 321
<212> TYPE: DNA
<213> ORGANISM: Homo sapiens

<400> SEQUENCE: 262

```
gatgtccaga tgacccagtc tccgtcttat cttgctgcgt ctcctggaga aagtgtttcc      60
atcagttgca aggcaagtaa gagcattact cattatttag cctggtatca acagaagcct    120
ggggaagcat ataaacttct tatctactct gggtcaactt tgcaatctgg aactccatca    180
aggttcattg gcactggagc tgttacagat ttcactctca ccatcagaag cctggagcct    240
gaagattttg gactctatta ctgtcaacag tattatgaaa aaccgtacac gtttggagct    300
gggaccaagc tggaactgaa a                                                321
```

<210> SEQ ID NO 263
<211> LENGTH: 107
<212> TYPE: PRT
<213> ORGANISM: Homo sapiens

<400> SEQUENCE: 263

```
Asp Val Gln Met Thr Gln Ser Pro Ser Tyr Leu Ala Ala Ser Pro Gly
1               5                   10                  15

Glu Ser Val Ser Ile Ser Cys Lys Ala Ser Lys Ser Ile Thr His Tyr
            20                  25                  30

Leu Ala Trp Tyr Gln Gln Lys Pro Gly Glu Ala Tyr Lys Leu Leu Ile
        35                  40                  45

Tyr Ser Gly Ser Thr Leu Gln Ser Gly Thr Pro Ser Arg Phe Ile Gly
    50                  55                  60
```

-continued

```
Thr Gly Ala Val Thr Asp Phe Thr Leu Thr Ile Arg Ser Leu Glu Pro
 65                  70                  75                  80

Glu Asp Phe Gly Leu Tyr Tyr Cys Gln Gln Tyr Tyr Glu Lys Pro Tyr
                 85                  90                  95

Thr Phe Gly Ala Gly Thr Lys Leu Glu Leu Lys
            100                 105
```

<210> SEQ ID NO 264
<211> LENGTH: 11
<212> TYPE: PRT
<213> ORGANISM: Homo sapiens

<400> SEQUENCE: 264

```
Lys Ala Ser Lys Ser Ile Thr His Tyr Leu Ala
 1               5                   10
```

<210> SEQ ID NO 265
<211> LENGTH: 7
<212> TYPE: PRT
<213> ORGANISM: Homo sapiens

<400> SEQUENCE: 265

```
Ser Gly Ser Thr Leu Gln Ser
 1               5
```

<210> SEQ ID NO 266
<211> LENGTH: 9
<212> TYPE: PRT
<213> ORGANISM: Homo sapiens

<400> SEQUENCE: 266

```
Gln Gln Tyr Tyr Glu Lys Pro Tyr Thr
 1               5
```

<210> SEQ ID NO 267
<211> LENGTH: 23
<212> TYPE: PRT
<213> ORGANISM: Homo sapiens

<400> SEQUENCE: 267

```
Asp Val Gln Met Thr Gln Ser Pro Ser Tyr Leu Ala Ala Ser Pro Gly
 1               5                   10                  15

Glu Ser Val Ser Ile Ser Cys
            20
```

<210> SEQ ID NO 268
<211> LENGTH: 15
<212> TYPE: PRT
<213> ORGANISM: Homo sapiens

<400> SEQUENCE: 268

```
Trp Tyr Gln Gln Lys Pro Gly Glu Ala Tyr Lys Leu Leu Ile Tyr
 1               5                   10                  15
```

<210> SEQ ID NO 269
<211> LENGTH: 32
<212> TYPE: PRT
<213> ORGANISM: Homo sapiens

<400> SEQUENCE: 269

```
Gly Thr Pro Ser Arg Phe Ile Gly Thr Gly Ala Val Thr Asp Phe Thr
 1               5                   10                  15

Leu Thr Ile Arg Ser Leu Glu Pro Glu Asp Phe Gly Leu Tyr Tyr Cys
```

<210> SEQ ID NO 270
<211> LENGTH: 10
<212> TYPE: PRT
<213> ORGANISM: Homo sapiens

<400> SEQUENCE: 270

Phe Gly Ala Gly Thr Lys Leu Glu Leu Lys
1               5                   10

<210> SEQ ID NO 271
<211> LENGTH: 357
<212> TYPE: DNA
<213> ORGANISM: Homo sapiens

<400> SEQUENCE: 271
caggtgcagc tgaaggagtc aggacctggt ctggtgcagc cctcacagac cctgtccctc    60
acctgcactg tctctgggtt ctcactaacc cgctatgatg tgcactgggt tcgccagcct   120
ccaggaaagg gtctggagtg gatgggagga atatggggtg atggaagcac agattataat   180
tcagctctca atcccgact gagcatcagc agggacacct ccaagagtca agtgttctta   240
aaaatgaaca gtctgcaaac tgaagacaca gccatttact tctgtaccag atctctggac   300
tacagtggtg acgggtttgg ttattggggc caaggcactc tggtcactgt ctcttca      357

<210> SEQ ID NO 272
<211> LENGTH: 119
<212> TYPE: PRT
<213> ORGANISM: Homo sapiens

<400> SEQUENCE: 272

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Arg Tyr
            20                  25                  30

Asp Val His Trp Val Arg Gln Pro Pro Gly Lys Gly Leu Glu Trp Met
        35                  40                  45

Gly Gly Ile Trp Gly Asp Gly Ser Thr Asp Tyr Asn Ser Ala Leu Lys
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Ala Ile Tyr Phe Cys Thr
                85                  90                  95

Arg Ser Leu Asp Tyr Ser Gly Asp Gly Phe Gly Tyr Trp Gly Gln Gly
            100                 105                 110

Thr Leu Val Thr Val Ser Ser
        115

<210> SEQ ID NO 273
<211> LENGTH: 5
<212> TYPE: PRT
<213> ORGANISM: Homo sapiens

<400> SEQUENCE: 273

Arg Tyr Asp Val His
1               5

<210> SEQ ID NO 274
<211> LENGTH: 16

```
<212> TYPE: PRT
<213> ORGANISM: Homo sapiens

<400> SEQUENCE: 274

Gly Ile Trp Gly Asp Gly Ser Thr Asp Tyr Asn Ser Ala Leu Lys Ser
1               5                   10                  15

<210> SEQ ID NO 275
<211> LENGTH: 11
<212> TYPE: PRT
<213> ORGANISM: Homo sapiens

<400> SEQUENCE: 275

Ser Leu Asp Tyr Ser Gly Asp Gly Phe Gly Tyr
1               5                   10

<210> SEQ ID NO 276
<211> LENGTH: 30
<212> TYPE: PRT
<213> ORGANISM: Homo sapiens

<400> SEQUENCE: 276

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr
                20                  25                  30

<210> SEQ ID NO 277
<211> LENGTH: 14
<212> TYPE: PRT
<213> ORGANISM: Homo sapiens

<400> SEQUENCE: 277

Trp Val Arg Gln Pro Pro Gly Lys Gly Leu Glu Trp Met Gly
1               5                   10

<210> SEQ ID NO 278
<211> LENGTH: 32
<212> TYPE: PRT
<213> ORGANISM: Homo sapiens

<400> SEQUENCE: 278

Arg Leu Ser Ile Ser Arg Asp Thr Ser Lys Ser Gln Val Phe Leu Lys
1               5                   10                  15

Met Asn Ser Leu Gln Thr Glu Asp Thr Ala Ile Tyr Phe Cys Thr Arg
                20                  25                  30

<210> SEQ ID NO 279
<211> LENGTH: 11
<212> TYPE: PRT
<213> ORGANISM: Homo sapiens

<400> SEQUENCE: 279

Trp Gly Gln Gly Thr Leu Val Thr Val Ser Ser
1               5                   10

<210> SEQ ID NO 280
<211> LENGTH: 321
<212> TYPE: DNA
<213> ORGANISM: Homo sapiens

<400> SEQUENCE: 280
gacatccaga tgacacagtc tcctccctcc ctgtctgcat ctctgggaga caaagtcacc     60
```

| | |
|---|---|
| atcacttgcc aggcaagtca aaacattaac aagtatatag cttggtatca gcaaaagcct | 120 |
| ggaaaagctc ctaggcagct catacgttac acatctgcac tagtgtcagg cacctcatcg | 180 |
| aggttcagtg gcagtggatc tgggagagat tattcattca gcatcagcaa cgtggagtct | 240 |
| gaagatattg caagttatta ctgtctacag tacgataacc ttccgtacac atttggagct | 300 |
| gggaccaagc tggaactgaa a | 321 |

<210> SEQ ID NO 281
<211> LENGTH: 107
<212> TYPE: PRT
<213> ORGANISM: Homo sapiens

<400> SEQUENCE: 281

Asp Ile Gln Met Thr Gln Ser Pro Ser Leu Ser Ala Ser Leu Gly
1               5                   10                  15

Asp Lys Val Thr Ile Thr Cys Gln Ala Ser Gln Asn Ile Asn Lys Tyr
            20                  25                  30

Ile Ala Trp Tyr Gln Gln Lys Pro Gly Lys Ala Pro Arg Gln Leu Ile
        35                  40                  45

Arg Tyr Thr Ser Ala Leu Val Ser Gly Thr Ser Ser Arg Phe Ser Gly
    50                  55                  60

Ser Gly Ser Gly Arg Asp Tyr Ser Phe Ser Ile Ser Asn Val Glu Ser
65                  70                  75                  80

Glu Asp Ile Ala Ser Tyr Tyr Cys Leu Gln Tyr Asp Asn Leu Pro Tyr
                85                  90                  95

Thr Phe Gly Ala Gly Thr Lys Leu Glu Leu Lys
            100                 105

<210> SEQ ID NO 282
<211> LENGTH: 11
<212> TYPE: PRT
<213> ORGANISM: Homo sapiens

<400> SEQUENCE: 282

Gln Ala Ser Gln Asn Ile Asn Lys Tyr Ile Ala
1               5                   10

<210> SEQ ID NO 283
<211> LENGTH: 7
<212> TYPE: PRT
<213> ORGANISM: Homo sapiens

<400> SEQUENCE: 283

Tyr Thr Ser Ala Leu Val Ser
1               5

<210> SEQ ID NO 284
<211> LENGTH: 9
<212> TYPE: PRT
<213> ORGANISM: Homo sapiens

<400> SEQUENCE: 284

Leu Gln Tyr Asp Asn Leu Pro Tyr Thr
1               5

<210> SEQ ID NO 285
<211> LENGTH: 23
<212> TYPE: PRT
<213> ORGANISM: Homo sapiens

<400> SEQUENCE: 285

Asp Ile Gln Met Thr Gln Ser Pro Ser Leu Ser Ala Ser Leu Gly
1               5                   10                  15

Asp Lys Val Thr Ile Thr Cys
            20

<210> SEQ ID NO 286
<211> LENGTH: 15
<212> TYPE: PRT
<213> ORGANISM: Homo sapiens

<400> SEQUENCE: 286

Trp Tyr Gln Gln Lys Pro Gly Lys Ala Pro Arg Gln Leu Ile Arg
1               5                   10                  15

<210> SEQ ID NO 287
<211> LENGTH: 32
<212> TYPE: PRT
<213> ORGANISM: Homo sapiens

<400> SEQUENCE: 287

Gly Thr Ser Ser Arg Phe Ser Gly Ser Gly Ser Gly Arg Asp Tyr Ser
1               5                   10                  15

Phe Ser Ile Ser Asn Val Glu Ser Glu Asp Ile Ala Ser Tyr Tyr Cys
                20                  25                  30

<210> SEQ ID NO 288
<211> LENGTH: 10
<212> TYPE: PRT
<213> ORGANISM: Homo sapiens

<400> SEQUENCE: 288

Phe Gly Ala Gly Thr Lys Leu Glu Leu Lys
1               5                   10

<210> SEQ ID NO 289
<211> LENGTH: 360
<212> TYPE: DNA
<213> ORGANISM: Homo sapiens

<400> SEQUENCE: 289
caggttactc tgaaagagtc tggccctggg atattgcagc cttcccagac cctcagtctg      60
acttgctctt tctctgggtt ttcactgaac acttatggta tatgtgtgag ctggattcgt     120
cagccttcag gaagggtct ggagtggctg gcaactattt gttgggagga tagtaaggtc     180
tacaacccct ctctgaagaa ccggctcaca atctccaagg acacctccaa caaccaagca     240
ttcctcaaga tcaccagtgt ggacactgca gataccgcca tatactactg tgctcggagg     300
agggtttggt catactactt tgattactgg ggccaaggag tcatggtcac agtctcctca     360

<210> SEQ ID NO 290
<211> LENGTH: 120
<212> TYPE: PRT
<213> ORGANISM: Homo sapiens

<400> SEQUENCE: 290

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Asn Thr Tyr
                20                  25                  30

Gly Ile Cys Val Ser Trp Ile Arg Gln Pro Ser Gly Lys Gly Leu Glu
            35                  40                  45

Trp Leu Ala Thr Ile Cys Trp Glu Asp Ser Lys Val Tyr Asn Pro Ser
            50                  55                  60

Leu Lys Asn Arg Leu Thr Ile Ser Lys Asp Thr Ser Asn Asn Gln Ala
 65                  70                  75                  80

Phe Leu Lys Ile Thr Ser Val Asp Thr Ala Asp Thr Ala Ile Tyr Tyr
                    85                  90                  95

Cys Ala Arg Arg Arg Val Trp Ser Tyr Tyr Phe Asp Tyr Trp Gly Gln
                100                 105                 110

Gly Val Met Val Thr Val Ser Ser
            115                 120

<210> SEQ ID NO 291
<211> LENGTH: 7
<212> TYPE: PRT
<213> ORGANISM: Homo sapiens

<400> SEQUENCE: 291

Thr Tyr Gly Ile Cys Val Ser
 1               5

<210> SEQ ID NO 292
<211> LENGTH: 16
<212> TYPE: PRT
<213> ORGANISM: Homo sapiens

<400> SEQUENCE: 292

Thr Ile Cys Trp Glu Asp Ser Lys Val Tyr Asn Pro Ser Leu Lys Asn
 1               5                  10                  15

<210> SEQ ID NO 293
<211> LENGTH: 10
<212> TYPE: PRT
<213> ORGANISM: Homo sapiens

<400> SEQUENCE: 293

Arg Arg Val Trp Ser Tyr Tyr Phe Asp Tyr
 1               5                  10

<210> SEQ ID NO 294
<211> LENGTH: 30
<212> TYPE: PRT
<213> ORGANISM: Homo sapiens

<400> SEQUENCE: 294

Gln Val Thr Leu Lys Glu Ser Gly Pro Gly Ile Leu Gln Pro Ser Gln
 1               5                  10                  15

Thr Leu Ser Leu Thr Cys Ser Phe Ser Gly Phe Ser Leu Asn
            20                  25                  30

<210> SEQ ID NO 295
<211> LENGTH: 14
<212> TYPE: PRT
<213> ORGANISM: Homo sapiens

<400> SEQUENCE: 295

Trp Ile Arg Gln Pro Ser Gly Lys Gly Leu Glu Trp Leu Ala
 1               5                  10

<210> SEQ ID NO 296
<211> LENGTH: 32
<212> TYPE: PRT
<213> ORGANISM: Homo sapiens

<400> SEQUENCE: 296

Arg Leu Thr Ile Ser Lys Asp Thr Ser Asn Asn Gln Ala Phe Leu Lys
1               5                   10                  15

Ile Thr Ser Val Asp Thr Ala Asp Thr Ala Ile Tyr Tyr Cys Ala Arg
            20                  25                  30

<210> SEQ ID NO 297
<211> LENGTH: 11
<212> TYPE: PRT
<213> ORGANISM: Homo sapiens

<400> SEQUENCE: 297

Trp Gly Gln Gly Val Met Val Thr Val Ser Ser
1               5                   10

<210> SEQ ID NO 298
<211> LENGTH: 321
<212> TYPE: DNA
<213> ORGANISM: Homo sapiens

<400> SEQUENCE: 298
gacatccaga tgacacagtc tcctgcctcc ctgtctgcat ctctggaaga aattgtcacc      60
atcacatgcc aggcaagcca agacattggt aattggttgg catggtatca gcagaaaccg     120
gggaaatctc ctcagctcct gatttatgat gcaaccagct tggcagatgg ggtcccatca     180
cggttcagcg gcagtagatc tggcacacag tattctctta agatcagcag actacaggtt    240
gaagatattg gaagctatta ctgtcaacag gctcatacta atccgctcac gttcggttct    300
gggaccaagc tggagatcaa a                                               321

<210> SEQ ID NO 299
<211> LENGTH: 107
<212> TYPE: PRT
<213> ORGANISM: Homo sapiens

<400> SEQUENCE: 299

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ala Trp Tyr Gln Gln Lys Pro Gly Lys Ser Pro Gln Leu Leu Ile
        35                  40                  45

Tyr Asp Ala Thr Ser Leu Ala Asp Gly Val Pro Ser Arg Phe Ser Gly
    50                  55                  60

Ser Arg Ser Gly Thr Gln Tyr Ser Leu Lys Ile Ser Arg Leu Gln Val
65                  70                  75                  80

Glu Asp Ile Gly Ser Tyr Tyr Cys Gln Gln Ala His Thr Asn Pro Leu
                85                  90                  95

Thr Phe Gly Ser Gly Thr Lys Leu Glu Ile Lys
            100                 105

<210> SEQ ID NO 300
<211> LENGTH: 11
<212> TYPE: PRT
<213> ORGANISM: Homo sapiens

<400> SEQUENCE: 300

Gln Ala Ser Gln Asp Ile Gly Asn Trp Leu Ala
1               5                   10

<210> SEQ ID NO 301
<211> LENGTH: 7
<212> TYPE: PRT
<213> ORGANISM: Homo sapiens

<400> SEQUENCE: 301

Asp Ala Thr Ser Leu Ala Asp
1               5

<210> SEQ ID NO 302
<211> LENGTH: 9
<212> TYPE: PRT
<213> ORGANISM: Homo sapiens

<400> SEQUENCE: 302

Gln Gln Ala His Thr Asn Pro Leu Thr
1               5

<210> SEQ ID NO 303
<211> LENGTH: 23
<212> TYPE: PRT
<213> ORGANISM: Homo sapiens

<400> SEQUENCE: 303

Asp Ile Gln Met Thr Gln Ser Pro Ala Ser Leu Ser Ala Ser Leu Glu
1               5                   10                  15

Glu Ile Val Thr Ile Thr Cys
            20

<210> SEQ ID NO 304
<211> LENGTH: 15
<212> TYPE: PRT
<213> ORGANISM: Homo sapiens

<400> SEQUENCE: 304

Trp Tyr Gln Gln Lys Pro Gly Lys Ser Pro Gln Leu Leu Ile Tyr
1               5                   10                  15

<210> SEQ ID NO 305
<211> LENGTH: 32
<212> TYPE: PRT
<213> ORGANISM: Homo sapiens

<400> SEQUENCE: 305

Gly Val Pro Ser Arg Phe Ser Gly Ser Arg Ser Gly Thr Gln Tyr Ser
1               5                   10                  15

Leu Lys Ile Ser Arg Leu Gln Val Glu Asp Ile Gly Ser Tyr Tyr Cys
            20                  25                  30

<210> SEQ ID NO 306
<211> LENGTH: 10
<212> TYPE: PRT
<213> ORGANISM: Homo sapiens

<400> SEQUENCE: 306

Phe Gly Ser Gly Thr Lys Leu Glu Ile Lys
1               5                   10

<210> SEQ ID NO 307
<211> LENGTH: 351
<212> TYPE: DNA
<213> ORGANISM: Homo sapiens

<400> SEQUENCE: 307

```
gagatacagc tgcaggagtc aggacctggc cttgtgaaac cttcacagtc actctccctc      60
acctgttctg tcactggtta caccattacc agtggttttg attggagctg gttccggaag     120
ttcccaggaa ataaaatgga gtggatggga tacataagct acagtggtag cactaactac     180
aacccatcgc tcaaaagtcg aatctccatt accagagaca catccaagaa tcagttcttc     240
ctgcagttga actctgtaac tactgaagat acagccacat attactgtgc aagaggggtc     300
tcctccctgt ctgcttactg gggccaaggc actctggtca ctgtctcttc a              351
```

<210> SEQ ID NO 308
<211> LENGTH: 117
<212> TYPE: PRT
<213> ORGANISM: Homo sapiens

<400> SEQUENCE: 308

```
Glu Ile Gln Leu Gln Glu Ser Gly Pro Gly Leu Val Lys Pro Ser Gln
1               5                   10                  15

Ser Leu Ser Leu Thr Cys Ser Val Thr Gly Tyr Thr Ile Thr Ser Gly
            20                  25                  30

Phe Asp Trp Ser Trp Phe Arg Lys Phe Pro Gly Asn Lys Met Glu Trp
        35                  40                  45

Met Gly Tyr Ile Ser Tyr Ser Gly Ser Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Gly Val Ser Ser Leu Ser Ala Tyr Trp Gly Gln Gly Thr Leu
            100                 105                 110

Val Thr Val Ser Ser
        115
```

<210> SEQ ID NO 309
<211> LENGTH: 4
<212> TYPE: PRT
<213> ORGANISM: Homo sapiens

<400> SEQUENCE: 309

```
Ser Gly Phe Asp
1
```

<210> SEQ ID NO 310
<211> LENGTH: 18
<212> TYPE: PRT
<213> ORGANISM: Homo sapiens

<400> SEQUENCE: 310

```
Met Gly Tyr Ile Ser Tyr Ser Gly Ser Thr Asn Tyr Asn Pro Ser Leu
1               5                   10                  15

Lys Ser
```

<210> SEQ ID NO 311
<211> LENGTH: 8
<212> TYPE: PRT
<213> ORGANISM: Homo sapiens

<400> SEQUENCE: 311

```
Gly Val Ser Ser Leu Ser Ala Tyr
```

<210> SEQ ID NO 312
<211> LENGTH: 30
<212> TYPE: PRT
<213> ORGANISM: Homo sapiens

<400> SEQUENCE: 312

Glu Ile Gln Leu Gln Glu Ser Gly Pro Gly Leu Val Lys Pro Ser Gln
1               5                   10                  15
Ser Leu Ser Leu Thr Cys Ser Val Thr Gly Tyr Thr Ile Thr
            20                  25                  30

<210> SEQ ID NO 313
<211> LENGTH: 14
<212> TYPE: PRT
<213> ORGANISM: Homo sapiens

<400> SEQUENCE: 313

Trp Ser Trp Phe Arg Lys Phe Pro Gly Asn Lys Met Glu Trp
1               5                   10

<210> SEQ ID NO 314
<211> LENGTH: 32
<212> TYPE: PRT
<213> ORGANISM: Homo sapiens

<400> SEQUENCE: 314

Arg Ile Ser Ile Thr Arg Asp Thr Ser Lys Asn Gln Phe Phe Leu Gln
1               5                   10                  15
Leu Asn Ser Val Thr Thr Glu Asp Thr Ala Thr Tyr Tyr Cys Ala Arg
            20                  25                  30

<210> SEQ ID NO 315
<211> LENGTH: 11
<212> TYPE: PRT
<213> ORGANISM: Homo sapiens

<400> SEQUENCE: 315

Trp Gly Gln Gly Thr Leu Val Thr Val Ser Ser
1               5                   10

<210> SEQ ID NO 316
<211> LENGTH: 321
<212> TYPE: DNA
<213> ORGANISM: Homo sapiens

<400> SEQUENCE: 316
gatgtccaga tgacccagtc tccgtcttat cttgctgcgt ctcctggaga gagtgtttcc      60
atcagttgca aggcaagtaa gctcattact aattatttag cctggtatca acagaaacct     120
ggggaaccat ataaccttct tatctactct gggtcaactt tgcaatctgg cactccatca     180
aggttcagtg gcagtagatc tggtacagat ttcactctca ccatcagaag cctgcagcct     240
gaagattttg gactctatta ctgtcaacag tattatgaaa aaccgtacac gtttggaggt     300
gggaccaagc tggaactgaa a                                                321

<210> SEQ ID NO 317
<211> LENGTH: 107
<212> TYPE: PRT
<213> ORGANISM: Homo sapiens

<400> SEQUENCE: 317

```
Asp Val Gln Met Thr Gln Ser Pro Ser Tyr Leu Ala Ala Ser Pro Gly
1               5                   10                  15

Glu Ser Val Ser Ile Ser Cys Lys Ala Ser Lys Leu Ile Thr Asn Tyr
            20                  25                  30

Leu Ala Trp Tyr Gln Lys Pro Gly Glu Pro Tyr Asn Leu Leu Ile
        35                  40                  45

Tyr Ser Gly Ser Thr Leu Gln Ser Gly Thr Pro Ser Arg Phe Ser Gly
    50                  55                  60

Ser Arg Ser Gly Thr Asp Phe Thr Leu Thr Ile Arg Ser Leu Gln Pro
65                  70                  75                  80

Glu Asp Phe Gly Leu Tyr Tyr Cys Gln Gln Tyr Tyr Glu Lys Pro Tyr
                85                  90                  95

Thr Phe Gly Gly Gly Thr Lys Leu Glu Leu Lys
            100                 105
```

<210> SEQ ID NO 318
<211> LENGTH: 11
<212> TYPE: PRT
<213> ORGANISM: Homo sapiens

<400> SEQUENCE: 318

```
Lys Ala Ser Lys Leu Ile Thr Asn Tyr Leu Ala
1               5                   10
```

<210> SEQ ID NO 319
<211> LENGTH: 7
<212> TYPE: PRT
<213> ORGANISM: Homo sapiens

<400> SEQUENCE: 319

```
Ser Gly Ser Thr Leu Gln Ser
1               5
```

<210> SEQ ID NO 320
<211> LENGTH: 9
<212> TYPE: PRT
<213> ORGANISM: Homo sapiens

<400> SEQUENCE: 320

```
Gln Gln Tyr Tyr Glu Lys Pro Tyr Thr
1               5
```

<210> SEQ ID NO 321
<211> LENGTH: 23
<212> TYPE: PRT
<213> ORGANISM: Homo sapiens

<400> SEQUENCE: 321

```
Asp Val Gln Met Thr Gln Ser Pro Ser Tyr Leu Ala Ala Ser Pro Gly
1               5                   10                  15

Glu Ser Val Ser Ile Ser Cys
            20
```

<210> SEQ ID NO 322
<211> LENGTH: 15
<212> TYPE: PRT
<213> ORGANISM: Homo sapiens

<400> SEQUENCE: 322

```
Trp Tyr Gln Gln Lys Pro Gly Glu Pro Tyr Asn Leu Leu Ile Tyr
1               5                   10                  15
```

<210> SEQ ID NO 323
<211> LENGTH: 32
<212> TYPE: PRT
<213> ORGANISM: Homo sapiens

<400> SEQUENCE: 323

Gly Thr Pro Ser Arg Phe Ser Gly Ser Arg Gly Thr Asp Phe Thr
1               5                   10                  15

Leu Thr Ile Arg Ser Leu Gln Pro Glu Asp Phe Gly Leu Tyr Tyr Cys
            20                  25                  30

<210> SEQ ID NO 324
<211> LENGTH: 10
<212> TYPE: PRT
<213> ORGANISM: Homo sapiens

<400> SEQUENCE: 324

Phe Gly Gly Gly Thr Lys Leu Glu Leu Lys
1               5                   10

<210> SEQ ID NO 325
<211> LENGTH: 366
<212> TYPE: DNA
<213> ORGANISM: Homo sapiens

<400> SEQUENCE: 325
caggtgcagc tgaaggagtc aggacctggc ctggtgaagc cctcagagac cctgtctctc      60
acctgcactg tctctgggtt ctcattaacc agctatcatg taagctgggt tcgacagcct     120
ccaggaaagg gtctggagtg gatgggaata atatggggtg atggaagcac agcatataat     180
tcagctctca atcccgact gagcatcagc agggacacct cgaagagcca agttttctta      240
aaaatgaaca gtctgcaaac tgaagacaca gccacttact actgtgtcag agccggacat     300
tattctgatg gtagttatta ctacggggct tactggggcc aaggcactct ggtcactgtc     360
tcttca                                                                 366

<210> SEQ ID NO 326
<211> LENGTH: 122
<212> TYPE: PRT
<213> ORGANISM: Homo sapiens

<400> SEQUENCE: 326

Gln Val Gln Leu Lys Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

His Val Ser Trp Val Arg Gln Pro Pro Gly Lys Gly Leu Glu Trp Met
        35                  40                  45

Gly Ile Ile Trp Gly Asp Gly Ser Thr Ala Tyr Asn Ser Ala Leu Lys
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Ala Thr Tyr Tyr Cys Val
                85                  90                  95

Arg Ala Gly His Tyr Ser Asp Gly Ser Tyr Tyr Tyr Gly Ala Tyr Trp
            100                 105                 110

Gly Gln Gly Thr Leu Val Thr Val Ser Ser
        115                 120

<210> SEQ ID NO 327
<211> LENGTH: 5
<212> TYPE: PRT
<213> ORGANISM: Homo sapiens

<400> SEQUENCE: 327

Ser Tyr His Val Ser
1               5

<210> SEQ ID NO 328
<211> LENGTH: 16
<212> TYPE: PRT
<213> ORGANISM: Homo sapiens

<400> SEQUENCE: 328

Ile Ile Trp Gly Asp Gly Ser Thr Ala Tyr Asn Ser Ala Leu Lys Ser
1               5                   10                  15

<210> SEQ ID NO 329
<211> LENGTH: 14
<212> TYPE: PRT
<213> ORGANISM: Homo sapiens

<400> SEQUENCE: 329

Ala Gly His Tyr Ser Asp Gly Ser Tyr Tyr Tyr Gly Ala Tyr
1               5                   10

<210> SEQ ID NO 330
<211> LENGTH: 30
<212> TYPE: PRT
<213> ORGANISM: Homo sapiens

<400> SEQUENCE: 330

Gln Val Gln Leu Lys Glu Ser Gly Pro Gly Leu Val Lys Pro Ser Glu
1               5                   10                  15

Thr Leu Ser Leu Thr Cys Thr Val Ser Gly Phe Ser Leu Thr
            20                  25                  30

<210> SEQ ID NO 331
<211> LENGTH: 14
<212> TYPE: PRT
<213> ORGANISM: Homo sapiens

<400> SEQUENCE: 331

Trp Val Arg Gln Pro Pro Gly Lys Gly Leu Glu Trp Met Gly
1               5                   10

<210> SEQ ID NO 332
<211> LENGTH: 32
<212> TYPE: PRT
<213> ORGANISM: Homo sapiens

<400> SEQUENCE: 332

Arg Leu Ser Ile Ser Arg Asp Thr Ser Lys Ser Gln Val Phe Leu Lys
1               5                   10                  15

Met Asn Ser Leu Gln Thr Glu Asp Thr Ala Thr Tyr Tyr Cys Val Arg
            20                  25                  30

<210> SEQ ID NO 333
<211> LENGTH: 11
<212> TYPE: PRT
<213> ORGANISM: Homo sapiens

<400> SEQUENCE: 333

Trp Gly Gln Gly Thr Leu Val Thr Val Ser Ser
1               5                   10

<210> SEQ ID NO 334
<211> LENGTH: 321
<212> TYPE: DNA
<213> ORGANISM: Homo sapiens

<400> SEQUENCE: 334

```
gacatccaga tgacacagtc tcctgcctcc ctgtctgcat ctctggaaga gattgtcacc     60
atcacatgcc aggcaagcca agacattggt aattggttgg catggtatca gcagaagccg    120
gggaaatctc ctcagctcct gatttatgat gcaaccacct tggcagatgg ggtcccatca    180
cggttcagcg gcagtagatc tggcacacag tattctctta agatcagcag actacaggtt    240
gaagatattg gaagctatta ctgtcaacag actcatagtc atcctcggac gttcggtgga    300
ggcaccaacc tggaattgaa a                                              321
```

<210> SEQ ID NO 335
<211> LENGTH: 107
<212> TYPE: PRT
<213> ORGANISM: Homo sapiens

<400> SEQUENCE: 335

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ala Trp Tyr Gln Gln Lys Pro Gly Lys Ser Pro Gln Leu Leu Ile
        35                  40                  45

Tyr Asp Ala Thr Thr Leu Ala Asp Gly Val Pro Ser Arg Phe Ser Gly
    50                  55                  60

Ser Arg Ser Gly Thr Gln Tyr Ser Leu Lys Ile Ser Arg Leu Gln Val
65                  70                  75                  80

Glu Asp Ile Gly Ser Tyr Tyr Cys Gln Gln Thr His Ser His Pro Arg
                85                  90                  95

Thr Phe Gly Gly Gly Thr Asn Leu Glu Leu Lys
            100                 105

<210> SEQ ID NO 336
<211> LENGTH: 11
<212> TYPE: PRT
<213> ORGANISM: Homo sapiens

<400> SEQUENCE: 336

Gln Ala Ser Gln Asp Ile Gly Asn Trp Leu Ala
1               5                   10

<210> SEQ ID NO 337
<211> LENGTH: 7
<212> TYPE: PRT
<213> ORGANISM: Homo sapiens

<400> SEQUENCE: 337

Asp Ala Thr Thr Leu Ala Asp
1               5

<210> SEQ ID NO 338
<211> LENGTH: 9

```
<212> TYPE: PRT
<213> ORGANISM: Homo sapiens

<400> SEQUENCE: 338

Gln Gln Thr His Ser His Pro Arg Thr
1               5

<210> SEQ ID NO 339
<211> LENGTH: 23
<212> TYPE: PRT
<213> ORGANISM: Homo sapiens

<400> SEQUENCE: 339

Asp Ile Gln Met Thr Gln Ser Pro Ala Ser Leu Ser Ala Ser Leu Glu
1               5                   10                  15

Glu Ile Val Thr Ile Thr Cys
            20

<210> SEQ ID NO 340
<211> LENGTH: 15
<212> TYPE: PRT
<213> ORGANISM: Homo sapiens

<400> SEQUENCE: 340

Trp Tyr Gln Gln Lys Pro Gly Lys Ser Pro Gln Leu Leu Ile Tyr
1               5                   10                  15

<210> SEQ ID NO 341
<211> LENGTH: 32
<212> TYPE: PRT
<213> ORGANISM: Homo sapiens

<400> SEQUENCE: 341

Gly Val Pro Ser Arg Phe Ser Gly Ser Arg Ser Gly Thr Gln Tyr Ser
1               5                   10                  15

Leu Lys Ile Ser Arg Leu Gln Val Glu Asp Ile Gly Ser Tyr Tyr Cys
            20                  25                  30

<210> SEQ ID NO 342
<211> LENGTH: 10
<212> TYPE: PRT
<213> ORGANISM: Homo sapiens

<400> SEQUENCE: 342

Phe Gly Gly Gly Thr Asn Leu Glu Leu Lys
1               5                   10

<210> SEQ ID NO 343
<211> LENGTH: 351
<212> TYPE: DNA
<213> ORGANISM: Homo sapiens

<400> SEQUENCE: 343
gagatacagc tgcaggagtc aggacctggc cttgtgaaac cttcacagtc actctccctc    60
acctgttctg tcactggtta caccattacc agtggttttg attggagctg gttccggaag   120
ttcccaggaa ataaaatgga gtggatggga tacattagct acagtggtat cactaactac   180
aacccatcgc tcaaaagtcg aatctccatt accagagaca catccaagaa tcagttcttc   240
ctgcagttga actctgtaac tactgaagat acagccacat attactgtgc aagaggggtc   300 tcctcccctgt ctgcttactg gggccaaggc actctggtca ctgtctcttc a          351
```

-continued

```
<210> SEQ ID NO 344
<211> LENGTH: 117
<212> TYPE: PRT
<213> ORGANISM: Homo sapiens

<400> SEQUENCE: 344
```

Glu Ile Gln Leu Gln Glu Ser Gly Pro Gly Leu Val Lys Pro Ser Gln
1               5                   10                  15

Ser Leu Ser Leu Thr Cys Ser Val Thr Gly Tyr Thr Ile Thr Ser Gly
            20                  25                  30

Phe Asp Trp Ser Trp Phe Arg Lys Phe Pro Gly Asn Lys Met Glu Trp
        35                  40                  45

Met Gly Tyr Ile Ser Tyr Ser Gly Ile Thr Asn Tyr Asn Pro Ser Leu
50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Gly Val Ser Ser Leu Ser Ala Tyr Trp Gly Gln Gly Thr Leu
            100                 105                 110

Val Thr Val Ser Ser
        115

```
<210> SEQ ID NO 345
<211> LENGTH: 4
<212> TYPE: PRT
<213> ORGANISM: Homo sapiens

<400> SEQUENCE: 345
```

Ser Gly Phe Asp
1

```
<210> SEQ ID NO 346
<211> LENGTH: 18
<212> TYPE: PRT
<213> ORGANISM: Homo sapiens

<400> SEQUENCE: 346
```

Met Gly Tyr Ile Ser Tyr Ser Gly Ile Thr Asn Tyr Asn Pro Ser Leu
1               5                   10                  15

Lys Ser

```
<210> SEQ ID NO 347
<211> LENGTH: 8
<212> TYPE: PRT
<213> ORGANISM: Homo sapiens

<400> SEQUENCE: 347
```

Gly Val Ser Ser Leu Ser Ala Tyr
1               5

```
<210> SEQ ID NO 348
<211> LENGTH: 30
<212> TYPE: PRT
<213> ORGANISM: Homo sapiens

<400> SEQUENCE: 348
```

Glu Ile Gln Leu Gln Glu Ser Gly Pro Gly Leu Val Lys Pro Ser Gln
1               5                   10                  15

Ser Leu Ser Leu Thr Cys Ser Val Thr Gly Tyr Thr Ile Thr
            20                  25                  30

<210> SEQ ID NO 349
<211> LENGTH: 14
<212> TYPE: PRT
<213> ORGANISM: Homo sapiens

<400> SEQUENCE: 349

Trp Ser Trp Phe Arg Lys Phe Pro Gly Asn Lys Met Glu Trp
1               5                   10

<210> SEQ ID NO 350
<211> LENGTH: 32
<212> TYPE: PRT
<213> ORGANISM: Homo sapiens

<400> SEQUENCE: 350

Arg Ile Ser Ile Thr Arg Asp Thr Ser Lys Asn Gln Phe Phe Leu Gln
1               5                   10                  15

Leu Asn Ser Val Thr Thr Glu Asp Thr Ala Thr Tyr Tyr Cys Ala Arg
            20                  25                  30

<210> SEQ ID NO 351
<211> LENGTH: 11
<212> TYPE: PRT
<213> ORGANISM: Homo sapiens

<400> SEQUENCE: 351

Trp Gly Gln Gly Thr Leu Val Thr Val Ser Ser
1               5                   10

<210> SEQ ID NO 352
<211> LENGTH: 321
<212> TYPE: DNA
<213> ORGANISM: Homo sapiens

<400> SEQUENCE: 352
gatgtccaga tgacccagtc tccgtcttat cttgctgcgt ctcctggaga aagtgtttcc      60
atcagttgca aggcaagtaa gatcattact aattatttag cctggtatca acagaaacct    120
ggggaaccat ataaccttct tatccactct gggtcaactt tgcaatctgg cactccatca    180
aggttcagtg gcagtagatc tggtacagat ttcactctca ccatcagaag cctgcagcct    240
gaagattttg gactctatta ctgccaacag tattatgaaa acccgtacac gtttggagct    300
gggaccaagc tggaactgaa a                                              321

<210> SEQ ID NO 353
<211> LENGTH: 107
<212> TYPE: PRT
<213> ORGANISM: Homo sapiens

<400> SEQUENCE: 353

Asp Val Gln Met Thr Gln Ser Pro Ser Tyr Leu Ala Ala Ser Pro Gly
1               5                   10                  15

Glu Ser Val Ser Ile Ser Cys Lys Ala Ser Lys Ile Ile Thr Asn Tyr
            20                  25                  30

Leu Ala Trp Tyr Gln Gln Lys Pro Gly Glu Pro Tyr Asn Leu Leu Ile
        35                  40                  45

His Ser Gly Ser Thr Leu Gln Ser Gly Thr Pro Ser Arg Phe Ser Gly
    50                  55                  60

Ser Arg Ser Gly Thr Asp Phe Thr Leu Thr Ile Arg Ser Leu Gln Pro
65                  70                  75                  80

-continued

Glu Asp Phe Gly Leu Tyr Tyr Cys Gln Gln Tyr Tyr Glu Asn Pro Tyr
            85                  90                  95

Thr Phe Gly Ala Gly Thr Lys Leu Glu Leu Lys
            100                 105

<210> SEQ ID NO 354
<211> LENGTH: 11
<212> TYPE: PRT
<213> ORGANISM: Homo sapiens

<400> SEQUENCE: 354

Lys Ala Ser Lys Ile Ile Thr Asn Tyr Leu Ala
1               5                   10

<210> SEQ ID NO 355
<211> LENGTH: 7
<212> TYPE: PRT
<213> ORGANISM: Homo sapiens

<400> SEQUENCE: 355

Ser Gly Ser Thr Leu Gln Ser
1               5

<210> SEQ ID NO 356
<211> LENGTH: 9
<212> TYPE: PRT
<213> ORGANISM: Homo sapiens

<400> SEQUENCE: 356

Gln Gln Tyr Tyr Glu Asn Pro Tyr Thr
1               5

<210> SEQ ID NO 357
<211> LENGTH: 23
<212> TYPE: PRT
<213> ORGANISM: Homo sapiens

<400> SEQUENCE: 357

Asp Val Gln Met Thr Gln Ser Pro Ser Tyr Leu Ala Ala Ser Pro Gly
1               5                   10                  15

Glu Ser Val Ser Ile Ser Cys
            20

<210> SEQ ID NO 358
<211> LENGTH: 15
<212> TYPE: PRT
<213> ORGANISM: Homo sapiens

<400> SEQUENCE: 358

Trp Tyr Gln Gln Lys Pro Gly Glu Pro Tyr Asn Leu Leu Ile His
1               5                   10                  15

<210> SEQ ID NO 359
<211> LENGTH: 32
<212> TYPE: PRT
<213> ORGANISM: Homo sapiens

<400> SEQUENCE: 359

Gly Thr Pro Ser Arg Phe Ser Gly Ser Arg Ser Gly Thr Asp Phe Thr
1               5                   10                  15

Leu Thr Ile Arg Ser Leu Gln Pro Glu Asp Phe Gly Leu Tyr Tyr Cys
            20                  25                  30

<210> SEQ ID NO 360
<211> LENGTH: 10
<212> TYPE: PRT
<213> ORGANISM: Homo sapiens

<400> SEQUENCE: 360

Phe Gly Ala Gly Thr Lys Leu Glu Leu Lys
1               5                   10

<210> SEQ ID NO 361
<211> LENGTH: 366
<212> TYPE: DNA
<213> ORGANISM: Homo sapiens

<400> SEQUENCE: 361
caggtgcagc tgaaggagtc aggacctggc ctggtgaagc cctcagagac cctgtctctc      60
acctgcactg tctctgggtt ctcattaacc agctatcatg tgagctgggt tcgacagcct     120
ccaggaaagg gtctggaatg gatgggagta atatggggtg atggaagcac agcatttaat     180
tcagctctca aatcccgact gagcatcagc aggacacct cgaagagcca agttttctta      240
aaaatgaaca gtctgcaaac tgaagacaca gccacttact actgtgccag agccggggtt     300
tactatgatg gtagttatta ctactttgct tactggggcc aaggcactct ggtcactgtc     360
tcttca                                                                366

<210> SEQ ID NO 362
<211> LENGTH: 122
<212> TYPE: PRT
<213> ORGANISM: Homo sapiens

<400> SEQUENCE: 362

Gln Val Gln Leu Lys Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
                20                  25                  30

His Val Ser Trp Val Arg Gln Pro Pro Gly Lys Gly Leu Glu Trp Met
            35                  40                  45

Gly Val Ile Trp Gly Asp Gly Ser Thr Ala Phe Asn Ser Ala Leu Lys
        50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Ala Thr Tyr Tyr Cys Ala
                85                  90                  95

Arg Ala Gly Val Tyr Tyr Asp Gly Ser Tyr Tyr Phe Ala Tyr Trp
            100                 105                 110

Gly Gln Gly Thr Leu Val Thr Val Ser Ser
        115                 120

<210> SEQ ID NO 363
<211> LENGTH: 5
<212> TYPE: PRT
<213> ORGANISM: Homo sapiens

<400> SEQUENCE: 363

Ser Tyr His Val Ser
1               5

<210> SEQ ID NO 364
<211> LENGTH: 16

```
<212> TYPE: PRT
<213> ORGANISM: Homo sapiens

<400> SEQUENCE: 364

Val Ile Trp Gly Asp Gly Ser Thr Ala Phe Asn Ser Ala Leu Lys Ser
1               5                   10                  15

<210> SEQ ID NO 365
<211> LENGTH: 14
<212> TYPE: PRT
<213> ORGANISM: Homo sapiens

<400> SEQUENCE: 365

Ala Gly Val Tyr Tyr Asp Gly Ser Tyr Tyr Phe Ala Tyr
1               5                   10

<210> SEQ ID NO 366
<211> LENGTH: 30
<212> TYPE: PRT
<213> ORGANISM: Homo sapiens

<400> SEQUENCE: 366

Gln Val Gln Leu Lys Glu Ser Gly Pro Gly Leu Val Lys Pro Ser Glu
1               5                   10                  15

Thr Leu Ser Leu Thr Cys Thr Val Ser Gly Phe Ser Leu Thr
                20                  25                  30

<210> SEQ ID NO 367
<211> LENGTH: 14
<212> TYPE: PRT
<213> ORGANISM: Homo sapiens

<400> SEQUENCE: 367

Trp Val Arg Gln Pro Pro Gly Lys Gly Leu Glu Trp Met Gly
1               5                   10

<210> SEQ ID NO 368
<211> LENGTH: 32
<212> TYPE: PRT
<213> ORGANISM: Homo sapiens

<400> SEQUENCE: 368

Arg Leu Ser Ile Ser Arg Asp Thr Ser Lys Ser Gln Val Phe Leu Lys
1               5                   10                  15

Met Asn Ser Leu Gln Thr Glu Asp Thr Ala Thr Tyr Tyr Cys Ala Arg
                20                  25                  30

<210> SEQ ID NO 369
<211> LENGTH: 11
<212> TYPE: PRT
<213> ORGANISM: Homo sapiens

<400> SEQUENCE: 369

Trp Gly Gln Gly Thr Leu Val Thr Val Ser Ser
1               5                   10

<210> SEQ ID NO 370
<211> LENGTH: 321
<212> TYPE: DNA
<213> ORGANISM: Homo sapiens

<400> SEQUENCE: 370
gacatccaga tgacacagtc tcctgcctcc ctgtctgcat ctctgggaga aattgtcacc     60
```

-continued

| | |
|---|---|
| atcacatgcc aggcaagcca agacattggt aattggttgg catggtatca gcagaaaccg | 120 |
| gggaaatctc ctcacctcct gatttatgat gcaaccacct tggcagatgg ggtcccatca | 180 |
| cggttcagcg gcagtagatc tggcacacag tattctctta agatcagcag actacaagtt | 240 |
| gaagatattg aagctatta ctgtcaaaag gctcatagta atccgtggac gttcggtgga | 300 |
| ggcaccaagc tggaattgaa a | 321 |

<210> SEQ ID NO 371
<211> LENGTH: 107
<212> TYPE: PRT
<213> ORGANISM: Homo sapiens

<400> SEQUENCE: 371

Asp Ile Gln Met Thr Gln Ser Pro Ala Ser Leu Ser Ala Ser Leu Gly
1               5                   10                  15

Glu Ile Val Thr Ile Thr Cys Gln Ala Ser Gln Asp Ile Gly Asn Trp
            20                  25                  30

Leu Ala Trp Tyr Gln Gln Lys Pro Gly Lys Ser Pro His Leu Leu Ile
        35                  40                  45

Tyr Asp Ala Thr Thr Leu Ala Asp Gly Val Pro Ser Arg Phe Ser Gly
    50                  55                  60

Ser Arg Ser Gly Thr Gln Tyr Ser Leu Lys Ile Ser Arg Leu Gln Val
65                  70                  75                  80

Glu Asp Ile Gly Ser Tyr Tyr Cys Gln Lys Ala His Ser Asn Pro Trp
                85                  90                  95

Thr Phe Gly Gly Gly Thr Lys Leu Glu Leu Lys
            100                 105

<210> SEQ ID NO 372
<211> LENGTH: 11
<212> TYPE: PRT
<213> ORGANISM: Homo sapiens

<400> SEQUENCE: 372

Gln Ala Ser Gln Asp Ile Gly Asn Trp Leu Ala
1               5                   10

<210> SEQ ID NO 373
<211> LENGTH: 7
<212> TYPE: PRT
<213> ORGANISM: Homo sapiens

<400> SEQUENCE: 373

Asp Ala Thr Thr Leu Ala Asp
1               5

<210> SEQ ID NO 374
<211> LENGTH: 9
<212> TYPE: PRT
<213> ORGANISM: Homo sapiens

<400> SEQUENCE: 374

Gln Lys Ala His Ser Asn Pro Trp Thr
1               5

<210> SEQ ID NO 375
<211> LENGTH: 23
<212> TYPE: PRT
<213> ORGANISM: Homo sapiens

<400> SEQUENCE: 375

Asp Ile Gln Met Thr Gln Ser Pro Ala Ser Leu Ser Ala Ser Leu Gly
1               5                   10                  15

Glu Ile Val Thr Ile Thr Cys
            20

<210> SEQ ID NO 376
<211> LENGTH: 15
<212> TYPE: PRT
<213> ORGANISM: Homo sapiens

<400> SEQUENCE: 376

Trp Tyr Gln Gln Lys Pro Gly Lys Ser Pro His Leu Leu Ile Tyr
1               5                   10                  15

<210> SEQ ID NO 377
<211> LENGTH: 32
<212> TYPE: PRT
<213> ORGANISM: Homo sapiens

<400> SEQUENCE: 377

Gly Val Pro Ser Arg Phe Ser Gly Ser Arg Ser Gly Thr Gln Tyr Ser
1               5                   10                  15

Leu Lys Ile Ser Arg Leu Gln Val Glu Asp Ile Gly Ser Tyr Tyr Cys
            20                  25                  30

<210> SEQ ID NO 378
<211> LENGTH: 10
<212> TYPE: PRT
<213> ORGANISM: Homo sapiens

<400> SEQUENCE: 378

Phe Gly Gly Gly Thr Lys Leu Glu Leu Lys
1               5                   10

<210> SEQ ID NO 379
<211> LENGTH: 375
<212> TYPE: DNA
<213> ORGANISM: Homo sapiens

<400> SEQUENCE: 379
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gcggcactgg     300
gactggtgga gtacttattc gggtccaact gcttttgatc tctggggcag aggcaccctg     360
gtcaccgtct cgagt                                                       375

<210> SEQ ID NO 380
<211> LENGTH: 125
<212> TYPE: PRT
<213> ORGANISM: Homo sapiens

<400> SEQUENCE: 380

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Trp Asp Trp Trp Ser Thr Tyr Ser Gly Pro Thr Ala Phe
            100                 105                 110

Asp Leu Trp Gly Arg Gly Thr Leu Val Thr Val Ser Ser
        115                 120                 125

<210> SEQ ID NO 381
<211> LENGTH: 5
<212> TYPE: PRT
<213> ORGANISM: Homo sapiens

<400> SEQUENCE: 381

Ser Tyr Ala Met Ser
1               5

<210> SEQ ID NO 382
<211> LENGTH: 17
<212> TYPE: PRT
<213> ORGANISM: Homo sapiens

<400> SEQUENCE: 382

Ala Ile Ser Gly Ser Gly Gly Ser Thr Tyr Tyr Ala Asp Ser Val Lys
1               5                   10                  15

Gly

<210> SEQ ID NO 383
<211> LENGTH: 16
<212> TYPE: PRT
<213> ORGANISM: Homo sapiens

<400> SEQUENCE: 383

His Trp Asp Trp Trp Ser Thr Tyr Ser Gly Pro Thr Ala Phe Asp Leu
1               5                   10                  15

<210> SEQ ID NO 384
<211> LENGTH: 30
<212> TYPE: PRT
<213> ORGANISM: Homo sapiens

<400> SEQUENCE: 384

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 385
<211> LENGTH: 14
<212> TYPE: PRT
<213> ORGANISM: Homo sapiens

<400> SEQUENCE: 385

Trp Val Arg Gln Ala Pro Gly Lys Gly Leu Glu Trp Val Ser
1               5                   10

-continued

<210> SEQ ID NO 386
<211> LENGTH: 32
<212> TYPE: PRT
<213> ORGANISM: Homo sapiens

<400> SEQUENCE: 386

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 387
<211> LENGTH: 11
<212> TYPE: PRT
<213> ORGANISM: Homo sapiens

<400> SEQUENCE: 387

Trp Gly Arg Gly Thr Leu Val Thr Val Ser Ser
1               5                   10

<210> SEQ ID NO 388
<211> LENGTH: 324
<212> TYPE: DNA
<213> ORGANISM: Homo sapiens

<400> SEQUENCE: 388
tcctatgagc tggctcagcc accctcggtg tcagtgtccc caggacagac ggccaggatc     60
acctgctctg gagatgcatt gccaaggcaa tatgcttact ggtaccagca gaagccaggc    120
caggcccctc tactggtgat atataaagac agtgagaggc cctcagggat ccctgagcga    180
ttctctggct ccggctcagg gacaacagtc acgttgacca tcagtggagt ccaggcagaa    240
gacgaggctg actattactg tcaatcagca gacagcagtg gtacctatgt ggtattcggc    300
ggagggacca aggtcaccgt ccta                                           324

<210> SEQ ID NO 389
<211> LENGTH: 108
<212> TYPE: PRT
<213> ORGANISM: Homo sapiens

<400> SEQUENCE: 389

Ser Tyr Glu Leu Ala Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Leu Leu Val Ile Tyr
        35                  40                  45

Lys Asp Ser Glu Arg Pro Ser Gly Ile Pro Glu Arg Phe Ser Gly Ser
50                  55                  60

Gly Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Val Val Phe Gly Gly Gly Thr Lys Val Thr Val Leu
            100                 105

<210> SEQ ID NO 390
<211> LENGTH: 11
<212> TYPE: PRT
<213> ORGANISM: Homo sapiens

```
<400> SEQUENCE: 390

Ser Gly Asp Ala Leu Pro Arg Gln Tyr Ala Tyr
1               5                   10

<210> SEQ ID NO 391
<211> LENGTH: 7
<212> TYPE: PRT
<213> ORGANISM: Homo sapiens

<400> SEQUENCE: 391

Lys Asp Ser Glu Arg Pro Ser
1               5

<210> SEQ ID NO 392
<211> LENGTH: 11
<212> TYPE: PRT
<213> ORGANISM: Homo sapiens

<400> SEQUENCE: 392

Gln Ser Ala Asp Ser Ser Gly Thr Tyr Val Val
1               5                   10

<210> SEQ ID NO 393
<211> LENGTH: 22
<212> TYPE: PRT
<213> ORGANISM: Homo sapiens

<400> SEQUENCE: 393

Ser Tyr Glu Leu Ala Gln Pro Pro Ser Val Ser Val Ser Pro Gly Gln
1               5                   10                  15

Thr Ala Arg Ile Thr Cys
            20

<210> SEQ ID NO 394
<211> LENGTH: 15
<212> TYPE: PRT
<213> ORGANISM: Homo sapiens

<400> SEQUENCE: 394

Trp Tyr Gln Gln Lys Pro Gly Gln Ala Pro Leu Leu Val Ile Tyr
1               5                   10                  15

<210> SEQ ID NO 395
<211> LENGTH: 32
<212> TYPE: PRT
<213> ORGANISM: Homo sapiens

<400> SEQUENCE: 395

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 396
<211> LENGTH: 10
<212> TYPE: PRT
<213> ORGANISM: Homo sapiens

<400> SEQUENCE: 396

Phe Gly Gly Gly Thr Lys Val Thr Val Leu
1               5                   10

<210> SEQ ID NO 397
```

-continued

```
<211> LENGTH: 375
<212> TYPE: DNA
<213> ORGANISM: Homo sapiens

<400> SEQUENCE: 397
gaggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcaaatga acagcctgag agccgaggac acggccgtgt attactgtgc cagggacatg    300
gactactgga gtacttattc gggtccaact gcttttgatc tctggggcag aggcaccctg    360
gtcaccgtct cgagt                                                     375

<210> SEQ ID NO 398
<211> LENGTH: 125
<212> TYPE: PRT
<213> ORGANISM: Homo sapiens

<400> SEQUENCE: 398

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Met Asp Tyr Trp Ser Thr Tyr Ser Gly Pro Thr Ala Phe
            100                 105                 110

Asp Leu Trp Gly Arg Gly Thr Leu Val Thr Val Ser Ser
        115                 120                 125

<210> SEQ ID NO 399
<211> LENGTH: 5
<212> TYPE: PRT
<213> ORGANISM: Homo sapiens

<400> SEQUENCE: 399

Ser Tyr Ala Met Ser
1               5

<210> SEQ ID NO 400
<211> LENGTH: 17
<212> TYPE: PRT
<213> ORGANISM: Homo sapiens

<400> SEQUENCE: 400

Ala Ile Ser Gly Ser Gly Gly Ser Thr Tyr Tyr Ala Asp Ser Val Lys
1               5                   10                  15

Gly

<210> SEQ ID NO 401
<211> LENGTH: 16
```

<212> TYPE: PRT
<213> ORGANISM: Homo sapiens

<400> SEQUENCE: 401

Asp Met Asp Tyr Trp Ser Thr Tyr Ser Gly Pro Thr Ala Phe Asp Leu
1               5                   10                  15

<210> SEQ ID NO 402
<211> LENGTH: 30
<212> TYPE: PRT
<213> ORGANISM: Homo sapiens

<400> SEQUENCE: 402

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 403
<211> LENGTH: 14
<212> TYPE: PRT
<213> ORGANISM: Homo sapiens

<400> SEQUENCE: 403

Trp Val Arg Gln Ala Pro Gly Lys Gly Leu Glu Trp Val Ser
1               5                   10

<210> SEQ ID NO 404
<211> LENGTH: 32
<212> TYPE: PRT
<213> ORGANISM: Homo sapiens

<400> SEQUENCE: 404

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 405
<211> LENGTH: 11
<212> TYPE: PRT
<213> ORGANISM: Homo sapiens

<400> SEQUENCE: 405

Trp Gly Arg Gly Thr Leu Val Thr Val Ser Ser
1               5                   10

<210> SEQ ID NO 406
<211> LENGTH: 324
<212> TYPE: DNA
<213> ORGANISM: Homo sapiens

<400> SEQUENCE: 406
tcctatgagc tggctcagcc accctcggtg tcagtgtccc caggacagac ggccaggatc      60
acctgctctg gagatgcatt gccaaggcaa tatgcttact ggtaccagca gaagccaggc     120
caggcccctc tactggtgat atataaagac agtgagaggc cctcagggat ccctgagcga     180
ttctctggct ccggctcagg gacaacagtc acgttgacca tcagtggagt ccaggcagaa     240
gacgaggctg actattactg tcaatcagca gacagcagtg gtacctatgt ggtattcggc     300
ggagggacca aggtcaccgt ccta                                            324

-continued

```
<210> SEQ ID NO 407
<211> LENGTH: 108
<212> TYPE: PRT
<213> ORGANISM: Homo sapiens

<400> SEQUENCE: 407

Ser Tyr Glu Leu Ala Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Leu Leu Val Ile Tyr
        35                  40                  45

Lys Asp Ser Glu Arg Pro Ser Gly Ile Pro Glu Arg Phe Ser Gly Ser
    50                  55                  60

Gly Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Val Val Phe Gly Gly Gly Thr Lys Val Thr Val Leu
            100                 105

<210> SEQ ID NO 408
<211> LENGTH: 11
<212> TYPE: PRT
<213> ORGANISM: Homo sapiens

<400> SEQUENCE: 408

Ser Gly Asp Ala Leu Pro Arg Gln Tyr Ala Tyr
1               5                   10

<210> SEQ ID NO 409
<211> LENGTH: 7
<212> TYPE: PRT
<213> ORGANISM: Homo sapiens

<400> SEQUENCE: 409

Lys Asp Ser Glu Arg Pro Ser
1               5

<210> SEQ ID NO 410
<211> LENGTH: 11
<212> TYPE: PRT
<213> ORGANISM: Homo sapiens

<400> SEQUENCE: 410

Gln Ser Ala Asp Ser Ser Gly Thr Tyr Val Val
1               5                   10

<210> SEQ ID NO 411
<211> LENGTH: 22
<212> TYPE: PRT
<213> ORGANISM: Homo sapiens

<400> SEQUENCE: 411

Ser Tyr Glu Leu Ala Gln Pro Pro Ser Val Ser Val Ser Pro Gly Gln
1               5                   10                  15

Thr Ala Arg Ile Thr Cys
            20

<210> SEQ ID NO 412
<211> LENGTH: 15
<212> TYPE: PRT
```

<213> ORGANISM: Homo sapiens

<400> SEQUENCE: 412

Trp Tyr Gln Gln Lys Pro Gly Gln Ala Pro Leu Leu Val Ile Tyr
1               5                   10                  15

<210> SEQ ID NO 413
<211> LENGTH: 32
<212> TYPE: PRT
<213> ORGANISM: Homo sapiens

<400> SEQUENCE: 413

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 414
<211> LENGTH: 10
<212> TYPE: PRT
<213> ORGANISM: Homo sapiens

<400> SEQUENCE: 414

Phe Gly Gly Gly Thr Lys Val Thr Val Leu
1               5                   10

<210> SEQ ID NO 415
<211> LENGTH: 375
<212> TYPE: DNA
<213> ORGANISM: Homo sapiens

<400> SEQUENCE: 415

```
gaggtgcagc tgttggagtc tgggggaggc ttggtacagc ctgggggtc cctgagactc         60
tcctgtgcag cctctggatt cacctttagc agctatgcca tgagctgggt ccgccaggct       120
ccagggaagg ggctggagtg ggtctcagct attagtggta gtggtggtag cacatactac       180
gcagactccg tgaagggccg gttcaccatc tccagagaca attccaagaa cacgctgtat       240
ctgcaaatga acagcctgag agccgaggac acggccgtgt attactgtgc ccgggaccac       300
gactactgga gtacttattc gggtccaact gcttttgatc tctggggcag aggcaccctg       360
gtcaccgtct cgagt                                                        375
```

<210> SEQ ID NO 416
<211> LENGTH: 125
<212> TYPE: PRT
<213> ORGANISM: Homo sapiens

<400> SEQUENCE: 416

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Arg Asp His Asp Tyr Trp Ser Thr Tyr Ser Gly Pro Thr Ala Phe
            100                 105                 110

Asp Leu Trp Gly Arg Gly Thr Leu Val Thr Val Ser Ser
            115                 120                 125
```

<210> SEQ ID NO 417
<211> LENGTH: 5
<212> TYPE: PRT
<213> ORGANISM: Homo sapiens

<400> SEQUENCE: 417

```
Ser Tyr Ala Met Ser
1               5
```

<210> SEQ ID NO 418
<211> LENGTH: 17
<212> TYPE: PRT
<213> ORGANISM: Homo sapiens

<400> SEQUENCE: 418

```
Ala Ile Ser Gly Ser Gly Gly Ser Thr Tyr Tyr Ala Asp Ser Val Lys
1               5                   10                  15

Gly
```

<210> SEQ ID NO 419
<211> LENGTH: 16
<212> TYPE: PRT
<213> ORGANISM: Homo sapiens

<400> SEQUENCE: 419

```
Asp His Asp Tyr Trp Ser Thr Tyr Ser Gly Pro Thr Ala Phe Asp Leu
1               5                   10                  15
```

<210> SEQ ID NO 420
<211> LENGTH: 30
<212> TYPE: PRT
<213> ORGANISM: Homo sapiens

<400> SEQUENCE: 420

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30
```

<210> SEQ ID NO 421
<211> LENGTH: 14
<212> TYPE: PRT
<213> ORGANISM: Homo sapiens

<400> SEQUENCE: 421

```
Trp Val Arg Gln Ala Pro Gly Lys Gly Leu Glu Trp Val Ser
1               5                   10
```

<210> SEQ ID NO 422
<211> LENGTH: 32
<212> TYPE: PRT
<213> ORGANISM: Homo sapiens

<400> SEQUENCE: 422

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
```

<210> SEQ ID NO 423
<211> LENGTH: 11
<212> TYPE: PRT
<213> ORGANISM: Homo sapiens

<400> SEQUENCE: 423

Trp Gly Arg Gly Thr Leu Val Thr Val Ser Ser
1               5                   10

<210> SEQ ID NO 424
<211> LENGTH: 324
<212> TYPE: DNA
<213> ORGANISM: Homo sapiens

<400> SEQUENCE: 424
tcctatgagc tggctcagcc accctcggtg tcagtgtccc caggacagac ggccaggatc    60
acctgctctg gagatgcatt gccaaggcaa tatgcttact ggtaccagca gaagccaggc   120
caggcccctc tactggtgat atataaagac agtgagaggc cctcagggat ccctgagcga   180
ttctctggct ccggctcagg gacaacagtc acgttgacca tcagtggagt ccaggcagaa   240
gacgaggctg actattactg tcaatcagca gacagcagtg gtacctatgt ggtattcggc   300
ggagggacca aggtcaccgt ccta                                          324

<210> SEQ ID NO 425
<211> LENGTH: 108
<212> TYPE: PRT
<213> ORGANISM: Homo sapiens

<400> SEQUENCE: 425

Ser Tyr Glu Leu Ala Gln Pro Pro Ser Val Ser Val Pro Gly Gln
1               5                   10                  15

Thr Ala Arg Ile Thr Cys Ser Gly Asp Ala Leu Pro Arg Gln Tyr Ala
                20                  25                  30

Tyr Trp Tyr Gln Gln Lys Pro Gly Gln Ala Pro Leu Leu Val Ile Tyr
            35                  40                  45

Lys Asp Ser Glu Arg Pro Ser Gly Ile Pro Glu Arg Phe Ser Gly Ser
50                  55                  60

Gly Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Val Val Phe Gly Gly Gly Thr Lys Val Thr Val Leu
            100                 105

<210> SEQ ID NO 426
<211> LENGTH: 11
<212> TYPE: PRT
<213> ORGANISM: Homo sapiens

<400> SEQUENCE: 426

Ser Gly Asp Ala Leu Pro Arg Gln Tyr Ala Tyr
1               5                   10

<210> SEQ ID NO 427
<211> LENGTH: 7
<212> TYPE: PRT
<213> ORGANISM: Homo sapiens

```
<400> SEQUENCE: 427

Lys Asp Ser Glu Arg Pro Ser
1               5

<210> SEQ ID NO 428
<211> LENGTH: 11
<212> TYPE: PRT
<213> ORGANISM: Homo sapiens

<400> SEQUENCE: 428

Gln Ser Ala Asp Ser Ser Gly Thr Tyr Val Val
1               5                   10

<210> SEQ ID NO 429
<211> LENGTH: 22
<212> TYPE: PRT
<213> ORGANISM: Homo sapiens

<400> SEQUENCE: 429

Ser Tyr Glu Leu Ala Gln Pro Pro Ser Val Ser Val Ser Pro Gly Gln
1               5                   10                  15

Thr Ala Arg Ile Thr Cys
            20

<210> SEQ ID NO 430
<211> LENGTH: 15
<212> TYPE: PRT
<213> ORGANISM: Homo sapiens

<400> SEQUENCE: 430

Trp Tyr Gln Gln Lys Pro Gly Gln Ala Pro Leu Leu Val Ile Tyr
1               5                   10                  15

<210> SEQ ID NO 431
<211> LENGTH: 32
<212> TYPE: PRT
<213> ORGANISM: Homo sapiens

<400> SEQUENCE: 431

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 432
<211> LENGTH: 10
<212> TYPE: PRT
<213> ORGANISM: Homo sapiens

<400> SEQUENCE: 432

Phe Gly Gly Gly Thr Lys Val Thr Val Leu
1               5                   10

<210> SEQ ID NO 433
<211> LENGTH: 375
<212> TYPE: DNA
<213> ORGANISM: Homo sapiens

<400> SEQUENCE: 433
gaggtgcagc tgttggagtc tgggggaggc ttggtacagc ctggggggtc cctgagactc      60
tcctgtgcag cctctggatt caccttagc agctatgcca tgagctgggt ccgccaggct      120
ccagggaagg ggctggagtg ggtctcagct attagtggta gtggtggtag cacatactac     180
```

-continued

```
gcagactccg tgaagggccg gttcaccatc tccagagaca attccaagaa cacgctgtat      240
ctgcaaatga acagcctgag agccgaggac acggccgtgt attactgttc gcggcagttc      300
gactactgga gtacttattc gggtccaact gcttttgatc tctggggcag aggcaccctg      360
gtcaccgtct cgagt                                                       375
```

<210> SEQ ID NO 434
<211> LENGTH: 125
<212> TYPE: PRT
<213> ORGANISM: Homo sapiens

<400> SEQUENCE: 434

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Arg Gln Phe Asp Tyr Trp Ser Thr Tyr Ser Gly Pro Thr Ala Phe
            100                 105                 110

Asp Leu Trp Gly Arg Gly Thr Leu Val Thr Val Ser Ser
        115                 120                 125

<210> SEQ ID NO 435
<211> LENGTH: 5
<212> TYPE: PRT
<213> ORGANISM: Homo sapiens

<400> SEQUENCE: 435

Ser Tyr Ala Met Ser
1               5

<210> SEQ ID NO 436
<211> LENGTH: 17
<212> TYPE: PRT
<213> ORGANISM: Homo sapiens

<400> SEQUENCE: 436

Ala Ile Ser Gly Ser Gly Gly Ser Thr Tyr Tyr Ala Asp Ser Val Lys
1               5                   10                  15

Gly

<210> SEQ ID NO 437
<211> LENGTH: 16
<212> TYPE: PRT
<213> ORGANISM: Homo sapiens

<400> SEQUENCE: 437

Gln Phe Asp Tyr Trp Ser Thr Tyr Ser Gly Pro Thr Ala Phe Asp Leu
1               5                   10                  15

<210> SEQ ID NO 438
<211> LENGTH: 30

<212> TYPE: PRT
<213> ORGANISM: Homo sapiens

<400> SEQUENCE: 438

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 439
<211> LENGTH: 14
<212> TYPE: PRT
<213> ORGANISM: Homo sapiens

<400> SEQUENCE: 439

Trp Val Arg Gln Ala Pro Gly Lys Gly Leu Glu Trp Val Ser
1               5                   10

<210> SEQ ID NO 440
<211> LENGTH: 32
<212> TYPE: PRT
<213> ORGANISM: Homo sapiens

<400> SEQUENCE: 440

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ser Arg
            20                  25                  30

<210> SEQ ID NO 441
<211> LENGTH: 11
<212> TYPE: PRT
<213> ORGANISM: Homo sapiens

<400> SEQUENCE: 441

Trp Gly Arg Gly Thr Leu Val Thr Val Ser Ser
1               5                   10

<210> SEQ ID NO 442
<211> LENGTH: 324
<212> TYPE: DNA
<213> ORGANISM: Homo sapiens

<400> SEQUENCE: 442
tcctatgagc tggctcagcc accctcggtg tcagtgtccc caggacagac ggccaggatc      60
acctgctctg gagatgcatt gccaaggcaa tatgcttact ggtaccagca gaagccaggc     120
caggcccctc tactggtgat atataaagac agtgagaggc cctcagggat ccctgagcga     180
ttctctggct ccggctcagg gacaacagtc acgttgacca tcagtggagt ccaggcagaa     240
gacgaggctg actattactg tcaatcagca gacagcagtg gtacctatgt ggtattcggc     300
ggagggacca aggtcaccgt ccta                                             324

<210> SEQ ID NO 443
<211> LENGTH: 108
<212> TYPE: PRT
<213> ORGANISM: Homo sapiens

<400> SEQUENCE: 443

Ser Tyr Glu Leu Ala Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala

```
                20                  25                  30
Tyr Trp Tyr Gln Gln Lys Pro Gly Gln Ala Pro Leu Leu Val Ile Tyr
             35                  40                  45

Lys Asp Ser Glu Arg Pro Ser Gly Ile Pro Glu Arg Phe Ser Gly Ser
 50                  55                  60

Gly Ser Gly Thr Thr Val Thr Leu Thr Ile Ser Gly Val Gln Ala Glu
 65                  70                  75                  80

Asp Glu Ala Asp Tyr Tyr Cys Gln Ser Ala Asp Ser Ser Gly Thr Tyr
                 85                  90                  95

Val Val Phe Gly Gly Gly Thr Lys Val Thr Val Leu
                100                 105
```

<210> SEQ ID NO 444
<211> LENGTH: 11
<212> TYPE: PRT
<213> ORGANISM: Homo sapiens

<400> SEQUENCE: 444

```
Ser Gly Asp Ala Leu Pro Arg Gln Tyr Ala Tyr
 1               5                  10
```

<210> SEQ ID NO 445
<211> LENGTH: 7
<212> TYPE: PRT
<213> ORGANISM: Homo sapiens

<400> SEQUENCE: 445

```
Lys Asp Ser Glu Arg Pro Ser
 1               5
```

<210> SEQ ID NO 446
<211> LENGTH: 11
<212> TYPE: PRT
<213> ORGANISM: Homo sapiens

<400> SEQUENCE: 446

```
Gln Ser Ala Asp Ser Ser Gly Thr Tyr Val Val
 1               5                  10
```

<210> SEQ ID NO 447
<211> LENGTH: 22
<212> TYPE: PRT
<213> ORGANISM: Homo sapiens

<400> SEQUENCE: 447

```
Ser Tyr Glu Leu Ala Gln Pro Pro Ser Val Ser Val Ser Pro Gly Gln
 1               5                  10                  15

Thr Ala Arg Ile Thr Cys
             20
```

<210> SEQ ID NO 448
<211> LENGTH: 15
<212> TYPE: PRT
<213> ORGANISM: Homo sapiens

<400> SEQUENCE: 448

```
Trp Tyr Gln Gln Lys Pro Gly Gln Ala Pro Leu Leu Val Ile Tyr
 1               5                  10                  15
```

<210> SEQ ID NO 449
<211> LENGTH: 32
<212> TYPE: PRT

<213> ORGANISM: Homo sapiens

<400> SEQUENCE: 449

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 450
<211> LENGTH: 10
<212> TYPE: PRT
<213> ORGANISM: Homo sapiens

<400> SEQUENCE: 450

Phe Gly Gly Gly Thr Lys Val Thr Val Leu
1               5                   10

<210> SEQ ID NO 451
<211> LENGTH: 375
<212> TYPE: DNA
<213> ORGANISM: Homo sapiens

<400> SEQUENCE: 451
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gagagatagg     300
gattttggga gtaaccggcc gtcccccacc gcttttgatc tctggggcag aggcaccctg     360
gtcaccgtct cgagt                                                     375

<210> SEQ ID NO 452
<211> LENGTH: 125
<212> TYPE: PRT
<213> ORGANISM: Homo sapiens

<400> SEQUENCE: 452

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Asp Phe Trp Ser Asn Arg Pro Ser Pro Thr Ala Phe
            100                 105                 110

Asp Leu Trp Gly Arg Gly Thr Leu Val Thr Val Ser Ser
        115                 120                 125

<210> SEQ ID NO 453
<211> LENGTH: 5
<212> TYPE: PRT

<213> ORGANISM: Homo sapiens

<400> SEQUENCE: 453

Ser Tyr Ala Met Ser
1               5

<210> SEQ ID NO 454
<211> LENGTH: 17
<212> TYPE: PRT
<213> ORGANISM: Homo sapiens

<400> SEQUENCE: 454

Ala Ile Ser Gly Ser Gly Gly Ser Thr Tyr Tyr Ala Asp Ser Val Lys
1               5                   10                  15

Gly

<210> SEQ ID NO 455
<211> LENGTH: 16
<212> TYPE: PRT
<213> ORGANISM: Homo sapiens

<400> SEQUENCE: 455

Asp Arg Asp Phe Trp Ser Asn Arg Pro Ser Pro Thr Ala Phe Asp Leu
1               5                   10                  15

<210> SEQ ID NO 456
<211> LENGTH: 30
<212> TYPE: PRT
<213> ORGANISM: Homo sapiens

<400> SEQUENCE: 456

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
                20                  25                  30

<210> SEQ ID NO 457
<211> LENGTH: 14
<212> TYPE: PRT
<213> ORGANISM: Homo sapiens

<400> SEQUENCE: 457

Trp Val Arg Gln Ala Pro Gly Lys Gly Leu Glu Trp Val Ser
1               5                   10

<210> SEQ ID NO 458
<211> LENGTH: 32
<212> TYPE: PRT
<213> ORGANISM: Homo sapiens

<400> SEQUENCE: 458

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
                20                  25                  30

<210> SEQ ID NO 459
<211> LENGTH: 11
<212> TYPE: PRT
<213> ORGANISM: Homo sapiens

<400> SEQUENCE: 459

Trp Gly Arg Gly Thr Leu Val Thr Val Ser Ser

```
1               5                    10
```

<210> SEQ ID NO 460
<211> LENGTH: 324
<212> TYPE: DNA
<213> ORGANISM: Homo sapiens

<400> SEQUENCE: 460

| | | | | | |
|---|---|---|---|---|---|
| tcctatgagc | tggctcagcc | accctcggtg | tcagtgtccc | caggacagac | ggccaggatc | 60 |
| acctgctctg | gagatgcatt | gccaaggcaa | tatgcttact | ggtaccagca | gaagccaggc | 120 |
| caggcccctc | tactggtgat | atataaagac | agtgagaggc | cctcagggat | ccctgagcga | 180 |
| ttctctggct | ccggctcagg | gacaacagtc | acgttgacca | tcagtggagt | ccaggcagaa | 240 |
| gacgaggctg | actattactg | tcaatcagca | gacagcagtg | gtacctatgt | ggtattcggc | 300 |
| ggagggacca | aggtcaccgt | ccta | | | | 324 |

<210> SEQ ID NO 461
<211> LENGTH: 108
<212> TYPE: PRT
<213> ORGANISM: Homo sapiens

<400> SEQUENCE: 461

Ser Tyr Glu Leu Ala Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Leu Leu Val Ile Tyr
        35                  40                  45

Lys Asp Ser Glu Arg Pro Ser Gly Ile Pro Glu Arg Phe Ser Gly Ser
    50                  55                  60

Gly Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Val Val Phe Gly Gly Gly Thr Lys Val Thr Val Leu
            100                 105

<210> SEQ ID NO 462
<211> LENGTH: 11
<212> TYPE: PRT
<213> ORGANISM: Homo sapiens

<400> SEQUENCE: 462

Ser Gly Asp Ala Leu Pro Arg Gln Tyr Ala Tyr
1               5                   10

<210> SEQ ID NO 463
<211> LENGTH: 7
<212> TYPE: PRT
<213> ORGANISM: Homo sapiens

<400> SEQUENCE: 463

Lys Asp Ser Glu Arg Pro Ser
1               5

<210> SEQ ID NO 464
<211> LENGTH: 11
<212> TYPE: PRT
<213> ORGANISM: Homo sapiens

<400> SEQUENCE: 464

Gln Ser Ala Asp Ser Ser Gly Thr Tyr Val Val
1               5                   10

<210> SEQ ID NO 465
<211> LENGTH: 22
<212> TYPE: PRT
<213> ORGANISM: Homo sapiens

<400> SEQUENCE: 465

Ser Tyr Glu Leu Ala Gln Pro Pro Ser Val Ser Val Ser Pro Gly Gln
1               5                   10                  15

Thr Ala Arg Ile Thr Cys
            20

<210> SEQ ID NO 466
<211> LENGTH: 15
<212> TYPE: PRT
<213> ORGANISM: Homo sapiens

<400> SEQUENCE: 466

Trp Tyr Gln Gln Lys Pro Gly Gln Ala Pro Leu Leu Val Ile Tyr
1               5                   10                  15

<210> SEQ ID NO 467
<211> LENGTH: 32
<212> TYPE: PRT
<213> ORGANISM: Homo sapiens

<400> SEQUENCE: 467

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 468
<211> LENGTH: 10
<212> TYPE: PRT
<213> ORGANISM: Homo sapiens

<400> SEQUENCE: 468

Phe Gly Gly Gly Thr Lys Val Thr Val Leu
1               5                   10

<210> SEQ ID NO 469
<211> LENGTH: 375
<212> TYPE: DNA
<213> ORGANISM: Homo sapiens

<400> SEQUENCE: 469
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gagagatagg     300 gattttttgga gtggcgcgaa ccggatgacc gcttttgatc tctggggcag aggcaccctg     360
gtcaccgtct cgagt                                                      375

<210> SEQ ID NO 470

```
<211> LENGTH: 125
<212> TYPE: PRT
<213> ORGANISM: Homo sapiens

<400> SEQUENCE: 470

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Asp Phe Trp Ser Gly Ala Asn Arg Met Thr Ala Phe
            100                 105                 110

Asp Leu Trp Gly Arg Gly Thr Leu Val Thr Val Ser Ser
        115                 120                 125

<210> SEQ ID NO 471
<211> LENGTH: 5
<212> TYPE: PRT
<213> ORGANISM: Homo sapiens

<400> SEQUENCE: 471

Ser Tyr Ala Met Ser
1               5

<210> SEQ ID NO 472
<211> LENGTH: 17
<212> TYPE: PRT
<213> ORGANISM: Homo sapiens

<400> SEQUENCE: 472

Ala Ile Ser Gly Ser Gly Gly Ser Thr Tyr Tyr Ala Asp Ser Val Lys
1               5                   10                  15

Gly

<210> SEQ ID NO 473
<211> LENGTH: 16
<212> TYPE: PRT
<213> ORGANISM: Homo sapiens

<400> SEQUENCE: 473

Asp Arg Asp Phe Trp Ser Gly Ala Asn Arg Met Thr Ala Phe Asp Leu
1               5                   10                  15

<210> SEQ ID NO 474
<211> LENGTH: 30
<212> TYPE: PRT
<213> ORGANISM: Homo sapiens

<400> SEQUENCE: 474

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30
```

<210> SEQ ID NO 475
<211> LENGTH: 14
<212> TYPE: PRT
<213> ORGANISM: Homo sapiens

<400> SEQUENCE: 475

Trp Val Arg Gln Ala Pro Gly Lys Gly Leu Glu Trp Val Ser
1               5                   10

<210> SEQ ID NO 476
<211> LENGTH: 32
<212> TYPE: PRT
<213> ORGANISM: Homo sapiens

<400> SEQUENCE: 476

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 477
<211> LENGTH: 11
<212> TYPE: PRT
<213> ORGANISM: Homo sapiens

<400> SEQUENCE: 477

Trp Gly Arg Gly Thr Leu Val Thr Val Ser Ser
1               5                   10

<210> SEQ ID NO 478
<211> LENGTH: 324
<212> TYPE: DNA
<213> ORGANISM: Homo sapiens

<400> SEQUENCE: 478
tcctatgagc tggctcagcc accctcggtg tcagtgtccc caggacagac ggccaggatc      60
acctgctctg gagatgcatt gccaaggcaa tatgcttact ggtaccagca gaagccaggc     120
caggcccctc tactggtgat atataaagac agtgagaggc cctcagggat ccctgagcga     180
ttctctggct ccggctcagg gacaacagtc acgttgacca tcagtggagt ccaggcagaa     240
gacgaggctg actattactg tcaatcagca gacagcagtg gtacctatgt ggtattcggc     300
ggagggacca aggtcaccgt ccta                                            324

<210> SEQ ID NO 479
<211> LENGTH: 108
<212> TYPE: PRT
<213> ORGANISM: Homo sapiens

<400> SEQUENCE: 479

Ser Tyr Glu Leu Ala Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Leu Leu Val Ile Tyr
        35                  40                  45

Lys Asp Ser Glu Arg Pro Ser Gly Ile Pro Glu Arg Phe Ser Gly Ser
    50                  55                  60

Gly Ser Gly Thr Thr Val Thr Leu Thr Ile Ser Gly Val Gln Ala Glu
65                  70                  75                  80

```
Asp Glu Ala Asp Tyr Tyr Cys Gln Ser Ala Asp Ser Ser Gly Thr Tyr
            85                  90                  95

Val Val Phe Gly Gly Gly Thr Lys Val Thr Val Leu
            100                 105
```

<210> SEQ ID NO 480
<211> LENGTH: 11
<212> TYPE: PRT
<213> ORGANISM: Homo sapiens

<400> SEQUENCE: 480

```
Ser Gly Asp Ala Leu Pro Arg Gln Tyr Ala Tyr
1               5                   10
```

<210> SEQ ID NO 481
<211> LENGTH: 7
<212> TYPE: PRT
<213> ORGANISM: Homo sapiens

<400> SEQUENCE: 481

```
Lys Asp Ser Glu Arg Pro Ser
1               5
```

<210> SEQ ID NO 482
<211> LENGTH: 11
<212> TYPE: PRT
<213> ORGANISM: Homo sapiens

<400> SEQUENCE: 482

```
Gln Ser Ala Asp Ser Ser Gly Thr Tyr Val Val
1               5                   10
```

<210> SEQ ID NO 483
<211> LENGTH: 22
<212> TYPE: PRT
<213> ORGANISM: Homo sapiens

<400> SEQUENCE: 483

```
Ser Tyr Glu Leu Ala Gln Pro Pro Ser Val Ser Val Ser Pro Gly Gln
1               5                   10                  15

Thr Ala Arg Ile Thr Cys
            20
```

<210> SEQ ID NO 484
<211> LENGTH: 15
<212> TYPE: PRT
<213> ORGANISM: Homo sapiens

<400> SEQUENCE: 484

```
Trp Tyr Gln Gln Lys Pro Gly Gln Ala Pro Leu Leu Val Ile Tyr
1               5                   10                  15
```

<210> SEQ ID NO 485
<211> LENGTH: 32
<212> TYPE: PRT
<213> ORGANISM: Homo sapiens

<400> SEQUENCE: 485

```
Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30
```

<210> SEQ ID NO 486
<211> LENGTH: 10
<212> TYPE: PRT
<213> ORGANISM: Homo sapiens

<400> SEQUENCE: 486

Phe Gly Gly Gly Thr Lys Val Thr Val Leu
1               5                   10

<210> SEQ ID NO 487
<211> LENGTH: 375
<212> TYPE: DNA
<213> ORGANISM: Homo sapiens

<400> SEQUENCE: 487
gaggtgcagc tgttggagtc tgggggaggc ttggtacagc ctgggggtc cctgagactc      60 tcctgtgcag cctctggatt caccttagc agctatgcca tgagctgggt ccgccaggct     120
ccagggaagg gctggagtg gtctcagct attagtggta gtggtggtag cacatactac      180
gcagactccg tgaagggccg gttcaccatc tccagagaca attccaagaa cacgctgtat    240
ctgcaaatga acagcctgag agccgaggac acggccgtgt attactgtgc gagagatagg    300 gattttttgga gtggctccag caaggccacg gcttttgatc tctggggcag aggcaccctg   360
gtcaccgtct cgagt                                                    375

<210> SEQ ID NO 488
<211> LENGTH: 125
<212> TYPE: PRT
<213> ORGANISM: Homo sapiens

<400> SEQUENCE: 488

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Asp Phe Trp Ser Gly Ser Ser Lys Ala Thr Ala Phe
            100                 105                 110

Asp Leu Trp Gly Arg Gly Thr Leu Val Thr Val Ser Ser
        115                 120                 125

<210> SEQ ID NO 489
<211> LENGTH: 5
<212> TYPE: PRT
<213> ORGANISM: Homo sapiens

<400> SEQUENCE: 489

Ser Tyr Ala Met Ser
1               5

<210> SEQ ID NO 490
<211> LENGTH: 17
<212> TYPE: PRT

<213> ORGANISM: Homo sapiens

<400> SEQUENCE: 490

Ala Ile Ser Gly Ser Gly Gly Ser Thr Tyr Tyr Ala Asp Ser Val Lys
1               5                   10                  15

Gly

<210> SEQ ID NO 491
<211> LENGTH: 16
<212> TYPE: PRT
<213> ORGANISM: Homo sapiens

<400> SEQUENCE: 491

Asp Arg Asp Phe Trp Ser Gly Ser Ser Lys Ala Thr Ala Phe Asp Leu
1               5                   10                  15

<210> SEQ ID NO 492
<211> LENGTH: 30
<212> TYPE: PRT
<213> ORGANISM: Homo sapiens

<400> SEQUENCE: 492

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 493
<211> LENGTH: 14
<212> TYPE: PRT
<213> ORGANISM: Homo sapiens

<400> SEQUENCE: 493

Trp Val Arg Gln Ala Pro Gly Lys Gly Leu Glu Trp Val Ser
1               5                   10

<210> SEQ ID NO 494
<211> LENGTH: 32
<212> TYPE: PRT
<213> ORGANISM: Homo sapiens

<400> SEQUENCE: 494

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 495
<211> LENGTH: 11
<212> TYPE: PRT
<213> ORGANISM: Homo sapiens

<400> SEQUENCE: 495

Trp Gly Arg Gly Thr Leu Val Thr Val Ser Ser
1               5                   10

<210> SEQ ID NO 496
<211> LENGTH: 324
<212> TYPE: DNA
<213> ORGANISM: Homo sapiens

<400> SEQUENCE: 496
tcctatgagc tggctcagcc accctcggtg tcagtgtccc caggacagac ggccaggatc       60

```
acctgctctg gagatgcatt gccaaggcaa tatgcttact ggtaccagca gaagccaggc    120
caggcccctc tactggtgat atataaagac agtgagaggc cctcagggat ccctgagcga    180
ttctctggct ccggctcagg gacaacagtc acgttgacca tcagtggagt ccaggcagaa    240
gacgaggctg actattactg tcaatcagca gacagcagtg gtacctatgt ggtattcggc    300
ggagggacca aggtcaccgt ccta                                            324
```

<210> SEQ ID NO 497
<211> LENGTH: 108
<212> TYPE: PRT
<213> ORGANISM: Homo sapiens

<400> SEQUENCE: 497

Ser Tyr Glu Leu Ala Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Leu Leu Val Ile Tyr
        35                  40                  45

Lys Asp Ser Glu Arg Pro Ser Gly Ile Pro Glu Arg Phe Ser Gly Ser
    50                  55                  60

Gly Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Val Val Phe Gly Gly Gly Thr Lys Val Thr Val Leu
            100                 105

<210> SEQ ID NO 498
<211> LENGTH: 11
<212> TYPE: PRT
<213> ORGANISM: Homo sapiens

<400> SEQUENCE: 498

Ser Gly Asp Ala Leu Pro Arg Gln Tyr Ala Tyr
1               5                   10

<210> SEQ ID NO 499
<211> LENGTH: 7
<212> TYPE: PRT
<213> ORGANISM: Homo sapiens

<400> SEQUENCE: 499

Lys Asp Ser Glu Arg Pro Ser
1               5

<210> SEQ ID NO 500
<211> LENGTH: 11
<212> TYPE: PRT
<213> ORGANISM: Homo sapiens

<400> SEQUENCE: 500

Gln Ser Ala Asp Ser Ser Gly Thr Tyr Val Val
1               5                   10

<210> SEQ ID NO 501
<211> LENGTH: 22
<212> TYPE: PRT
<213> ORGANISM: Homo sapiens

```
<400> SEQUENCE: 501

Ser Tyr Glu Leu Ala Gln Pro Pro Ser Val Ser Val Ser Pro Gly Gln
1               5                   10                  15

Thr Ala Arg Ile Thr Cys
            20

<210> SEQ ID NO 502
<211> LENGTH: 15
<212> TYPE: PRT
<213> ORGANISM: Homo sapiens

<400> SEQUENCE: 502

Trp Tyr Gln Gln Lys Pro Gly Gln Ala Pro Leu Leu Val Ile Tyr
1               5                   10                  15

<210> SEQ ID NO 503
<211> LENGTH: 32
<212> TYPE: PRT
<213> ORGANISM: Homo sapiens

<400> SEQUENCE: 503

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 504
<211> LENGTH: 10
<212> TYPE: PRT
<213> ORGANISM: Homo sapiens

<400> SEQUENCE: 504

Phe Gly Gly Gly Thr Lys Val Thr Val Leu
1               5                   10

<210> SEQ ID NO 505
<211> LENGTH: 375
<212> TYPE: DNA
<213> ORGANISM: Homo sapiens

<400> SEQUENCE: 505
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg gctggagtg gtctcagct attagtggta gtggtggtag cacatactac       180
gcagactccg tgaagggccg gttcaccatc tccagagaca attccaagaa cacgctgtat     240
ctgcaaatga acagcctgag agccgaggac acggccgtgt attactgtgc gagagatagg     300 gattttttgga gtcccgggac cggcctcacc gcttttgatc tctggggcag aggcaccctg    360
gtcaccgtct cgagt                                                     375

<210> SEQ ID NO 506
<211> LENGTH: 125
<212> TYPE: PRT
<213> ORGANISM: Homo sapiens

<400> SEQUENCE: 506

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Arg Asp Phe Trp Ser Pro Gly Thr Gly Leu Thr Ala Phe
            100                 105                 110
Asp Leu Trp Gly Arg Gly Thr Leu Val Thr Val Ser Ser
            115                 120                 125

<210> SEQ ID NO 507
<211> LENGTH: 5
<212> TYPE: PRT
<213> ORGANISM: Homo sapiens

<400> SEQUENCE: 507

Ser Tyr Ala Met Ser
1               5

<210> SEQ ID NO 508
<211> LENGTH: 17
<212> TYPE: PRT
<213> ORGANISM: Homo sapiens

<400> SEQUENCE: 508

Ala Ile Ser Gly Ser Gly Gly Ser Thr Tyr Tyr Ala Asp Ser Val Lys
1               5                   10                  15
Gly

<210> SEQ ID NO 509
<211> LENGTH: 16
<212> TYPE: PRT
<213> ORGANISM: Homo sapiens

<400> SEQUENCE: 509

Asp Arg Asp Phe Trp Ser Pro Gly Thr Gly Leu Thr Ala Phe Asp Leu
1               5                   10                  15

<210> SEQ ID NO 510
<211> LENGTH: 30
<212> TYPE: PRT
<213> ORGANISM: Homo sapiens

<400> SEQUENCE: 510

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser
            20                  25                  30

<210> SEQ ID NO 511
<211> LENGTH: 14
<212> TYPE: PRT
<213> ORGANISM: Homo sapiens

<400> SEQUENCE: 511

Trp Val Arg Gln Ala Pro Gly Lys Gly Leu Glu Trp Val Ser
1               5                   10
```

<210> SEQ ID NO 512
<211> LENGTH: 32
<212> TYPE: PRT
<213> ORGANISM: Homo sapiens

<400> SEQUENCE: 512

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 513
<211> LENGTH: 11
<212> TYPE: PRT
<213> ORGANISM: Homo sapiens

<400> SEQUENCE: 513

Trp Gly Arg Gly Thr Leu Val Thr Val Ser Ser
1               5                   10

<210> SEQ ID NO 514
<211> LENGTH: 324
<212> TYPE: DNA
<213> ORGANISM: Homo sapiens

<400> SEQUENCE: 514
tcctatgagc tggctcagcc accctcggtg tcagtgtccc caggacagac ggccaggatc      60
acctgctctg gagatgcatt gccaaggcaa tatgcttact ggtaccagca gaagccaggc     120
caggcccctc tactggtgat atataaagac agtgagaggc cctcagggat ccctgagcga     180
ttctctggct ccggctcagg gacaacagtc acgttgacca tcagtggagt ccaggcagaa     240
gacgaggctg actattactg tcaatcagca gacagcagtg gtacctatgt ggtattcggc     300
ggagggacca aggtcaccgt ccta                                            324

<210> SEQ ID NO 515
<211> LENGTH: 108
<212> TYPE: PRT
<213> ORGANISM: Homo sapiens

<400> SEQUENCE: 515

Ser Tyr Glu Leu Ala Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Leu Leu Val Ile Tyr
        35                  40                  45

Lys Asp Ser Glu Arg Pro Ser Gly Ile Pro Glu Arg Phe Ser Gly Ser
    50                  55                  60

Gly Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Val Val Phe Gly Gly Gly Thr Lys Val Thr Val Leu
            100                 105

<210> SEQ ID NO 516
<211> LENGTH: 11
<212> TYPE: PRT
<213> ORGANISM: Homo sapiens

```
<400> SEQUENCE: 516

Ser Gly Asp Ala Leu Pro Arg Gln Tyr Ala Tyr
1               5                   10

<210> SEQ ID NO 517
<211> LENGTH: 7
<212> TYPE: PRT
<213> ORGANISM: Homo sapiens

<400> SEQUENCE: 517

Lys Asp Ser Glu Arg Pro Ser
1               5

<210> SEQ ID NO 518
<211> LENGTH: 11
<212> TYPE: PRT
<213> ORGANISM: Homo sapiens

<400> SEQUENCE: 518

Gln Ser Ala Asp Ser Ser Gly Thr Tyr Val Val
1               5                   10

<210> SEQ ID NO 519
<211> LENGTH: 22
<212> TYPE: PRT
<213> ORGANISM: Homo sapiens

<400> SEQUENCE: 519

Ser Tyr Glu Leu Ala Gln Pro Pro Ser Val Ser Val Ser Pro Gly Gln
1               5                   10                  15

Thr Ala Arg Ile Thr Cys
            20

<210> SEQ ID NO 520
<211> LENGTH: 15
<212> TYPE: PRT
<213> ORGANISM: Homo sapiens

<400> SEQUENCE: 520

Trp Tyr Gln Gln Lys Pro Gly Gln Ala Pro Leu Leu Val Ile Tyr
1               5                   10                  15

<210> SEQ ID NO 521
<211> LENGTH: 32
<212> TYPE: PRT
<213> ORGANISM: Homo sapiens

<400> SEQUENCE: 521

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 522
<211> LENGTH: 10
<212> TYPE: PRT
<213> ORGANISM: Homo sapiens

<400> SEQUENCE: 522

Phe Gly Gly Gly Thr Lys Val Thr Val Leu
1               5                   10
```

```
<210> SEQ ID NO 523
<211> LENGTH: 375
<212> TYPE: DNA
<213> ORGANISM: Homo sapiens

<400> SEQUENCE: 523
gaggtgcagc tgctggagtc tgggggaggc ttggtacagc ctggggggtc cctgagactc      60
tcctgtgcag cctctggatt cacctttagc agctttgcca tgagctgggt ccgccaggct     120
cctgggaagg ggctggagtg gtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gagagatagg     300
gatttttgga gtacttattc gggtccaact gcttttgatc tctggggcag aggcaccctg     360
gtcaccgtct cctca                                                      375

<210> SEQ ID NO 524
<211> LENGTH: 125
<212> TYPE: PRT
<213> ORGANISM: Homo sapiens

<400> SEQUENCE: 524

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Asp Phe Trp Ser Thr Tyr Ser Gly Pro Thr Ala Phe
            100                 105                 110

Asp Leu Trp Gly Arg Gly Thr Leu Val Thr Val Ser Ser
        115                 120                 125

<210> SEQ ID NO 525
<211> LENGTH: 5
<212> TYPE: PRT
<213> ORGANISM: Homo sapiens

<400> SEQUENCE: 525

Ser Phe Ala Met Ser
1               5

<210> SEQ ID NO 526
<211> LENGTH: 17
<212> TYPE: PRT
<213> ORGANISM: Homo sapiens

<400> SEQUENCE: 526

Ala Ile Ser Gly Ser Gly Gly Ser Thr Tyr Tyr Ala Asp Ser Val Lys
1               5                   10                  15

Gly

<210> SEQ ID NO 527
```

```
<211> LENGTH: 16
<212> TYPE: PRT
<213> ORGANISM: Homo sapiens

<400> SEQUENCE: 527

Asp Arg Asp Phe Trp Ser Thr Tyr Ser Gly Pro Thr Ala Phe Asp Leu
1               5                   10                  15

<210> SEQ ID NO 528
<211> LENGTH: 30
<212> TYPE: PRT
<213> ORGANISM: Homo sapiens

<400> SEQUENCE: 528

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 529
<211> LENGTH: 14
<212> TYPE: PRT
<213> ORGANISM: Homo sapiens

<400> SEQUENCE: 529

Trp Val Arg Gln Ala Pro Gly Lys Gly Leu Glu Trp Val Ser
1               5                   10

<210> SEQ ID NO 530
<211> LENGTH: 32
<212> TYPE: PRT
<213> ORGANISM: Homo sapiens

<400> SEQUENCE: 530

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 531
<211> LENGTH: 11
<212> TYPE: PRT
<213> ORGANISM: Homo sapiens

<400> SEQUENCE: 531

Trp Gly Arg Gly Thr Leu Val Thr Val Ser Ser
1               5                   10

<210> SEQ ID NO 532
<211> LENGTH: 324
<212> TYPE: DNA
<213> ORGANISM: Homo sapiens

<400> SEQUENCE: 532
tcctatgagc tggctcagcc accctcggtg tcagtgtccc caggacagac ggccaggatc      60
acctgctctg gagatgcatt gccaaggcaa tatgcttact ggtaccagca gaagccaggc     120
caggcccctc tactggtgat atataaagac agtgagaggc cctcagggat ccctgagcga     180
ttctctggct ccggctcagg gacaacagtc acgttgacca tcagtggagt ccaggcagaa     240
gacgaggctg actattactg tcaatcagca gacagcagtg gtacctatgt ggtattcggc     300
ggagggacca aggtcaccgt ccta                                            324
```

<210> SEQ ID NO 533
<211> LENGTH: 108
<212> TYPE: PRT
<213> ORGANISM: Homo sapiens

<400> SEQUENCE: 533

Ser Tyr Glu Leu Ala Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Leu Leu Val Ile Tyr
        35                  40                  45

Lys Asp Ser Glu Arg Pro Ser Gly Ile Pro Glu Arg Phe Ser Gly Ser
    50                  55                  60

Gly Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Val Val Phe Gly Gly Gly Thr Lys Val Thr Val Leu
            100                 105

<210> SEQ ID NO 534
<211> LENGTH: 11
<212> TYPE: PRT
<213> ORGANISM: Homo sapiens

<400> SEQUENCE: 534

Ser Gly Asp Ala Leu Pro Arg Gln Tyr Ala Tyr
1               5                   10

<210> SEQ ID NO 535
<211> LENGTH: 7
<212> TYPE: PRT
<213> ORGANISM: Homo sapiens

<400> SEQUENCE: 535

Lys Asp Ser Glu Arg Pro Ser
1               5

<210> SEQ ID NO 536
<211> LENGTH: 11
<212> TYPE: PRT
<213> ORGANISM: Homo sapiens

<400> SEQUENCE: 536

Gln Ser Ala Asp Ser Ser Gly Thr Tyr Val Val
1               5                   10

<210> SEQ ID NO 537
<211> LENGTH: 22
<212> TYPE: PRT
<213> ORGANISM: Homo sapiens

<400> SEQUENCE: 537

Ser Tyr Glu Leu Ala Gln Pro Pro Ser Val Ser Val Ser Pro Gly Gln
1               5                   10                  15

Thr Ala Arg Ile Thr Cys
            20

<210> SEQ ID NO 538
<211> LENGTH: 15

<212> TYPE: PRT
<213> ORGANISM: Homo sapiens

<400> SEQUENCE: 538

Trp Tyr Gln Gln Lys Pro Gly Gln Ala Pro Leu Leu Val Ile Tyr
1               5                   10                  15

<210> SEQ ID NO 539
<211> LENGTH: 32
<212> TYPE: PRT
<213> ORGANISM: Homo sapiens

<400> SEQUENCE: 539

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 540
<211> LENGTH: 10
<212> TYPE: PRT
<213> ORGANISM: Homo sapiens

<400> SEQUENCE: 540

Phe Gly Gly Gly Thr Lys Val Thr Val Leu
1               5                   10

<210> SEQ ID NO 541
<211> LENGTH: 375
<212> TYPE: DNA
<213> ORGANISM: Homo sapiens

<400> SEQUENCE: 541
gaggtgcagc tgttggagtc tgggggaggc ttggtacagc ctggggggtc cctgagactc     60
tcctgtgcag cctctggatt cacctttagc agctttgcca tgagctgggt ccgccaggct    120
ccagggaagg ggctggagtg ggtctcagct attagtggta gtggtggtag cacatactac    180
gcagactccg tgaagggccg gctcaccatc tccagagaca attccaagaa cacgctgtat    240
ctgcaaatga acagcctgag agccgaggac acggccgtgt attactgtgc gagagatagg    300
gattttggga gtacttattc gggtccaact gcttttgatc tctggggcag aggcaccctg    360
gtcaccgtct cgagt                                                    375

<210> SEQ ID NO 542
<211> LENGTH: 125
<212> TYPE: PRT
<213> ORGANISM: Homo sapiens

<400> SEQUENCE: 542

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Leu Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys 85                  90                  95
Ala Arg Asp Arg Asp Phe Trp Ser Thr Tyr Ser Gly Pro Thr Ala Phe
            100                 105                 110

Asp Leu Trp Gly Arg Gly Thr Leu Val Thr Val Ser Ser
            115                 120                 125

<210> SEQ ID NO 543
<211> LENGTH: 5
<212> TYPE: PRT
<213> ORGANISM: Homo sapiens

<400> SEQUENCE: 543

Ser Phe Ala Met Ser
1               5

<210> SEQ ID NO 544
<211> LENGTH: 17
<212> TYPE: PRT
<213> ORGANISM: Homo sapiens

<400> SEQUENCE: 544

Ala Ile Ser Gly Ser Gly Gly Ser Thr Tyr Tyr Ala Asp Ser Val Lys
1               5                   10                  15

Gly

<210> SEQ ID NO 545
<211> LENGTH: 16
<212> TYPE: PRT
<213> ORGANISM: Homo sapiens

<400> SEQUENCE: 545

Asp Arg Asp Phe Trp Ser Thr Tyr Ser Gly Pro Thr Ala Phe Asp Leu
1               5                   10                  15

<210> SEQ ID NO 546
<211> LENGTH: 30
<212> TYPE: PRT
<213> ORGANISM: Homo sapiens

<400> SEQUENCE: 546

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 547
<211> LENGTH: 14
<212> TYPE: PRT
<213> ORGANISM: Homo sapiens

<400> SEQUENCE: 547

Trp Val Arg Gln Ala Pro Gly Lys Gly Leu Glu Trp Val Ser
1               5                   10

<210> SEQ ID NO 548
<211> LENGTH: 32
<212> TYPE: PRT
<213> ORGANISM: Homo sapiens

<400> SEQUENCE: 548

Arg Leu Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 549
<211> LENGTH: 11
<212> TYPE: PRT
<213> ORGANISM: Homo sapiens

<400> SEQUENCE: 549

Trp Gly Arg Gly Thr Leu Val Thr Val Ser Ser
1               5                   10

<210> SEQ ID NO 550
<211> LENGTH: 324
<212> TYPE: DNA
<213> ORGANISM: Homo sapiens

<400> SEQUENCE: 550
tcctatgagc tggctcagcc accctcggtg tcagtgtccc caggacagac ggccaggatc      60
acctgctctg gagatgcatt gccaaggcaa tatgcttact ggtaccagca gaagccaggc     120
caggccsctc tactggtgat atataaagac agtgagaggc cctcagggat ccctgagcga     180
ttctctggct ccggctcagg gacaacagtc acgttgacca tcagtggagt ccaggcagaa     240
gacgaggctg actattactg tcaatcagca gacagcagtg gtacctatgt ggtattcggc     300
ggagggacca aggtcaccgt ccta                                            324

<210> SEQ ID NO 551
<211> LENGTH: 108
<212> TYPE: PRT
<213> ORGANISM: Homo sapiens

<400> SEQUENCE: 551

Ser Tyr Glu Leu Ala Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Leu Leu Val Ile Tyr
        35                  40                  45

Lys Asp Ser Glu Arg Pro Ser Gly Ile Pro Glu Arg Phe Ser Gly Ser
    50                  55                  60

Gly Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Val Val Phe Gly Gly Gly Thr Lys Val Thr Val Leu
            100                 105

<210> SEQ ID NO 552
<211> LENGTH: 11
<212> TYPE: PRT
<213> ORGANISM: Homo sapiens

<400> SEQUENCE: 552

Ser Gly Asp Ala Leu Pro Arg Gln Tyr Ala Tyr
1               5                   10

<210> SEQ ID NO 553
<211> LENGTH: 7
<212> TYPE: PRT
<213> ORGANISM: Homo sapiens

<400> SEQUENCE: 553

Lys Asp Ser Glu Arg Pro Ser
1               5

<210> SEQ ID NO 554
<211> LENGTH: 11
<212> TYPE: PRT
<213> ORGANISM: Homo sapiens

<400> SEQUENCE: 554

Gln Ser Ala Asp Ser Ser Gly Thr Tyr Val Val
1               5                   10

<210> SEQ ID NO 555
<211> LENGTH: 22
<212> TYPE: PRT
<213> ORGANISM: Homo sapiens

<400> SEQUENCE: 555

Ser Tyr Glu Leu Ala Gln Pro Pro Ser Val Ser Val Ser Pro Gly Gln
1               5                   10                  15

Thr Ala Arg Ile Thr Cys
            20

<210> SEQ ID NO 556
<211> LENGTH: 15
<212> TYPE: PRT
<213> ORGANISM: Homo sapiens

<400> SEQUENCE: 556

Trp Tyr Gln Gln Lys Pro Gly Gln Ala Pro Leu Leu Val Ile Tyr
1               5                   10                  15

<210> SEQ ID NO 557
<211> LENGTH: 32
<212> TYPE: PRT
<213> ORGANISM: Homo sapiens

<400> SEQUENCE: 557

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 558
<211> LENGTH: 10
<212> TYPE: PRT
<213> ORGANISM: Homo sapiens

<400> SEQUENCE: 558

Phe Gly Gly Gly Thr Lys Val Thr Val Leu
1               5                   10

<210> SEQ ID NO 559
<211> LENGTH: 375
<212> TYPE: DNA
<213> ORGANISM: Homo sapiens

<400> SEQUENCE: 559
gaggtgcggc tgttggagtc tgggggaggc ttggtacagc ctggggggtc cctgagactc      60
tcctgtgcag cctctggatt cacctttagc agctttgcca tgagctgggt ccgccaggct     120

```
ccagggaagg ggctggagtg ggtctcagct attagtggta gtggtggtag cacatactac    180
gcagactccg tgaagggccg gttcaccatc tctagagaca attccaagaa cacgctgtat    240
ctgcaaatga acagcctgag agccgaggac acggccgtgt attactgtgc gagagatagg    300 gattttttgga gtacttattc gggtccaact gcttttgatc tctggggcag aggcaccctg    360
gtcaccgtct cgagt                                                     375
```

<210> SEQ ID NO 560
<211> LENGTH: 125
<212> TYPE: PRT
<213> ORGANISM: Homo sapiens

<400> SEQUENCE: 560

```
Glu Val Arg Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Asp Phe Trp Ser Thr Tyr Ser Gly Pro Thr Ala Phe
            100                 105                 110

Asp Leu Trp Gly Arg Gly Thr Leu Val Thr Val Ser Ser
        115                 120                 125
```

<210> SEQ ID NO 561
<211> LENGTH: 5
<212> TYPE: PRT
<213> ORGANISM: Homo sapiens

<400> SEQUENCE: 561

```
Ser Phe Ala Met Ser
1               5
```

<210> SEQ ID NO 562
<211> LENGTH: 17
<212> TYPE: PRT
<213> ORGANISM: Homo sapiens

<400> SEQUENCE: 562

```
Ala Ile Ser Gly Ser Gly Gly Ser Thr Tyr Tyr Ala Asp Ser Val Lys
1               5                   10                  15

Gly
```

<210> SEQ ID NO 563
<211> LENGTH: 16
<212> TYPE: PRT
<213> ORGANISM: Homo sapiens

<400> SEQUENCE: 563

```
Asp Arg Asp Phe Trp Ser Thr Tyr Ser Gly Pro Thr Ala Phe Asp Leu
1               5                   10                  15
```

<210> SEQ ID NO 564

```
<211> LENGTH: 30
<212> TYPE: PRT
<213> ORGANISM: Homo sapiens

<400> SEQUENCE: 564

Glu Val Arg Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 565
<211> LENGTH: 14
<212> TYPE: PRT
<213> ORGANISM: Homo sapiens

<400> SEQUENCE: 565

Trp Val Arg Gln Ala Pro Gly Lys Gly Leu Glu Trp Val Ser
1               5                   10

<210> SEQ ID NO 566
<211> LENGTH: 32
<212> TYPE: PRT
<213> ORGANISM: Homo sapiens

<400> SEQUENCE: 566

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 567
<211> LENGTH: 11
<212> TYPE: PRT
<213> ORGANISM: Homo sapiens

<400> SEQUENCE: 567

Trp Gly Arg Gly Thr Leu Val Thr Val Ser Ser
1               5                   10

<210> SEQ ID NO 568
<211> LENGTH: 324
<212> TYPE: DNA
<213> ORGANISM: Homo sapiens

<400> SEQUENCE: 568
tcctatgagc tggctcagcc accctcggtg tcagtgtccc caggacagac ggccaggatc    60
acctgctctg gtgatgcatt gccaaggcaa tacgcttact ggtaccagca gaagccaggc   120
caggcccctc tactggtgat atataaagac agtgagaggc cctcagggat cccagagcga   180
ttctctggct ccggctcagg gacaacagtc acgttgacca tcagtggagt ccaggcagaa   240
gacgaggctg actattactg tcaatcagca gacagcagtg gtacctatgt ggtattcggc   300
ggagggacca aggtcaccgt ccta                                          324

<210> SEQ ID NO 569
<211> LENGTH: 108
<212> TYPE: PRT
<213> ORGANISM: Homo sapiens

<400> SEQUENCE: 569

Ser Tyr Glu Leu Ala Gln Pro Pro Ser Val Ser Val Pro Gly Gln
1               5                   10                  15
```

```
Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Leu Leu Val Ile Tyr
        35                  40                  45

Lys Asp Ser Glu Arg Pro Ser Gly Ile Pro Glu Arg Phe Ser Gly Ser
    50                  55                  60

Gly Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Val Val Phe Gly Gly Gly Thr Lys Val Thr Val Leu
            100                 105
```

<210> SEQ ID NO 570
<211> LENGTH: 11
<212> TYPE: PRT
<213> ORGANISM: Homo sapiens

<400> SEQUENCE: 570

```
Ser Gly Asp Ala Leu Pro Arg Gln Tyr Ala Tyr
1               5                   10
```

<210> SEQ ID NO 571
<211> LENGTH: 7
<212> TYPE: PRT
<213> ORGANISM: Homo sapiens

<400> SEQUENCE: 571

```
Lys Asp Ser Glu Arg Pro Ser
1               5
```

<210> SEQ ID NO 572
<211> LENGTH: 11
<212> TYPE: PRT
<213> ORGANISM: Homo sapiens

<400> SEQUENCE: 572

```
Gln Ser Ala Asp Ser Ser Gly Thr Tyr Val Val
1               5                   10
```

<210> SEQ ID NO 573
<211> LENGTH: 22
<212> TYPE: PRT
<213> ORGANISM: Homo sapiens

<400> SEQUENCE: 573

```
Ser Tyr Glu Leu Ala Gln Pro Pro Ser Val Ser Val Ser Pro Gly Gln
1               5                   10                  15

Thr Ala Arg Ile Thr Cys
            20
```

<210> SEQ ID NO 574
<211> LENGTH: 15
<212> TYPE: PRT
<213> ORGANISM: Homo sapiens

<400> SEQUENCE: 574

```
Trp Tyr Gln Gln Lys Pro Gly Gln Ala Pro Leu Leu Val Ile Tyr
1               5                   10                  15
```

<210> SEQ ID NO 575
<211> LENGTH: 32

<212> TYPE: PRT
<213> ORGANISM: Homo sapiens

<400> SEQUENCE: 575

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 576
<211> LENGTH: 10
<212> TYPE: PRT
<213> ORGANISM: Homo sapiens

<400> SEQUENCE: 576

Phe Gly Gly Gly Thr Lys Val Thr Val Leu
1               5                   10

<210> SEQ ID NO 577
<211> LENGTH: 375
<212> TYPE: DNA
<213> ORGANISM: Homo sapiens

<400> SEQUENCE: 577
gaggtgcagc tgatggagtc tgggggaggc ttggtacagc ctggggggtc cctgaggctc      60
tcctgtgcag cctctggatt cacctttagc agctttgcca tgagctgggt ccgccaggct     120
ccagggaagg ggctggagtg ggtctcagct attagtggta gtggtggtag cacatactac     180
gcagactccg cgaagggccg gttcaccatc tccagagaca attccaagaa cacgctgtat     240
ctgcaaatga acagcctgag agccgaggac acggccgtgt attactgtgc gagagatagg     300
gattttggga gtacttattc gggtccaact gcttttgatc tctggggcag aggcaccctg     360
gtcaccgtct cctca                                                      375

<210> SEQ ID NO 578
<211> LENGTH: 125
<212> TYPE: PRT
<213> ORGANISM: Homo sapiens

<400> SEQUENCE: 578

Glu Val Gln Leu Met Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Asp Phe Trp Ser Thr Tyr Ser Gly Pro Thr Ala Phe
            100                 105                 110

Asp Leu Trp Gly Arg Gly Thr Leu Val Thr Val Ser Ser
        115                 120                 125

<210> SEQ ID NO 579
<211> LENGTH: 5

```
<212> TYPE: PRT
<213> ORGANISM: Homo sapiens

<400> SEQUENCE: 579

Ser Phe Ala Met Ser
1               5

<210> SEQ ID NO 580
<211> LENGTH: 17
<212> TYPE: PRT
<213> ORGANISM: Homo sapiens

<400> SEQUENCE: 580

Ala Ile Ser Gly Ser Gly Gly Ser Thr Tyr Tyr Ala Asp Ser Ala Lys
1               5                   10                  15

Gly

<210> SEQ ID NO 581
<211> LENGTH: 16
<212> TYPE: PRT
<213> ORGANISM: Homo sapiens

<400> SEQUENCE: 581

Asp Arg Asp Phe Trp Ser Thr Tyr Ser Gly Pro Thr Ala Phe Asp Leu
1               5                   10                  15

<210> SEQ ID NO 582
<211> LENGTH: 30
<212> TYPE: PRT
<213> ORGANISM: Homo sapiens

<400> SEQUENCE: 582

Glu Val Gln Leu Met Glu Ser Gly Gly Gly Leu Val Gln Pro Gly Gly
1               5                   10                  15

Ser Leu Arg Leu Ser Cys Ala Ala Ser Gly Phe Thr Phe Ser
                20                  25                  30

<210> SEQ ID NO 583
<211> LENGTH: 14
<212> TYPE: PRT
<213> ORGANISM: Homo sapiens

<400> SEQUENCE: 583

Trp Val Arg Gln Ala Pro Gly Lys Gly Leu Glu Trp Val Ser
1               5                   10

<210> SEQ ID NO 584
<211> LENGTH: 32
<212> TYPE: PRT
<213> ORGANISM: Homo sapiens

<400> SEQUENCE: 584

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
                20                  25                  30

<210> SEQ ID NO 585
<211> LENGTH: 11
<212> TYPE: PRT
<213> ORGANISM: Homo sapiens

<400> SEQUENCE: 585
```

Trp Gly Arg Gly Thr Leu Val Thr Val Ser Ser
1               5                   10

<210> SEQ ID NO 586
<211> LENGTH: 324
<212> TYPE: DNA
<213> ORGANISM: Homo sapiens

<400> SEQUENCE: 586

| tcctatgagc tggctcagcc accctcggtg tcagtgtccc caggacagac ggccaggatc | 60 |
| acctgctctg gagatgcatt gccaaggcaa tatgcttact ggtaccagca gaagccaggc | 120 |
| caggcccctc taccggtgat atataaagac agtgagaggc cctcagggat ccctgagcga | 180 |
| ttctctggct ccggctcagg gacaacagtc acgttgacca tcagtggagt ccaggcagaa | 240 |
| gacgaggctg actattactg tcaatcagca gacagcagtg gtacctatgt ggtattcggc | 300 |
| ggagggacca aggtcaccgt ccta | 324 |

<210> SEQ ID NO 587
<211> LENGTH: 108
<212> TYPE: PRT
<213> ORGANISM: Homo sapiens

<400> SEQUENCE: 587

Ser Tyr Glu Leu Ala Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Leu Pro Val Ile Tyr
        35                  40                  45

Lys Asp Ser Glu Arg Pro Ser Gly Ile Pro Glu Arg Phe Ser Gly Ser
    50                  55                  60

Gly Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Val Val Phe Gly Gly Gly Thr Lys Val Thr Val Leu
            100                 105

<210> SEQ ID NO 588
<211> LENGTH: 11
<212> TYPE: PRT
<213> ORGANISM: Homo sapiens

<400> SEQUENCE: 588

Ser Gly Asp Ala Leu Pro Arg Gln Tyr Ala Tyr
1               5                   10

<210> SEQ ID NO 589
<211> LENGTH: 7
<212> TYPE: PRT
<213> ORGANISM: Homo sapiens

<400> SEQUENCE: 589

Lys Asp Ser Glu Arg Pro Ser
1               5

<210> SEQ ID NO 590
<211> LENGTH: 11
<212> TYPE: PRT
<213> ORGANISM: Homo sapiens -continued

<400> SEQUENCE: 590

Gln Ser Ala Asp Ser Ser Gly Thr Tyr Val Val
1               5                   10

<210> SEQ ID NO 591
<211> LENGTH: 22
<212> TYPE: PRT
<213> ORGANISM: Homo sapiens

<400> SEQUENCE: 591

Ser Tyr Glu Leu Ala Gln Pro Pro Ser Val Ser Val Ser Pro Gly Gln
1               5                   10                  15

Thr Ala Arg Ile Thr Cys
            20

<210> SEQ ID NO 592
<211> LENGTH: 15
<212> TYPE: PRT
<213> ORGANISM: Homo sapiens

<400> SEQUENCE: 592

Trp Tyr Gln Gln Lys Pro Gly Gln Ala Pro Leu Pro Val Ile Tyr
1               5                   10                  15

<210> SEQ ID NO 593
<211> LENGTH: 32
<212> TYPE: PRT
<213> ORGANISM: Homo sapiens

<400> SEQUENCE: 593

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 594
<211> LENGTH: 10
<212> TYPE: PRT
<213> ORGANISM: Homo sapiens

<400> SEQUENCE: 594

Phe Gly Gly Gly Thr Lys Val Thr Val Leu
1               5                   10

<210> SEQ ID NO 595
<211> LENGTH: 375
<212> TYPE: DNA
<213> ORGANISM: Homo sapiens

<400> SEQUENCE: 595
gaggtgcagc tgttggagtc tgggggaggc ttggtacagc ctggggggcc cctgagactc      60
tcctgtgcag cctctggatt caccttttagc agctatgcca tgagctgggt ccgccaggct    120
ccagggaagg ggctggagtg ggtctcggct attagtggta gtggtggtag cacatactac    180
gcagactccg tgaagggccg gttcaccatc tccagagaca attccaagaa cacgctgtat    240
ctgcaaatga acagcctgag agccgaggac acggccgcgt attactgtgc gagagattgg    300 gattttttgga gtacttattc gggtccaact gcttttgatc tctggggcag aggcaccctg    360
gtcaccgtct cgagt                                                       375

```
<210> SEQ ID NO 596
<211> LENGTH: 125
<212> TYPE: PRT
<213> ORGANISM: Homo sapiens

<400> SEQUENCE: 596

Glu Val Gln Leu Leu Glu Ser Gly Gly Gly Leu Val Gln Pro Gly Gly
1               5                   10                  15

Pro Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ala Tyr Tyr Cys
                85                  90                  95

Ala Arg Asp Trp Asp Phe Trp Ser Thr Tyr Ser Gly Pro Thr Ala Phe
            100                 105                 110

Asp Leu Trp Gly Arg Gly Thr Leu Val Thr Val Ser Ser
        115                 120                 125

<210> SEQ ID NO 597
<211> LENGTH: 5
<212> TYPE: PRT
<213> ORGANISM: Homo sapiens

<400> SEQUENCE: 597

Ser Tyr Ala Met Ser
1               5

<210> SEQ ID NO 598
<211> LENGTH: 17
<212> TYPE: PRT
<213> ORGANISM: Homo sapiens

<400> SEQUENCE: 598

Ala Ile Ser Gly Ser Gly Gly Ser Thr Tyr Tyr Ala Asp Ser Val Lys
1               5                   10                  15

Gly

<210> SEQ ID NO 599
<211> LENGTH: 16
<212> TYPE: PRT
<213> ORGANISM: Homo sapiens

<400> SEQUENCE: 599

Asp Trp Asp Phe Trp Ser Thr Tyr Ser Gly Pro Thr Ala Phe Asp Leu
1               5                   10                  15

<210> SEQ ID NO 600
<211> LENGTH: 30
<212> TYPE: PRT
<213> ORGANISM: Homo sapiens

<400> SEQUENCE: 600

Glu Val Gln Leu Leu Glu Ser Gly Gly Gly Leu Val Gln Pro Gly Gly
1               5                   10                  15

Pro Leu Arg Leu Ser Cys Ala Ala Ser Gly Phe Thr Phe Ser
            20                  25                  30
```

<210> SEQ ID NO 601
<211> LENGTH: 14
<212> TYPE: PRT
<213> ORGANISM: Homo sapiens

<400> SEQUENCE: 601

Trp Val Arg Gln Ala Pro Gly Lys Gly Leu Glu Trp Val Ser
1               5                   10

<210> SEQ ID NO 602
<211> LENGTH: 32
<212> TYPE: PRT
<213> ORGANISM: Homo sapiens

<400> SEQUENCE: 602

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Ala Tyr Tyr Cys Ala Arg
            20                  25                  30

<210> SEQ ID NO 603
<211> LENGTH: 11
<212> TYPE: PRT
<213> ORGANISM: Homo sapiens

<400> SEQUENCE: 603

Trp Gly Arg Gly Thr Leu Val Thr Val Ser Ser
1               5                   10

<210> SEQ ID NO 604
<211> LENGTH: 324
<212> TYPE: DNA
<213> ORGANISM: Homo sapiens

<400> SEQUENCE: 604
tcctatgagc tggctcagcc accctcggtg tcagtgtccc caggacagac ggccaggatc      60
acctgctctg gagatgcatt gccaaggcaa tatgcttact ggtaccagca gaagccaggc     120 caggccccc tactggtgat atataaagac agtgagaggc cctcagggat ccctgagcga     180
ttctctggct ccggctcagg gacaacagtc acgttgacca tcagtggagt ccaggcagaa     240
gacgaggctg actattactg tcaatcagca gacagcagtg gtacctatgt ggtattcggc     300
ggagggacca aggtcaccgt ccta                                            324

<210> SEQ ID NO 605
<211> LENGTH: 108
<212> TYPE: PRT
<213> ORGANISM: Homo sapiens

<400> SEQUENCE: 605

Ser Tyr Glu Leu Ala Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Leu Leu Val Ile Tyr
        35                  40                  45

Lys Asp Ser Glu Arg Pro Ser Gly Ile Pro Glu Arg Phe Ser Gly Ser
    50                  55                  60

Gly Ser Gly Thr Thr Val Thr Leu Thr Ile Ser Gly Val Gln Ala Glu
65                  70                  75                  80

```
Asp Glu Ala Asp Tyr Tyr Cys Gln Ser Ala Asp Ser Ser Gly Thr Tyr
                85                  90                  95

Val Val Phe Gly Gly Gly Thr Lys Val Thr Val Leu
            100                 105

<210> SEQ ID NO 606
<211> LENGTH: 11
<212> TYPE: PRT
<213> ORGANISM: Homo sapiens

<400> SEQUENCE: 606

Ser Gly Asp Ala Leu Pro Arg Gln Tyr Ala Tyr
1               5                   10

<210> SEQ ID NO 607
<211> LENGTH: 7
<212> TYPE: PRT
<213> ORGANISM: Homo sapiens

<400> SEQUENCE: 607

Lys Asp Ser Glu Arg Pro Ser
1               5

<210> SEQ ID NO 608
<211> LENGTH: 11
<212> TYPE: PRT
<213> ORGANISM: Homo sapiens

<400> SEQUENCE: 608

Gln Ser Ala Asp Ser Ser Gly Thr Tyr Val Val
1               5                   10

<210> SEQ ID NO 609
<211> LENGTH: 22
<212> TYPE: PRT
<213> ORGANISM: Homo sapiens

<400> SEQUENCE: 609

Ser Tyr Glu Leu Ala Gln Pro Pro Ser Val Ser Val Ser Pro Gly Gln
1               5                   10                  15

Thr Ala Arg Ile Thr Cys
            20

<210> SEQ ID NO 610
<211> LENGTH: 15
<212> TYPE: PRT
<213> ORGANISM: Homo sapiens

<400> SEQUENCE: 610

Trp Tyr Gln Gln Lys Pro Gly Gln Ala Pro Leu Leu Val Ile Tyr
1               5                   10                  15

<210> SEQ ID NO 611
<211> LENGTH: 32
<212> TYPE: PRT
<213> ORGANISM: Homo sapiens

<400> SEQUENCE: 611

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30
```

<210> SEQ ID NO 612
<211> LENGTH: 10
<212> TYPE: PRT
<213> ORGANISM: Homo sapiens

<400> SEQUENCE: 612

Phe Gly Gly Gly Thr Lys Val Thr Val Leu
1               5                   10

<210> SEQ ID NO 613
<211> LENGTH: 375
<212> TYPE: DNA
<213> ORGANISM: Homo sapiens

<400> SEQUENCE: 613

```
gaggtgcagc tgttggagtc tgggggaggc ttggtacagc ctgggggtc cctgagactc      60 tcctgtgcag cctctggatt caccttagc agctttgcca tgagctgggt ccgccaggct     120
ccagggaagg ggctggagtg ggtctcagct attagtggta gtggtagtag cacatactac    180
gcagactccg tgaagggccg gttcgccatc tccagagaca attccaagaa cacgctgtat    240
ctgcaaatga acagcctgag agccgaggac acggccgtgt attactgtgc gagagatagg    300
gattttggga gtacttattc gggtccaact gcttttgatc tctggggcag aggcaccctg    360
gtcaccgtct cgagt                                                     375
```

<210> SEQ ID NO 614
<211> LENGTH: 125
<212> TYPE: PRT
<213> ORGANISM: Homo sapiens

<400> SEQUENCE: 614

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Ser Thr Tyr Tyr Ala Asp Ser Val
    50                  55                  60

Lys Gly Arg Phe Ala Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Asp Phe Trp Ser Thr Tyr Ser Gly Pro Thr Ala Phe
            100                 105                 110

Asp Leu Trp Gly Arg Gly Thr Leu Val Thr Val Ser Ser
        115                 120                 125

<210> SEQ ID NO 615
<211> LENGTH: 5
<212> TYPE: PRT
<213> ORGANISM: Homo sapiens

<400> SEQUENCE: 615

Ser Phe Ala Met Ser
1               5

<210> SEQ ID NO 616
<211> LENGTH: 17

```
<212> TYPE: PRT
<213> ORGANISM: Homo sapiens

<400> SEQUENCE: 616

Ala Ile Ser Gly Ser Gly Ser Ser Thr Tyr Tyr Ala Asp Ser Val Lys
1               5                   10                  15

Gly

<210> SEQ ID NO 617
<211> LENGTH: 16
<212> TYPE: PRT
<213> ORGANISM: Homo sapiens

<400> SEQUENCE: 617

Asp Arg Asp Phe Trp Ser Thr Tyr Ser Gly Pro Thr Ala Phe Asp Leu
1               5                   10                  15

<210> SEQ ID NO 618
<211> LENGTH: 30
<212> TYPE: PRT
<213> ORGANISM: Homo sapiens

<400> SEQUENCE: 618

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 619
<211> LENGTH: 14
<212> TYPE: PRT
<213> ORGANISM: Homo sapiens

<400> SEQUENCE: 619

Trp Val Arg Gln Ala Pro Gly Lys Gly Leu Glu Trp Val Ser
1               5                   10

<210> SEQ ID NO 620
<211> LENGTH: 32
<212> TYPE: PRT
<213> ORGANISM: Homo sapiens

<400> SEQUENCE: 620

Arg Phe Ala Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 621
<211> LENGTH: 11
<212> TYPE: PRT
<213> ORGANISM: Homo sapiens

<400> SEQUENCE: 621

Trp Gly Arg Gly Thr Leu Val Thr Val Ser Ser
1               5                   10

<210> SEQ ID NO 622
<211> LENGTH: 324
<212> TYPE: DNA
<213> ORGANISM: Homo sapiens

<400> SEQUENCE: 622
```

```
tcctatgagc tggcccagcc accctcggtg tcagtgtccc caggacagac ggccaggatc     60
acctgctctg gagatgcatt gccaaggcaa tatgcttact ggtaccagca gaagccaggc    120
caggcccctc tactggtgat atataaagac agtgagaggc cctcagggat ccctgagcga    180
ttctctggct ccggctcagg gacaacagtc acgttgacca tcagtggagt ccaggcagaa    240
gacgaggctg actattactg tcaatcagcg gacagcagtg gtacctatgc ggtattcggc    300
ggagggacca aggtcaccgt ccta                                           324
```

<210> SEQ ID NO 623
<211> LENGTH: 108
<212> TYPE: PRT
<213> ORGANISM: Homo sapiens

<400> SEQUENCE: 623

Ser Tyr Glu Leu Ala Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
                20                  25                  30

Tyr Trp Tyr Gln Gln Lys Pro Gly Gln Ala Pro Leu Leu Val Ile Tyr
            35                  40                  45

Lys Asp Ser Glu Arg Pro Ser Gly Ile Pro Glu Arg Phe Ser Gly Ser
        50                  55                  60

Gly Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Ala Val Phe Gly Gly Gly Thr Lys Val Thr Val Leu
            100                 105

<210> SEQ ID NO 624
<211> LENGTH: 11
<212> TYPE: PRT
<213> ORGANISM: Homo sapiens

<400> SEQUENCE: 624

Ser Gly Asp Ala Leu Pro Arg Gln Tyr Ala Tyr
1               5                   10

<210> SEQ ID NO 625
<211> LENGTH: 7
<212> TYPE: PRT
<213> ORGANISM: Homo sapiens

<400> SEQUENCE: 625

Lys Asp Ser Glu Arg Pro Ser
1               5

<210> SEQ ID NO 626
<211> LENGTH: 11
<212> TYPE: PRT
<213> ORGANISM: Homo sapiens

<400> SEQUENCE: 626

Gln Ser Ala Asp Ser Ser Gly Thr Tyr Ala Val
1               5                   10

<210> SEQ ID NO 627
<211> LENGTH: 22
<212> TYPE: PRT
<213> ORGANISM: Homo sapiens

<400> SEQUENCE: 627

Ser Tyr Glu Leu Ala Gln Pro Pro Ser Val Ser Val Ser Pro Gly Gln
1               5                   10                  15

Thr Ala Arg Ile Thr Cys
            20

<210> SEQ ID NO 628
<211> LENGTH: 15
<212> TYPE: PRT
<213> ORGANISM: Homo sapiens

<400> SEQUENCE: 628

Trp Tyr Gln Gln Lys Pro Gly Gln Ala Pro Leu Leu Val Ile Tyr
1               5                   10                  15

<210> SEQ ID NO 629
<211> LENGTH: 32
<212> TYPE: PRT
<213> ORGANISM: Homo sapiens

<400> SEQUENCE: 629

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 630
<211> LENGTH: 10
<212> TYPE: PRT
<213> ORGANISM: Homo sapiens

<400> SEQUENCE: 630

Phe Gly Gly Gly Thr Lys Val Thr Val Leu
1               5                   10

<210> SEQ ID NO 631
<211> LENGTH: 375
<212> TYPE: DNA
<213> ORGANISM: Homo sapiens

<400> SEQUENCE: 631
gaggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg gctggagtg gtctcagct attagtggta gtggtggtag cacatactac      180
gcagactccg tgaagggccg gttcgccatc tccagagaca attccaagaa cacgctgtat    240
ctgcaaatga acagcctgag agccgaggac acggccgtgt attactgttc gcggcagttc    300
gactactgga gtacttattc gggtccaact gcttttgatc tctggggcag aggcaccctg    360
gtcaccgtct cgagt                                                     375

<210> SEQ ID NO 632
<211> LENGTH: 125
<212> TYPE: PRT
<213> ORGANISM: Homo sapiens

<400> SEQUENCE: 632

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr

```
            20                  25                  30
Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Ala Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Arg Gln Phe Asp Tyr Trp Ser Thr Tyr Ser Gly Pro Thr Ala Phe
            100                 105                 110

Asp Leu Trp Gly Arg Gly Thr Leu Val Thr Val Ser Ser
            115                 120                 125

<210> SEQ ID NO 633
<211> LENGTH: 5
<212> TYPE: PRT
<213> ORGANISM: Homo sapiens

<400> SEQUENCE: 633

Ser Tyr Ala Met Ser
1               5

<210> SEQ ID NO 634
<211> LENGTH: 17
<212> TYPE: PRT
<213> ORGANISM: Homo sapiens

<400> SEQUENCE: 634

Ala Ile Ser Gly Ser Gly Gly Ser Thr Tyr Tyr Ala Asp Ser Val Lys
1               5                   10                  15

Gly

<210> SEQ ID NO 635
<211> LENGTH: 16
<212> TYPE: PRT
<213> ORGANISM: Homo sapiens

<400> SEQUENCE: 635

Gln Phe Asp Tyr Trp Ser Thr Tyr Ser Gly Pro Thr Ala Phe Asp Leu
1               5                   10                  15

<210> SEQ ID NO 636
<211> LENGTH: 30
<212> TYPE: PRT
<213> ORGANISM: Homo sapiens

<400> SEQUENCE: 636

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 637
<211> LENGTH: 14
<212> TYPE: PRT
<213> ORGANISM: Homo sapiens

<400> SEQUENCE: 637

Trp Val Arg Gln Ala Pro Gly Lys Gly Leu Glu Trp Val Ser
1               5                   10
```

<210> SEQ ID NO 638
<211> LENGTH: 32
<212> TYPE: PRT
<213> ORGANISM: Homo sapiens

<400> SEQUENCE: 638

Arg Phe Ala Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ser Arg
            20                  25                  30

<210> SEQ ID NO 639
<211> LENGTH: 11
<212> TYPE: PRT
<213> ORGANISM: Homo sapiens

<400> SEQUENCE: 639

Trp Gly Arg Gly Thr Leu Val Thr Val Ser Ser
1               5                   10

<210> SEQ ID NO 640
<211> LENGTH: 324
<212> TYPE: DNA
<213> ORGANISM: Homo sapiens

<400> SEQUENCE: 640
tcctatgagc tggctcagcc accctcggtg tcagtgtccc caggacagac ggccaggatc        60
acctgctctg gagatgcatt gccaaggcaa tatgcttact ggtaccagca gaagccaggc       120
caggcccctc tactggtgat atataaagac agtttcaggc cctcagggat ccctgagcga       180
ttctctggct ccggctcagg gacaacagtc acgttgacca tcagtggagt ccaggcagaa       240
gacgaggctg actattactg tcaatcagca gacagcagtg gtacctatgc ggtattcggc       300
ggagggacca aggtcaccgt ccta                                              324

<210> SEQ ID NO 641
<211> LENGTH: 108
<212> TYPE: PRT
<213> ORGANISM: Homo sapiens

<400> SEQUENCE: 641

Ser Tyr Glu Leu Ala Gln Pro Pro Ser Val Ser Val Ser Pro Gly Gln
1               5                   10                  15
Thr Ala Arg Ile Thr Cys Ser Gly Asp Ala Leu Pro Arg Gln Tyr Ala
            20                  25                  30
Tyr Trp Tyr Gln Gln Lys Pro Gly Gln Ala Pro Leu Leu Val Ile Tyr
        35                  40                  45
Lys Asp Ser Phe Arg Pro Ser Gly Ile Pro Glu Arg Phe Ser Gly Ser
    50                  55                  60
Gly Ser Gly Thr Thr Val Thr Leu Thr Ile Ser Gly Val Gln Ala Glu
65                  70                  75                  80
Asp Glu Ala Asp Tyr Tyr Cys Gln Ser Ala Asp Ser Ser Gly Thr Tyr
                85                  90                  95
Ala Val Phe Gly Gly Gly Thr Lys Val Thr Val Leu
            100                 105

<210> SEQ ID NO 642
<211> LENGTH: 11
<212> TYPE: PRT

```
<213> ORGANISM: Homo sapiens

<400> SEQUENCE: 642

Ser Gly Asp Ala Leu Pro Arg Gln Tyr Ala Tyr
1               5                   10

<210> SEQ ID NO 643
<211> LENGTH: 7
<212> TYPE: PRT
<213> ORGANISM: Homo sapiens

<400> SEQUENCE: 643

Lys Asp Ser Phe Arg Pro Ser
1               5

<210> SEQ ID NO 644
<211> LENGTH: 11
<212> TYPE: PRT
<213> ORGANISM: Homo sapiens

<400> SEQUENCE: 644

Gln Ser Ala Asp Ser Ser Gly Thr Tyr Ala Val
1               5                   10

<210> SEQ ID NO 645
<211> LENGTH: 22
<212> TYPE: PRT
<213> ORGANISM: Homo sapiens

<400> SEQUENCE: 645

Ser Tyr Glu Leu Ala Gln Pro Pro Ser Val Ser Val Ser Pro Gly Gln
1               5                   10                  15

Thr Ala Arg Ile Thr Cys
            20

<210> SEQ ID NO 646
<211> LENGTH: 15
<212> TYPE: PRT
<213> ORGANISM: Homo sapiens

<400> SEQUENCE: 646

Trp Tyr Gln Gln Lys Pro Gly Gln Ala Pro Leu Leu Val Ile Tyr
1               5                   10                  15

<210> SEQ ID NO 647
<211> LENGTH: 32
<212> TYPE: PRT
<213> ORGANISM: Homo sapiens

<400> SEQUENCE: 647

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 648
<211> LENGTH: 10
<212> TYPE: PRT
<213> ORGANISM: Homo sapiens

<400> SEQUENCE: 648

Phe Gly Gly Gly Thr Lys Val Thr Val Leu
1               5                   10
```

<210> SEQ ID NO 649
<211> LENGTH: 375
<212> TYPE: DNA
<213> ORGANISM: Homo sapiens

<400> SEQUENCE: 649

```
gaggtgcagc tgttggagtc tgggggaggc ttggtacagc ctgggggtc cctgagactc      60
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcgccatc tccagagaca attccaagaa cacgctgtat    240
ctgcaaatga acagcctgag agccgaggac acggccgtgt attactgttc gcggcagttc    300
gactactgga gtacttattc gggtccaact gcttttgatc tctggggcag aggcaccctg    360
gtcaccgtct cgagt                                                      375
```

<210> SEQ ID NO 650
<211> LENGTH: 125
<212> TYPE: PRT
<213> ORGANISM: Homo sapiens

<400> SEQUENCE: 650

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Ala Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ser Arg Gln Phe Asp Tyr Trp Ser Thr Tyr Ser Gly Pro Thr Ala Phe
            100                 105                 110
Asp Leu Trp Gly Arg Gly Thr Leu Val Thr Val Ser Ser
        115                 120                 125
```

<210> SEQ ID NO 651
<211> LENGTH: 5
<212> TYPE: PRT
<213> ORGANISM: Homo sapiens

<400> SEQUENCE: 651

```
Ser Tyr Ala Met Ser
1               5
```

<210> SEQ ID NO 652
<211> LENGTH: 17
<212> TYPE: PRT
<213> ORGANISM: Homo sapiens

<400> SEQUENCE: 652

```
Ala Ile Ser Gly Ser Gly Gly Ser Thr Tyr Tyr Ala Asp Ser Val Lys
1               5                   10                  15
Gly
```

```
<210> SEQ ID NO 653
<211> LENGTH: 16
<212> TYPE: PRT
<213> ORGANISM: Homo sapiens

<400> SEQUENCE: 653

Gln Phe Asp Tyr Trp Ser Thr Tyr Ser Gly Pro Thr Ala Phe Asp Leu
1               5                   10                  15

<210> SEQ ID NO 654
<211> LENGTH: 30
<212> TYPE: PRT
<213> ORGANISM: Homo sapiens

<400> SEQUENCE: 654

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 655
<211> LENGTH: 14
<212> TYPE: PRT
<213> ORGANISM: Homo sapiens

<400> SEQUENCE: 655

Trp Val Arg Gln Ala Pro Gly Lys Gly Leu Glu Trp Val Ser
1               5                   10

<210> SEQ ID NO 656
<211> LENGTH: 32
<212> TYPE: PRT
<213> ORGANISM: Homo sapiens

<400> SEQUENCE: 656

Arg Phe Ala Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ser Arg
            20                  25                  30

<210> SEQ ID NO 657
<211> LENGTH: 11
<212> TYPE: PRT
<213> ORGANISM: Homo sapiens

<400> SEQUENCE: 657

Trp Gly Arg Gly Thr Leu Val Thr Val Ser Ser
1               5                   10

<210> SEQ ID NO 658
<211> LENGTH: 324
<212> TYPE: DNA
<213> ORGANISM: Homo sapiens

<400> SEQUENCE: 658
tcctatgagc tggctcagcc accctcggtg tcagtgtccc caggacagac ggccaggatc     60
acctgctctg gagatgcatt gccaaggcaa tatgcttact ggtaccagca gaagccaggc    120
caggcccctc tactggtgat atataaagac agtgagaggc cctcagggat ccctgagcga    180
ttctctggct ccggctcagg gacaacagtc acgttgacca tcagtggagt ccaggcagaa    240
gacgaggctg actattactg tcaatcagca gacagcagtg gtacctatgt ggtattcggc    300
ggagggacca aggtcaccgt ccta                                           324
```

```
<210> SEQ ID NO 659
<211> LENGTH: 108
<212> TYPE: PRT
<213> ORGANISM: Homo sapiens

<400> SEQUENCE: 659

Ser Tyr Glu Leu Ala Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Leu Leu Val Ile Tyr
        35                  40                  45

Lys Asp Ser Glu Arg Pro Ser Gly Ile Pro Glu Arg Phe Ser Gly Ser
    50                  55                  60

Gly Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Val Val Phe Gly Gly Gly Thr Lys Val Thr Val Leu
            100                 105

<210> SEQ ID NO 660
<211> LENGTH: 11
<212> TYPE: PRT
<213> ORGANISM: Homo sapiens

<400> SEQUENCE: 660

Ser Gly Asp Ala Leu Pro Arg Gln Tyr Ala Tyr
1               5                   10

<210> SEQ ID NO 661
<211> LENGTH: 7
<212> TYPE: PRT
<213> ORGANISM: Homo sapiens

<400> SEQUENCE: 661

Lys Asp Ser Glu Arg Pro Ser
1               5

<210> SEQ ID NO 662
<211> LENGTH: 11
<212> TYPE: PRT
<213> ORGANISM: Homo sapiens

<400> SEQUENCE: 662

Gln Ser Ala Asp Ser Ser Gly Thr Tyr Val Val
1               5                   10

<210> SEQ ID NO 663
<211> LENGTH: 22
<212> TYPE: PRT
<213> ORGANISM: Homo sapiens

<400> SEQUENCE: 663

Ser Tyr Glu Leu Ala Gln Pro Pro Ser Val Ser Val Ser Pro Gly Gln
1               5                   10                  15

Thr Ala Arg Ile Thr Cys
            20

<210> SEQ ID NO 664
```

<211> LENGTH: 15
<212> TYPE: PRT
<213> ORGANISM: Homo sapiens

<400> SEQUENCE: 664

Trp Tyr Gln Gln Lys Pro Gly Gln Ala Pro Leu Leu Val Ile Tyr
1               5                   10                  15

<210> SEQ ID NO 665
<211> LENGTH: 32
<212> TYPE: PRT
<213> ORGANISM: Homo sapiens

<400> SEQUENCE: 665

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 666
<211> LENGTH: 10
<212> TYPE: PRT
<213> ORGANISM: Homo sapiens

<400> SEQUENCE: 666

Phe Gly Gly Gly Thr Lys Val Thr Val Leu
1               5                   10

<210> SEQ ID NO 667
<211> LENGTH: 375
<212> TYPE: DNA
<213> ORGANISM: Homo sapiens

<400> SEQUENCE: 667
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcgccatc tccagagaca attccaagaa cacgctgtat     240
ctgcaaatga acagcctgag agccgaggac acggccgtgt attactgttc gcggcagttc     300
gactactgga gtacttattc gggtccaact gcttttgatc tctggggcag aggcaccctg     360
gtcaccgtct cgagt                                                      375

<210> SEQ ID NO 668
<211> LENGTH: 125
<212> TYPE: PRT
<213> ORGANISM: Homo sapiens

<400> SEQUENCE: 668

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Ala Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ser Arg Gln Phe Asp Tyr Trp Ser Thr Tyr Ser Gly Pro Thr Ala Phe
            100                 105                 110

Asp Leu Trp Gly Arg Gly Thr Leu Val Thr Val Ser Ser
        115                 120                 125

<210> SEQ ID NO 669
<211> LENGTH: 5
<212> TYPE: PRT
<213> ORGANISM: Homo sapiens

<400> SEQUENCE: 669

Ser Tyr Ala Met Ser
1               5

<210> SEQ ID NO 670
<211> LENGTH: 17
<212> TYPE: PRT
<213> ORGANISM: Homo sapiens

<400> SEQUENCE: 670

Ala Ile Ser Gly Ser Gly Gly Ser Thr Tyr Tyr Ala Asp Ser Val Lys
1               5                   10                  15

Gly

<210> SEQ ID NO 671
<211> LENGTH: 16
<212> TYPE: PRT
<213> ORGANISM: Homo sapiens

<400> SEQUENCE: 671

Gln Phe Asp Tyr Trp Ser Thr Tyr Ser Gly Pro Thr Ala Phe Asp Leu
1               5                   10                  15

<210> SEQ ID NO 672
<211> LENGTH: 30
<212> TYPE: PRT
<213> ORGANISM: Homo sapiens

<400> SEQUENCE: 672

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 673
<211> LENGTH: 14
<212> TYPE: PRT
<213> ORGANISM: Homo sapiens

<400> SEQUENCE: 673

Trp Val Arg Gln Ala Pro Gly Lys Gly Leu Glu Trp Val Ser
1               5                   10

<210> SEQ ID NO 674
<211> LENGTH: 32
<212> TYPE: PRT
<213> ORGANISM: Homo sapiens

<400> SEQUENCE: 674

Arg Phe Ala Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ser Arg
            20                  25                  30

<210> SEQ ID NO 675
<211> LENGTH: 11
<212> TYPE: PRT
<213> ORGANISM: Homo sapiens

<400> SEQUENCE: 675

Trp Gly Arg Gly Thr Leu Val Thr Val Ser Ser
1               5                   10

<210> SEQ ID NO 676
<211> LENGTH: 324
<212> TYPE: DNA
<213> ORGANISM: Homo sapiens

<400> SEQUENCE: 676
tcctatgagc tggctcagcc accctcggtg tcagtgtccc caggacagac ggccaggatc      60
acctgctctg gagatgcatt gccaaggcaa tatgcttact ggtaccagca gaagccaggc     120
caggcccctc tactggtgat atataaagac agtgagaggc cctcagggat ccctgagcga     180
ttctctggct ccggctcagg gacaacagtc acgttgacca tcagtggagt ccaggcagaa     240
gacgaggctg actattactg tcaatcagca gacagcagtg gtacctatgc ggtattcggc     300
ggagggacca aggtcaccgt ccta                                            324

<210> SEQ ID NO 677
<211> LENGTH: 108
<212> TYPE: PRT
<213> ORGANISM: Homo sapiens

<400> SEQUENCE: 677

Ser Tyr Glu Leu Ala Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Leu Leu Val Ile Tyr
        35                  40                  45

Lys Asp Ser Glu Arg Pro Ser Gly Ile Pro Glu Arg Phe Ser Gly Ser
    50                  55                  60

Gly Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Ala Val Phe Gly Gly Gly Thr Lys Val Thr Val Leu
            100                 105

<210> SEQ ID NO 678
<211> LENGTH: 11
<212> TYPE: PRT
<213> ORGANISM: Homo sapiens

<400> SEQUENCE: 678

Ser Gly Asp Ala Leu Pro Arg Gln Tyr Ala Tyr
1               5                   10

<210> SEQ ID NO 679
<211> LENGTH: 7
<212> TYPE: PRT

<213> ORGANISM: Homo sapiens

<400> SEQUENCE: 679

Lys Asp Ser Glu Arg Pro Ser
1               5

<210> SEQ ID NO 680
<211> LENGTH: 11
<212> TYPE: PRT
<213> ORGANISM: Homo sapiens

<400> SEQUENCE: 680

Gln Ser Ala Asp Ser Ser Gly Thr Tyr Ala Val
1               5                   10

<210> SEQ ID NO 681
<211> LENGTH: 22
<212> TYPE: PRT
<213> ORGANISM: Homo sapiens

<400> SEQUENCE: 681

Ser Tyr Glu Leu Ala Gln Pro Pro Ser Val Ser Val Ser Pro Gly Gln
1               5                   10                  15

Thr Ala Arg Ile Thr Cys
            20

<210> SEQ ID NO 682
<211> LENGTH: 15
<212> TYPE: PRT
<213> ORGANISM: Homo sapiens

<400> SEQUENCE: 682

Trp Tyr Gln Gln Lys Pro Gly Gln Ala Pro Leu Leu Val Ile Tyr
1               5                   10                  15

<210> SEQ ID NO 683
<211> LENGTH: 32
<212> TYPE: PRT
<213> ORGANISM: Homo sapiens

<400> SEQUENCE: 683

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 684
<211> LENGTH: 10
<212> TYPE: PRT
<213> ORGANISM: Homo sapiens

<400> SEQUENCE: 684

Phe Gly Gly Gly Thr Lys Val Thr Val Leu
1               5                   10

<210> SEQ ID NO 685
<211> LENGTH: 375
<212> TYPE: DNA
<213> ORGANISM: Homo sapiens

<400> SEQUENCE: 685
gaggtgcagc tgttggagtc tgggggaggc ttggtacagc ctgggggtc cctgagactc      60 tcctgtgcag cctctggatt caccttagc agctatgcca tgagctgggt ccgccaggct     120

```
ccagggaagg ggctggagtg ggtctcagct attagtggta gtggtagtag cacatactac    180
gcagactccg tgaagggccg gttcaccatc tccagagaca attccaagaa cacgctgtat    240
ctgcaaatga acagcctgag agccgaggac acggccgtgt attactgtgc gagagatagg    300
gattttggga gtacttattc gggtccaact gcttttgatc tctggggcag aggcaccctg    360
gtcaccgtct cgagt                                                    375
```

<210> SEQ ID NO 686
<211> LENGTH: 125
<212> TYPE: PRT
<213> ORGANISM: Homo sapiens

<400> SEQUENCE: 686

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Asp Phe Trp Ser Thr Tyr Ser Gly Pro Thr Ala Phe
            100                 105                 110

Asp Leu Trp Gly Arg Gly Thr Leu Val Thr Val Ser Ser
        115                 120                 125
```

<210> SEQ ID NO 687
<211> LENGTH: 5
<212> TYPE: PRT
<213> ORGANISM: Homo sapiens

<400> SEQUENCE: 687

```
Ser Tyr Ala Met Ser
1               5
```

<210> SEQ ID NO 688
<211> LENGTH: 17
<212> TYPE: PRT
<213> ORGANISM: Homo sapiens

<400> SEQUENCE: 688

```
Ala Ile Ser Gly Ser Gly Ser Ser Thr Tyr Tyr Ala Asp Ser Val Lys
1               5                   10                  15

Gly
```

<210> SEQ ID NO 689
<211> LENGTH: 16
<212> TYPE: PRT
<213> ORGANISM: Homo sapiens

<400> SEQUENCE: 689

```
Asp Arg Asp Phe Trp Ser Thr Tyr Ser Gly Pro Thr Ala Phe Asp Leu
1               5                   10                  15
```

<210> SEQ ID NO 690
<211> LENGTH: 30
<212> TYPE: PRT
<213> ORGANISM: Homo sapiens

<400> SEQUENCE: 690

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser
        20                  25                  30

<210> SEQ ID NO 691
<211> LENGTH: 14
<212> TYPE: PRT
<213> ORGANISM: Homo sapiens

<400> SEQUENCE: 691

Trp Val Arg Gln Ala Pro Gly Lys Gly Leu Glu Trp Val Ser
1               5                   10

<210> SEQ ID NO 692
<211> LENGTH: 32
<212> TYPE: PRT
<213> ORGANISM: Homo sapiens

<400> SEQUENCE: 692

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ala Arg
        20                  25                  30

<210> SEQ ID NO 693
<211> LENGTH: 11
<212> TYPE: PRT
<213> ORGANISM: Homo sapiens

<400> SEQUENCE: 693

Trp Gly Arg Gly Thr Leu Val Thr Val Ser Ser
1               5                   10

<210> SEQ ID NO 694
<211> LENGTH: 324
<212> TYPE: DNA
<213> ORGANISM: Homo sapiens

<400> SEQUENCE: 694
tcctatgagc tggctcagcc accctcggtg tcagtgtccc caggacagac ggccaggatc        60
acctgctctg gagatgcatt gccaaggcaa tatgcttact ggtaccagca gaagccaggc       120
caggcccctc tactggtgat atataaagac agtgagaggc cctcagggat ccctgagcga       180
ttctctggct ccggctcagg gacaacagtc acgttgacca tcagtggagt ccaggcagaa       240
gacgaggctg actattactg tcaatcagca gacagcagtg gtacctatgt ggtattcggc       300
ggagggacca aggtcaccgt ccta                                              324

<210> SEQ ID NO 695
<211> LENGTH: 108
<212> TYPE: PRT
<213> ORGANISM: Homo sapiens

<400> SEQUENCE: 695

Ser Tyr Glu Leu Ala Gln Pro Pro Ser Val Ser Val Pro Gly Gln
1               5                   10                  15

```
Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Leu Leu Val Ile Tyr
            35                  40                  45

Lys Asp Ser Glu Arg Pro Ser Gly Ile Pro Glu Arg Phe Ser Gly Ser
50                  55                  60

Gly Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Val Val Phe Gly Gly Gly Thr Lys Val Thr Val Leu
            100                 105
```

<210> SEQ ID NO 696
<211> LENGTH: 11
<212> TYPE: PRT
<213> ORGANISM: Homo sapiens

<400> SEQUENCE: 696

```
Ser Gly Asp Ala Leu Pro Arg Gln Tyr Ala Tyr
1               5                   10
```

<210> SEQ ID NO 697
<211> LENGTH: 7
<212> TYPE: PRT
<213> ORGANISM: Homo sapiens

<400> SEQUENCE: 697

```
Lys Asp Ser Glu Arg Pro Ser
1               5
```

<210> SEQ ID NO 698
<211> LENGTH: 11
<212> TYPE: PRT
<213> ORGANISM: Homo sapiens

<400> SEQUENCE: 698

```
Gln Ser Ala Asp Ser Ser Gly Thr Tyr Val Val
1               5                   10
```

<210> SEQ ID NO 699
<211> LENGTH: 22
<212> TYPE: PRT
<213> ORGANISM: Homo sapiens

<400> SEQUENCE: 699

```
Ser Tyr Glu Leu Ala Gln Pro Pro Ser Val Ser Val Ser Pro Gly Gln
1               5                   10                  15

Thr Ala Arg Ile Thr Cys
            20
```

<210> SEQ ID NO 700
<211> LENGTH: 15
<212> TYPE: PRT
<213> ORGANISM: Homo sapiens

<400> SEQUENCE: 700

```
Trp Tyr Gln Gln Lys Pro Gly Gln Ala Pro Leu Leu Val Ile Tyr
1               5                   10                  15
```

<210> SEQ ID NO 701

<211> LENGTH: 32
<212> TYPE: PRT
<213> ORGANISM: Homo sapiens

<400> SEQUENCE: 701

```
Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30
```

<210> SEQ ID NO 702
<211> LENGTH: 10
<212> TYPE: PRT
<213> ORGANISM: Homo sapiens

<400> SEQUENCE: 702

```
Phe Gly Gly Gly Thr Lys Val Thr Val Leu
1               5                   10
```

<210> SEQ ID NO 703
<211> LENGTH: 375
<212> TYPE: DNA
<213> ORGANISM: Homo sapiens

<400> SEQUENCE: 703

```
gaggtgcagc tgttggagtc tgggggaggc ttggtacagc ctggggggtc cctgagactc    60
tcctgtgcag cctctggatt cacctttagc agctatgcca tgagctgggt ccgccaggct   120
ccagggaagg gctggagtg gtctcagct attagtggta gtggtggtag cacatactac    180
gcagactccg tgaagggccg gttcgccatc tccagagaca attccaagaa cacgctgtat   240
ctgcaaatga acagcctgag agccgaggac acggccgtgt attactgtgc gagagatagg   300 gattttttgga gtacttattc gggtccaact gcttttgatc tctggggcag aggcaccctg   360
gtcaccgtct cgagt                                                    375
```

<210> SEQ ID NO 704
<211> LENGTH: 125
<212> TYPE: PRT
<213> ORGANISM: Homo sapiens

<400> SEQUENCE: 704

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Ala Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Asp Phe Trp Ser Thr Tyr Ser Gly Pro Thr Ala Phe
            100                 105                 110

Asp Leu Trp Gly Arg Gly Thr Leu Val Thr Val Ser Ser
        115                 120                 125
```

<210> SEQ ID NO 705

```
<211> LENGTH: 5
<212> TYPE: PRT
<213> ORGANISM: Homo sapiens

<400> SEQUENCE: 705

Ser Tyr Ala Met Ser
1               5

<210> SEQ ID NO 706
<211> LENGTH: 17
<212> TYPE: PRT
<213> ORGANISM: Homo sapiens

<400> SEQUENCE: 706

Ala Ile Ser Gly Ser Gly Gly Ser Thr Tyr Tyr Ala Asp Ser Val Lys
1               5                   10                  15

Gly

<210> SEQ ID NO 707
<211> LENGTH: 16
<212> TYPE: PRT
<213> ORGANISM: Homo sapiens

<400> SEQUENCE: 707

Asp Arg Asp Phe Trp Ser Thr Tyr Ser Gly Pro Thr Ala Phe Asp Leu
1               5                   10                  15

<210> SEQ ID NO 708
<211> LENGTH: 30
<212> TYPE: PRT
<213> ORGANISM: Homo sapiens

<400> SEQUENCE: 708

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 709
<211> LENGTH: 14
<212> TYPE: PRT
<213> ORGANISM: Homo sapiens

<400> SEQUENCE: 709

Trp Val Arg Gln Ala Pro Gly Lys Gly Leu Glu Trp Val Ser
1               5                   10

<210> SEQ ID NO 710
<211> LENGTH: 32
<212> TYPE: PRT
<213> ORGANISM: Homo sapiens

<400> SEQUENCE: 710

Arg Phe Ala Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 711
<211> LENGTH: 11
<212> TYPE: PRT
<213> ORGANISM: Homo sapiens

<400> SEQUENCE: 711
```

Trp Gly Arg Gly Thr Leu Val Thr Val Ser Ser
1               5                   10

<210> SEQ ID NO 712
<211> LENGTH: 324
<212> TYPE: DNA
<213> ORGANISM: Homo sapiens

<400> SEQUENCE: 712
tcctatgagc tggctcagcc accctcggtg tcagtgtccc caggacagac ggccaggatc     60
acctgctctg gagatgcatt gccaaggcaa tatgcttact ggtaccagca gaagccaggc    120
caggcccctc tactggtgat atataaagac agtgagaggc cctcagggat ccctgagcga    180
ttctctggct ccggctcagg acaacagtc acgttgacca tcagtggagt ccaggcagaa    240
gacgaggctg actattactg tcaatcagca gacagcagtg gtacctatgt ggtattcggc    300
ggagggacca aggtcaccgt ccta                                           324

<210> SEQ ID NO 713
<211> LENGTH: 108
<212> TYPE: PRT
<213> ORGANISM: Homo sapiens

<400> SEQUENCE: 713

Ser Tyr Glu Leu Ala Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Leu Leu Val Ile Tyr
        35                  40                  45

Lys Asp Ser Glu Arg Pro Ser Gly Ile Pro Glu Arg Phe Ser Gly Ser
    50                  55                  60

Gly Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Val Val Phe Gly Gly Gly Thr Lys Val Thr Val Leu
            100                 105

<210> SEQ ID NO 714
<211> LENGTH: 11
<212> TYPE: PRT
<213> ORGANISM: Homo sapiens

<400> SEQUENCE: 714

Ser Gly Asp Ala Leu Pro Arg Gln Tyr Ala Tyr
1               5                   10

<210> SEQ ID NO 715
<211> LENGTH: 7
<212> TYPE: PRT
<213> ORGANISM: Homo sapiens

<400> SEQUENCE: 715

Lys Asp Ser Glu Arg Pro Ser
1               5

<210> SEQ ID NO 716
<211> LENGTH: 11
<212> TYPE: PRT

<213> ORGANISM: Homo sapiens

<400> SEQUENCE: 716

Gln Ser Ala Asp Ser Ser Gly Thr Tyr Val Val
1               5                   10

<210> SEQ ID NO 717
<211> LENGTH: 22
<212> TYPE: PRT
<213> ORGANISM: Homo sapiens

<400> SEQUENCE: 717

Ser Tyr Glu Leu Ala Gln Pro Pro Ser Val Ser Val Ser Pro Gly Gln
1               5                   10                  15

Thr Ala Arg Ile Thr Cys
            20

<210> SEQ ID NO 718
<211> LENGTH: 15
<212> TYPE: PRT
<213> ORGANISM: Homo sapiens

<400> SEQUENCE: 718

Trp Tyr Gln Gln Lys Pro Gly Gln Ala Pro Leu Leu Val Ile Tyr
1               5                   10                  15

<210> SEQ ID NO 719
<211> LENGTH: 32
<212> TYPE: PRT
<213> ORGANISM: Homo sapiens

<400> SEQUENCE: 719

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 720
<211> LENGTH: 10
<212> TYPE: PRT
<213> ORGANISM: Homo sapiens

<400> SEQUENCE: 720

Phe Gly Gly Gly Thr Lys Val Thr Val Leu
1               5                   10

<210> SEQ ID NO 721
<211> LENGTH: 375
<212> TYPE: DNA
<213> ORGANISM: Homo sapiens

<400> SEQUENCE: 721

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gagagatagg     300 gattttttgga gtacttattc gggtccaact gcttttgatc tctggggcag aggcaccctg     360
gtcaccgtct cgagt                                                       375
```

<210> SEQ ID NO 722
<211> LENGTH: 125
<212> TYPE: PRT
<213> ORGANISM: Homo sapiens

<400> SEQUENCE: 722

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Asp Phe Trp Ser Thr Tyr Ser Gly Pro Thr Ala Phe
            100                 105                 110

Asp Leu Trp Gly Arg Gly Thr Leu Val Thr Val Ser Ser
        115                 120                 125

<210> SEQ ID NO 723
<211> LENGTH: 5
<212> TYPE: PRT
<213> ORGANISM: Homo sapiens

<400> SEQUENCE: 723

Ser Tyr Ala Met Ser
1               5

<210> SEQ ID NO 724
<211> LENGTH: 17
<212> TYPE: PRT
<213> ORGANISM: Homo sapiens

<400> SEQUENCE: 724

Ala Ile Ser Gly Ser Gly Gly Ser Thr Tyr Tyr Ala Asp Ser Val Lys
1               5                   10                  15

Gly

<210> SEQ ID NO 725
<211> LENGTH: 16
<212> TYPE: PRT
<213> ORGANISM: Homo sapiens

<400> SEQUENCE: 725

Asp Arg Asp Phe Trp Ser Thr Tyr Ser Gly Pro Thr Ala Phe Asp Leu
1               5                   10                  15

<210> SEQ ID NO 726
<211> LENGTH: 30
<212> TYPE: PRT
<213> ORGANISM: Homo sapiens

<400> SEQUENCE: 726

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser

<210> SEQ ID NO 727
<211> LENGTH: 14
<212> TYPE: PRT
<213> ORGANISM: Homo sapiens

<400> SEQUENCE: 727

Trp Val Arg Gln Ala Pro Gly Lys Gly Leu Glu Trp Val Ser
1               5                   10

<210> SEQ ID NO 728
<211> LENGTH: 32
<212> TYPE: PRT
<213> ORGANISM: Homo sapiens

<400> SEQUENCE: 728

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 729
<211> LENGTH: 11
<212> TYPE: PRT
<213> ORGANISM: Homo sapiens

<400> SEQUENCE: 729

Trp Gly Arg Gly Thr Leu Val Thr Val Ser Ser
1               5                   10

<210> SEQ ID NO 730
<211> LENGTH: 324
<212> TYPE: DNA
<213> ORGANISM: Homo sapiens

<400> SEQUENCE: 730
tcctatgagc tggctcagcc accctcggtg tcagtgtccc caggacagac ggccaggatc      60
acctgctctg gagatgcatt gccaaggcaa tatgcttact ggtaccagca gaagccaggc     120
caggcccctc tactggtgat atataaagac agtgagaggc cctcagggat ccctgagcga     180
ttctctggct ccggctcagg gacaacagtc acgttgacca tcagtggagt ccaggcagaa     240
gacgaggctg actattactg tcaatcagca gacagcagtg gtacctatgc ggtattcggc     300
ggagggacca aggtcaccgt ccta                                             324

<210> SEQ ID NO 731
<211> LENGTH: 108
<212> TYPE: PRT
<213> ORGANISM: Homo sapiens

<400> SEQUENCE: 731

Ser Tyr Glu Leu Ala Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Leu Leu Val Ile Tyr
        35                  40                  45

Lys Asp Ser Glu Arg Pro Ser Gly Ile Pro Glu Arg Phe Ser Gly Ser
    50                  55                  60

Gly Ser Gly Thr Thr Val Thr Leu Thr Ile Ser Gly Val Gln Ala Glu

```
                65                  70                  75                  80
Asp Glu Ala Asp Tyr Tyr Cys Gln Ser Ala Asp Ser Ser Gly Thr Tyr
                    85                  90                  95
Ala Val Phe Gly Gly Gly Thr Lys Val Thr Val Leu
            100                 105

<210> SEQ ID NO 732
<211> LENGTH: 11
<212> TYPE: PRT
<213> ORGANISM: Homo sapiens

<400> SEQUENCE: 732

Ser Gly Asp Ala Leu Pro Arg Gln Tyr Ala Tyr
1               5                   10

<210> SEQ ID NO 733
<211> LENGTH: 7
<212> TYPE: PRT
<213> ORGANISM: Homo sapiens

<400> SEQUENCE: 733

Lys Asp Ser Glu Arg Pro Ser
1               5

<210> SEQ ID NO 734
<211> LENGTH: 11
<212> TYPE: PRT
<213> ORGANISM: Homo sapiens

<400> SEQUENCE: 734

Gln Ser Ala Asp Ser Ser Gly Thr Tyr Ala Val
1               5                   10

<210> SEQ ID NO 735
<211> LENGTH: 22
<212> TYPE: PRT
<213> ORGANISM: Homo sapiens

<400> SEQUENCE: 735

Ser Tyr Glu Leu Ala Gln Pro Pro Ser Val Ser Val Ser Pro Gly Gln
1               5                   10                  15

Thr Ala Arg Ile Thr Cys
            20

<210> SEQ ID NO 736
<211> LENGTH: 15
<212> TYPE: PRT
<213> ORGANISM: Homo sapiens

<400> SEQUENCE: 736

Trp Tyr Gln Gln Lys Pro Gly Gln Ala Pro Leu Leu Val Ile Tyr
1               5                   10                  15

<210> SEQ ID NO 737
<211> LENGTH: 32
<212> TYPE: PRT
<213> ORGANISM: Homo sapiens

<400> SEQUENCE: 737

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30
```

<210> SEQ ID NO 738
<211> LENGTH: 10
<212> TYPE: PRT
<213> ORGANISM: Homo sapiens

<400> SEQUENCE: 738

Phe Gly Gly Gly Thr Lys Val Thr Val Leu
1               5                   10

<210> SEQ ID NO 739
<211> LENGTH: 375
<212> TYPE: DNA
<213> ORGANISM: Homo sapiens

<400> SEQUENCE: 739

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcgccatc tccagagaca attccaagaa cacgctgtat     240
ctgcaaatga acagcctgag agccgaggac acggccgtgt attactgttc gcggcagttc     300
gactactgga gtacttattc gggtccaact gcttttgatc tctggggcag aggcaccctg     360
gtcaccgtct cgagt                                                      375
```

<210> SEQ ID NO 740
<211> LENGTH: 125
<212> TYPE: PRT
<213> ORGANISM: Homo sapiens

<400> SEQUENCE: 740

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Ala Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Arg Gln Phe Asp Tyr Trp Ser Thr Tyr Ser Gly Pro Thr Ala Phe
            100                 105                 110

Asp Leu Trp Gly Arg Gly Thr Leu Val Thr Val Ser Ser
        115                 120                 125

<210> SEQ ID NO 741
<211> LENGTH: 5
<212> TYPE: PRT
<213> ORGANISM: Homo sapiens

<400> SEQUENCE: 741

Ser Tyr Ala Met Ser
1               5

<210> SEQ ID NO 742

```
<211> LENGTH: 17
<212> TYPE: PRT
<213> ORGANISM: Homo sapiens

<400> SEQUENCE: 742

Ala Ile Ser Gly Ser Gly Gly Ser Thr Tyr Tyr Ala Asp Ser Val Lys
1               5                   10                  15
Gly

<210> SEQ ID NO 743
<211> LENGTH: 16
<212> TYPE: PRT
<213> ORGANISM: Homo sapiens

<400> SEQUENCE: 743

Gln Phe Asp Tyr Trp Ser Thr Tyr Ser Gly Pro Thr Ala Phe Asp Leu
1               5                   10                  15

<210> SEQ ID NO 744
<211> LENGTH: 30
<212> TYPE: PRT
<213> ORGANISM: Homo sapiens

<400> SEQUENCE: 744

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 745
<211> LENGTH: 14
<212> TYPE: PRT
<213> ORGANISM: Homo sapiens

<400> SEQUENCE: 745

Trp Val Arg Gln Ala Pro Gly Lys Gly Leu Glu Trp Val Ser
1               5                   10

<210> SEQ ID NO 746
<211> LENGTH: 32
<212> TYPE: PRT
<213> ORGANISM: Homo sapiens

<400> SEQUENCE: 746

Arg Phe Ala Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ser Arg
            20                  25                  30

<210> SEQ ID NO 747
<211> LENGTH: 11
<212> TYPE: PRT
<213> ORGANISM: Homo sapiens

<400> SEQUENCE: 747

Trp Gly Arg Gly Thr Leu Val Thr Val Ser Ser
1               5                   10

<210> SEQ ID NO 748
<211> LENGTH: 324
<212> TYPE: DNA
<213> ORGANISM: Homo sapiens

<400> SEQUENCE: 748
```

```
tcctatgagc tggctcagcc accctcggtg tcagtgtccc caggacagac ggccaggatc    60
acctgctctg gagatgcatt gccaaggcaa tatgcttact ggtaccagca gaagccaggc   120
caggcccctc tactggtgat atataaagac agtttcaggc cctcagggat ccctgagcga   180
ttctctggct ccggctcagg gacaacagtc acgttgacca tcagtggagt ccaggcagaa   240
gacgaggctg actattactg tcaatcagca gacagcagtg gtacctatgt ggtattcggc   300
ggagggacca aggtcaccgt ccta                                          324
```

<210> SEQ ID NO 749
<211> LENGTH: 108
<212> TYPE: PRT
<213> ORGANISM: Homo sapiens

<400> SEQUENCE: 749

Ser Tyr Glu Leu Ala Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Leu Leu Val Ile Tyr
        35                  40                  45

Lys Asp Ser Phe Arg Pro Ser Gly Ile Pro Glu Arg Phe Ser Gly Ser
    50                  55                  60

Gly Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Val Val Phe Gly Gly Gly Thr Lys Val Thr Val Leu
            100                 105

<210> SEQ ID NO 750
<211> LENGTH: 11
<212> TYPE: PRT
<213> ORGANISM: Homo sapiens

<400> SEQUENCE: 750

Ser Gly Asp Ala Leu Pro Arg Gln Tyr Ala Tyr
1               5                   10

<210> SEQ ID NO 751
<211> LENGTH: 7
<212> TYPE: PRT
<213> ORGANISM: Homo sapiens

<400> SEQUENCE: 751

Lys Asp Ser Phe Arg Pro Ser
1               5

<210> SEQ ID NO 752
<211> LENGTH: 11
<212> TYPE: PRT
<213> ORGANISM: Homo sapiens

<400> SEQUENCE: 752

Gln Ser Ala Asp Ser Ser Gly Thr Tyr Val Val
1               5                   10

<210> SEQ ID NO 753
<211> LENGTH: 22
<212> TYPE: PRT

<213> ORGANISM: Homo sapiens

<400> SEQUENCE: 753

Ser Tyr Glu Leu Ala Gln Pro Pro Ser Val Ser Val Ser Pro Gly Gln
1               5                   10                  15

Thr Ala Arg Ile Thr Cys
            20

<210> SEQ ID NO 754
<211> LENGTH: 15
<212> TYPE: PRT
<213> ORGANISM: Homo sapiens

<400> SEQUENCE: 754

Trp Tyr Gln Gln Lys Pro Gly Gln Ala Pro Leu Leu Val Ile Tyr
1               5                   10                  15

<210> SEQ ID NO 755
<211> LENGTH: 32
<212> TYPE: PRT
<213> ORGANISM: Homo sapiens

<400> SEQUENCE: 755

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 756
<211> LENGTH: 10
<212> TYPE: PRT
<213> ORGANISM: Homo sapiens

<400> SEQUENCE: 756

Phe Gly Gly Gly Thr Lys Val Thr Val Leu
1               5                   10

<210> SEQ ID NO 757
<211> LENGTH: 375
<212> TYPE: DNA
<213> ORGANISM: Homo sapiens

<400> SEQUENCE: 757
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgttc gcggcagttc     300
gactactgga gtacttattc gggtccaact gcttttgatc tctggggcag aggcaccctg     360
gtcaccgtct cgagt                                                      375

<210> SEQ ID NO 758
<211> LENGTH: 125
<212> TYPE: PRT
<213> ORGANISM: Homo sapiens

<400> SEQUENCE: 758

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Arg Gln Phe Asp Tyr Trp Ser Thr Tyr Ser Gly Pro Thr Ala Phe
            100                 105                 110

Asp Leu Trp Gly Arg Gly Thr Leu Val Thr Val Ser Ser
        115                 120                 125

<210> SEQ ID NO 759
<211> LENGTH: 5
<212> TYPE: PRT
<213> ORGANISM: Homo sapiens

<400> SEQUENCE: 759

Ser Tyr Ala Met Ser
1               5

<210> SEQ ID NO 760
<211> LENGTH: 17
<212> TYPE: PRT
<213> ORGANISM: Homo sapiens

<400> SEQUENCE: 760

Ala Ile Ser Gly Ser Gly Gly Ser Thr Tyr Tyr Ala Asp Ser Val Lys
1               5                   10                  15

Gly

<210> SEQ ID NO 761
<211> LENGTH: 16
<212> TYPE: PRT
<213> ORGANISM: Homo sapiens

<400> SEQUENCE: 761

Gln Phe Asp Tyr Trp Ser Thr Tyr Ser Gly Pro Thr Ala Phe Asp Leu
1               5                   10                  15

<210> SEQ ID NO 762
<211> LENGTH: 30
<212> TYPE: PRT
<213> ORGANISM: Homo sapiens

<400> SEQUENCE: 762

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 763
<211> LENGTH: 14
<212> TYPE: PRT
<213> ORGANISM: Homo sapiens

<400> SEQUENCE: 763

Trp Val Arg Gln Ala Pro Gly Lys Gly Leu Glu Trp Val Ser
```

<210> SEQ ID NO 764
<211> LENGTH: 32
<212> TYPE: PRT
<213> ORGANISM: Homo sapiens

<400> SEQUENCE: 764

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ser Arg
            20                  25                  30

<210> SEQ ID NO 765
<211> LENGTH: 11
<212> TYPE: PRT
<213> ORGANISM: Homo sapiens

<400> SEQUENCE: 765

Trp Gly Arg Gly Thr Leu Val Thr Val Ser Ser
1               5                   10

<210> SEQ ID NO 766
<211> LENGTH: 324
<212> TYPE: DNA
<213> ORGANISM: Homo sapiens

<400> SEQUENCE: 766
tcctatgagc tggctcagcc accctcggtg tcagtgtccc caggacagac ggccaggatc      60
acctgctctg gagatgcatt gccaaggcaa tatgcttact ggtaccagca gaagccaggc     120
caggcccctc tactggtgat atataaagac agtgagaggc cctcagggat ccctgagcga     180
ttctctggct ccggctcagg gacaacagtc acgttgacca tcagtggagt ccaggcagaa     240
gacgaggctg actattactg tcaatcagca gacagcagtg gtacctatgc ggtattcggc     300
ggagggacca aggtcaccgt ccta                                            324

<210> SEQ ID NO 767
<211> LENGTH: 108
<212> TYPE: PRT
<213> ORGANISM: Homo sapiens

<400> SEQUENCE: 767

Ser Tyr Glu Leu Ala Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Leu Leu Val Ile Tyr
        35                  40                  45

Lys Asp Ser Glu Arg Pro Ser Gly Ile Pro Glu Arg Phe Ser Gly Ser
    50                  55                  60

Gly Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Ala Val Phe Gly Gly Gly Thr Lys Val Thr Val Leu
            100                 105

<210> SEQ ID NO 768
<211> LENGTH: 11

```
<212> TYPE: PRT
<213> ORGANISM: Homo sapiens

<400> SEQUENCE: 768

Ser Gly Asp Ala Leu Pro Arg Gln Tyr Ala Tyr
1               5                   10

<210> SEQ ID NO 769
<211> LENGTH: 7
<212> TYPE: PRT
<213> ORGANISM: Homo sapiens

<400> SEQUENCE: 769

Lys Asp Ser Glu Arg Pro Ser
1               5

<210> SEQ ID NO 770
<211> LENGTH: 11
<212> TYPE: PRT
<213> ORGANISM: Homo sapiens

<400> SEQUENCE: 770

Gln Ser Ala Asp Ser Ser Gly Thr Tyr Ala Val
1               5                   10

<210> SEQ ID NO 771
<211> LENGTH: 22
<212> TYPE: PRT
<213> ORGANISM: Homo sapiens

<400> SEQUENCE: 771

Ser Tyr Glu Leu Ala Gln Pro Pro Ser Val Ser Val Ser Pro Gly Gln
1               5                   10                  15

Thr Ala Arg Ile Thr Cys
            20

<210> SEQ ID NO 772
<211> LENGTH: 15
<212> TYPE: PRT
<213> ORGANISM: Homo sapiens

<400> SEQUENCE: 772

Trp Tyr Gln Gln Lys Pro Gly Gln Ala Pro Leu Leu Val Ile Tyr
1               5                   10                  15

<210> SEQ ID NO 773
<211> LENGTH: 32
<212> TYPE: PRT
<213> ORGANISM: Homo sapiens

<400> SEQUENCE: 773

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 774
<211> LENGTH: 10
<212> TYPE: PRT
<213> ORGANISM: Homo sapiens

<400> SEQUENCE: 774

Phe Gly Gly Gly Thr Lys Val Thr Val Leu
1               5                   10
```

<210> SEQ ID NO 775
<211> LENGTH: 375
<212> TYPE: DNA
<213> ORGANISM: Homo sapiens

<400> SEQUENCE: 775

```
gaggtgcagc tgttggagtc tgggggaggc ttggtacagc ctgggggtc cctgagactc      60
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcgccatc tccagagaca attccaagaa cacgctgtat    240
ctgcaaatga acagcctgag agccgaggac acggccgtgt attactgtgc gagagatagg    300
gattttttgga gtacttattc gggtccaact gcttttgatc tctggggcag aggcaccctg    360
gtcaccgtct cgagt                                                      375
```

<210> SEQ ID NO 776
<211> LENGTH: 125
<212> TYPE: PRT
<213> ORGANISM: Homo sapiens

<400> SEQUENCE: 776

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Ala Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Asp Phe Trp Ser Thr Tyr Ser Gly Pro Thr Ala Phe
            100                 105                 110

Asp Leu Trp Gly Arg Gly Thr Leu Val Thr Val Ser Ser
        115                 120                 125

<210> SEQ ID NO 777
<211> LENGTH: 5
<212> TYPE: PRT
<213> ORGANISM: Homo sapiens

<400> SEQUENCE: 777

Ser Tyr Ala Met Ser
1               5

<210> SEQ ID NO 778
<211> LENGTH: 17
<212> TYPE: PRT
<213> ORGANISM: Homo sapiens

<400> SEQUENCE: 778

Ala Ile Ser Gly Ser Gly Gly Ser Thr Tyr Tyr Ala Asp Ser Val Lys
1               5                   10                  15

Gly

<210> SEQ ID NO 779
<211> LENGTH: 16
<212> TYPE: PRT
<213> ORGANISM: Homo sapiens

<400> SEQUENCE: 779

Asp Arg Asp Phe Trp Ser Thr Tyr Ser Gly Pro Thr Ala Phe Asp Leu
1               5                   10                  15

<210> SEQ ID NO 780
<211> LENGTH: 30
<212> TYPE: PRT
<213> ORGANISM: Homo sapiens

<400> SEQUENCE: 780

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 781
<211> LENGTH: 14
<212> TYPE: PRT
<213> ORGANISM: Homo sapiens

<400> SEQUENCE: 781

Trp Val Arg Gln Ala Pro Gly Lys Gly Leu Glu Trp Val Ser
1               5                   10

<210> SEQ ID NO 782
<211> LENGTH: 32
<212> TYPE: PRT
<213> ORGANISM: Homo sapiens

<400> SEQUENCE: 782

Arg Phe Ala Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 783
<211> LENGTH: 11
<212> TYPE: PRT
<213> ORGANISM: Homo sapiens

<400> SEQUENCE: 783

Trp Gly Arg Gly Thr Leu Val Thr Val Ser Ser
1               5                   10

<210> SEQ ID NO 784
<211> LENGTH: 324
<212> TYPE: DNA
<213> ORGANISM: Homo sapiens

<400> SEQUENCE: 784
tcctatgagc tggctcagcc acccctcggtg tcagtgtccc caggacagac ggccaggatc    60
acctgctctg gagatgcatt gccaaggcaa tatgcttact ggtaccagca gaagccaggc   120
caggcccctc tactggtgat atataaagac agtgagaggc cctcagggat ccctgagcga   180
ttctctggct ccggctcagg gacaacagtc acgttgacca tcagtggagt ccaggcagaa   240
gacgaggctg actattactg tcaatcagca gacagcagtg gtacctatgc ggtattcggc   300
ggagggacca aggtcaccgt ccta                                                  324

<210> SEQ ID NO 785
<211> LENGTH: 108
<212> TYPE: PRT
<213> ORGANISM: Homo sapiens

<400> SEQUENCE: 785

Ser Tyr Glu Leu Ala Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Leu Leu Val Ile Tyr
        35                  40                  45

Lys Asp Ser Glu Arg Pro Ser Gly Ile Pro Glu Arg Phe Ser Gly Ser
    50                  55                  60

Gly Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Ala Val Phe Gly Gly Gly Thr Lys Val Thr Val Leu
            100                 105

<210> SEQ ID NO 786
<211> LENGTH: 11
<212> TYPE: PRT
<213> ORGANISM: Homo sapiens

<400> SEQUENCE: 786

Ser Gly Asp Ala Leu Pro Arg Gln Tyr Ala Tyr
1               5                   10

<210> SEQ ID NO 787
<211> LENGTH: 7
<212> TYPE: PRT
<213> ORGANISM: Homo sapiens

<400> SEQUENCE: 787

Lys Asp Ser Glu Arg Pro Ser
1               5

<210> SEQ ID NO 788
<211> LENGTH: 11
<212> TYPE: PRT
<213> ORGANISM: Homo sapiens

<400> SEQUENCE: 788

Gln Ser Ala Asp Ser Ser Gly Thr Tyr Ala Val
1               5                   10

<210> SEQ ID NO 789
<211> LENGTH: 22
<212> TYPE: PRT
<213> ORGANISM: Homo sapiens

<400> SEQUENCE: 789

Ser Tyr Glu Leu Ala Gln Pro Pro Ser Val Ser Val Ser Pro Gly Gln
1               5                   10                  15

Thr Ala Arg Ile Thr Cys
            20

-continued

```
<210> SEQ ID NO 790
<211> LENGTH: 15
<212> TYPE: PRT
<213> ORGANISM: Homo sapiens

<400> SEQUENCE: 790

Trp Tyr Gln Gln Lys Pro Gly Gln Ala Pro Leu Leu Val Ile Tyr
1               5                   10                  15

<210> SEQ ID NO 791
<211> LENGTH: 32
<212> TYPE: PRT
<213> ORGANISM: Homo sapiens

<400> SEQUENCE: 791

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 792
<211> LENGTH: 10
<212> TYPE: PRT
<213> ORGANISM: Homo sapiens

<400> SEQUENCE: 792

Phe Gly Gly Gly Thr Lys Val Thr Val Leu
1               5                   10

<210> SEQ ID NO 793
<211> LENGTH: 375
<212> TYPE: DNA
<213> ORGANISM: Homo sapiens

<400> SEQUENCE: 793
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgttc gcggcagttc     300
gactactgga gtacttattc gggtccaact gcttttgatc tctggggcag aggcaccctg     360
gtcaccgtct cgagt                                                      375

<210> SEQ ID NO 794
<211> LENGTH: 125
<212> TYPE: PRT
<213> ORGANISM: Homo sapiens

<400> SEQUENCE: 794

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ser Arg Gln Phe Asp Tyr Trp Ser Thr Tyr Ser Gly Pro Thr Ala Phe
            100                 105                 110

Asp Leu Trp Gly Arg Gly Thr Leu Val Thr Val Ser Ser
        115                 120                 125

<210> SEQ ID NO 795
<211> LENGTH: 5
<212> TYPE: PRT
<213> ORGANISM: Homo sapiens

<400> SEQUENCE: 795

Ser Tyr Ala Met Ser
1               5

<210> SEQ ID NO 796
<211> LENGTH: 17
<212> TYPE: PRT
<213> ORGANISM: Homo sapiens

<400> SEQUENCE: 796

Ala Ile Ser Gly Ser Gly Gly Ser Thr Tyr Tyr Ala Asp Ser Val Lys
1               5                   10                  15

Gly

<210> SEQ ID NO 797
<211> LENGTH: 16
<212> TYPE: PRT
<213> ORGANISM: Homo sapiens

<400> SEQUENCE: 797

Gln Phe Asp Tyr Trp Ser Thr Tyr Ser Gly Pro Thr Ala Phe Asp Leu
1               5                   10                  15

<210> SEQ ID NO 798
<211> LENGTH: 30
<212> TYPE: PRT
<213> ORGANISM: Homo sapiens

<400> SEQUENCE: 798

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 799
<211> LENGTH: 14
<212> TYPE: PRT
<213> ORGANISM: Homo sapiens

<400> SEQUENCE: 799

Trp Val Arg Gln Ala Pro Gly Lys Gly Leu Glu Trp Val Ser
1               5                   10

<210> SEQ ID NO 800
<211> LENGTH: 32
<212> TYPE: PRT
<213> ORGANISM: Homo sapiens

<400> SEQUENCE: 800

Arg Phe Thr Ile Ser Arg Asp Asn Ser Lys Asn Thr Leu Tyr Leu Gln
```

```
                1               5                   10                  15
            Met Asn Ser Leu Arg Ala Glu Asp Thr Ala Val Tyr Tyr Cys Ser Arg
                            20                  25                  30
```

<210> SEQ ID NO 801
<211> LENGTH: 11
<212> TYPE: PRT
<213> ORGANISM: Homo sapiens

<400> SEQUENCE: 801

```
Trp Gly Arg Gly Thr Leu Val Thr Val Ser Ser
1               5                   10
```

<210> SEQ ID NO 802
<211> LENGTH: 324
<212> TYPE: DNA
<213> ORGANISM: Homo sapiens

<400> SEQUENCE: 802

| | | |
|---|---|---|
| tcctatgagc tggctcagcc accctcggtg tcagtgtccc caggacagac ggccaggatc | 60 |
| acctgctctg gagatgcatt gccaaggcaa tatgcttact ggtaccagca gaagccaggc | 120 |
| caggcccctc tactggtgat atataaagac agtttcaggc cctcagggat ccctgagcga | 180 |
| ttctctggct ccggctcagg gacaacagtc acgttgacca tcagtggagt ccaggcagaa | 240 |
| gacgaggctg actattactg tcaatcagca gacagcagtg gtacctatgt ggtattcggc | 300 |
| ggagggacca aggtcaccgt ccta | 324 |

<210> SEQ ID NO 803
<211> LENGTH: 108
<212> TYPE: PRT
<213> ORGANISM: Homo sapiens

<400> SEQUENCE: 803

```
Ser Tyr Glu Leu Ala Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
                20                  25                  30

Tyr Trp Tyr Gln Gln Lys Pro Gly Gln Ala Pro Leu Leu Val Ile Tyr
            35                  40                  45

Lys Asp Ser Phe Arg Pro Ser Gly Ile Pro Glu Arg Phe Ser Gly Ser
    50                  55                  60

Gly Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Val Val Phe Gly Gly Gly Thr Lys Val Thr Val Leu
                100                 105
```

<210> SEQ ID NO 804
<211> LENGTH: 11
<212> TYPE: PRT
<213> ORGANISM: Homo sapiens

<400> SEQUENCE: 804

```
Ser Gly Asp Ala Leu Pro Arg Gln Tyr Ala Tyr
1               5                   10
```

<210> SEQ ID NO 805
<211> LENGTH: 7

```
<212> TYPE: PRT
<213> ORGANISM: Homo sapiens

<400> SEQUENCE: 805

Lys Asp Ser Phe Arg Pro Ser
1               5

<210> SEQ ID NO 806
<211> LENGTH: 11
<212> TYPE: PRT
<213> ORGANISM: Homo sapiens

<400> SEQUENCE: 806

Gln Ser Ala Asp Ser Ser Gly Thr Tyr Val Val
1               5                   10

<210> SEQ ID NO 807
<211> LENGTH: 22
<212> TYPE: PRT
<213> ORGANISM: Homo sapiens

<400> SEQUENCE: 807

Ser Tyr Glu Leu Ala Gln Pro Pro Ser Val Ser Val Ser Pro Gly Gln
1               5                   10                  15

Thr Ala Arg Ile Thr Cys
            20

<210> SEQ ID NO 808
<211> LENGTH: 15
<212> TYPE: PRT
<213> ORGANISM: Homo sapiens

<400> SEQUENCE: 808

Trp Tyr Gln Gln Lys Pro Gly Gln Ala Pro Leu Leu Val Ile Tyr
1               5                   10                  15

<210> SEQ ID NO 809
<211> LENGTH: 32
<212> TYPE: PRT
<213> ORGANISM: Homo sapiens

<400> SEQUENCE: 809

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 810
<211> LENGTH: 10
<212> TYPE: PRT
<213> ORGANISM: Homo sapiens

<400> SEQUENCE: 810

Phe Gly Gly Gly Thr Lys Val Thr Val Leu
1               5                   10

<210> SEQ ID NO 811
<211> LENGTH: 375
<212> TYPE: DNA
<213> ORGANISM: Homo sapiens

<400> SEQUENCE: 811
gaggtgcagc tgttggagtc tgggggaggc ttggtacagc ctggggggtc cctgagactc      60
```

```
tcctgtgcag cctctggatt cacctttagc agctttgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgttc gcggcagttc    300
gactactgga gtacttattc gggtccaact gcttttgatc tctggggcag aggcaccctg    360
gtcaccgtct cgagt                                                     375
```

<210> SEQ ID NO 812
<211> LENGTH: 125
<212> TYPE: PRT
<213> ORGANISM: Homo sapiens

<400> SEQUENCE: 812

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Arg Gln Phe Asp Tyr Trp Ser Thr Tyr Ser Gly Pro Thr Ala Phe
            100                 105                 110

Asp Leu Trp Gly Arg Gly Thr Leu Val Thr Val Ser Ser
        115                 120                 125
```

<210> SEQ ID NO 813
<211> LENGTH: 5
<212> TYPE: PRT
<213> ORGANISM: Homo sapiens

<400> SEQUENCE: 813

```
Ser Phe Ala Met Ser
1               5
```

<210> SEQ ID NO 814
<211> LENGTH: 17
<212> TYPE: PRT
<213> ORGANISM: Homo sapiens

<400> SEQUENCE: 814

```
Ala Ile Ser Gly Ser Gly Gly Ser Thr Tyr Tyr Ala Asp Ser Val Lys
1               5                   10                  15

Gly
```

<210> SEQ ID NO 815
<211> LENGTH: 16
<212> TYPE: PRT
<213> ORGANISM: Homo sapiens

<400> SEQUENCE: 815

```
Gln Phe Asp Tyr Trp Ser Thr Tyr Ser Gly Pro Thr Ala Phe Asp Leu
1               5                   10                  15
```

<210> SEQ ID NO 816
<211> LENGTH: 30
<212> TYPE: PRT
<213> ORGANISM: Homo sapiens

<400> SEQUENCE: 816

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser
            20                  25                  30

<210> SEQ ID NO 817
<211> LENGTH: 14
<212> TYPE: PRT
<213> ORGANISM: Homo sapiens

<400> SEQUENCE: 817

Trp Val Arg Gln Ala Pro Gly Lys Gly Leu Glu Trp Val Ser
1               5                   10

<210> SEQ ID NO 818
<211> LENGTH: 32
<212> TYPE: PRT
<213> ORGANISM: Homo sapiens

<400> SEQUENCE: 818

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ser Arg
            20                  25                  30

<210> SEQ ID NO 819
<211> LENGTH: 11
<212> TYPE: PRT
<213> ORGANISM: Homo sapiens

<400> SEQUENCE: 819

Trp Gly Arg Gly Thr Leu Val Thr Val Ser Ser
1               5                   10

<210> SEQ ID NO 820
<211> LENGTH: 324
<212> TYPE: DNA
<213> ORGANISM: Homo sapiens

<400> SEQUENCE: 820
tcctatgagc tggctcagcc accctcggtg tcagtgtccc caggacagac ggccaggatc      60
acctgctctg gagatgcatt gccaaggcaa tatgcttact ggtaccagca gaagccaggc     120
caggcccctc tactggtgat atataaagac agtgagaggc cctcagggat ccctgagcga     180
ttctctggct ccggctcagg gacaacagtc acgttgacca tcagtggagt ccaggcagaa     240
gacgaggctg actattactg tcaatcagca gacagcagtg gtacctatgt ggtattcggc     300
ggagggacca aggtcaccgt ccta                                            324

<210> SEQ ID NO 821
<211> LENGTH: 108
<212> TYPE: PRT
<213> ORGANISM: Homo sapiens

<400> SEQUENCE: 821

Ser Tyr Glu Leu Ala Gln Pro Pro Ser Val Ser Val Ser Pro Gly Gln

```
                1               5                  10                  15
            Thr Ala Arg Ile Thr Cys Ser Gly Asp Ala Leu Pro Arg Gln Tyr Ala
                            20                  25                  30
            Tyr Trp Tyr Gln Gln Lys Pro Gly Gln Ala Pro Leu Leu Val Ile Tyr
                            35                  40                  45
            Lys Asp Ser Glu Arg Pro Ser Gly Ile Pro Glu Arg Phe Ser Gly Ser
                            50                  55                  60
            Gly Ser Gly Thr Thr Val Thr Leu Thr Ile Ser Gly Val Gln Ala Glu
             65                  70                  75                  80
            Asp Glu Ala Asp Tyr Tyr Cys Gln Ser Ala Asp Ser Ser Gly Thr Tyr
                            85                  90                  95
            Val Val Phe Gly Gly Gly Thr Lys Val Thr Val Leu
                           100                 105
```

<210> SEQ ID NO 822
<211> LENGTH: 11
<212> TYPE: PRT
<213> ORGANISM: Homo sapiens

<400> SEQUENCE: 822

```
Ser Gly Asp Ala Leu Pro Arg Gln Tyr Ala Tyr
 1               5                  10
```

<210> SEQ ID NO 823
<211> LENGTH: 7
<212> TYPE: PRT
<213> ORGANISM: Homo sapiens

<400> SEQUENCE: 823

```
Lys Asp Ser Glu Arg Pro Ser
 1               5
```

<210> SEQ ID NO 824
<211> LENGTH: 11
<212> TYPE: PRT
<213> ORGANISM: Homo sapiens

<400> SEQUENCE: 824

```
Gln Ser Ala Asp Ser Ser Gly Thr Tyr Val Val
 1               5                  10
```

<210> SEQ ID NO 825
<211> LENGTH: 22
<212> TYPE: PRT
<213> ORGANISM: Homo sapiens

<400> SEQUENCE: 825

```
Ser Tyr Glu Leu Ala Gln Pro Pro Ser Val Ser Val Ser Pro Gly Gln
 1               5                  10                  15
Thr Ala Arg Ile Thr Cys
                20
```

<210> SEQ ID NO 826
<211> LENGTH: 15
<212> TYPE: PRT
<213> ORGANISM: Homo sapiens

<400> SEQUENCE: 826

```
Trp Tyr Gln Gln Lys Pro Gly Gln Ala Pro Leu Leu Val Ile Tyr
 1               5                  10                  15
```

```
<210> SEQ ID NO 827
<211> LENGTH: 32
<212> TYPE: PRT
<213> ORGANISM: Homo sapiens

<400> SEQUENCE: 827
```

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30

```
<210> SEQ ID NO 828
<211> LENGTH: 10
<212> TYPE: PRT
<213> ORGANISM: Homo sapiens

<400> SEQUENCE: 828
```

Phe Gly Gly Gly Thr Lys Val Thr Val Leu
1               5                   10

```
<210> SEQ ID NO 829
<211> LENGTH: 375
<212> TYPE: DNA
<213> ORGANISM: Homo sapiens

<400> SEQUENCE: 829
```

| | | | |
|---|---|---|---|
| gaggtgcagc tgttggagtc tgggggaggc ttggtacagc ctggggggtc cctgagactc | | | 60 |
| tcctgtgcag cctctggatt cacctttagc agctttgcca tgagctgggt ccgccaggct | | | 120 |
| ccagggaagg gctggagtg gtctcagct attagtggta gtggtggtag cacatactac | | | 180 |
| gcagactccg tgaagggccg gttcaccatc tccagagaca attccaagaa cacgctgtat | | | 240 |
| ctgcaaatga acagcctgag agccgaggac acggccgtgt attactgttc gcggcagttc | | | 300 |
| gactactgga gtacttattc gggtccaact gcttttgatc tctggggcag aggcaccctg | | | 360 |
| gtcaccgtct cgagt | | | 375 |

```
<210> SEQ ID NO 830
<211> LENGTH: 125
<212> TYPE: PRT
<213> ORGANISM: Homo sapiens

<400> SEQUENCE: 830
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Arg Gln Phe Asp Tyr Trp Ser Thr Tyr Ser Gly Pro Thr Ala Phe
            100                 105                 110

Asp Leu Trp Gly Arg Gly Thr Leu Val Thr Val Ser Ser
        115                 120                 125

```
<210> SEQ ID NO 831
<211> LENGTH: 5
<212> TYPE: PRT
<213> ORGANISM: Homo sapiens

<400> SEQUENCE: 831

Ser Phe Ala Met Ser
1               5

<210> SEQ ID NO 832
<211> LENGTH: 17
<212> TYPE: PRT
<213> ORGANISM: Homo sapiens

<400> SEQUENCE: 832

Ala Ile Ser Gly Ser Gly Gly Ser Thr Tyr Tyr Ala Asp Ser Val Lys
1               5                   10                  15

Gly

<210> SEQ ID NO 833
<211> LENGTH: 16
<212> TYPE: PRT
<213> ORGANISM: Homo sapiens

<400> SEQUENCE: 833

Gln Phe Asp Tyr Trp Ser Thr Tyr Ser Gly Pro Thr Ala Phe Asp Leu
1               5                   10                  15

<210> SEQ ID NO 834
<211> LENGTH: 30
<212> TYPE: PRT
<213> ORGANISM: Homo sapiens

<400> SEQUENCE: 834

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 835
<211> LENGTH: 14
<212> TYPE: PRT
<213> ORGANISM: Homo sapiens

<400> SEQUENCE: 835

Trp Val Arg Gln Ala Pro Gly Lys Gly Leu Glu Trp Val Ser
1               5                   10

<210> SEQ ID NO 836
<211> LENGTH: 32
<212> TYPE: PRT
<213> ORGANISM: Homo sapiens

<400> SEQUENCE: 836

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ser Arg
            20                  25                  30

<210> SEQ ID NO 837
<211> LENGTH: 11
<212> TYPE: PRT
<213> ORGANISM: Homo sapiens
```

<400> SEQUENCE: 837

Trp Gly Arg Gly Thr Leu Val Thr Val Ser Ser
1               5                   10

<210> SEQ ID NO 838
<211> LENGTH: 324
<212> TYPE: DNA
<213> ORGANISM: Homo sapiens

<400> SEQUENCE: 838
tcctatgagc tggctcagcc accctcggtg tcagtgtccc caggacagac ggccaggatc    60
acctgctctg gagatgcatt gccaaggcaa tatgcttact ggtaccagca gaagccaggc   120
caggcccctc tactggtgat atataaagac agtttcaggc cctcagggat ccctgagcga   180
ttctctggct ccggctcagg gacaacagtc acgttgacca tcagtggagt ccaggcagaa   240
gacgaggctg actattactg tcaatcagca gacagcagtg gtacctatgt ggtattcggc   300
ggagggacca aggtcaccgt ccta                                          324

<210> SEQ ID NO 839
<211> LENGTH: 108
<212> TYPE: PRT
<213> ORGANISM: Homo sapiens

<400> SEQUENCE: 839

Ser Tyr Glu Leu Ala Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Leu Leu Val Ile Tyr
        35                  40                  45

Lys Asp Ser Phe Arg Pro Ser Gly Ile Pro Glu Arg Phe Ser Gly Ser
    50                  55                  60

Gly Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Val Val Phe Gly Gly Gly Thr Lys Val Thr Val Leu
            100                 105

<210> SEQ ID NO 840
<211> LENGTH: 11
<212> TYPE: PRT
<213> ORGANISM: Homo sapiens

<400> SEQUENCE: 840

Ser Gly Asp Ala Leu Pro Arg Gln Tyr Ala Tyr
1               5                   10

<210> SEQ ID NO 841
<211> LENGTH: 7
<212> TYPE: PRT
<213> ORGANISM: Homo sapiens

<400> SEQUENCE: 841

Lys Asp Ser Phe Arg Pro Ser
1               5

<210> SEQ ID NO 842
<211> LENGTH: 11

```
<212> TYPE: PRT
<213> ORGANISM: Homo sapiens

<400> SEQUENCE: 842

Gln Ser Ala Asp Ser Ser Gly Thr Tyr Val Val
1               5                   10

<210> SEQ ID NO 843
<211> LENGTH: 22
<212> TYPE: PRT
<213> ORGANISM: Homo sapiens

<400> SEQUENCE: 843

Ser Tyr Glu Leu Ala Gln Pro Pro Ser Val Ser Val Ser Pro Gly Gln
1               5                   10                  15

Thr Ala Arg Ile Thr Cys
            20

<210> SEQ ID NO 844
<211> LENGTH: 15
<212> TYPE: PRT
<213> ORGANISM: Homo sapiens

<400> SEQUENCE: 844

Trp Tyr Gln Gln Lys Pro Gly Gln Ala Pro Leu Leu Val Ile Tyr
1               5                   10                  15

<210> SEQ ID NO 845
<211> LENGTH: 32
<212> TYPE: PRT
<213> ORGANISM: Homo sapiens

<400> SEQUENCE: 845

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 846
<211> LENGTH: 10
<212> TYPE: PRT
<213> ORGANISM: Homo sapiens

<400> SEQUENCE: 846

Phe Gly Gly Gly Thr Lys Val Thr Val Leu
1               5                   10

<210> SEQ ID NO 847
<211> LENGTH: 375
<212> TYPE: DNA
<213> ORGANISM: Homo sapiens

<400> SEQUENCE: 847
gaggtgcagc tgttggagtc tgggggaggc ttggtacagc ctggggggtc cctgagactc       60
tcctgtgcag cctctggatt cacctttagc agctatgcca tgagctgggt ccgccaggct      120
ccagggaagg ggctggagtg gtctcagct attagtggta gtggtagtag cacatactac      180
gcagactccg tgaagggccg gttcgccatc tccagagaca attccaagaa cacgctgtat      240
ctgcaaatga acagcctgag agccgaggac acggccgtgt attactgttc gcggcagttc      300
gactactgga gtacttattc gggtccaact gcttttgatc tctggggcag aggcaccctg      360
gtcaccgtct cgagt                                                       375
```

<210> SEQ ID NO 848
<211> LENGTH: 125
<212> TYPE: PRT
<213> ORGANISM: Homo sapiens

<400> SEQUENCE: 848

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Ser Thr Tyr Tyr Ala Asp Ser Val
    50                  55                  60

Lys Gly Arg Phe Ala Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Arg Gln Phe Asp Tyr Trp Ser Thr Tyr Ser Gly Pro Thr Ala Phe
            100                 105                 110

Asp Leu Trp Gly Arg Gly Thr Leu Val Thr Val Ser Ser
        115                 120                 125
```

<210> SEQ ID NO 849
<211> LENGTH: 5
<212> TYPE: PRT
<213> ORGANISM: Homo sapiens

<400> SEQUENCE: 849

```
Ser Tyr Ala Met Ser
1               5
```

<210> SEQ ID NO 850
<211> LENGTH: 17
<212> TYPE: PRT
<213> ORGANISM: Homo sapiens

<400> SEQUENCE: 850

```
Ala Ile Ser Gly Ser Gly Ser Ser Thr Tyr Tyr Ala Asp Ser Val Lys
1               5                   10                  15

Gly
```

<210> SEQ ID NO 851
<211> LENGTH: 16
<212> TYPE: PRT
<213> ORGANISM: Homo sapiens

<400> SEQUENCE: 851

```
Gln Phe Asp Tyr Trp Ser Thr Tyr Ser Gly Pro Thr Ala Phe Asp Leu
1               5                   10                  15
```

<210> SEQ ID NO 852
<211> LENGTH: 30
<212> TYPE: PRT
<213> ORGANISM: Homo sapiens

<400> SEQUENCE: 852

```
Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser
            20                  25                  30

<210> SEQ ID NO 853
<211> LENGTH: 14
<212> TYPE: PRT
<213> ORGANISM: Homo sapiens

<400> SEQUENCE: 853

Trp Val Arg Gln Ala Pro Gly Lys Gly Leu Glu Trp Val Ser
1               5                   10

<210> SEQ ID NO 854
<211> LENGTH: 32
<212> TYPE: PRT
<213> ORGANISM: Homo sapiens

<400> SEQUENCE: 854

Arg Phe Ala Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ser Arg
            20                  25                  30

<210> SEQ ID NO 855
<211> LENGTH: 11
<212> TYPE: PRT
<213> ORGANISM: Homo sapiens

<400> SEQUENCE: 855

Trp Gly Arg Gly Thr Leu Val Thr Val Ser Ser
1               5                   10

<210> SEQ ID NO 856
<211> LENGTH: 324
<212> TYPE: DNA
<213> ORGANISM: Homo sapiens

<400> SEQUENCE: 856
tcctatgagc tggctcagcc accctcggtg tcagtgtccc caggacagac ggccaggatc     60
acctgctctg gagatgcatt gccaaggcaa tatgcttact ggtaccagca gaagccaggc    120
caggcccctc tactggtgat atataaagac agtgagaggc cctcagggat ccctgagcga    180
ttctctggct ccggctcagg gacaacagtc acgttgacca tcagtggagt ccaggcagaa    240
gacgaggctg actattactg tcaatcagca gacagcagtg gtacctatgc ggtattcggc    300
ggagggacca aggtcaccgt ccta                                            324

<210> SEQ ID NO 857
<211> LENGTH: 108
<212> TYPE: PRT
<213> ORGANISM: Homo sapiens

<400> SEQUENCE: 857

Ser Tyr Glu Leu Ala Gln Pro Pro Ser Val Ser Val Ser Pro Gly Gln
1               5                   10                  15

Thr Ala Arg Ile Thr Cys Ser Gly Asp Ala Leu Pro Arg Gln Tyr Ala
            20                  25                  30

Tyr Trp Tyr Gln Gln Lys Pro Gly Gln Ala Pro Leu Leu Val Ile Tyr
        35                  40                  45

Lys Asp Ser Glu Arg Pro Ser Gly Ile Pro Glu Arg Phe Ser Gly Ser
    50                  55                  60

-continued

Gly Ser Gly Thr Thr Val Thr Leu Thr Ile Ser Gly Val Gln Ala Glu
 65                  70                  75                  80

Asp Glu Ala Asp Tyr Tyr Cys Gln Ser Ala Asp Ser Ser Gly Thr Tyr
                 85                  90                  95

Ala Val Phe Gly Gly Gly Thr Lys Val Thr Val Leu
            100                 105

<210> SEQ ID NO 858
<211> LENGTH: 11
<212> TYPE: PRT
<213> ORGANISM: Homo sapiens

<400> SEQUENCE: 858

Ser Gly Asp Ala Leu Pro Arg Gln Tyr Ala Tyr
1               5                   10

<210> SEQ ID NO 859
<211> LENGTH: 7
<212> TYPE: PRT
<213> ORGANISM: Homo sapiens

<400> SEQUENCE: 859

Lys Asp Ser Glu Arg Pro Ser
1               5

<210> SEQ ID NO 860
<211> LENGTH: 11
<212> TYPE: PRT
<213> ORGANISM: Homo sapiens

<400> SEQUENCE: 860

Gln Ser Ala Asp Ser Ser Gly Thr Tyr Ala Val
1               5                   10

<210> SEQ ID NO 861
<211> LENGTH: 22
<212> TYPE: PRT
<213> ORGANISM: Homo sapiens

<400> SEQUENCE: 861

Ser Tyr Glu Leu Ala Gln Pro Pro Ser Val Ser Val Ser Pro Gly Gln
1               5                   10                  15

Thr Ala Arg Ile Thr Cys
            20

<210> SEQ ID NO 862
<211> LENGTH: 15
<212> TYPE: PRT
<213> ORGANISM: Homo sapiens

<400> SEQUENCE: 862

Trp Tyr Gln Gln Lys Pro Gly Gln Ala Pro Leu Leu Val Ile Tyr
1               5                   10                  15

<210> SEQ ID NO 863
<211> LENGTH: 32
<212> TYPE: PRT
<213> ORGANISM: Homo sapiens

<400> SEQUENCE: 863

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys

<210> SEQ ID NO 864
<211> LENGTH: 10
<212> TYPE: PRT
<213> ORGANISM: Homo sapiens

<400> SEQUENCE: 864

Phe Gly Gly Gly Thr Lys Val Thr Val Leu
1               5                   10

<210> SEQ ID NO 865
<211> LENGTH: 375
<212> TYPE: DNA
<213> ORGANISM: Homo sapiens

<400> SEQUENCE: 865
gaggtgcagc tgttggagtc tgggggaggc ttggtacagc ctggggggtc cctgagactc     60
tcctgtgcag cctctggatt cacctttagc agctttgcca tgagctgggt ccgccaggct    120
ccagggaagg ggctggagtg ggtctcagct attagtggta gtggtagtag cacatactac    180
gcagactccg tgaagggccg gttcgccatc tccagagaca attccaagaa cacgctgtat    240
ctgcaaatga acagcctgag agccgaggac acggccgtgt attactgtgc gagagatagg    300
gattttggga gtacttattc gggtccaact gcttttgatc tctggggcag aggcaccctg    360
gtcaccgtct cgagt                                                     375

<210> SEQ ID NO 866
<211> LENGTH: 125
<212> TYPE: PRT
<213> ORGANISM: Homo sapiens

<400> SEQUENCE: 866

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Ser Thr Tyr Tyr Ala Asp Ser Val
    50                  55                  60

Lys Gly Arg Phe Ala Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Asp Phe Trp Ser Thr Tyr Ser Gly Pro Thr Ala Phe
            100                 105                 110

Asp Leu Trp Gly Arg Gly Thr Leu Val Thr Val Ser Ser
        115                 120                 125

<210> SEQ ID NO 867
<211> LENGTH: 5
<212> TYPE: PRT
<213> ORGANISM: Homo sapiens

<400> SEQUENCE: 867

Ser Phe Ala Met Ser
1               5

```
<210> SEQ ID NO 868
<211> LENGTH: 17
<212> TYPE: PRT
<213> ORGANISM: Homo sapiens

<400> SEQUENCE: 868

Ala Ile Ser Gly Ser Gly Ser Ser Thr Tyr Tyr Ala Asp Ser Val Lys
1               5                   10                  15
Gly

<210> SEQ ID NO 869
<211> LENGTH: 16
<212> TYPE: PRT
<213> ORGANISM: Homo sapiens

<400> SEQUENCE: 869

Asp Arg Asp Phe Trp Ser Thr Tyr Ser Gly Pro Thr Ala Phe Asp Leu
1               5                   10                  15

<210> SEQ ID NO 870
<211> LENGTH: 30
<212> TYPE: PRT
<213> ORGANISM: Homo sapiens

<400> SEQUENCE: 870

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 871
<211> LENGTH: 14
<212> TYPE: PRT
<213> ORGANISM: Homo sapiens

<400> SEQUENCE: 871

Trp Val Arg Gln Ala Pro Gly Lys Gly Leu Glu Trp Val Ser
1               5                   10

<210> SEQ ID NO 872
<211> LENGTH: 32
<212> TYPE: PRT
<213> ORGANISM: Homo sapiens

<400> SEQUENCE: 872

Arg Phe Ala Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 873
<211> LENGTH: 11
<212> TYPE: PRT
<213> ORGANISM: Homo sapiens

<400> SEQUENCE: 873

Trp Gly Arg Gly Thr Leu Val Thr Val Ser Ser
1               5                   10

<210> SEQ ID NO 874
<211> LENGTH: 324
<212> TYPE: DNA
<213> ORGANISM: Homo sapiens
```

<400> SEQUENCE: 874

```
tcctatgagc tggcccagcc accctcggtg tcagtgtccc caggacagac ggccaggatc    60
acctgctctg gagatgcatt gccaaggcaa tatgcttact ggtaccagca gaagccaggc   120
caggcccctc tactggtgat atataaagac agtttcaggc cctcagggat ccctgagcga   180
ttctctggct ccggctcagg gacaacagtc acgttgacca tcagtggagt ccaggcagaa   240
gacgaggctg actattactg tcaatcagcg gacagcagtg gtacctatgc ggtattcggc   300
ggagggacca aggtcaccgt ccta                                          324
```

<210> SEQ ID NO 875
<211> LENGTH: 108
<212> TYPE: PRT
<213> ORGANISM: Homo sapiens

<400> SEQUENCE: 875

```
Ser Tyr Glu Leu Ala Gln Pro Pro Ser Val Ser Val Ser Pro Gly Gln
1               5                   10                  15
Thr Ala Arg Ile Thr Cys Ser Gly Asp Ala Leu Pro Arg Gln Tyr Ala
            20                  25                  30
Tyr Trp Tyr Gln Gln Lys Pro Gly Gln Ala Pro Leu Leu Val Ile Tyr
        35                  40                  45
Lys Asp Ser Phe Arg Pro Ser Gly Ile Pro Glu Arg Phe Ser Gly Ser
    50                  55                  60
Gly Ser Gly Thr Thr Val Thr Leu Thr Ile Ser Gly Val Gln Ala Glu
65                  70                  75                  80
Asp Glu Ala Asp Tyr Tyr Cys Gln Ser Ala Asp Ser Ser Gly Thr Tyr
                85                  90                  95
Ala Val Phe Gly Gly Gly Thr Lys Val Thr Val Leu
            100                 105
```

<210> SEQ ID NO 876
<211> LENGTH: 11
<212> TYPE: PRT
<213> ORGANISM: Homo sapiens

<400> SEQUENCE: 876

```
Ser Gly Asp Ala Leu Pro Arg Gln Tyr Ala Tyr
1               5                   10
```

<210> SEQ ID NO 877
<211> LENGTH: 7
<212> TYPE: PRT
<213> ORGANISM: Homo sapiens

<400> SEQUENCE: 877

```
Lys Asp Ser Phe Arg Pro Ser
1               5
```

<210> SEQ ID NO 878
<211> LENGTH: 11
<212> TYPE: PRT
<213> ORGANISM: Homo sapiens

<400> SEQUENCE: 878

```
Gln Ser Ala Asp Ser Ser Gly Thr Tyr Ala Val
1               5                   10
```

<210> SEQ ID NO 879
<211> LENGTH: 22

```
<212> TYPE: PRT
<213> ORGANISM: Homo sapiens

<400> SEQUENCE: 879

Ser Tyr Glu Leu Ala Gln Pro Pro Ser Val Ser Val Ser Pro Gly Gln
1               5                   10                  15

Thr Ala Arg Ile Thr Cys
            20

<210> SEQ ID NO 880
<211> LENGTH: 15
<212> TYPE: PRT
<213> ORGANISM: Homo sapiens

<400> SEQUENCE: 880

Trp Tyr Gln Gln Lys Pro Gly Gln Ala Pro Leu Leu Val Ile Tyr
1               5                   10                  15

<210> SEQ ID NO 881
<211> LENGTH: 32
<212> TYPE: PRT
<213> ORGANISM: Homo sapiens

<400> SEQUENCE: 881

Gly Ile Pro Glu Arg Phe Ser Gly Ser Gly Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 882
<211> LENGTH: 10
<212> TYPE: PRT
<213> ORGANISM: Homo sapiens

<400> SEQUENCE: 882

Phe Gly Gly Gly Thr Lys Val Thr Val Leu
1               5                   10

<210> SEQ ID NO 883
<211> LENGTH: 366
<212> TYPE: DNA
<213> ORGANISM: Rattus rattus

<400> SEQUENCE: 883
caggtgcagc tgaaggagtc aggacctggc ctggtgaagc cctcagagac cctgtctctc      60
acctgcactg tctctgggtt ctcattaacc aactatcatg taaactgggt tcgacagcct     120
ccaggaaagg gtctggagtg gatgggagta atatgggtg atggaagcac agcatataat      180
tcagctctca atcccgact gagcatcagc agggacacct cgaagagcca agttttctta      240
aaaatgaaca gtctgcaaac tgaagacaca gccacttact actgtgccag aggcggggat     300
tactatgatg gtagttatta ctacgagggc tactggggcc aaggagtcat ggtcaccgtc     360
tcctca                                                               366

<210> SEQ ID NO 884
<211> LENGTH: 122
<212> TYPE: PRT
<213> ORGANISM: Rattus rattus

<400> SEQUENCE: 884

Gln Val Gln Leu Lys Glu Ser Gly Pro Gly Leu Val Lys Pro Ser Glu
1               5                   10                  15
```

```
Thr Leu Ser Leu Thr Cys Thr Val Ser Gly Phe Ser Leu Thr Asn Tyr
            20                  25                  30

His Val Asn Trp Val Arg Gln Pro Pro Gly Lys Gly Leu Glu Trp Met
            35                  40                  45

Gly Val Ile Trp Gly Asp Gly Ser Thr Ala Tyr Asn Ser Ala Leu Lys
 50                  55                  60

Ser Arg Leu Ser Ile Ser Arg Asp Thr Ser Lys Ser Gln Val Phe Leu
 65                  70                  75                  80

Lys Met Asn Ser Leu Gln Thr Glu Asp Thr Ala Thr Tyr Tyr Cys Ala
                 85                  90                  95

Arg Gly Gly Asp Tyr Tyr Asp Gly Ser Tyr Tyr Glu Gly Tyr Trp
            100                 105                 110

Gly Gln Gly Val Met Val Thr Val Ser Ser
        115                 120
```

<210> SEQ ID NO 885
<211> LENGTH: 5
<212> TYPE: PRT
<213> ORGANISM: Rattus rattus

<400> SEQUENCE: 885

```
Asn Tyr His Val Asn
1               5
```

<210> SEQ ID NO 886
<211> LENGTH: 16
<212> TYPE: PRT
<213> ORGANISM: Rattus rattus

<400> SEQUENCE: 886

```
Val Ile Trp Gly Asp Gly Ser Thr Ala Tyr Asn Ser Ala Leu Lys Ser
1               5                   10                  15
```

<210> SEQ ID NO 887
<211> LENGTH: 14
<212> TYPE: PRT
<213> ORGANISM: Rattus rattus

<400> SEQUENCE: 887

```
Gly Gly Asp Tyr Tyr Asp Gly Ser Tyr Tyr Glu Gly Tyr
1               5                   10
```

<210> SEQ ID NO 888
<211> LENGTH: 30
<212> TYPE: PRT
<213> ORGANISM: Rattus rattus

<400> SEQUENCE: 888

```
Gln Val Gln Leu Lys Glu Ser Gly Pro Gly Leu Val Lys Pro Ser Glu
1               5                   10                  15

Thr Leu Ser Leu Thr Cys Thr Val Ser Gly Phe Ser Leu Thr
            20                  25                  30
```

<210> SEQ ID NO 889
<211> LENGTH: 14
<212> TYPE: PRT
<213> ORGANISM: Rattus rattus

<400> SEQUENCE: 889

```
Trp Val Arg Gln Pro Pro Gly Lys Gly Leu Glu Trp Met Gly
1               5                   10
```

<210> SEQ ID NO 890
<211> LENGTH: 32
<212> TYPE: PRT
<213> ORGANISM: Rattus rattus

<400> SEQUENCE: 890

Arg Leu Ser Ile Ser Arg Asp Thr Ser Lys Ser Gln Val Phe Leu Lys
1               5                   10                  15

Met Asn Ser Leu Gln Thr Glu Asp Thr Ala Thr Tyr Tyr Cys Ala Arg
            20                  25                  30

<210> SEQ ID NO 891
<211> LENGTH: 11
<212> TYPE: PRT
<213> ORGANISM: Rattus rattus

<400> SEQUENCE: 891

Trp Gly Gln Gly Val Met Val Thr Val Ser Ser
1               5                   10

<210> SEQ ID NO 892
<211> LENGTH: 321
<212> TYPE: DNA
<213> ORGANISM: Rattus rattus

<400> SEQUENCE: 892
gacatccaga tgacacagtc tcctgcctcc ctgtctgcat ctctggaaga aattgtcacc      60
atcacatgcc aggcaagcca ggacattggt aattggttat catggtatca gcagaaacca     120
gggaaatctc ctcagctcct gatctatggt gcaaccagct ggcagatggg gtcccatca      180 aggttcagcg gcagtagatc tggcacacag ttttctctta agatcagcag actacaggtt     240
gaagatattg gaatctatta ctgtctacag gcttatagtg ctccgtggac gttcggtgga     300
ggcaccaagc tggaattgaa a                                               321

<210> SEQ ID NO 893
<211> LENGTH: 107
<212> TYPE: PRT
<213> ORGANISM: Rattus rattus

<400> SEQUENCE: 893

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ser Trp Tyr Gln Gln Lys Pro Gly Lys Ser Pro Gln Leu Leu Ile
        35                  40                  45

Tyr Gly Ala Thr Ser Leu Ala Asp Gly Val Pro Ser Arg Phe Ser Gly
    50                  55                  60

Ser Arg Ser Gly Thr Gln Phe Ser Leu Lys Ile Ser Arg Leu Gln Val
65                  70                  75                  80

Glu Asp Ile Gly Ile Tyr Tyr Cys Leu Gln Ala Tyr Ser Ala Pro Trp
                85                  90                  95

Thr Phe Gly Gly Gly Thr Lys Leu Glu Leu Lys
            100                 105

<210> SEQ ID NO 894
<211> LENGTH: 11
<212> TYPE: PRT

<213> ORGANISM: Rattus rattus

<400> SEQUENCE: 894

Gln Ala Ser Gln Asp Ile Gly Asn Trp Leu Ser
1               5                   10

<210> SEQ ID NO 895
<211> LENGTH: 7
<212> TYPE: PRT
<213> ORGANISM: Rattus rattus

<400> SEQUENCE: 895

Gly Ala Thr Ser Leu Ala Asp
1               5

<210> SEQ ID NO 896
<211> LENGTH: 9
<212> TYPE: PRT
<213> ORGANISM: Rattus rattus

<400> SEQUENCE: 896

Leu Gln Ala Tyr Ser Ala Pro Trp Thr
1               5

<210> SEQ ID NO 897
<211> LENGTH: 23
<212> TYPE: PRT
<213> ORGANISM: Rattus rattus

<400> SEQUENCE: 897

Asp Ile Gln Met Thr Gln Ser Pro Ala Ser Leu Ser Ala Ser Leu Glu
1               5                   10                  15

Glu Ile Val Thr Ile Thr Cys
            20

<210> SEQ ID NO 898
<211> LENGTH: 15
<212> TYPE: PRT
<213> ORGANISM: Rattus rattus

<400> SEQUENCE: 898

Trp Tyr Gln Gln Lys Pro Gly Lys Ser Pro Gln Leu Leu Ile Tyr
1               5                   10                  15

<210> SEQ ID NO 899
<211> LENGTH: 32
<212> TYPE: PRT
<213> ORGANISM: Rattus rattus

<400> SEQUENCE: 899

Gly Val Pro Ser Arg Phe Ser Gly Ser Arg Ser Gly Thr Gln Phe Ser
1               5                   10                  15

Leu Lys Ile Ser Arg Leu Gln Val Glu Asp Ile Gly Ile Tyr Tyr Cys
            20                  25                  30

<210> SEQ ID NO 900
<211> LENGTH: 10
<212> TYPE: PRT
<213> ORGANISM: Rattus rattus

<400> SEQUENCE: 900

Phe Gly Gly Gly Thr Lys Leu Glu Leu Lys
1               5                   10

<210> SEQ ID NO 901
<211> LENGTH: 366
<212> TYPE: DNA
<213> ORGANISM: Rattus rattus

<400> SEQUENCE: 901

```
caggtgcagc tgaaggagtc aggacctggc ctggtgaagc cctcagagac cctgtctctc    60
acctgcactg tctctgggtt ctcattaacc aactatcatg taaactgggt tcgacagcct   120
ccaggaaagg gtctggagtg gatgggagta atatggggtg atggaagcac agcatataat   180
tcagctctca atcccgact gagcatcagc agggacacct cgaagagcca agttttctta   240
aaaatgaaca gtctgcaaac tgaagacaca gccacttact actgtgccag aggcggggat   300
tactatgatg gtagttatta ctacgagggc tactggggcc aaggagtcat ggtcaccgtc   360
tcctca                                                              366
```

<210> SEQ ID NO 902
<211> LENGTH: 122
<212> TYPE: PRT
<213> ORGANISM: Rattus rattus

<400> SEQUENCE: 902

Gln Val Gln Leu Lys Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

His Val Asn Trp Val Arg Gln Pro Pro Gly Lys Gly Leu Glu Trp Met
        35                  40                  45

Gly Val Ile Trp Gly Asp Gly Ser Thr Ala Tyr Asn Ser Ala Leu Lys
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Ala Thr Tyr Tyr Cys Ala
                85                  90                  95

Arg Gly Gly Asp Tyr Tyr Asp Gly Ser Tyr Tyr Tyr Glu Gly Tyr Trp
            100                 105                 110

Gly Gln Gly Val Met Val Thr Val Ser Ser
        115                 120

<210> SEQ ID NO 903
<211> LENGTH: 5
<212> TYPE: PRT
<213> ORGANISM: Rattus rattus

<400> SEQUENCE: 903

Asn Tyr His Val Asn
1               5

<210> SEQ ID NO 904
<211> LENGTH: 16
<212> TYPE: PRT
<213> ORGANISM: Rattus rattus

<400> SEQUENCE: 904

Val Ile Trp Gly Asp Gly Ser Thr Ala Tyr Asn Ser Ala Leu Lys Ser
1               5                   10                  15

<210> SEQ ID NO 905
<211> LENGTH: 14

```
<212> TYPE: PRT
<213> ORGANISM: Rattus rattus

<400> SEQUENCE: 905

Gly Gly Asp Tyr Tyr Asp Gly Ser Tyr Tyr Tyr Glu Gly Tyr
1               5                   10

<210> SEQ ID NO 906
<211> LENGTH: 30
<212> TYPE: PRT
<213> ORGANISM: Rattus rattus

<400> SEQUENCE: 906

Gln Val Gln Leu Lys Glu Ser Gly Pro Gly Leu Val Lys Pro Ser Glu
1               5                   10                  15

Thr Leu Ser Leu Thr Cys Thr Val Ser Gly Phe Ser Leu Thr
            20                  25                  30

<210> SEQ ID NO 907
<211> LENGTH: 14
<212> TYPE: PRT
<213> ORGANISM: Rattus rattus

<400> SEQUENCE: 907

Trp Val Arg Gln Pro Pro Gly Lys Gly Leu Glu Trp Met Gly
1               5                   10

<210> SEQ ID NO 908
<211> LENGTH: 32
<212> TYPE: PRT
<213> ORGANISM: Rattus rattus

<400> SEQUENCE: 908

Arg Leu Ser Ile Ser Arg Asp Thr Ser Lys Ser Gln Val Phe Leu Lys
1               5                   10                  15

Met Asn Ser Leu Gln Thr Glu Asp Thr Ala Thr Tyr Tyr Cys Ala Arg
            20                  25                  30

<210> SEQ ID NO 909
<211> LENGTH: 11
<212> TYPE: PRT
<213> ORGANISM: Rattus rattus

<400> SEQUENCE: 909

Trp Gly Gln Gly Val Met Val Thr Val Ser Ser
1               5                   10

<210> SEQ ID NO 910
<211> LENGTH: 321
<212> TYPE: DNA
<213> ORGANISM: Rattus rattus

<400> SEQUENCE: 910
gacatccaga tgacacagtc tcctgcctcc ctgtctgcat ctctggaaga aattgtcacc      60
atcacatgcc aggcaagcca agacattggt aattggttgg catggtatca gcagaaaccg     120
gggaaatctc ctcagctcct gatttatgat gcaaccagct ggcagatggg gtcccatca     180 cggttcagcg gcagtagatc tggcacacag tattctctta agatcagcag actacaggtt    240
gaagatattg aagctatta ctgtcaccag gctcatagta atcctcggac gttcggtgga     300
ggcaccaagc tggaattgaa a                                               321
```

```
<210> SEQ ID NO 911
<211> LENGTH: 107
<212> TYPE: PRT
<213> ORGANISM: Rattus rattus

<400> SEQUENCE: 911

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ala Trp Tyr Gln Gln Lys Pro Gly Lys Ser Pro Gln Leu Leu Ile
        35                  40                  45

Tyr Asp Ala Thr Ser Leu Ala Asp Gly Val Pro Ser Arg Phe Ser Gly
    50                  55                  60

Ser Arg Ser Gly Thr Gln Tyr Ser Leu Lys Ile Ser Arg Leu Gln Val
65                  70                  75                  80

Glu Asp Ile Gly Ser Tyr Tyr Cys His Gln Ala His Ser Asn Pro Arg
                85                  90                  95

Thr Phe Gly Gly Gly Thr Lys Leu Glu Leu Lys
            100                 105

<210> SEQ ID NO 912
<211> LENGTH: 11
<212> TYPE: PRT
<213> ORGANISM: Rattus rattus

<400> SEQUENCE: 912

Gln Ala Ser Gln Asp Ile Gly Asn Trp Leu Ala
1               5                   10

<210> SEQ ID NO 913
<211> LENGTH: 7
<212> TYPE: PRT
<213> ORGANISM: Rattus rattus

<400> SEQUENCE: 913

Asp Ala Thr Ser Leu Ala Asp
1               5

<210> SEQ ID NO 914
<211> LENGTH: 9
<212> TYPE: PRT
<213> ORGANISM: Rattus rattus

<400> SEQUENCE: 914

His Gln Ala His Ser Asn Pro Arg Thr
1               5

<210> SEQ ID NO 915
<211> LENGTH: 23
<212> TYPE: PRT
<213> ORGANISM: Rattus rattus

<400> SEQUENCE: 915

Asp Ile Gln Met Thr Gln Ser Pro Ala Ser Leu Ser Ala Ser Leu Glu
1               5                   10                  15

Glu Ile Val Thr Ile Thr Cys
            20

<210> SEQ ID NO 916
<211> LENGTH: 15
<212> TYPE: PRT
```

<213> ORGANISM: Rattus rattus

<400> SEQUENCE: 916

Trp Tyr Gln Gln Lys Pro Gly Lys Ser Pro Gln Leu Leu Ile Tyr
1               5                   10                  15

<210> SEQ ID NO 917
<211> LENGTH: 32
<212> TYPE: PRT
<213> ORGANISM: Rattus rattus

<400> SEQUENCE: 917

Gly Val Pro Ser Arg Phe Ser Gly Ser Arg Gly Thr Gln Tyr Ser
1               5                   10                  15

Leu Lys Ile Ser Arg Leu Gln Val Glu Asp Ile Gly Ser Tyr Tyr Cys
            20                  25                  30

<210> SEQ ID NO 918
<211> LENGTH: 10
<212> TYPE: PRT
<213> ORGANISM: Rattus rattus

<400> SEQUENCE: 918

Phe Gly Gly Gly Thr Lys Leu Glu Leu Lys
1               5                   10

<210> SEQ ID NO 919
<211> LENGTH: 366
<212> TYPE: DNA
<213> ORGANISM: Rattus rattus

<400> SEQUENCE: 919
caggtgcagc tgaaggagtc aggacctggc ctggtgaagc cctcagagac cctgtctctc    60
acctgcactg tctctgggtt ctcattaacc aactatcatg taaactgggt tcgacagcct   120
ccaggaaagg gtctggagtg gatgggagta atatggggtg atggaagcac agcatataat   180
tcagctctca aatcccgact gagcatcagc aggacacct cgaagagcca gttttcttta    240
aaaatgaaca gtctgcaaac tgaagacaca gccacttact actgtgccag aggcggggat   300
tactatgatg gtagttatta ctacgagggc tactgggcc aaggagtcat ggtcaccgtc    360
tcctca                                                             366

<210> SEQ ID NO 920
<211> LENGTH: 122
<212> TYPE: PRT
<213> ORGANISM: Rattus rattus

<400> SEQUENCE: 920

Gln Val Gln Leu Lys Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

His Val Asn Trp Val Arg Gln Pro Pro Gly Lys Gly Leu Glu Trp Met
        35                  40                  45

Gly Val Ile Trp Gly Asp Gly Ser Thr Ala Tyr Asn Ser Ala Leu Lys
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Ala Thr Tyr Tyr Cys Ala
                85                  90                  95

Arg Gly Gly Asp Tyr Tyr Asp Gly Ser Tyr Tyr Tyr Glu Gly Tyr Trp
            100                 105                 110
Gly Gln Gly Val Met Val Thr Val Ser Ser
        115                 120

<210> SEQ ID NO 921
<211> LENGTH: 5
<212> TYPE: PRT
<213> ORGANISM: Rattus rattus

<400> SEQUENCE: 921

Asn Tyr His Val Asn
1               5

<210> SEQ ID NO 922
<211> LENGTH: 16
<212> TYPE: PRT
<213> ORGANISM: Rattus rattus

<400> SEQUENCE: 922

Val Ile Trp Gly Asp Gly Ser Thr Ala Tyr Asn Ser Ala Leu Lys Ser
1               5                   10                  15

<210> SEQ ID NO 923
<211> LENGTH: 14
<212> TYPE: PRT
<213> ORGANISM: Rattus rattus

<400> SEQUENCE: 923

Gly Gly Asp Tyr Tyr Asp Gly Ser Tyr Tyr Tyr Glu Gly Tyr
1               5                   10

<210> SEQ ID NO 924
<211> LENGTH: 30
<212> TYPE: PRT
<213> ORGANISM: Rattus rattus

<400> SEQUENCE: 924

Gln Val Gln Leu Lys Glu Ser Gly Pro Gly Leu Val Lys Pro Ser Glu
1               5                   10                  15
Thr Leu Ser Leu Thr Cys Thr Val Ser Gly Phe Ser Leu Thr
            20                  25                  30

<210> SEQ ID NO 925
<211> LENGTH: 14
<212> TYPE: PRT
<213> ORGANISM: Rattus rattus

<400> SEQUENCE: 925

Trp Val Arg Gln Pro Pro Gly Lys Gly Leu Glu Trp Met Gly
1               5                   10

<210> SEQ ID NO 926
<211> LENGTH: 32
<212> TYPE: PRT
<213> ORGANISM: Rattus rattus

<400> SEQUENCE: 926

Arg Leu Ser Ile Ser Arg Asp Thr Ser Lys Ser Gln Val Phe Leu Lys
1               5                   10                  15
Met Asn Ser Leu Gln Thr Glu Asp Thr Ala Thr Tyr Tyr Cys Ala Arg
            20                  25                  30

<210> SEQ ID NO 927
<211> LENGTH: 11
<212> TYPE: PRT
<213> ORGANISM: Rattus rattus

<400> SEQUENCE: 927

Trp Gly Gln Gly Val Met Val Thr Val Ser Ser
1               5                   10

<210> SEQ ID NO 928
<211> LENGTH: 321
<212> TYPE: DNA
<213> ORGANISM: Rattus rattus

<400> SEQUENCE: 928
gacatccaga tgacacagtc tcctgcctcc ctgtctgcat ctctggaaga aattgtcacc      60
atcacatgcc aggcaagcca agacattggt aattggttgg catggtatca gcagaaaccg     120
gggaaatctc ctcaactcct gatttatgat gcaaccagct tggcagatgg ggtcccatca     180
cggttcagcg gcagtagatc tggcacacag tattctctta agatcagcag actacaggtt     240
gaagatattg gaatctatta ctgtctacag gcttatagtg ctccgtggac gttcggtgga     300
ggcaccaagc tggaattgaa a                                              321

<210> SEQ ID NO 929
<211> LENGTH: 107
<212> TYPE: PRT
<213> ORGANISM: Rattus rattus

<400> SEQUENCE: 929

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ala Trp Tyr Gln Gln Lys Pro Gly Lys Ser Pro Gln Leu Leu Ile
        35                  40                  45

Tyr Asp Ala Thr Ser Leu Ala Asp Gly Val Pro Ser Arg Phe Ser Gly
    50                  55                  60

Ser Arg Ser Gly Thr Gln Tyr Ser Leu Lys Ile Ser Arg Leu Gln Val
65                  70                  75                  80

Glu Asp Ile Gly Ile Tyr Tyr Cys Leu Gln Ala Tyr Ser Ala Pro Trp
                85                  90                  95

Thr Phe Gly Gly Gly Thr Lys Leu Glu Leu Lys
            100                 105

<210> SEQ ID NO 930
<211> LENGTH: 11
<212> TYPE: PRT
<213> ORGANISM: Rattus rattus

<400> SEQUENCE: 930

Gln Ala Ser Gln Asp Ile Gly Asn Trp Leu Ala
1               5                   10

<210> SEQ ID NO 931
<211> LENGTH: 7
<212> TYPE: PRT
<213> ORGANISM: Rattus rattus

<400> SEQUENCE: 931

```
Asp Ala Thr Ser Leu Ala Asp
1               5

<210> SEQ ID NO 932
<211> LENGTH: 9
<212> TYPE: PRT
<213> ORGANISM: Rattus rattus

<400> SEQUENCE: 932

Leu Gln Ala Tyr Ser Ala Pro Trp Thr
1               5

<210> SEQ ID NO 933
<211> LENGTH: 23
<212> TYPE: PRT
<213> ORGANISM: Rattus rattus

<400> SEQUENCE: 933

Asp Ile Gln Met Thr Gln Ser Pro Ala Ser Leu Ser Ala Ser Leu Glu
1               5                   10                  15

Glu Ile Val Thr Ile Thr Cys
            20

<210> SEQ ID NO 934
<211> LENGTH: 15
<212> TYPE: PRT
<213> ORGANISM: Rattus rattus

<400> SEQUENCE: 934

Trp Tyr Gln Gln Lys Pro Gly Lys Ser Pro Gln Leu Leu Ile Tyr
1               5                   10                  15

<210> SEQ ID NO 935
<211> LENGTH: 32
<212> TYPE: PRT
<213> ORGANISM: Rattus rattus

<400> SEQUENCE: 935

Gly Val Pro Ser Arg Phe Ser Gly Ser Arg Ser Gly Thr Gln Tyr Ser
1               5                   10                  15

Leu Lys Ile Ser Arg Leu Gln Val Glu Asp Ile Gly Ile Tyr Tyr Cys
            20                  25                  30

<210> SEQ ID NO 936
<211> LENGTH: 10
<212> TYPE: PRT
<213> ORGANISM: Rattus rattus

<400> SEQUENCE: 936

Phe Gly Gly Gly Thr Lys Leu Glu Leu Lys
1               5                   10

<210> SEQ ID NO 937
<211> LENGTH: 360
<212> TYPE: DNA
<213> ORGANISM: Mus musculus

<400> SEQUENCE: 937
caggtgcagc tgaaggagtc tggacctggc ctggtggcgc cctcacagag cctgtccatc      60
acttgcactg tctctgggtt ttcattaacc acctatggta tacactgggt tcgccagcct     120
ccaggaaagg gtctggagtg gctgggagta atatggactc gtggaagcac aaattataat     180
tcggctctca tgtccagact gagcatcagc aaagacaact ccaagagcca gttttctta      240
```

```
aaaatgaaca gtctgcaaac tgatgacaca gccatgtact tctgtgccag agatggttac      300
tacggttatt actatgcttt ggactactgg ggtcaaggaa cctcagtcac cgtctcctca      360
```

<210> SEQ ID NO 938
<211> LENGTH: 120
<212> TYPE: PRT
<213> ORGANISM: Mus musculus

<400> SEQUENCE: 938

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Tyr
            20                  25                  30

Gly Ile His Trp Val Arg Gln Pro Pro Gly Lys Gly Leu Glu Trp Leu
        35                  40                  45

Gly Val Ile Trp Thr Arg Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Phe Cys Ala
                85                  90                  95

Arg Asp Gly Tyr Tyr Gly Tyr Tyr Tyr Ala Leu Asp Tyr Trp Gly Gln
            100                 105                 110

Gly Thr Ser Val Thr Val Ser Ser
        115                 120

<210> SEQ ID NO 939
<211> LENGTH: 5
<212> TYPE: PRT
<213> ORGANISM: Mus musculus

<400> SEQUENCE: 939

Thr Tyr Gly Ile His
1               5

<210> SEQ ID NO 940
<211> LENGTH: 16
<212> TYPE: PRT
<213> ORGANISM: Mus musculus

<400> SEQUENCE: 940

Val Ile Trp Thr Arg Gly Ser Thr Asn Tyr Asn Ser Ala Leu Met Ser
1               5                   10                  15

<210> SEQ ID NO 941
<211> LENGTH: 12
<212> TYPE: PRT
<213> ORGANISM: Mus musculus

<400> SEQUENCE: 941

Asp Gly Tyr Tyr Gly Tyr Tyr Tyr Ala Leu Asp Tyr
1               5                   10

<210> SEQ ID NO 942
<211> LENGTH: 30
<212> TYPE: PRT
<213> ORGANISM: Mus musculus

<400> SEQUENCE: 942

Gln Val Gln Leu Lys Glu Ser Gly Pro Gly Leu Val Ala Pro Ser Gln

```
                1               5                  10                  15
Ser Leu Ser Ile Thr Cys Thr Val Ser Gly Phe Ser Leu Thr
            20                  25                  30

<210> SEQ ID NO 943
<211> LENGTH: 14
<212> TYPE: PRT
<213> ORGANISM: Mus musculus

<400> SEQUENCE: 943

Trp Val Arg Gln Pro Pro Gly Lys Gly Leu Glu Trp Leu Gly
1               5                   10

<210> SEQ ID NO 944
<211> LENGTH: 32
<212> TYPE: PRT
<213> ORGANISM: Mus musculus

<400> SEQUENCE: 944

Arg Leu Ser Ile Ser Lys Asp Asn Ser Lys Ser Gln Val Phe Leu Lys
1               5                   10                  15

Met Asn Ser Leu Gln Thr Asp Asp Thr Ala Met Tyr Phe Cys Ala Arg
            20                  25                  30

<210> SEQ ID NO 945
<211> LENGTH: 11
<212> TYPE: PRT
<213> ORGANISM: Mus musculus

<400> SEQUENCE: 945

Trp Gly Gln Gly Thr Ser Val Thr Val Ser Ser
1               5                   10

<210> SEQ ID NO 946
<211> LENGTH: 321
<212> TYPE: DNA
<213> ORGANISM: Mus musculus

<400> SEQUENCE: 946
caaattgttc tcaaacagtc tccagcaatc atgtctgcat ctccagggga gaaggtcacc      60
atgacctgca gtgccagctc aagtgtaagt tacatgtact ggtaccagca gaagccagga     120
tcctccccca gactcctgat ttatgacaca tccaacctgg cttctggagt ccctgttcgc     180
ttcagttaca gtgggtctgg gacctcttac tctctcacaa tcagccgaat ggaggctgaa     240
gatgctgcca cttattactg ccagcagtgg agtagttacc cacccatgac gttcggtgga     300
ggcaccaagc tggaaatcaa a                                               321

<210> SEQ ID NO 947
<211> LENGTH: 107
<212> TYPE: PRT
<213> ORGANISM: Mus musculus

<400> SEQUENCE: 947

Gln Ile Val Leu Lys Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Tyr Ser
```

```
                    50                  55                  60
Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Trp Ser Ser Tyr Pro Pro Met
                 85                  90                  95

Thr Phe Gly Gly Gly Thr Lys Leu Glu Ile Lys
            100                 105
```

<210> SEQ ID NO 948
<211> LENGTH: 10
<212> TYPE: PRT
<213> ORGANISM: Mus musculus

<400> SEQUENCE: 948

```
Ser Ala Ser Ser Val Ser Tyr Met Tyr
1               5                   10
```

<210> SEQ ID NO 949
<211> LENGTH: 7
<212> TYPE: PRT
<213> ORGANISM: Mus musculus

<400> SEQUENCE: 949

```
Asp Thr Ser Asn Leu Ala Ser
1               5
```

<210> SEQ ID NO 950
<211> LENGTH: 10
<212> TYPE: PRT
<213> ORGANISM: Mus musculus

<400> SEQUENCE: 950

```
Gln Gln Trp Ser Ser Tyr Pro Pro Met Thr
1               5                   10
```

<210> SEQ ID NO 951
<211> LENGTH: 23
<212> TYPE: PRT
<213> ORGANISM: Mus musculus

<400> SEQUENCE: 951

```
Gln Ile Val Leu Lys Gln Ser Pro Ala Ile Met Ser Ala Ser Pro Gly
1               5                   10                  15

Glu Lys Val Thr Met Thr Cys
            20
```

<210> SEQ ID NO 952
<211> LENGTH: 15
<212> TYPE: PRT
<213> ORGANISM: Mus musculus

<400> SEQUENCE: 952

```
Trp Tyr Gln Gln Lys Pro Gly Ser Ser Pro Arg Leu Leu Ile Tyr
1               5                   10                  15
```

<210> SEQ ID NO 953
<211> LENGTH: 32
<212> TYPE: PRT
<213> ORGANISM: Mus musculus

<400> SEQUENCE: 953

```
Gly Val Pro Val Arg Phe Ser Tyr Ser Gly Ser Gly Thr Ser Tyr Ser
1               5                   10                  15
```

Leu Thr Ile Ser Arg Met Glu Ala Glu Asp Ala Ala Thr Tyr Tyr Cys
            20                  25                  30

<210> SEQ ID NO 954
<211> LENGTH: 10
<212> TYPE: PRT
<213> ORGANISM: Mus musculus

<400> SEQUENCE: 954

Phe Gly Gly Gly Thr Lys Leu Glu Ile Lys
1               5                   10

<210> SEQ ID NO 955
<211> LENGTH: 369
<212> TYPE: DNA
<213> ORGANISM: Mus musculus

<400> SEQUENCE: 955
caggtccagc ttcagcagtc tggggctgaa ctggcaaaac ccggggcctc agtgaggatg      60
tcctgcaaga cttctggcta cacctttagt acctactgga tgcactgggt aaaacagagg     120
cctggacagg gtctggaatg gattggatac attaatcctc ccactggtta tactgagtat     180
aatcagaagt tcaaggacaa ggccacattg actgcagaca atcctccag cacagcctac      240 atgcaactga tcagcctgac atctgaagac tctgcagtct attactgtgt gcatgagggg     300
ggtatgatta cgaccgactt tcatgctttg gactactggg gtcaaggaac ctcagtcacc     360
gtctcctca                                                             369

<210> SEQ ID NO 956
<211> LENGTH: 123
<212> TYPE: PRT
<213> ORGANISM: Mus musculus

<400> SEQUENCE: 956

Gln Val Gln Leu Gln Gln Ser Gly Ala Glu Leu Ala Lys Pro Gly Ala
1               5                   10                  15

Ser Val Arg Met Ser Cys Lys Thr Ser Gly Tyr Thr Phe Ser Thr Tyr
            20                  25                  30

Trp Met His Trp Val Lys Gln Arg Pro Gly Gln Gly Leu Glu Trp Ile
        35                  40                  45

Gly Tyr Ile Asn Pro Pro Thr Gly Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ile Ser Leu Thr Ser Glu Asp Ser Ala Val Tyr Tyr Cys
                85                  90                  95

Val His Glu Gly Gly Met Ile Thr Thr Asp Phe His Ala Leu Asp Tyr
            100                 105                 110

Trp Gly Gln Gly Thr Ser Val Thr Val Ser Ser
        115                 120

<210> SEQ ID NO 957
<211> LENGTH: 5
<212> TYPE: PRT
<213> ORGANISM: Mus musculus

<400> SEQUENCE: 957

Thr Tyr Trp Met His
1               5

<210> SEQ ID NO 958
<211> LENGTH: 17
<212> TYPE: PRT
<213> ORGANISM: Mus musculus

<400> SEQUENCE: 958

Tyr Ile Asn Pro Pro Thr Gly Tyr Thr Glu Tyr Asn Gln Lys Phe Lys
1               5                   10                  15

Asp

<210> SEQ ID NO 959
<211> LENGTH: 14
<212> TYPE: PRT
<213> ORGANISM: Mus musculus

<400> SEQUENCE: 959

Glu Gly Gly Met Ile Thr Thr Asp Phe His Ala Leu Asp Tyr
1               5                   10

<210> SEQ ID NO 960
<211> LENGTH: 30
<212> TYPE: PRT
<213> ORGANISM: Mus musculus

<400> SEQUENCE: 960

Gln Val Gln Leu Gln Gln Ser Gly Ala Glu Leu Ala Lys Pro Gly Ala
1               5                   10                  15

Ser Val Arg Met Ser Cys Lys Thr Ser Gly Tyr Thr Phe Ser
            20                  25                  30

<210> SEQ ID NO 961
<211> LENGTH: 14
<212> TYPE: PRT
<213> ORGANISM: Mus musculus

<400> SEQUENCE: 961

Trp Val Lys Gln Arg Pro Gly Gln Gly Leu Glu Trp Ile Gly
1               5                   10

<210> SEQ ID NO 962
<211> LENGTH: 32
<212> TYPE: PRT
<213> ORGANISM: Mus musculus

<400> SEQUENCE: 962

Lys Ala Thr Leu Thr Ala Asp Lys Ser Ser Ser Thr Ala Tyr Met Gln
1               5                   10                  15

Leu Ile Ser Leu Thr Ser Glu Asp Ser Ala Val Tyr Tyr Cys Val His
            20                  25                  30

<210> SEQ ID NO 963
<211> LENGTH: 11
<212> TYPE: PRT
<213> ORGANISM: Mus musculus

<400> SEQUENCE: 963

Trp Gly Gln Gly Thr Ser Val Thr Val Ser Ser
1               5                   10

<210> SEQ ID NO 964
<211> LENGTH: 336
<212> TYPE: DNA

<213> ORGANISM: Mus musculus

<400> SEQUENCE: 964

```
gacattgtga tgtcacagtc tccatcctcc ctggctgtgt cagcaggaga gaaggtcact    60
atgagctgca atccagtca gagtctgctc aacagtagaa cccgaaagaa ctacttggct   120
tggtaccagc agaaaccagg gcagtctcct aaactgctga tctactgggc atccactagg   180
gaatctgggg tccctgatcg cttcacaggc agtggatctg ggacagattt cactctcacc   240
atcagcagtg tgcaggctga agacctggca gtttattact gcaagcaatc ttataatctg   300
tacacgttcg gagggggac caagctggaa ataaaa                              336
```

<210> SEQ ID NO 965
<211> LENGTH: 112
<212> TYPE: PRT
<213> ORGANISM: Mus musculus

<400> SEQUENCE: 965

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Tyr Thr Phe Gly Gly Gly Thr Lys Leu Glu Ile Lys
            100                 105                 110

<210> SEQ ID NO 966
<211> LENGTH: 17
<212> TYPE: PRT
<213> ORGANISM: Mus musculus

<400> SEQUENCE: 966

Lys Ser Ser Gln Ser Leu Leu Asn Ser Arg Thr Arg Lys Asn Tyr Leu
1               5                   10                  15

Ala

<210> SEQ ID NO 967
<211> LENGTH: 7
<212> TYPE: PRT
<213> ORGANISM: Mus musculus

<400> SEQUENCE: 967

Trp Ala Ser Thr Arg Glu Ser
1               5

<210> SEQ ID NO 968
<211> LENGTH: 8
<212> TYPE: PRT
<213> ORGANISM: Mus musculus

<400> SEQUENCE: 968

Lys Gln Ser Tyr Asn Leu Tyr Thr
1               5

<210> SEQ ID NO 969
<211> LENGTH: 23
<212> TYPE: PRT
<213> ORGANISM: Mus musculus

<400> SEQUENCE: 969

Asp Ile Val Met Ser Gln Ser Pro Ser Ser Leu Ala Val Ser Ala Gly
1               5                   10                  15

Glu Lys Val Thr Met Ser Cys
            20

<210> SEQ ID NO 970
<211> LENGTH: 15
<212> TYPE: PRT
<213> ORGANISM: Mus musculus

<400> SEQUENCE: 970

Trp Tyr Gln Gln Lys Pro Gly Gln Ser Pro Lys Leu Leu Ile Tyr
1               5                   10                  15

<210> SEQ ID NO 971
<211> LENGTH: 32
<212> TYPE: PRT
<213> ORGANISM: Mus musculus

<400> SEQUENCE: 971

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 972
<211> LENGTH: 10
<212> TYPE: PRT
<213> ORGANISM: Mus musculus

<400> SEQUENCE: 972

Phe Gly Gly Gly Thr Lys Leu Glu Ile Lys
1               5                   10

<210> SEQ ID NO 973
<211> LENGTH: 360
<212> TYPE: DNA
<213> ORGANISM: Mus musculus

<400> SEQUENCE: 973
caggtgcagc tgaagcagtc aggacctggc ctagtgcagc cctcacagag cctgtccatc      60
acctgcacag tctctggttt ctcattaact acctatggtg tacactgggt tcgccagtct     120
ccaggaaagg gtctggagtg gctgggagtg atatggagtg gtggatccac agactataat     180
gcagctttca tatccagact gagcatcacc aaggacaatt ccaagagcca agttttcttt     240
aaaatgaaca gtctgcaagc taatgacaca gccatatatt actgtgccag ggatggttac     300
tacgcccttt actatgctat ggactactgg ggtcaaggaa cctcagtcac cgtctcctca     360

<210> SEQ ID NO 974
<211> LENGTH: 120
<212> TYPE: PRT
<213> ORGANISM: Mus musculus

<400> SEQUENCE: 974

-continued

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Thr Tyr
            20                  25                  30

Gly Val His Trp Val Arg Gln Ser Pro Gly Lys Gly Leu Glu Trp Leu
            35                  40                  45

Gly Val Ile Trp Ser Gly Gly Ser Thr Asp Tyr Asn Ala Ala Phe Ile
        50                  55                  60

Ser Arg Leu Ser Ile Thr Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala
                85                  90                  95

Arg Asp Gly Tyr Tyr Ala Leu Tyr Tyr Ala Met Asp Tyr Trp Gly Gln
            100                 105                 110

Gly Thr Ser Val Thr Val Ser Ser
        115                 120

<210> SEQ ID NO 975
<211> LENGTH: 5
<212> TYPE: PRT
<213> ORGANISM: Mus musculus

<400> SEQUENCE: 975

Thr Tyr Gly Val His
1               5

<210> SEQ ID NO 976
<211> LENGTH: 16
<212> TYPE: PRT
<213> ORGANISM: Mus musculus

<400> SEQUENCE: 976

Val Ile Trp Ser Gly Gly Ser Thr Asp Tyr Asn Ala Ala Phe Ile Ser
1               5                   10                  15

<210> SEQ ID NO 977
<211> LENGTH: 12
<212> TYPE: PRT
<213> ORGANISM: Mus musculus

<400> SEQUENCE: 977

Asp Gly Tyr Tyr Ala Leu Tyr Tyr Ala Met Asp Tyr
1               5                   10

<210> SEQ ID NO 978
<211> LENGTH: 30
<212> TYPE: PRT
<213> ORGANISM: Mus musculus

<400> SEQUENCE: 978

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr
            20                  25                  30

<210> SEQ ID NO 979
<211> LENGTH: 14
<212> TYPE: PRT
<213> ORGANISM: Mus musculus

<400> SEQUENCE: 979
```

Trp Val Arg Gln Ser Pro Gly Lys Gly Leu Glu Trp Leu Gly
1               5                   10

<210> SEQ ID NO 980
<211> LENGTH: 32
<212> TYPE: PRT
<213> ORGANISM: Mus musculus

<400> SEQUENCE: 980

Arg Leu Ser Ile Thr Lys Asp Asn Ser Lys Ser Gln Val Phe Phe Lys
1               5                   10                  15

Met Asn Ser Leu Gln Ala Asn Asp Thr Ala Ile Tyr Tyr Cys Ala Arg
            20                  25                  30

<210> SEQ ID NO 981
<211> LENGTH: 11
<212> TYPE: PRT
<213> ORGANISM: Mus musculus

<400> SEQUENCE: 981

Trp Gly Gln Gly Thr Ser Val Thr Val Ser Ser
1               5                   10

<210> SEQ ID NO 982
<211> LENGTH: 321
<212> TYPE: DNA
<213> ORGANISM: Mus musculus

<400> SEQUENCE: 982
gacattgtga tgacccagtc tcacaaattc atgtccacat cagtaggaga cagggtcagc       60
atcacctgca aggccagtca ggatgtgagt actgctgtag cctggtatca acagaaacca      120
ggacaatctc ctaaactact gatttactcg gcatcctacc ggtacactgg agtccctgat      180
cgcttcactg gcagtggatc tgggacggat ttcactttca ccatcagcag tgtgcaggct      240
gaagacctgg cagtttatta ctgtcagcaa cattatagta ctccgtggac gttcggtgga      300
ggcaccaagc tggaaatcaa a                                                321

<210> SEQ ID NO 983
<211> LENGTH: 107
<212> TYPE: PRT
<213> ORGANISM: Mus musculus

<400> SEQUENCE: 983

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys
            100                 105

<210> SEQ ID NO 984

<211> LENGTH: 11
<212> TYPE: PRT
<213> ORGANISM: Mus musculus

<400> SEQUENCE: 984

Lys Ala Ser Gln Asp Val Ser Thr Ala Val Ala
1               5                   10

<210> SEQ ID NO 985
<211> LENGTH: 7
<212> TYPE: PRT
<213> ORGANISM: Mus musculus

<400> SEQUENCE: 985

Ser Ala Ser Tyr Arg Tyr Thr
1               5

<210> SEQ ID NO 986
<211> LENGTH: 9
<212> TYPE: PRT
<213> ORGANISM: Mus musculus

<400> SEQUENCE: 986

Gln Gln His Tyr Ser Thr Pro Trp Thr
1               5

<210> SEQ ID NO 987
<211> LENGTH: 23
<212> TYPE: PRT
<213> ORGANISM: Mus musculus

<400> SEQUENCE: 987

Asp Ile Val Met Thr Gln Ser His Lys Phe Met Ser Thr Ser Val Gly
1               5                   10                  15

Asp Arg Val Ser Ile Thr Cys
            20

<210> SEQ ID NO 988
<211> LENGTH: 15
<212> TYPE: PRT
<213> ORGANISM: Mus musculus

<400> SEQUENCE: 988

Trp Tyr Gln Gln Lys Pro Gly Gln Ser Pro Lys Leu Leu Ile Tyr
1               5                   10                  15

<210> SEQ ID NO 989
<211> LENGTH: 32
<212> TYPE: PRT
<213> ORGANISM: Mus musculus

<400> SEQUENCE: 989

Gly Val Pro Asp Arg Phe Thr Gly Ser Gly Ser Gly Thr Asp Phe Thr
1               5                   10                  15

Phe Thr Ile Ser Ser Val Gln Ala Glu Asp Leu Ala Val Tyr Tyr Cys
            20                  25                  30

<210> SEQ ID NO 990
<211> LENGTH: 10
<212> TYPE: PRT
<213> ORGANISM: Mus musculus

<400> SEQUENCE: 990

Phe Gly Gly Gly Thr Lys Leu Glu Ile Lys

<210> SEQ ID NO 991
<211> LENGTH: 354
<212> TYPE: DNA
<213> ORGANISM: Rattus rattus

<400> SEQUENCE: 991

```
caggtgcagc tgaaggagtc aggacctggc ctggtgaagc cctcagagac cctgtctctc    60
acctgcactg tgtctgggtt ctcattaacc aactatccta taagctgggt tcgacagcct   120
ccaggaaagg gtctggagtg gatgggagta atatggggtg atggaagcac atcatataat   180
ttagctctca atcccgact gagcatcagc aggacacct cgaagagcca agttttatta   240
aaaatgaaca gtctggaaac tgaagacaca gccacttact actgtgccag agtaggagta   300
tactacggat tattaggtta ctggggccaa ggagtcatgg tcaccgtctc ctca         354
```

<210> SEQ ID NO 992
<211> LENGTH: 118
<212> TYPE: PRT
<213> ORGANISM: Rattus rattus

<400> SEQUENCE: 992

Gln Val Gln Leu Lys Glu Ser Gly Pro Gly Leu Val Lys Pro Ser Glu
1               5                   10                  15
Thr Leu Ser Leu Thr Cys Thr Val Ser Gly Phe Ser Leu Thr Asn Tyr
            20                  25                  30
Pro Ile Ser Trp Val Arg Gln Pro Pro Gly Lys Gly Leu Glu Trp Met
        35                  40                  45
Gly Val Ile Trp Gly Asp Gly Ser Thr Ser Tyr Asn Leu Ala Leu Lys
    50                  55                  60
Ser Arg Leu Ser Ile Ser Arg Asp Thr Ser Lys Ser Gln Val Leu Leu
65                  70                  75                  80
Lys Met Asn Ser Leu Glu Thr Glu Asp Thr Ala Thr Tyr Tyr Cys Ala
                85                  90                  95
Arg Val Gly Val Tyr Tyr Gly Leu Leu Gly Tyr Trp Gly Gln Gly Val
            100                 105                 110
Met Val Thr Val Ser Ser
        115

<210> SEQ ID NO 993
<211> LENGTH: 5
<212> TYPE: PRT
<213> ORGANISM: Rattus rattus

<400> SEQUENCE: 993

Asn Tyr Pro Ile Ser
1               5

<210> SEQ ID NO 994
<211> LENGTH: 16
<212> TYPE: PRT
<213> ORGANISM: Rattus rattus

<400> SEQUENCE: 994

Val Ile Trp Gly Asp Gly Ser Thr Ser Tyr Asn Leu Ala Leu Lys Ser
1               5                   10                  15

<210> SEQ ID NO 995
<211> LENGTH: 10

```
<212> TYPE: PRT
<213> ORGANISM: Rattus rattus

<400> SEQUENCE: 995

Val Gly Val Tyr Tyr Gly Leu Leu Gly Tyr
1               5                   10

<210> SEQ ID NO 996
<211> LENGTH: 30
<212> TYPE: PRT
<213> ORGANISM: Rattus rattus

<400> SEQUENCE: 996

Gln Val Gln Leu Lys Glu Ser Gly Pro Gly Leu Val Lys Pro Ser Glu
1               5                   10                  15

Thr Leu Ser Leu Thr Cys Thr Val Ser Gly Phe Ser Leu Thr
            20                  25                  30

<210> SEQ ID NO 997
<211> LENGTH: 14
<212> TYPE: PRT
<213> ORGANISM: Rattus rattus

<400> SEQUENCE: 997

Trp Val Arg Gln Pro Pro Gly Lys Gly Leu Glu Trp Met Gly
1               5                   10

<210> SEQ ID NO 998
<211> LENGTH: 32
<212> TYPE: PRT
<213> ORGANISM: Rattus rattus

<400> SEQUENCE: 998

Arg Leu Ser Ile Ser Arg Asp Thr Ser Lys Ser Gln Val Leu Leu Lys
1               5                   10                  15

Met Asn Ser Leu Glu Thr Glu Asp Thr Ala Thr Tyr Tyr Cys Ala Arg
            20                  25                  30

<210> SEQ ID NO 999
<211> LENGTH: 11
<212> TYPE: PRT
<213> ORGANISM: Rattus rattus

<400> SEQUENCE: 999

Trp Gly Gln Gly Val Met Val Thr Val Ser Ser
1               5                   10

<210> SEQ ID NO 1000
<211> LENGTH: 321
<212> TYPE: DNA
<213> ORGANISM: Rattus rattus

<400> SEQUENCE: 1000
aacactgtga tgactcagtc tcccacatcc atgttcagat cagtaggaga cagggtcacc      60
atgaactgca aggccagtca gaatgtgggt actaatgtag actggtacca acagaaaaca     120
gggcagtctc ctaaactgct tatctatggg gcatccaacc ggtacactgg agtccctgat     180
cgcttcacag gcagtggatc tggaacagat ttcactctca ccatcagcaa catgcaggct     240
gaagacttgg ctgtttatta ctgtttacag tataactaca atccgtacac gtttggagct     300
gggaccaagc tggaactgaa a                                               321
```

<210> SEQ ID NO 1001
<211> LENGTH: 107
<212> TYPE: PRT
<213> ORGANISM: Rattus rattus

<400> SEQUENCE: 1001

Asn Thr Val Met Thr Gln Ser Pro Thr Ser Met Phe Arg Ser Val Gly
1               5                   10                  15

Asp Arg Val Thr Met Asn Cys Lys Ala Ser Gln Asn Val Gly Thr Asn
            20                  25                  30

Val Asp Trp Tyr Gln Gln Lys Thr Gly Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ala
65                  70                  75                  80

Glu Asp Leu Ala Val Tyr Tyr Cys Leu Gln Tyr Asn Tyr Asn Pro Tyr
                85                  90                  95

Thr Phe Gly Ala Gly Thr Lys Leu Glu Leu Lys
            100                 105

<210> SEQ ID NO 1002
<211> LENGTH: 11
<212> TYPE: PRT
<213> ORGANISM: Rattus rattus

<400> SEQUENCE: 1002

Lys Ala Ser Gln Asn Val Gly Thr Asn Val Asp
1               5                   10

<210> SEQ ID NO 1003
<211> LENGTH: 7
<212> TYPE: PRT
<213> ORGANISM: Rattus rattus

<400> SEQUENCE: 1003

Gly Ala Ser Asn Arg Tyr Thr
1               5

<210> SEQ ID NO 1004
<211> LENGTH: 9
<212> TYPE: PRT
<213> ORGANISM: Rattus rattus

<400> SEQUENCE: 1004

Leu Gln Tyr Asn Tyr Asn Pro Tyr Thr
1               5

<210> SEQ ID NO 1005
<211> LENGTH: 23
<212> TYPE: PRT
<213> ORGANISM: Rattus rattus

<400> SEQUENCE: 1005

Asn Thr Val Met Thr Gln Ser Pro Thr Ser Met Phe Arg Ser Val Gly
1               5                   10                  15

Asp Arg Val Thr Met Asn Cys
            20

<210> SEQ ID NO 1006
<211> LENGTH: 15
<212> TYPE: PRT

```
<213> ORGANISM: Rattus rattus

<400> SEQUENCE: 1006

Trp Tyr Gln Gln Lys Thr Gly Gln Ser Pro Lys Leu Leu Ile Tyr
1               5                   10                  15

<210> SEQ ID NO 1007
<211> LENGTH: 32
<212> TYPE: PRT
<213> ORGANISM: Rattus rattus

<400> SEQUENCE: 1007

Gly Val Pro Asp Arg Phe Thr Gly Ser Gly Ser Gly Thr Asp Phe Thr
1               5                   10                  15

Leu Thr Ile Ser Asn Met Gln Ala Glu Asp Leu Ala Val Tyr Tyr Cys
            20                  25                  30

<210> SEQ ID NO 1008
<211> LENGTH: 10
<212> TYPE: PRT
<213> ORGANISM: Rattus rattus

<400> SEQUENCE: 1008

Phe Gly Ala Gly Thr Lys Leu Glu Leu Lys
1               5                   10

<210> SEQ ID NO 1009
<211> LENGTH: 5
<212> TYPE: PRT
<213> ORGANISM: Artificial Sequence
<220> FEATURE:
<223> OTHER INFORMATION: heavy chain variable region CDR1
<220> FEATURE:
<221> NAME/KEY: MISC_FEATURE
<222> LOCATION: (1)..(1)
<223> OTHER INFORMATION: Xaa is G, N, S, D, or R
<220> FEATURE:
<221> NAME/KEY: MISC_FEATURE
<222> LOCATION: (2)..(2)
<223> OTHER INFORMATION: Xaa is Y, A, H, F, or S
<220> FEATURE:
<221> NAME/KEY: MISC_FEATURE
<222> LOCATION: (3)..(3)
<223> OTHER INFORMATION: Xaa is A, W, Y, S, G, F, W, E, D, or P
<220> FEATURE:
<221> NAME/KEY: MISC_FEATURE
<222> LOCATION: (4)..(4)
<223> OTHER INFORMATION: Xaa is M, I, W, L, I, F, or V
<220> FEATURE:
<221> NAME/KEY: MISC_FEATURE
<222> LOCATION: (5)..(5)
<223> OTHER INFORMATION: Xaa is S, G, T, H, or N

<400> SEQUENCE: 1009

Xaa Xaa Xaa Xaa Xaa
1               5

<210> SEQ ID NO 1010
<211> LENGTH: 16
<212> TYPE: PRT
<213> ORGANISM: Artificial Sequence
<220> FEATURE:
<223> OTHER INFORMATION: heavy chain variable region CDR2
<220> FEATURE:
<221> NAME/KEY: MISC_FEATURE
<222> LOCATION: (1)..(1)
<223> OTHER INFORMATION: Xaa is A, R, I, T, E, S, A, V, W, N, G, E, R,
      or Y
<220> FEATURE:
<221> NAME/KEY: MISC_FEATURE
```

```
<222> LOCATION: (2)..(2)
<223> OTHER INFORMATION: Xaa is I or M
<220> FEATURE:
<221> NAME/KEY: MISC_FEATURE
<222> LOCATION: (3)..(3)
<223> OTHER INFORMATION: Xaa is S, K, Y, D, N, W, or I
<220> FEATURE:
<221> NAME/KEY: MISC_FEATURE
<222> LOCATION: (3)..(4)
<223> OTHER INFORMATION: optional insertion of 1-3 amino acids XaXbXc
      between positions 3 and 4, wherein Xa is G, S, P, W, Y, E, A, R,
      or N; and XbXc are KT, respectively
<220> FEATURE:
<221> NAME/KEY: MISC_FEATURE
<222> LOCATION: (4)..(4)
<223> OTHER INFORMATION: Xaa is S, D, G, H, N, R, Y, or V
<220> FEATURE:
<221> NAME/KEY: MISC_FEATURE
<222> LOCATION: (5)..(5)
<223> OTHER INFORMATION: Xaa is G, D, S, F, N, R, F, D, or T
<220> FEATURE:
<221> NAME/KEY: MISC_FEATURE
<222> LOCATION: (6)..(6)
<223> OTHER INFORMATION: Xaa is G, S, N, or T
<220> FEATURE:
<221> NAME/KEY: MISC_FEATURE
<222> LOCATION: (7)..(7)
<223> OTHER INFORMATION: Xaa is S, T, D, Y, N, A, E, M, F, or D
<220> FEATURE:
<221> NAME/KEY: MISC_FEATURE
<222> LOCATION: (8)..(8)
<223> OTHER INFORMATION: Xaa is T, I, K, or A
<220> FEATURE:
<221> NAME/KEY: MISC_FEATURE
<222> LOCATION: (9)..(9)
<223> OTHER INFORMATION: Xaa is Y, D, R, N, G, Q, E, H, or K
<220> FEATURE:
<221> NAME/KEY: MISC_FEATURE
<222> LOCATION: (10)..(10)
<223> OTHER INFORMATION: Xaa is Y, Q, S, or V
<220> FEATURE:
<221> NAME/KEY: MISC_FEATURE
<222> LOCATION: (11)..(11)
<223> OTHER INFORMATION: Xaa is A, S, N, or V
<220> FEATURE:
<221> NAME/KEY: MISC_FEATURE
<222> LOCATION: (12)..(12)
<223> OTHER INFORMATION: Xaa is D, A, P, R, or Q
<220> FEATURE:
<221> NAME/KEY: MISC_FEATURE
<222> LOCATION: (13)..(13)
<223> OTHER INFORMATION: Xaa is S, P, K, or N
<220> FEATURE:
<221> NAME/KEY: MISC_FEATURE
<222> LOCATION: (14)..(14)
<223> OTHER INFORMATION: Xaa is V, F, L, or A
<220> FEATURE:
<221> NAME/KEY: MISC_FEATURE
<222> LOCATION: (15)..(15)
<223> OTHER INFORMATION: Xaa is K, Q, or E
<220> FEATURE:
<221> NAME/KEY: MISC_FEATURE
<222> LOCATION: (16)..(16)
<223> OTHER INFORMATION: Xaa is G, S, A, or D

<400> SEQUENCE: 1010

Xaa Xaa Xaa Xaa Xaa Xaa Xaa Xaa Xaa Xaa Xaa Xaa Xaa Xaa Xaa Xaa
1               5                   10                  15

<210> SEQ ID NO 1011
<211> LENGTH: 8
<212> TYPE: PRT
<213> ORGANISM: Artificial Sequence
<220> FEATURE:
<223> OTHER INFORMATION: heavy chain variable region CDR3
<220> FEATURE:
<221> NAME/KEY: MISC_FEATURE
```

```
<222> LOCATION: (1)..(1)
<223> OTHER INFORMATION: Xaa is E, N, D, R, K, G, S, A, Y, V, P, or H
<220> FEATURE:
<221> NAME/KEY: MISC_FEATURE
<222> LOCATION: (2)..(2)
<223> OTHER INFORMATION: Xaa is E, L, R, Q, T, G, F, P, Y, K, A, S, V,
      or F
<220> FEATURE:
<221> NAME/KEY: MISC_FEATURE
<222> LOCATION: (3)..(3)
<223> OTHER INFORMATION: Xaa is R, A, T, G, V, S, M, W, Y, D, H, N, E,
      L, or I
<220> FEATURE:
<221> NAME/KEY: MISC_FEATURE
<222> LOCATION: (4)..(4)
<223> OTHER INFORMATION: Xaa is G, L, R, D, T, G, Y, S, E, F, Q, C, I,
      M, V, N, K, or P
<220> FEATURE:
<221> NAME/KEY: MISC_FEATURE
<222> LOCATION: (5)..(5)
<223> OTHER INFORMATION: Xaa is S, G, Y, D, W, T, S, N, I, D, V, E, or C
<220> FEATURE:
<221> NAME/KEY: MISC_FEATURE
<222> LOCATION: (6)..(6)
<223> OTHER INFORMATION: Xaa is Y, A, S, W, T, L, G, E, F, K, V, I, or D
<220> FEATURE:
<221> NAME/KEY: MISC_FEATURE
<222> LOCATION: (7)..(7)
<223> OTHER INFORMATION: Xaa is D, E, or G
<220> FEATURE:
<221> NAME/KEY: MISC_FEATURE
<222> LOCATION: (8)..(8)
<223> OTHER INFORMATION: Xaa is Y, S, V, L, M, Q, I, S, I, H, F, or D

<400> SEQUENCE: 1011

Xaa Xaa Xaa Xaa Xaa Xaa Xaa Xaa
1               5

<210> SEQ ID NO 1012
<211> LENGTH: 14
<212> TYPE: PRT
<213> ORGANISM: Artificial Sequence
<220> FEATURE:
<223> OTHER INFORMATION: optional insertion in heavy chain variable
      region CDR3
<220> FEATURE:
<221> NAME/KEY: MISC_FEATURE
<222> LOCATION: (1)..(1)
<223> OTHER INFORMATION: Xaa is F, R, S, Y, L, D, G, V, I, T, or A
<220> FEATURE:
<221> NAME/KEY: MISC_FEATURE
<222> LOCATION: (2)..(2)
<223> OTHER INFORMATION: Xaa is G, R, Y, F, T, D, S, G, V, M, D, or R
<220> FEATURE:
<221> NAME/KEY: MISC_FEATURE
<222> LOCATION: (3)..(3)
<223> OTHER INFORMATION: Xaa is F, W, A, G, T, I, S, F, Y, C, L, V, R,
      or N
<220> FEATURE:
<221> NAME/KEY: MISC_FEATURE
<222> LOCATION: (4)..(4)
<223> OTHER INFORMATION: Xaa is S, F, M, G, Y, L, S, A, D, L, R, V, C,
      or S
<220> FEATURE:
<221> NAME/KEY: MISC_FEATURE
<222> LOCATION: (5)..(5)
<223> OTHER INFORMATION: Xaa is G, Y, S, T, P, F, Y, R, A, E, G, Q, N,
      or L
<220> FEATURE:
<221> NAME/KEY: MISC_FEATURE
<222> LOCATION: (6)..(6)
<223> OTHER INFORMATION: Xaa is Y, N, G, T, R, F, A, M, W, P, or V
<220> FEATURE:
<221> NAME/KEY: MISC_FEATURE
<222> LOCATION: (7)..(7)
<223> OTHER INFORMATION: Xaa is Y, M, S, V, F, A, P, S, D, R, H, P, E,
      or R
```

```
<220> FEATURE:
<221> NAME/KEY: MISC_FEATURE
<222> LOCATION: (8)..(8)
<223> OTHER INFORMATION: Xaa is Y, G, M, F, G, P, V, F, H, T, or G
<220> FEATURE:
<221> NAME/KEY: MISC_FEATURE
<222> LOCATION: (9)..(9)
<223> OTHER INFORMATION: Xaa is T, I G, R, or F
<220> FEATURE:
<221> NAME/KEY: MISC_FEATURE
<222> LOCATION: (10)..(10)
<223> OTHER INFORMATION: Xaa is Y, G, H, or E
<220> FEATURE:
<221> NAME/KEY: MISC_FEATURE
<222> LOCATION: (11)..(11)
<223> OTHER INFORMATION: Xaa is Y, G, F, or N
<220> FEATURE:
<221> NAME/KEY: MISC_FEATURE
<222> LOCATION: (12)..(12)
<223> OTHER INFORMATION: Xaa is F, or N
<220> FEATURE:
<221> NAME/KEY: MISC_FEATURE
<222> LOCATION: (13)..(13)
<223> OTHER INFORMATION: Xaa is Y
<220> FEATURE:
<221> NAME/KEY: MISC_FEATURE
<222> LOCATION: (14)..(14)
<223> OTHER INFORMATION: Xaa is F

<400> SEQUENCE: 1012

Xaa Xaa Xaa Xaa Xaa Xaa Xaa Xaa Xaa Xaa Xaa Xaa Xaa Xaa
 1               5                  10

<210> SEQ ID NO 1013
<211> LENGTH: 11
<212> TYPE: PRT
<213> ORGANISM: Artificial Sequence
<220> FEATURE:
<223> OTHER INFORMATION: light chain variable region CDR1
<220> FEATURE:
<221> NAME/KEY: MISC_FEATURE
<222> LOCATION: (1)..(1)
<223> OTHER INFORMATION: Xaa is T, G, R, S, or Q
<220> FEATURE:
<221> NAME/KEY: MISC_FEATURE
<222> LOCATION: (2)..(2)
<223> OTHER INFORMATION: Xaa is G, A, or L
<220> FEATURE:
<221> NAME/KEY: MISC_FEATURE
<222> LOCATION: (3)..(3)
<223> OTHER INFORMATION: Xaa is S, T, D, or H
<220> FEATURE:
<221> NAME/KEY: MISC_FEATURE
<222> LOCATION: (4)..(4)
<223> OTHER INFORMATION: Xaa is S, N, K, A, Q, T, or V
<220> FEATURE:
<221> NAME/KEY: MISC_FEATURE
<222> LOCATION: (4)..(5)
<223> OTHER INFORMATION: optional insertion of between 1 and 3 amino
      acids Xa-Xc between positions 4 and 5, wherein Xa is S or G, Xb is
      N, D, or S, and Xc is I or V
<220> FEATURE:
<221> NAME/KEY: MISC_FEATURE
<222> LOCATION: (5)..(5)
<223> OTHER INFORMATION: Xaa is G, I, L, S, or D
<220> FEATURE:
<221> NAME/KEY: MISC_FEATURE
<222> LOCATION: (6)..(6)
<223> OTHER INFORMATION: Xaa is A, G, R, P, I, D, S, E, or T
<220> FEATURE:
<221> NAME/KEY: MISC_FEATURE
<222> LOCATION: (7)..(7)
<223> OTHER INFORMATION: Xaa is G, N, M, D, K, S, R, Y, or T
<220> FEATURE:
<221> NAME/KEY: MISC_FEATURE
<222> LOCATION: (8)..(8)
<223> OTHER INFORMATION: Xaa is Y, K, F, Q, S, N, Y, D, H, or R
```

```
<220> FEATURE:
<221> NAME/KEY: MISC_FEATURE
<222> LOCATION: (9)..(9)
<223> OTHER INFORMATION: Xaa is D, N, Y, W, F, M, G, or S
<220> FEATURE:
<221> NAME/KEY: MISC_FEATURE
<222> LOCATION: (10)..(10)
<223> OTHER INFORMATION: Xaa is V, A, L, I, G, or P
<220> FEATURE:
<221> NAME/KEY: MISC_FEATURE
<222> LOCATION: (11)..(11)
<223> OTHER INFORMATION: Xaa is H, T, S, Y, A, Q, Y, N, or F

<400> SEQUENCE: 1013

Xaa Xaa Xaa Xaa Xaa Xaa Xaa Xaa Xaa Xaa Xaa
1               5                   10

<210> SEQ ID NO 1014
<211> LENGTH: 7
<212> TYPE: PRT
<213> ORGANISM: Artificial Sequence
<220> FEATURE:
<223> OTHER INFORMATION: light chain variable region CDR2
<220> FEATURE:
<221> NAME/KEY: MISC_FEATURE
<222> LOCATION: (1)..(1)
<223> OTHER INFORMATION: Xaa is G, Y, Q, K, N, D, R, A, or E
<220> FEATURE:
<221> NAME/KEY: MISC_FEATURE
<222> LOCATION: (2)..(2)
<223> OTHER INFORMATION: Xaa is N, D, K, A, V, G, or T
<220> FEATURE:
<221> NAME/KEY: MISC_FEATURE
<222> LOCATION: (3)..(3)
<223> OTHER INFORMATION: Xaa is N, S, T, I, K, Y, or D
<220> FEATURE:
<221> NAME/KEY: MISC_FEATURE
<222> LOCATION: (4)..(4)
<223> OTHER INFORMATION: Xaa is N, D, Y, K, E, T, N, S, or Q
<220> FEATURE:
<221> NAME/KEY: MISC_FEATURE
<222> LOCATION: (5)..(5)
<223> OTHER INFORMATION: Xaa is R, or L
<220> FEATURE:
<221> NAME/KEY: MISC_FEATURE
<222> LOCATION: (6)..(6)
<223> OTHER INFORMATION: Xaa is P, E, A, S, or Q
<220> FEATURE:
<221> NAME/KEY: MISC_FEATURE
<222> LOCATION: (7)..(7)
<223> OTHER INFORMATION: Xaa is S, P, or T

<400> SEQUENCE: 1014

Xaa Xaa Xaa Xaa Xaa Xaa Xaa
1               5

<210> SEQ ID NO 1015
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Q, N, A, G, D, S, or L
<220> FEATURE:
<221> NAME/KEY: MISC_FEATURE
<222> LOCATION: (2)..(2)
<223> OTHER INFORMATION: Xaa is S, V, A, Q, T, L, or H
<220> FEATURE:
<221> NAME/KEY: MISC_FEATURE
<222> LOCATION: (3)..(3)
<223> OTHER INFORMATION: Xaa is Y, W, R, A, S, Q, T, or G
<220> FEATURE:
```

```
<221> NAME/KEY: MISC_FEATURE
<222> LOCATION: (4)..(4)
<223> OTHER INFORMATION: Xaa is D, Y, I, N, M, or H
<220> FEATURE:
<221> NAME/KEY: MISC_FEATURE
<222> LOCATION: (5)..(5)
<223> OTHER INFORMATION: Xaa is T, M, S, N, D, R, G, or K
<220> FEATURE:
<221> NAME/KEY: MISC_FEATURE
<222> LOCATION: (6)..(6)
<223> OTHER INFORMATION: Xaa is N, T, S, G, F, L, or D
<220> FEATURE:
<221> NAME/KEY: MISC_FEATURE
<222> LOCATION: (7)..(7)
<223> OTHER INFORMATION: Xaa is L, T, G, P, A, I, or N
<220> FEATURE:
<221> NAME/KEY: MISC_FEATURE
<222> LOCATION: (7)..(8)
<223> OTHER INFORMATION: optional insertion of between 1 and 3 amino
      acids Xa-Xc between positions 7 and 8, wherein Xa is D, N, A, T,
      S, I or H, Xb is H, Y, G, A, R, L, S, or P, Xc is S
<220> FEATURE:
<221> NAME/KEY: MISC_FEATURE
<222> LOCATION: (8)..(8)
<223> OTHER INFORMATION: Xaa is K, W, V, I, P, G, L, R, or Y
<220> FEATURE:
<221> NAME/KEY: MISC_FEATURE
<222> LOCATION: (9)..(9)
<223> OTHER INFORMATION: Xaa is V, L, or T
<220> FEATURE:
<221> NAME/KEY: MISC_FEATURE
<222> LOCATION: (9)..(9)
<223> OTHER INFORMATION: Xaa is V, L, or T

<400> SEQUENCE: 1015

Xaa Xaa Xaa Xaa Xaa Xaa Xaa Xaa Xaa
1               5

<210> SEQ ID NO 1016
<211> LENGTH: 5
<212> TYPE: PRT
<213> ORGANISM: Artificial Sequence
<220> FEATURE:
<223> OTHER INFORMATION: heavy chain variable region CDR1
<220> FEATURE:
<221> NAME/KEY: MISC_FEATURE
<222> LOCATION: (2)..(2)
<223> OTHER INFORMATION: Xaa is Y or F

<400> SEQUENCE: 1016

Ser Xaa Ala Met Ser
1               5

<210> SEQ ID NO 1017
<211> LENGTH: 17
<212> TYPE: PRT
<213> ORGANISM: Artificial Sequence
<220> FEATURE:
<223> OTHER INFORMATION: heavy chain variable region CDR2
<220> FEATURE:
<221> NAME/KEY: MISC_FEATURE
<222> LOCATION: (7)..(7)
<223> OTHER INFORMATION: Xaa is S or G

<400> SEQUENCE: 1017

Ala Ile Ser Gly Ser Gly Xaa Ser Thr Tyr Tyr Ala Asp Ser Val Lys
1               5                   10                  15

Gly

<210> SEQ ID NO 1018
<211> LENGTH: 16
<212> TYPE: PRT
```

```
<213> ORGANISM: Artificial Sequence
<220> FEATURE:
<223> OTHER INFORMATION: heavy chain variable region CDR3
<220> FEATURE:
<221> NAME/KEY: MISC_FEATURE
<222> LOCATION: (1)..(1)
<223> OTHER INFORMATION: Xaa is H, D or Q
<220> FEATURE:
<221> NAME/KEY: MISC_FEATURE
<222> LOCATION: (2)..(2)
<223> OTHER INFORMATION: Xaa is W, M, F, H, or R
<220> FEATURE:
<221> NAME/KEY: MISC_FEATURE
<222> LOCATION: (4)..(4)
<223> OTHER INFORMATION: Xaa is W, Y or F
<220> FEATURE:
<221> NAME/KEY: MISC_FEATURE
<222> LOCATION: (7)..(7)
<223> OTHER INFORMATION: Xaa is T, N, G, or P
<220> FEATURE:
<221> NAME/KEY: MISC_FEATURE
<222> LOCATION: (8)..(8)
<223> OTHER INFORMATION: Xaa is R, A, S, G, or Y
<220> FEATURE:
<221> NAME/KEY: MISC_FEATURE
<222> LOCATION: (9)..(9)
<223> OTHER INFORMATION: Xaa is S, P, N or T
<220> FEATURE:
<221> NAME/KEY: MISC_FEATURE
<222> LOCATION: (10)..(10)
<223> OTHER INFORMATION: Xaa is G, S, R, or K
<220> FEATURE:
<221> NAME/KEY: MISC_FEATURE
<222> LOCATION: (11)..(11)
<223> OTHER INFORMATION: Xaa is P, M, A or L

<400> SEQUENCE: 1018

Xaa Xaa Asp Xaa Trp Ser Xaa Xaa Xaa Xaa Xaa Thr Ala Phe Asp Leu
1               5                   10                  15

<210> SEQ ID NO 1019
<211> LENGTH: 11
<212> TYPE: PRT
<213> ORGANISM: Artificial Sequence
<220> FEATURE:
<223> OTHER INFORMATION: light chain variable region CDR1

<400> SEQUENCE: 1019

Ser Gly Asp Ala Leu Pro Arg Gln Tyr Ala Tyr
1               5                   10

<210> SEQ ID NO 1020
<211> LENGTH: 7
<212> TYPE: PRT
<213> ORGANISM: Artificial Sequence
<220> FEATURE:
<223> OTHER INFORMATION: light chain variable region CDR2
<220> FEATURE:
<221> NAME/KEY: MISC_FEATURE
<222> LOCATION: (4)..(4)
<223> OTHER INFORMATION: Xaa is E or F

<400> SEQUENCE: 1020

Lys Asp Ser Xaa Arg Pro Ser
1               5

<210> SEQ ID NO 1021
<211> LENGTH: 11
<212> TYPE: PRT
<213> ORGANISM: Artificial Sequence
<220> FEATURE:
<223> OTHER INFORMATION: light chain variable region CDR3
<220> FEATURE:
```

-continued

```
<221> NAME/KEY: MISC_FEATURE
<222> LOCATION: (10)..(10)
<223> OTHER INFORMATION: Xaa is V or A

<400> SEQUENCE: 1021

Gln Ser Ala Asp Ser Ser Gly Thr Tyr Xaa Val
1               5                   10

<210> SEQ ID NO 1022
<211> LENGTH: 5
<212> TYPE: PRT
<213> ORGANISM: Artificial Sequence
<220> FEATURE:
<223> OTHER INFORMATION: heavy chain variable region CDR1
<220> FEATURE:
<221> NAME/KEY: MISC_FEATURE
<222> LOCATION: (1)..(1)
<223> OTHER INFORMATION: Xaa is S, N, D, T, or R
<220> FEATURE:
<221> NAME/KEY: MISC_FEATURE
<222> LOCATION: (2)..(2)
<223> OTHER INFORMATION: Xaa is G, Y, or F
<220> FEATURE:
<221> NAME/KEY: MISC_FEATURE
<222> LOCATION: (3)..(3)
<223> OTHER INFORMATION: Xaa is Y, H, S, G, D, or F
<220> FEATURE:
<221> NAME/KEY: MISC_FEATURE
<222> LOCATION: (4)..(4)
<223> OTHER INFORMATION: Xaa is D, V, or I
<220> FEATURE:
<221> NAME/KEY: MISC_FEATURE
<222> LOCATION: (5)..(5)
<223> OTHER INFORMATION: Xaa is N, H, C, R, S or is absent
<220> FEATURE:
<221> NAME/KEY: MISC_FEATURE
<222> LOCATION: (6)..(7)
<223> OTHER INFORMATION: optional insertion of V at position 6 and S at
      position 7

<400> SEQUENCE: 1022

Xaa Xaa Xaa Xaa Xaa
1               5

<210> SEQ ID NO 1023
<211> LENGTH: 16
<212> TYPE: PRT
<213> ORGANISM: Artificial Sequence
<220> FEATURE:
<223> OTHER INFORMATION: heavy chain variable region CDR2
<220> FEATURE:
<221> NAME/KEY: MISC_FEATURE
<222> LOCATION: (1)..(1)
<223> OTHER INFORMATION: Xaa is M, V, L, I, A, G, or T
<220> FEATURE:
<221> NAME/KEY: MISC_FEATURE
<222> LOCATION: (2)..(2)
<223> OTHER INFORMATION: Xaa is G or I
<220> FEATURE:
<221> NAME/KEY: MISC_FEATURE
<222> LOCATION: (3)..(3)
<223> OTHER INFORMATION: Xaa is Y, W, N, or C
<220> FEATURE:
<221> NAME/KEY: MISC_FEATURE
<222> LOCATION: (3)..(4)
<223> OTHER INFORMATION: optional insertion of amino acids Xa and Xb
      between positions 3 and 4, wherein Xa is I or P and Xb is S
<220> FEATURE:
<221> NAME/KEY: MISC_FEATURE
<222> LOCATION: (4)..(4)
<223> OTHER INFORMATION: Xaa is Y, G, D, or W
<220> FEATURE:
<221> NAME/KEY: MISC_FEATURE
<222> LOCATION: (5)..(5)
<223> OTHER INFORMATION: Xaa is S, D, or E
```

```
<220> FEATURE:
<221> NAME/KEY: MISC_FEATURE
<222> LOCATION: (6)..(6)
<223> OTHER INFORMATION: Xaa is G or D
<220> FEATURE:
<221> NAME/KEY: MISC_FEATURE
<222> LOCATION: (7)..(7)
<223> OTHER INFORMATION: Xaa is S, Y, N, or I
<220> FEATURE:
<221> NAME/KEY: MISC_FEATURE
<222> LOCATION: (8)..(8)
<223> OTHER INFORMATION: Xaa is T, P, or K
<220> FEATURE:
<221> NAME/KEY: MISC_FEATURE
<222> LOCATION: (9)..(9)
<223> OTHER INFORMATION: Xaa is N, A, G, D, or V
<220> FEATURE:
<221> NAME/KEY: MISC_FEATURE
<222> LOCATION: (10)..(10)
<223> OTHER INFORMATION: Xaa is Y or F
<220> FEATURE:
<221> NAME/KEY: MISC_FEATURE
<222> LOCATION: (11)..(11)
<223> OTHER INFORMATION: Xaa is N
<220> FEATURE:
<221> NAME/KEY: MISC_FEATURE
<222> LOCATION: (12)..(12)
<223> OTHER INFORMATION: Xaa is P, S, or E
<220> FEATURE:
<221> NAME/KEY: MISC_FEATURE
<222> LOCATION: (13)..(13)
<223> OTHER INFORMATION: Xaa is S, A, or N
<220> FEATURE:
<221> NAME/KEY: MISC_FEATURE
<222> LOCATION: (14)..(14)
<223> OTHER INFORMATION: Xaa is L or F
<220> FEATURE:
<221> NAME/KEY: MISC_FEATURE
<222> LOCATION: (15)..(15)
<223> OTHER INFORMATION: Xaa is K
<220> FEATURE:
<221> NAME/KEY: MISC_FEATURE
<222> LOCATION: (16)..(16)
<223> OTHER INFORMATION: Xaa is S, G, or N

<400> SEQUENCE: 1023

Xaa Xaa Xaa Xaa Xaa Xaa Xaa Xaa Xaa Xaa Xaa Xaa Xaa Xaa Xaa Xaa
1               5                   10                  15

<210> SEQ ID NO 1024
<211> LENGTH: 8
<212> TYPE: PRT
<213> ORGANISM: Artificial Sequence
<220> FEATURE:
<223> OTHER INFORMATION: heavy chain variable region CDR3
<220> FEATURE:
<221> NAME/KEY: MISC_FEATURE
<222> LOCATION: (1)..(1)
<223> OTHER INFORMATION: Xaa is G, S, A, or R
<220> FEATURE:
<221> NAME/KEY: MISC_FEATURE
<222> LOCATION: (2)..(2)
<223> OTHER INFORMATION: Xaa is M, G, Y, S, L, R, or V
<220> FEATURE:
<221> NAME/KEY: MISC_FEATURE
<222> LOCATION: (3)..(3)
<223> OTHER INFORMATION: Xaa is M, D, I, V, H, M, or S
<220> FEATURE:
<221> NAME/KEY: MISC_FEATURE
<222> LOCATION: (4)..(4)
<223> OTHER INFORMATION: Xaa is V, Y, M, W, or S
<220> FEATURE:
<221> NAME/KEY: MISC_FEATURE
<222> LOCATION: (5)..(5)
<223> OTHER INFORMATION: Xaa is L, Y, S or absent
<220> FEATURE:
<221> NAME/KEY: MISC_FEATURE
```

```
<222> LOCATION: (6)..(6)
<223> OTHER INFORMATION: Xaa is I, D, V, T, G, S, Y, or absent
<220> FEATURE:
<221> NAME/KEY: MISC_FEATURE
<222> LOCATION: (7)..(7)
<223> OTHER INFORMATION: Xaa is P, G, D, S, or A
<220> FEATURE:
<221> NAME/KEY: MISC_FEATURE
<222> LOCATION: (8)..(8)
<223> OTHER INFORMATION: Xaa is N, Y, or T

<400> SEQUENCE: 1024

Xaa Xaa Xaa Xaa Xaa Xaa Xaa Xaa
1               5

<210> SEQ ID NO 1025
<211> LENGTH: 6
<212> TYPE: PRT
<213> ORGANISM: Artificial Sequence
<220> FEATURE:
<223> OTHER INFORMATION: optional insertion of 1 to 6 amino acids in
      heavy chain variable region CDR3
<220> FEATURE:
<221> NAME/KEY: MISC_FEATURE
<222> LOCATION: (1)..(1)
<223> OTHER INFORMATION: Xaa is G, T, D, or Y
<220> FEATURE:
<221> NAME/KEY: MISC_FEATURE
<222> LOCATION: (2)..(2)
<223> OTHER INFORMATION: Xaa is S, A, G, or F
<220> FEATURE:
<221> NAME/KEY: MISC_FEATURE
<222> LOCATION: (3)..(3)
<223> OTHER INFORMATION: Xaa is Y, V, P, or F
<220> FEATURE:
<221> NAME/KEY: MISC_FEATURE
<222> LOCATION: (4)..(4)
<223> OTHER INFORMATION: Xaa is Y or F
<220> FEATURE:
<221> NAME/KEY: MISC_FEATURE
<222> LOCATION: (5)..(5)
<223> OTHER INFORMATION: Xaa is Y
<220> FEATURE:
<221> NAME/KEY: MISC_FEATURE
<222> LOCATION: (6)..(6)
<223> OTHER INFORMATION: Xaa is E, F, or G

<400> SEQUENCE: 1025

Xaa Xaa Xaa Xaa Xaa Xaa
1               5

<210> SEQ ID NO 1026
<211> LENGTH: 11
<212> TYPE: PRT
<213> ORGANISM: Artificial Sequence
<220> FEATURE:
<223> OTHER INFORMATION: light chain variable region CDR1
<220> FEATURE:
<221> NAME/KEY: MISC_FEATURE
<222> LOCATION: (1)..(1)
<223> OTHER INFORMATION: Xaa is K, Q, or R
<220> FEATURE:
<221> NAME/KEY: MISC_FEATURE
<222> LOCATION: (2)..(2)
<223> OTHER INFORMATION: Xaa is A or T
<220> FEATURE:
<221> NAME/KEY: MISC_FEATURE
<222> LOCATION: (3)..(3)
<223> OTHER INFORMATION: Xaa is S, R, or N
<220> FEATURE:
<221> NAME/KEY: MISC_FEATURE
<222> LOCATION: (4)..(4)
<223> OTHER INFORMATION: Xaa is K or Q
<220> FEATURE:
<221> NAME/KEY: MISC_FEATURE
```

```
<222> LOCATION: (5)..(5)
<223> OTHER INFORMATION: Xaa is S, D, R, N, L, or I
<220> FEATURE:
<221> NAME/KEY: MISC_FEATURE
<222> LOCATION: (6)..(6)
<223> OTHER INFORMATION: Xaa is I or S
<220> FEATURE:
<221> NAME/KEY: MISC_FEATURE
<222> LOCATION: (7)..(7)
<223> OTHER INFORMATION: Xaa is T, G, V, or N
<220> FEATURE:
<221> NAME/KEY: MISC_FEATURE
<222> LOCATION: (8)..(8)
<223> OTHER INFORMATION: Xaa is N, S, H, or K
<220> FEATURE:
<221> NAME/KEY: MISC_FEATURE
<222> LOCATION: (9)..(9)
<223> OTHER INFORMATION: Xaa is Y or W
<220> FEATURE:
<221> NAME/KEY: MISC_FEATURE
<222> LOCATION: (10)..(10)
<223> OTHER INFORMATION: Xaa is L, M, or I
<220> FEATURE:
<221> NAME/KEY: MISC_FEATURE
<222> LOCATION: (11)..(11)
<223> OTHER INFORMATION: Xaa is A, S, or Y

<400> SEQUENCE: 1026

Xaa Xaa Xaa Xaa Xaa Xaa Xaa Xaa Xaa Xaa Xaa
1               5                   10

<210> SEQ ID NO 1027
<211> LENGTH: 7
<212> TYPE: PRT
<213> ORGANISM: Artificial Sequence
<220> FEATURE:
<223> OTHER INFORMATION: light chain variable region CDR2
<220> FEATURE:
<221> NAME/KEY: MISC_FEATURE
<222> LOCATION: (1)..(1)
<223> OTHER INFORMATION: Xaa is S, D, E, or Y
<220> FEATURE:
<221> NAME/KEY: MISC_FEATURE
<222> LOCATION: (2)..(2)
<223> OTHER INFORMATION: Xaa is G, A, or T
<220> FEATURE:
<221> NAME/KEY: MISC_FEATURE
<222> LOCATION: (3)..(3)
<223> OTHER INFORMATION: Xaa is S or T
<220> FEATURE:
<221> NAME/KEY: MISC_FEATURE
<222> LOCATION: (4)..(4)
<223> OTHER INFORMATION: Xaa is T, S, K, or A
<220> FEATURE:
<221> NAME/KEY: MISC_FEATURE
<222> LOCATION: (5)..(5)
<223> OTHER INFORMATION: Xaa is L
<220> FEATURE:
<221> NAME/KEY: MISC_FEATURE
<222> LOCATION: (6)..(6)
<223> OTHER INFORMATION: Xaa is Q, A, or V
<220> FEATURE:
<221> NAME/KEY: MISC_FEATURE
<222> LOCATION: (7)..(7)
<223> OTHER INFORMATION: Xaa is S or D

<400> SEQUENCE: 1027

Xaa Xaa Xaa Xaa Xaa Xaa Xaa
1               5

<210> SEQ ID NO 1028
<211> LENGTH: 9
<212> TYPE: PRT
<213> ORGANISM: Artificial Sequence
<220> FEATURE:
```

```
<223> OTHER INFORMATION: light chain variable region CDR3
<220> FEATURE:
<221> NAME/KEY: MISC_FEATURE
<222> LOCATION: (1)..(1)
<223> OTHER INFORMATION: Xaa is Q, L, or H
<220> FEATURE:
<221> NAME/KEY: MISC_FEATURE
<222> LOCATION: (2)..(2)
<223> OTHER INFORMATION: Xaa is Q or K
<220> FEATURE:
<221> NAME/KEY: MISC_FEATURE
<222> LOCATION: (3)..(3)
<223> OTHER INFORMATION: Xaa is Y, A, W, or T
<220> FEATURE:
<221> NAME/KEY: MISC_FEATURE
<222> LOCATION: (4)..(4)
<223> OTHER INFORMATION: Xaa is Y, H, S, or D
<220> FEATURE:
<221> NAME/KEY: MISC_FEATURE
<222> LOCATION: (5)..(5)
<223> OTHER INFORMATION: Xaa is E, S, R, T, or N
<220> FEATURE:
<221> NAME/KEY: MISC_FEATURE
<222> LOCATION: (6)..(6)
<223> OTHER INFORMATION: Xaa is K, N, T, L, or H
<220> FEATURE:
<221> NAME/KEY: MISC_FEATURE
<222> LOCATION: (7)..(7)
<223> OTHER INFORMATION: Xaa is P
<220> FEATURE:
<221> NAME/KEY: MISC_FEATURE
<222> LOCATION: (8)..(8)
<223> OTHER INFORMATION: Xaa is Y, W, L, N, P, or R
<220> FEATURE:
<221> NAME/KEY: MISC_FEATURE
<222> LOCATION: (9)..(9)
<223> OTHER INFORMATION: Xaa is T

<400> SEQUENCE: 1028

Xaa Xaa Xaa Xaa Xaa Xaa Xaa Xaa Xaa
1               5

<210> SEQ ID NO 1029
<211> LENGTH: 388
<212> TYPE: PRT
<213> ORGANISM: Homo sapiens

<400> SEQUENCE: 1029

Met Ala Gly Cys Cys Ala Ala Leu Ala Ala Phe Leu Phe Glu Tyr Asp
1               5                   10                  15

Thr Pro Arg Ile Val Leu Ile Arg Ser Arg Lys Val Gly Leu Met Asn
                20                  25                  30

Arg Ala Val Gln Leu Leu Ile Leu Ala Tyr Val Ile Gly Trp Val Phe
            35                  40                  45

Val Trp Glu Lys Gly Tyr Gln Glu Thr Asp Ser Val Val Ser Ser Val
    50                  55                  60

Thr Thr Lys Val Lys Gly Val Ala Val Thr Asn Thr Ser Lys Leu Gly
65                  70                  75                  80

Phe Arg Ile Trp Asp Val Ala Asp Tyr Val Ile Pro Ala Gln Glu Glu
                85                  90                  95

Asn Ser Leu Phe Val Met Thr Asn Val Ile Leu Thr Met Asn Gln Thr
            100                 105                 110

Gln Gly Leu Cys Pro Glu Ile Pro Asp Ala Thr Val Cys Lys Ser
        115                 120                 125

Asp Ala Ser Cys Thr Ala Gly Ser Ala Gly Thr His Ser Asn Gly Val
    130                 135                 140

Ser Thr Gly Arg Cys Val Ala Phe Asn Gly Ser Val Lys Thr Cys Glu
```

145                 150                 155                 160
Val Ala Ala Trp Cys Pro Val Glu Asp Asp Thr His Val Pro Gln Pro
                165                 170                 175

Ala Phe Leu Lys Ala Ala Glu Asn Phe Thr Leu Leu Val Lys Asn Asn
                180                 185                 190

Ile Trp Tyr Pro Lys Phe Asn Phe Ser Lys Arg Asn Ile Leu Pro Asn
                195                 200                 205

Ile Thr Thr Thr Tyr Leu Lys Ser Cys Ile Tyr Asp Ala Lys Thr Asp
    210                 215                 220

Pro Phe Cys Pro Ile Phe Arg Leu Gly Lys Ile Val Glu Asn Ala Gly
225                 230                 235                 240

His Ser Phe Gln Asp Met Ala Val Glu Gly Ile Met Gly Ile Gln
                245                 250                 255

Val Asn Trp Asp Cys Asn Leu Asp Arg Ala Ala Ser Leu Cys Leu Pro
                260                 265                 270

Arg Tyr Ser Phe Arg Arg Leu Asp Thr Arg Asp Val Glu His Asn Val
                275                 280                 285

Ser Pro Gly Tyr Asn Phe Arg Phe Ala Lys Tyr Tyr Arg Asp Leu Ala
                290                 295                 300

Gly Asn Glu Gln Arg Thr Leu Ile Lys Ala Tyr Gly Ile Arg Phe Asp
305                 310                 315                 320

Ile Ile Val Phe Gly Lys Ala Gly Lys Phe Asp Ile Ile Pro Thr Met
                325                 330                 335

Ile Asn Ile Gly Ser Gly Leu Ala Leu Leu Gly Met Ala Thr Val Leu
                340                 345                 350

Cys Asp Ile Ile Val Leu Tyr Cys Met Lys Lys Arg Leu Tyr Tyr Arg
                355                 360                 365

Glu Lys Lys Tyr Lys Tyr Val Glu Asp Tyr Glu Gln Gly Leu Ala Ser
                370                 375                 380

Glu Leu Asp Gln
385

<210> SEQ ID NO 1030
<211> LENGTH: 388
<212> TYPE: PRT
<213> ORGANISM: Mus musculus

<400> SEQUENCE: 1030

Met Ala Gly Cys Cys Ser Val Leu Gly Ser Phe Leu Phe Glu Tyr Asp
1               5                   10                  15

Thr Pro Arg Ile Val Leu Ile Arg Ser Arg Lys Val Gly Leu Met Asn
                20                  25                  30

Arg Val Val Gln Leu Leu Ile Leu Ala Tyr Val Ile Gly Trp Val Phe
            35                  40                  45

Val Trp Glu Lys Gly Tyr Gln Glu Thr Asp Ser Val Val Ser Ser Val
        50                  55                  60

Thr Thr Lys Ala Lys Gly Val Ala Val Thr Asn Thr Ser Gln Leu Gly
65                  70                  75                  80

Phe Arg Ile Trp Asp Val Ala Asp Tyr Val Val Pro Ala Gln Glu Glu
                85                  90                  95

Asn Ser Leu Phe Ile Met Thr Asn Met Ile Val Thr Val Asn Gln Thr
                100                 105                 110

Gln Gly Thr Cys Pro Glu Ile Pro Asp Lys Thr Ser Ile Cys Asp Ser
            115                 120                 125

```
Asp Ala Asn Cys Thr Leu Gly Ser Ser Asp Thr His Ser Ser Gly Ile
    130                 135                 140

Gly Thr Gly Arg Cys Val Pro Phe Asn Ala Ser Val Lys Thr Cys Glu
145                 150                 155                 160

Val Ala Ala Trp Cys Pro Val Glu Asn Asp Ala Gly Val Pro Thr Pro
                165                 170                 175

Ala Phe Leu Lys Ala Ala Glu Asn Phe Thr Leu Leu Val Lys Asn Asn
            180                 185                 190

Ile Trp Tyr Pro Lys Phe Asn Phe Ser Lys Arg Asn Ile Leu Pro Asn
                195                 200                 205

Ile Thr Thr Ser Tyr Leu Lys Ser Cys Ile Tyr Asn Ala Arg Thr Asp
    210                 215                 220

Pro Phe Cys Pro Ile Phe Arg Leu Gly Gln Ile Val Ala Asp Ala Gly
225                 230                 235                 240

His Ser Phe Gln Glu Met Ala Val Glu Gly Ile Met Gly Ile Gln
                245                 250                 255

Ile Lys Trp Asp Cys Asn Leu Asp Arg Ala Ala Ser His Cys Leu Pro
                260                 265                 270

Arg Tyr Ser Phe Arg Arg Leu Asp Thr Arg Asp Leu Glu His Asn Val
    275                 280                 285

Ser Pro Gly Tyr Asn Phe Arg Phe Ala Lys Tyr Tyr Arg Asp Leu Ala
290                 295                 300

Gly Asn Glu Gln Arg Thr Leu Thr Lys Ala Tyr Gly Ile Arg Phe Asp
305                 310                 315                 320

Ile Ile Val Phe Gly Lys Ala Gly Lys Phe Asp Ile Ile Pro Thr Met
                325                 330                 335

Ile Asn Val Gly Ser Gly Leu Ala Leu Leu Gly Val Ala Thr Val Leu
                340                 345                 350

Cys Asp Val Ile Val Leu Tyr Cys Met Lys Lys Arg Tyr Tyr Tyr Arg
                355                 360                 365

Asp Lys Lys Tyr Lys Tyr Val Glu Asp Tyr Glu Gln Gly Leu Ser Gly
    370                 375                 380

Glu Met Asn Gln
385

<210> SEQ ID NO 1031
<211> LENGTH: 388
<212> TYPE: PRT
<213> ORGANISM: Rattus rattus

<400> SEQUENCE: 1031

Met Ala Gly Cys Cys Ser Val Leu Gly Ser Phe Leu Phe Glu Tyr Asp
1               5                   10                  15

Thr Pro Arg Ile Val Leu Ile Arg Ser Arg Lys Val Gly Leu Met Asn
                20                  25                  30

Arg Ala Val Gln Leu Leu Ile Leu Ala Tyr Val Ile Gly Trp Val Phe
            35                  40                  45

Val Trp Glu Lys Gly Tyr Gln Glu Thr Asp Ser Val Val Ser Ser Val
        50                  55                  60

Thr Thr Lys Ala Lys Gly Val Ala Val Thr Asn Thr Ser Gln Leu Gly
65                  70                  75                  80

Phe Arg Ile Trp Asp Val Ala Asp Tyr Val Ile Pro Ala Gln Glu Glu
                85                  90                  95

Asn Ser Leu Phe Ile Met Thr Asn Met Ile Val Thr Val Asn Gln Thr
                100                 105                 110
```

Gln Ser Thr Cys Pro Glu Ile Pro Asp Lys Thr Ser Ile Cys Asn Ser
            115                 120                 125

Asp Ala Asp Cys Thr Pro Gly Ser Val Asp Thr His Ser Ser Gly Val
        130                 135                 140

Ala Thr Gly Arg Cys Val Pro Phe Asn Glu Ser Val Lys Thr Cys Glu
145                 150                 155                 160

Val Ala Ala Trp Cys Pro Val Glu Asn Asp Val Gly Val Pro Thr Pro
                165                 170                 175

Ala Phe Leu Lys Ala Ala Glu Asn Phe Thr Leu Leu Val Lys Asn Asn
            180                 185                 190

Ile Trp Tyr Pro Lys Phe Asn Phe Ser Lys Arg Asn Ile Leu Pro Asn
        195                 200                 205

Ile Thr Thr Ser Tyr Leu Lys Ser Cys Ile Tyr Asn Ala Gln Thr Asp
    210                 215                 220

Pro Phe Cys Pro Ile Phe Arg Leu Gly Thr Ile Val Glu Asp Ala Gly
225                 230                 235                 240

His Ser Phe Gln Glu Met Ala Val Glu Gly Gly Ile Met Gly Ile Gln
                245                 250                 255

Ile Lys Trp Asp Cys Asn Leu Asp Arg Ala Ala Ser Leu Cys Leu Pro
            260                 265                 270

Arg Tyr Ser Phe Arg Arg Leu Asp Thr Arg Asp Leu Glu His Asn Val
        275                 280                 285

Ser Pro Gly Tyr Asn Phe Arg Phe Ala Lys Tyr Tyr Arg Asp Leu Ala
    290                 295                 300

Gly Lys Glu Gln Arg Thr Leu Thr Lys Ala Tyr Gly Ile Arg Phe Asp
305                 310                 315                 320

Ile Ile Val Phe Gly Lys Ala Gly Lys Phe Asp Ile Ile Pro Thr Met
                325                 330                 335

Ile Asn Val Gly Ser Gly Leu Ala Leu Leu Gly Val Ala Thr Val Leu
            340                 345                 350

Cys Asp Val Ile Val Leu Tyr Cys Met Lys Lys Lys Tyr Tyr Tyr Arg
        355                 360                 365

Asp Lys Lys Tyr Lys Tyr Val Glu Asp Tyr Gln Gly Leu Ser Gly
    370                 375                 380

Glu Met Asn Gln
385

<210> SEQ ID NO 1032
<211> LENGTH: 388
<212> TYPE: PRT
<213> ORGANISM: cynomolgus monkey

<400> SEQUENCE: 1032

Met Ala Gly Cys Cys Ala Ala Leu Ala Ala Phe Leu Phe Glu Tyr Asp
1               5                   10                  15

Thr Pro Arg Ile Val Leu Ile Arg Ser Arg Lys Val Gly Leu Met Asn
            20                  25                  30

Arg Ala Val Gln Leu Leu Ile Leu Ala Tyr Val Ile Gly Trp Val Phe
        35                  40                  45

Val Trp Glu Lys Gly Tyr Gln Glu Thr Asp Ser Val Val Ser Ser Val
    50                  55                  60

Thr Thr Lys Val Lys Gly Val Ala Val Thr Asn Thr Ser Lys Leu Gly
65                  70                  75                  80

Phe Arg Ile Trp Asp Val Ala Asp Tyr Val Ile Pro Ala Gln Gln Glu

```
                85                  90                  95
Asn Ser Leu Phe Val Met Thr Asn Met Ile Leu Thr Met Asn Gln Thr
            100                 105                 110

Gln Asp Leu Cys Pro Glu Ile Pro Asp Val Thr Thr Val Cys Lys Ser
            115                 120                 125

Asp Ala Asn Cys Thr Ala Gly Ser Ala Gly Thr His Ser Asn Gly Val
            130                 135                 140

Ser Thr Gly Arg Cys Val Pro Phe Asn Arg Ser Val Lys Thr Cys Glu
145                 150                 155                 160

Val Ala Ala Trp Cys Pro Val Glu Asp Thr His Val Pro Gln Pro
                165                 170                 175

Ala Phe Leu Lys Ala Ala Glu Asn Phe Thr Leu Leu Val Lys Asn Asn
                180                 185                 190

Ile Trp Tyr Pro Lys Phe Asn Phe Ser Lys Arg Asn Ile Leu Pro Asn
                195                 200                 205

Ile Thr Thr Thr Tyr Leu Lys Ser Cys Ile Tyr Asp Ala Lys Thr Asp
            210                 215                 220

Pro Phe Cys Pro Ile Phe Arg Leu Gly Lys Ile Val Glu Asn Ala Gly
225                 230                 235                 240

His Ser Phe Gln Asp Met Ala Val Glu Gly Ile Met Gly Ile Gln
                245                 250                 255

Val Asn Trp Asp Cys Asn Leu Asp Arg Ala Ala Ser Leu Cys Leu Pro
                260                 265                 270

Arg Tyr Ser Phe Arg Arg Leu Asp Thr Arg Asp Val Glu His Asn Val
                275                 280                 285

Ser Pro Gly Tyr Asn Phe Arg Phe Ala Lys Tyr Tyr Arg Asp Pro Ala
            290                 295                 300

Gly Lys Glu Gln Arg Thr Leu Ile Lys Ala Tyr Gly Ile Arg Phe Asp
305                 310                 315                 320

Ile Ile Val Phe Gly Lys Ala Gly Lys Phe Asp Ile Ile Pro Thr Met
                325                 330                 335

Ile Asn Ile Gly Ser Gly Leu Ala Leu Leu Gly Met Ala Thr Val Leu
            340                 345                 350

Cys Asp Ile Ile Val Leu Tyr Cys Met Lys Lys Arg Leu Tyr Tyr Arg
            355                 360                 365

Glu Lys Lys Tyr Lys Tyr Val Glu Asp Tyr Glu Gln Gly Leu Ala Ser
            370                 375                 380

Glu Leu Asp Pro
385

<210> SEQ ID NO 1033
<211> LENGTH: 2043
<212> TYPE: DNA
<213> ORGANISM: Homo sapiens

<400> SEQUENCE: 1033
aagtgctggg atgacaggtg tgagccaccg cccccggccc ctcgcccgcc ttttgaagga      60
gcctttcgtc ctcaagggcg aggccactcc cccccgcga gttccatgcc ccctagaggg     120
tcatcgttcc cgacggggag gtggcgccct ccccggggcc ccgggccccg accgccgtg     180 ctgcctcctt ccgggccctc ctccgcgatg acggcgccgc cagcaggcca ggcggactgg     240
gcggggctcc gagcggggac tgggacccag accgactagg ggactgggag cgggcggcgc     300
ggccatggcg ggctgctgcg ccgcgctggc ggccttcctg ttcgagtacg acaccgccgc     360
```

-continued

| | |
|---|---|
| catcgtgctc atccgcagcc gcaaagtggg gctcatgaac cgcgccgtgc aactgctcat | 420 |
| cctggcctac gtcatcgggt gggtgtttgt gtgggaaaag gctaccagg aaactgactc | 480 |
| cgtggtcagc tccgttacga ccaaggtcaa gggcgtggct gtgaccaaca cttctaaact | 540 |
| tggattccgg atctgggatg tggcggatta tgtgatacca gctcaggagg aaaactccct | 600 |
| cttcgtcatg accaacgtga tcctcaccat gaaccagaca cagggcctgt gccccgagat | 660 |
| tccagatgcg accactgtgt gtaaatcaga tgccagctgt actgccggct ctgccggcac | 720 |
| ccacagcaac ggagtctcaa caggcaggtg cgtagctttc aacgggtctg tcaagacgtg | 780 |
| tgaggtggcg gcctggtgcc cggtggagga tgacacacac gtgccacaac ctgctttttt | 840 |
| aaaggctgca gaaaacttca ctcttttggt taagaacaac atctggtatc ccaaatttaa | 900 |
| tttcagcaag aggaatatcc ttcccaacat caccactact tacctcaagt cgtgcattta | 960 |
| tgatgctaaa acagatccct tctgccccat attccgtctt ggcaaaatag tggagaacgc | 1020 |
| aggacacagt ttccaggaca tggcgtgga gggaggcatc atgggcatcc aggtcaactg | 1080 |
| ggactgcaac ctggacagag ccgcctccct ctgcttgccc aggtactcct tccgccgcct | 1140 |
| cgatacacgg gacgttgagc acaacgtatc tcctggctac aatttcaggt ttgccaagta | 1200 |
| ctacagagac ctggctggca acgagcagcg cacgctcatc aaggcctatg catccgcttt | 1260 |
| cgacatcatt gtgtttggga aggcagggaa atttgacatc atccccacta tgatcaacat | 1320 |
| cggctctggc ctggcactgc taggcatggc gaccgtgctg tgtgacatca tagtcctcta | 1380 |
| ctgcatgaag aaaagactct actatcggga gaagaaatat aaatatgtgg aagattacga | 1440 |
| gcagggtctt gctagtgagc tggaccagtg aggcctaccc cacacctggg ctctccacag | 1500 |
| ccccatcaaa gaacagagag gaggaggagg gagaaatggc caccacatca ccccagagaa | 1560 |
| atttctggaa tctgattgag tctccactcc acaagcactc agggttcccc agcagctcct | 1620 |
| gtgtgttgtg tgcaggatct gtttgcccac tcggcccagg aggtcagcag tctgttcttg | 1680 |
| gctgggtcaa ctctgctttt cccgcaacct ggggttgtcg ggggagcgct ggcccgacgc | 1740 |
| agtggcactg ctgtggcttt cagggctgga gctggctttg ctcagaagcc tcctgtctcc | 1800 |
| agctctctcc aggacaggcc cagtcctctg aggcacggcg gctctgttca agcactttat | 1860 |
| gcggcagggg aggccgcctg gctgcagtca ctagacttgt agcaggcctg gctgcaggc | 1920 |
| ttccccccga ccattccctg cagccatgcg gcagagctgg catttctcct cagagaagcg | 1980 |
| ctgtgctaag gtgatcgagg accagacatt aaagcgtgat tttcttaaaa aaaaaaaaaa | 2040 |
| aaa | 2043 |

<210> SEQ ID NO 1034
<211> LENGTH: 5
<212> TYPE: PRT
<213> ORGANISM: Artificial Sequence
<220> FEATURE:
<223> OTHER INFORMATION: sequence comprised in light chain variable
      region CDR1

<400> SEQUENCE: 1034

Ser Gly Asp Lys Leu
1               5

<210> SEQ ID NO 1035
<211> LENGTH: 8
<212> TYPE: PRT
<213> ORGANISM: Artificial Sequence
<220> FEATURE:
<223> OTHER INFORMATION: sequence comprised in light chain variable

```
                              region CDR1

<400> SEQUENCE: 1035

Ser Gly Ser Ser Ser Asn Ile Gly
1               5

<210> SEQ ID NO 1036
<211> LENGTH: 5
<212> TYPE: PRT
<213> ORGANISM: Artificial Sequence
<220> FEATURE:
<223> OTHER INFORMATION: sequence comprised in light chain variable
      region CDR1

<400> SEQUENCE: 1036

Ser Gly Asp Ala Leu
1               5

<210> SEQ ID NO 1037
<211> LENGTH: 11
<212> TYPE: PRT
<213> ORGANISM: Artificial Sequence
<220> FEATURE:
<223> OTHER INFORMATION: sequence comprised in light chain variable
      region CDR1

<400> SEQUENCE: 1037

Arg Ala Ser Gln Gly Ile Ser Ser Trp Leu Ala
1               5                   10

<210> SEQ ID NO 1038
<211> LENGTH: 11
<212> TYPE: PRT
<213> ORGANISM: Artificial Sequence
<220> FEATURE:
<223> OTHER INFORMATION: sequence comprised in light chain variable
      region CDR1

<400> SEQUENCE: 1038

Arg Ala Ser Gln Gly Ile Ser Arg Trp Leu Ala
1               5                   10

<210> SEQ ID NO 1039
<211> LENGTH: 7
<212> TYPE: PRT
<213> ORGANISM: Artificial Sequence
<220> FEATURE:
<223> OTHER INFORMATION: sequence comprised in light chain variable
      region CDR2
<220> FEATURE:
<221> NAME/KEY: MISC_FEATURE
<222> LOCATION: (2)..(2)
<223> OTHER INFORMATION: Xaa is T, S, K
<220> FEATURE:
<221> NAME/KEY: MISC_FEATURE
<222> LOCATION: (3)..(3)
<223> OTHER INFORMATION: Xaa is T, S, K

<400> SEQUENCE: 1039

Gly Xaa Xaa Tyr Arg Pro Ser
1               5

<210> SEQ ID NO 1040
<211> LENGTH: 7
<212> TYPE: PRT
<213> ORGANISM: Artificial Sequence
<220> FEATURE:
<223> OTHER INFORMATION: sequence comprised in light chain variable
      region CDR2
```

```
<400> SEQUENCE: 1040

Lys Asp Ser Glu Arg Pro Ser
1               5

<210> SEQ ID NO 1041
<211> LENGTH: 7
<212> TYPE: PRT
<213> ORGANISM: Artificial Sequence
<220> FEATURE:
<223> OTHER INFORMATION: sequence comprised in light chain variable
      region CDR2

<400> SEQUENCE: 1041

Lys Ala Ser Thr Leu Glu Ser
1               5

<210> SEQ ID NO 1042
<211> LENGTH: 7
<212> TYPE: PRT
<213> ORGANISM: Artificial Sequence
<220> FEATURE:
<223> OTHER INFORMATION: sequence comprised in light chain variable
      region CDR2
<220> FEATURE:
<221> NAME/KEY: MISC_FEATURE
<222> LOCATION: (3)..(3)

<400> SEQUENCE: 1042

Gln Asp Xaa Lys Arg Pro Ser
1               5

<210> SEQ ID NO 1043
<211> LENGTH: 7
<212> TYPE: PRT
<213> ORGANISM: Artificial Sequence
<220> FEATURE:
<223> OTHER INFORMATION: sequence comprised in light chain variable
      region CDR2

<400> SEQUENCE: 1043

Gln Asp Ile Glu Arg Pro Ser
1               5

<210> SEQ ID NO 1044
<211> LENGTH: 9
<212> TYPE: PRT
<213> ORGANISM: Artificial Sequence
<220> FEATURE:
<223> OTHER INFORMATION: sequence comprised in light chain variable
      region CDR3

<400> SEQUENCE: 1044

Gln Gln Ser Tyr Ser Thr Pro Trp Thr
1               5

<210> SEQ ID NO 1045
<211> LENGTH: 7
<212> TYPE: PRT
<213> ORGANISM: Artificial Sequence
<220> FEATURE:
<223> OTHER INFORMATION: sequence comprised in light chain variable
      region CDR3

<400> SEQUENCE: 1045

Ser Ser Gly Thr Tyr Val Val
1               5
```

<210> SEQ ID NO 1046
<211> LENGTH: 4
<212> TYPE: PRT
<213> ORGANISM: Artificial Sequence
<220> FEATURE:
<223> OTHER INFORMATION: sequence comprised in the heavy chain variable
      region CDR1

<400> SEQUENCE: 1046

Ser Gly Tyr Asp
1

<210> SEQ ID NO 1047
<211> LENGTH: 4
<212> TYPE: PRT
<213> ORGANISM: Artificial Sequence
<220> FEATURE:
<223> OTHER INFORMATION: sequence comprised in the heavy chain variable
      region CDR1

<400> SEQUENCE: 1047

Ser Gly Ser Asp
1

<210> SEQ ID NO 1048
<211> LENGTH: 4
<212> TYPE: PRT
<213> ORGANISM: Artificial Sequence
<220> FEATURE:
<223> OTHER INFORMATION: sequence comprised in the heavy chain variable
      region CDR1

<400> SEQUENCE: 1048

Ser Gly Phe Asp
1

<210> SEQ ID NO 1049
<211> LENGTH: 7
<212> TYPE: PRT
<213> ORGANISM: Artificial Sequence
<220> FEATURE:
<223> OTHER INFORMATION: sequence comprised in the heavy chain variable
      region CDR2

<400> SEQUENCE: 1049

Met Gly Tyr Ile Ser Tyr Ser
1               5

<210> SEQ ID NO 1050
<211> LENGTH: 9
<212> TYPE: PRT
<213> ORGANISM: Artificial Sequence
<220> FEATURE:
<223> OTHER INFORMATION: sequence comprised in the heavy chain variable
      region CDR2

<400> SEQUENCE: 1050

Val Ile Trp Gly Asp Gly Ser Thr Ala
1               5

<210> SEQ ID NO 1051
<211> LENGTH: 6
<212> TYPE: PRT
<213> ORGANISM: Artificial Sequence
<220> FEATURE:
<223> OTHER INFORMATION: sequence comprised in the heavy chain variable
      region CDR2

```
<400> SEQUENCE: 1051

Ser Thr Ala Tyr Asn Ser
1               5

<210> SEQ ID NO 1052
<211> LENGTH: 6
<212> TYPE: PRT
<213> ORGANISM: Artificial Sequence
<220> FEATURE:
<223> OTHER INFORMATION: sequence comprised in the heavy chain variable
      region CDR2

<400> SEQUENCE: 1052

Ser Thr Asn Tyr Asn Pro
1               5

<210> SEQ ID NO 1053
<211> LENGTH: 6
<212> TYPE: PRT
<213> ORGANISM: Artificial Sequence
<220> FEATURE:
<223> OTHER INFORMATION: sequence comprised in the heavy chain variable
      region CDR3

<400> SEQUENCE: 1053

Gly Met Met Val Leu Ile
1               5

<210> SEQ ID NO 1054
<211> LENGTH: 6
<212> TYPE: PRT
<213> ORGANISM: Artificial Sequence
<220> FEATURE:
<223> OTHER INFORMATION: sequence comprised in the heavy chain variable
      region CDR3

<400> SEQUENCE: 1054

Gly Val Ser Ser Leu Ser
1               5

<210> SEQ ID NO 1055
<211> LENGTH: 6
<212> TYPE: PRT
<213> ORGANISM: Artificial Sequence
<220> FEATURE:
<223> OTHER INFORMATION: sequence comprised in the heavy chain variable
      region CDR3
<220> FEATURE:
<221> NAME/KEY: MISC_FEATURE
<222> LOCATION: (6)..(6)
<223> OTHER INFORMATION: Xaa is E, G, or F

<400> SEQUENCE: 1055

Gly Ser Tyr Tyr Tyr Xaa
1               5

<210> SEQ ID NO 1056
<211> LENGTH: 7
<212> TYPE: PRT
<213> ORGANISM: Artificial Sequence
<220> FEATURE:
<223> OTHER INFORMATION: sequence contained in light chain variable
      region CDR1
<220> FEATURE:
<221> NAME/KEY: MISC_FEATURE
<222> LOCATION: (5)..(5)
<223> OTHER INFORMATION: Xaa is X, L, or I

<400> SEQUENCE: 1056
```

```
Lys Ala Ser Lys Xaa Ile Thr
1               5

<210> SEQ ID NO 1057
<211> LENGTH: 10
<212> TYPE: PRT
<213> ORGANISM: Artificial Sequence
<220> FEATURE:
<223> OTHER INFORMATION: sequence contained in light chain variable
      region CDR1

<400> SEQUENCE: 1057

Gln Ala Ser Gln Asp Ile Gly Asn Trp Leu
1               5                   10

<210> SEQ ID NO 1058
<211> LENGTH: 7
<212> TYPE: PRT
<213> ORGANISM: Artificial Sequence
<220> FEATURE:
<223> OTHER INFORMATION: sequence contained in light chain variable
      region CDR2

<400> SEQUENCE: 1058

Ser Gly Ser Thr Leu Gln Ser
1               5

<210> SEQ ID NO 1059
<211> LENGTH: 7
<212> TYPE: PRT
<213> ORGANISM: Artificial Sequence
<220> FEATURE:
<223> OTHER INFORMATION: sequence contained in light chain variable
      region CDR2

<400> SEQUENCE: 1059

Asp Ala Thr Ser Leu Ala Asp
1               5

<210> SEQ ID NO 1060
<211> LENGTH: 7
<212> TYPE: PRT
<213> ORGANISM: Artificial Sequence
<220> FEATURE:
<223> OTHER INFORMATION: sequence contained in light chain variable
      region CDR2

<400> SEQUENCE: 1060

Asp Ala Thr Thr Leu Ala Asp
1               5

<210> SEQ ID NO 1061
<211> LENGTH: 9
<212> TYPE: PRT
<213> ORGANISM: Artificial Sequence
<220> FEATURE:
<223> OTHER INFORMATION: sequence contained in light chain variable
      region CDR3
<220> FEATURE:
<221> NAME/KEY: misc_feature
<222> LOCATION: (8)..(8)
<223> OTHER INFORMATION: Xaa can be any naturally occurring amino acid

<400> SEQUENCE: 1061

Gln Gln Tyr Tyr Glu Lys Pro Xaa Thr
1               5
```

```
<210> SEQ ID NO 1062
<211> LENGTH: 9
<212> TYPE: PRT
<213> ORGANISM: Artificial Sequence
<220> FEATURE:
<223> OTHER INFORMATION: sequence contained in light chain variable
      region CDR3
<220> FEATURE:
<221> NAME/KEY: MISC_FEATURE
<222> LOCATION: (8)..(8)
<223> OTHER INFORMATION: Xaa is Y or L

<400> SEQUENCE: 1062

Gln Gln Tyr Tyr Glu Asn Pro Xaa Thr
1               5

<210> SEQ ID NO 1063
<211> LENGTH: 5
<212> TYPE: PRT
<213> ORGANISM: Artificial Sequence
<220> FEATURE:
<223> OTHER INFORMATION: heavy chain variable region CDR1
<220> FEATURE:
<221> NAME/KEY: MISC_FEATURE
<222> LOCATION: (3)..(3)
<223> OTHER INFORMATION: Xaa is A, W, Y, S, G, F, E, D, or P
<220> FEATURE:
<221> NAME/KEY: MISC_FEATURE
<222> LOCATION: (5)..(5)
<223> OTHER INFORMATION: Xaa is S, G, T, H, or N

<400> SEQUENCE: 1063

Ser Tyr Xaa Met Xaa
1               5

<210> SEQ ID NO 1064
<211> LENGTH: 5
<212> TYPE: PRT
<213> ORGANISM: Artificial Sequence
<220> FEATURE:
<223> OTHER INFORMATION: heavy chain variable region CDR1
<220> FEATURE:
<221> NAME/KEY: MISC_FEATURE
<222> LOCATION: (1)..(1)
<223> OTHER INFORMATION: Xaa is S, D, G, N or R

<400> SEQUENCE: 1064

Xaa Tyr Ala Met Ser
1               5

<210> SEQ ID NO 1065
<211> LENGTH: 5
<212> TYPE: PRT
<213> ORGANISM: Artificial Sequence
<220> FEATURE:
<223> OTHER INFORMATION: heavy chain variable region CDR1
<220> FEATURE:
<221> NAME/KEY: MISC_FEATURE
<222> LOCATION: (2)..(2)
<223> OTHER INFORMATION: Xaa is Y, A, H, F, or S

<400> SEQUENCE: 1065

Ser Xaa Ala Met Ser
1               5

<210> SEQ ID NO 1066
<211> LENGTH: 5
<212> TYPE: PRT
<213> ORGANISM: Artificial Sequence
<220> FEATURE:
<223> OTHER INFORMATION: heavy chain variable region CDR1
```

```
<220> FEATURE:
<221> NAME/KEY: MISC_FEATURE
<222> LOCATION: (3)..(3)
<223> OTHER INFORMATION: Xaa is A, W, Y, S, G, F, E, D, or P

<400> SEQUENCE: 1066

Ser Tyr Xaa Met Ser
1               5

<210> SEQ ID NO 1067
<211> LENGTH: 5
<212> TYPE: PRT
<213> ORGANISM: Artificial Sequence
<220> FEATURE:
<223> OTHER INFORMATION: heavy chain variable region CDR1
<220> FEATURE:
<221> NAME/KEY: MISC_FEATURE
<222> LOCATION: (4)..(4)
<223> OTHER INFORMATION: Xaa is M, I, W, L, F, or V

<400> SEQUENCE: 1067

Ser Tyr Ala Xaa Ser
1               5

<210> SEQ ID NO 1068
<211> LENGTH: 5
<212> TYPE: PRT
<213> ORGANISM: Artificial Sequence
<220> FEATURE:
<223> OTHER INFORMATION: heavy chain variable region CDR1
<220> FEATURE:
<221> NAME/KEY: MISC_FEATURE
<222> LOCATION: (5)..(5)
<223> OTHER INFORMATION: Xaa is S, G, T, H, or N

<400> SEQUENCE: 1068

Ser Tyr Ala Met Xaa
1               5

<210> SEQ ID NO 1069
<211> LENGTH: 17
<212> TYPE: PRT
<213> ORGANISM: Artificial Sequence
<220> FEATURE:
<223> OTHER INFORMATION: heavy chain variable region CDR2

<400> SEQUENCE: 1069

Ala Ile Ser Gly Ser Gly Gly Ser Thr Tyr Tyr Ala Asp Ser Val Lys
1               5                   10                  15

Gly

<210> SEQ ID NO 1070
<211> LENGTH: 17
<212> TYPE: PRT
<213> ORGANISM: Artificial Sequence
<220> FEATURE:
<223> OTHER INFORMATION: heavy chain variable region CDR2

<400> SEQUENCE: 1070

Ala Ile Ser Gly Ser Gly Gly Ser Thr Tyr Tyr Ala Asp Ser Val Glu
1               5                   10                  15

Gly

<210> SEQ ID NO 1071
<211> LENGTH: 6
<212> TYPE: PRT
<213> ORGANISM: Artificial Sequence
```

```
<220> FEATURE:
<223> OTHER INFORMATION: heavy chain variable region CDR3

<400> SEQUENCE: 1071

Asp Trp Tyr Phe Asp Leu
1               5

<210> SEQ ID NO 1072
<211> LENGTH: 6
<212> TYPE: PRT
<213> ORGANISM: Artificial Sequence
<220> FEATURE:
<223> OTHER INFORMATION: heavy chain variable region CDR3

<400> SEQUENCE: 1072

Asn Trp Tyr Leu Asp Leu
1               5
```

US 10,654,926 B2

P2X4 ANTIBODIES AND USES THEREOF

CROSS-REFERENCE TO RELATED APPLICATIONS

This application is a U.S. National Stage application of International Application No. PCT/EP2015/059633, filed on May 2, 2015, said International Application No. PCT/EP2015/059633 claims benefit under 35 U.S.C. § 119(e) of U.S. Provisional Application No. 61/987,929, filed on May 2, 2014. Each of the above listed applications is incorporated by reference herein in its entirety for all purposes.

REFERENCE TO THE SEQUENCE LISTING

This application incorporates by reference a Sequence Listing submitted with this application as a text file entitled "P2X4-100-US-PCT-SequenceListing", created on Oct. 3, 2019, and having a size of 379,460 bytes.

BACKGROUND OF THE INVENTION

Chronic pain serves no beneficial purpose, but arises from pathological alterations in nociceptive neural networks. Neuropathic pain is a form of chronic pain that arises after nerve injury caused by trauma, infection, or pathology. Neuropathic pain persists long after the initiating event has healed. While neurons are involved in neuropathic pain, they are unlikely to be the sole cell type mediating this condition. There is a growing body of evidence that supports a role for glia-neuron interactions in establishing and maintaining neuropathic pain. Microglia, in particular, have emerged as key players in neuropathic pain. The microglial P2X4 receptor appears to be important in the development and maintenance of neuropathic pain.

The ion channel P2X4 is one of seven members of a family of purinergic, cation permeable channels. Each P2X4 subunit has two transmembrane domains, separated by a large ~280 amino acid extracellular domain. Functional channels are formed of a trimeric arrangement of subunits with a central pore. The P2X4 channel is activated by binding of the ligand adenosine 5'-triphosphate (ATP) to residues contained within its extracellular domain. Activation of these receptors instigates a series of conformational changes that allow cations, such as $Ca^{2+}$ and $Na^+$, entry into the cell through a cation selective channel. P2X4 activation and upregulation is thought to be a key driver of neuropathic pain. Downstream of P2X4 activation, microglia release brain derived neurotrophic factor (BDNF), which acts on spinal lamina I neurons to reduce expression of a neuronal chloride transporter KCC2, thereby altering the electrochemical gradient for chloride and rendering one of the main inhibitory neurotransmitters GABA excitatory. Therefore, P2X4-mediated BDNF release in spinal cord is thought to be a key driver of neuropathic pain.

Neuropathic pain fails to respond to currently available analgesics, and is considered to be one of the most debilitating chronic pain conditions. Accordingly, improved methods for treating neuropathic pain, particularly pain mediated by P2X4 are urgently required.

SUMMARY OF THE INVENTION

As described below, the present invention provides antibodies that specifically bind a P2X4 polypeptide and modulate P2X4 channel activity, recombinant P2X4 polypeptides and methods for generating such polypeptides, as well as compositions and methods for generating anti-P2X4 antibodies, and methods of using P2X4 antibodies for the treatment of neuropathic pain and other indications.

In a first aspect, the invention provides an antibody or antigen binding fragment thereof that specifically binds a human P2X4 polypeptide and modulates channel activity. In one embodiment, the antibody is a P2X4 potentiator. In another embodiment, the antibody is a P2X4 antagonist. In another embodiment, the antibody is a P2X4 modulator. In another embodiment, the antibody is a P2X4 antagonist that reduces P2X4 biological activity by at least about 10, 25, 50, 75, 85, 90 or 95%. In another embodiment, the antibody binds an epitope containing human P2X4 amino acids 110-166. In another embodiment, the antibody binds an epitope containing one or more human P2X4 amino acids selected from any one or more of amino acids 118, 122-139, 145, 159, 180, 183, 184, 231, and 244. In another embodiment, an amino acid substitution at position 131 of P2X4 reduces or eliminates antibody binding to a human P2X4 polypeptide. In another embodiment, the serine at position 131 of human P2X4 is substituted by Asparagine.

In one embodiment of the previous aspect, the antibody or fragment thereof contains:

a. a heavy chain variable region CDR1 containing a sequence $$X_1X_2X_3X_4X_5, \text{ (SEQ ID NO: 1009)}$$

where $X_1$ is G, N, S, D, or R; $X_2$ is Y, A, H, F, or S; $X_3$ is A, W, Y, S, G, F, W, E, D, or P; $X_4$ is M, I, W, L, I, F, or V; $X_5$ is S, G, T, H, or N; and/or b. a heavy chain variable region CDR2 containing a sequence $$X_1X_2X_3X_4X_5X_6X_7X_8X_9X_{10}X_{11}X_{12}X_{13}X_{14}X_{15}X_{16}, \text{ (SEQ ID NO: 1029)}$$

where $X_1$ is A, R, I, T, E, S, A, V, W, N, G, E, R, or Y; $X_2$ is I or M; $X_3$ is S, K, Y, D, N, W, or I; $X_4$ is S, D, G, H, N, R, Y, or V; $X_5$ is G, D, S, F, N, R, F, D, or T; $X_6$ is G, S, N, or T; $X_7$ is S, T, D, Y, N, A, E, M, F, or D; $X_8$ is T, I, K, or A; $X_9$ is Y, D, R, N, G, Q, E, H, or K; $X_{10}$ is Y, Q, S, or V; $X_{11}$ is A, S, N, or V; $X_{12}$ is D, A, P, R, or Q; $X_{13}$ is S, P, K, or N; $X_{14}$ is V, F, L, or A; $X_{15}$ is K, Q, or E; $X_{16}$ is G, S, A, or D; and/or c. a heavy chain variable region CDR3 containing a sequence $$X_1X_2X_3X_4X_5X_6X_7X_8, \text{ (SEQ ID NO: 1011)}$$

where $X_1$ is E, N, D, R, K, G, S, A, Y, V, P, or H; $X_2$ is E, L, R, Q, T, G, F, P, Y, K, A, S, V, or F; $X_3$ is R, A, T, G, V, S, M, W, Y, D, H, N, E, L, or I; $X_4$ is G, L, R, D, T, G, Y, S, E, F, Q, C, I, M, V, N, K, or P; $X_5$ is S, G, Y, D, W, T, S, N, I, D, V, E, or C; $X_6$ is Y, A, S, W, T, L, G, E, F, K, V, I, or D; $X_7$ is D, E, or G; and $X_8$ is Y, S, V, L, M, Q, I, S, I, H, F, or D. In one embodiment, the heavy chain variable region CDR2 optionally contains an insertion of 1-3 amino acids, $X_aX_bX_c$ between amino acids X3 and X4, where $X_a$ is G, S, P, W, Y, E, A, R, or N; and XbXc are KT, respectively. In another embodiment, the heavy chain variable region CDR3 optionally contains an insertion of 1-14 amino acids Xa-Xn (SEQ ID NO: 1012), where $X_a$ is F, R, S, Y, L, D, G, V, I, T, or A; $X_b$ is G, R, Y, F, T, D, S, G, V, M, D, or R; $X_c$ is F, W, A, G, T, I, S, F, Y, C, L, V, R, or N; $X_d$ is S, F, M, G, Y, L, S, A, D, L, R, V, C, or S, $X_e$ is G, Y, S, T, P, F, Y, R, A, E, G, Q, N, or L; $X_f$ is Y, N, G, T, R, F, A, M, W, P, or V; $X_g$ is Y, M, S, V, F, A, P, S, D, R, H, P, E, or R $X_h$ is Y, G, M, F, G, P, V, F, H, T, or G, $X_i$ is T, I, G, R, or F; $X_j$ is Y, G, H, or E; $X_K$ is Y, G, F, or N; $X_L$ is F, or N; $X_m$ is Y; and $X_n$ is F. In one embodiment, the heavy chain variable region CDR1 contains the sequence $SYX_1MX_2$ (SEQ ID NO: 1063), where $X_1$ is A, W, Y, S, G, F, E, D, or P and $X_2$ is S, G, T, H, or N. In another embodiment, the heavy chain variable region CDR1 contains the sequence XYAMS (SEQ ID NO: 1064), where X is S, D, G, N or R; SXAMS (SEQ ID NO: 1065), where X is Y, A, H, F, or S; SYXMS (SEQ ID NO: 1066), where X is A, W, Y, S, G, F, E, D, or P; SYAXS (SEQ ID NO: 1067), where X is M, I, W, L, F, or V; SYAMX (SEQ ID NO: 1068), where X is S, G, T, H, or N. In another embodiment, the heavy chain variable region CDR1 contains amino acids SYAMS (SEQ ID NO: 57). In another embodiment, the heavy chain variable region CDR2 contains the sequence AISGSGGSTYYADSVKG (SEQ ID NO: 1069); or AISGSGGSTYYADSVEG (SEQ ID NO: 1070). In yet another embodiment, the heavy chain variable region CDR3 contains the sequence DWYFDL (SEQ ID NO: 1071) or NWYLDL (SEQ ID NO: 1072). In still another embodiment, the antibody or fragment thereof contains, a. a light chain variable region CDR1 containing a sequence $X_1X_2X_3X_4X_5X_6X_7X_8X_9X_{10}X_{11}$, (SEQ ID NO: 1013)

where $X_1$ is T, G, R, S, or Q; $X_2$ is G, A, or L; $X_3$ is S, T, D, or H; $X_4$ is S, N, K, A, Q, T, or V; $X_5$ is G, I, L, S, or D; $X_6$ is A, G, R, P, I, D, S, E, T; $X_7$ is G, N, M, D, K, S, R, Y, or T; $X_8$ is Y, K, F, Q, S, N, Y, D, H, or R; $X_9$ is D, N, Y, W, F, M, G, or S; $X_{10}$ is V, A, L, I, G, or P; $X_{11}$ is H, T, S, Y, A, Q, Y, N, or F, b. a light chain variable region CDR2 containing a sequence:

$X_1X_2X_3X_4X_5X_6X_7$, (SEQ ID NO: 1014)

where $X_1$ is G, Y, Q, K, N, D, R, A, or E; $X_2$ is N, D, K, A, V, G, or T, $X_3$ is N, S, T, I, K, Y, or D; $X_4$ is N, D, Y, K, E, T, N, S, or Q, $X_5$ is R, or L; $X_6$ is P, E, A, S, or Q; $X_7$ is S, P, or T;

c. a light chain variable region CDR3 containing a sequence $X_1X_2X_3X_4X_5X_6X_7X_8X_9$, (SEQ ID NO: 1015)

where $X_1$ is Q, N, A, G, D, S, or L; $X_2$ is S, V, A, Q, T, L, or H; $X_3$ is Y, W, R, A, S, Q, T, or G; $X_4$ is D, Y, I, N, M, or H, $X_5$ is T, M, S, N, D, R, G, or K, $X_6$ is N, T, S, G, F, L or D; $X_7$ is L, T, G, P, A, I, or N; $X_8$ is K, W, V, I, P, G, L, R, or Y; $X_9$ is V, L, or T. In one embodiment, the light chain variable region CDR1 optionally contains an insertion of between 1 and 3 amino acids Xa-Xc between X4 and X5, where Xa is S or G; Xb is N, D or S; and Xc is I or V. In another embodiment, the light chain variable region CDR3 optionally contains an insertion of between 1 and 3 amino acids Xa-Xc between X7 and $X_8$, where Xa is D, N, A, T, S, I or H; Xb is H, Y, G, A, R, L, S, or P; Xc is S. In still another embodiment, the light chain variable region CDR1 contains one of the following sequences: SGDKL (SEQ ID NO: 1034); S G S S S N I G (SEQ ID NO: 1035); S G D A L (SEQ ID NO: 1036); R A S Q G I S S W L A (SEQ ID NO: 1037); and R A S Q G I S R W L A (SEQ ID NO: 1038). In another embodiment, the light chain variable region CDR2 contains one of the following sequences: G X X Y R P S (SEQ ID NO: 1039), where X is T, S, K or K D S E R P S (SEQ ID NO: 1040); K A S T L E S (SEQ ID NO: 1041); Q D X K R P S (SEQ ID NO: 1042), where X is D or T; and Q D I E R P S (SEQ ID NO: 1043). In another embodiment, the light chain variable region CDR3 contains one of the following sequences: Q Q S Y S T P W T (SEQ ID NO: 1044) or S S G T Y V V (SEQ ID NO: 1045).

In various embodiments of the above aspects, the antibody contains a heavy chain variable region CDR1, CDR2, and CDR3. In other embodiments of the above aspects, the antibody contains a light chain variable region CDR1, CDR2, and CDR3. In other embodiments of the above aspects the antibody contains a heavy chain variable region CDR1, CDR2, and CDR3, and a light chain variable region CDR1, CDR2, and CDR3. In other embodiments of the above aspects the antibody is a phage display derived antibody selected from any one or more of Antibody Nos. 1-34. In particular embodiments, the antibody is Antibody No. 5, 8, 11, 18, 29, or 33.

In another embodiment of the above aspect, the antibody or fragment thereof contains:

a. a heavy chain variable region CDR1 containing a sequence:

$X_1X_2X_3X_4X_5$, (SEQ ID NO: 1022)

where $X_1$ is S, N, D, T, A, or R; $X_2$ is G, Y, or F; $X_3$ is Y, H, S, G, D, or F; $X_4$ is D, V, or I; $X_5$ is N, H, C, R, S or is absent;

b. a heavy chain variable region CDR2 containing a sequence:

$X_1X_2X_3X_4X_5X_6X_7X_8X_9X_{10}X_{11}X_{12}X_{13}X_{14}X_{15}, X_{16}$, (SEQ ID NO: 1023)

where $X_1$ is M, V, L, I, A, G, or T; $X_2$ is G or I; $X_3$ is Y, W, N, or C; $X_4$ is Y, G, D, or W; $X_5$ is S, D, or E; $X_6$ is G or D; $X_7$ is S, Y, N, or I; $X_8$ is T, P, or K; $X_9$ is N, A, G, D, or V; $X_{10}$ is Y or F; $X_{11}$ is N; $X_{12}$ is P, S, or E; $X_{13}$ is S, A, or N; $X_{14}$ is L or F; $X_{15}$ is K; $X_{16}$ is S, G, or N;

c. a heavy chain variable region CDR3 containing a sequence:

$X_1X_2X_3X_4X_5X_6X_7X_8$, (SEQ ID NO: 1024)

where $X_1$ is G, S, A, or R; $X_2$ is M, G, Y, S, L, R, or V; $X_3$ is M, D, I, V, H, M, or S; $X_4$ is V, Y, M, W, or S; $X_5$ is L, Y, S or absent; $X_6$ is I, D, V, T, G, S or absent; $X_7$ is P, G, D, S, or A; and $X_8$ is N, Y, or T. In one embodiment, the heavy chain variable region CDR1 optionally contains amino acids $X_6$ and $X_7$, which are V and S, respectively. In another embodiment, the heavy chain variable region CDR2 optionally contains an insertion of amino acids Xa and Xb between $X_3$ and $X_4$, where Xa is I or P and Xb is S. In another embodiment, the heavy chain variable region CDR3 optionally contains an insertion of between 1 and 6 amino acids Xa-Xf (SEQ ID NO: 1025) between $X_6$ and $X_7$, where Xa is G, T, D, or Y; Xb is S, A, G, or F; Xc is Y, V, P, or F; Xd is Y or F; Xe is Y; and Xf is E, F, or G. In another embodiment, the heavy chain variable region CDR1 contains the sequence S G Y D (SEQ ID NO: 1046); S G S D (SEQ ID NO: 1047); or S G F D (SEQ ID NO: 1048). In another embodiment, the heavy chain variable region CDR2 contains the sequence: M G Y I S Y S (SEQ ID NO: 1049);

V I W G D G S T A (SEQ ID NO: 1050); S T A Y N S (SEQ ID NO: 1051); or S T N Y N P (SEQ ID NO: 1052). In one embodiment, the heavy chain variable region CDR3 contains the sequence G M M V L I (SEQ ID NO: 1053); G V S S L S (SEQ ID NO: 1054); or GS Y Y Y X (SEQ ID NO: 1055), where X is E, G, or F.

In another embodiment of the above aspect, the antibody or fragment thereof contains:

a. a light chain variable region CDR1 containing a sequence:

$X_1X_2X_3X_4X_5X_6X_7X_8X_9X_{10}X_{11}$, (SEQ ID NO: 1026)

where $X_1$ is K, Q, or R; $X_2$ is A or T; $X_3$ is S, R, or N; $X_4$ is K or Q; $X_5$ is S, D, R, N, L, or I; $X_6$ is I or S; $X_7$ is T, G, V, or N; $X_8$ is N, S, H, or K; $X_9$ is Y or W; $X_{10}$ is L, M, or I; $X_{11}$ is A, S, or Y;

b. a light chain variable region CDR2 containing a sequence:

$X_1X_2X_3X_4X_5X_6X_7$, (SEQ ID NO: 1027)

where $X_1$ is S, D, E, or Y; $X_2$ is G, A, or T; $X_3$ is S or T; $X_4$ is T, S, K, or A; $X_5$ is L; $X_6$ is Q, A, or V; $X_7$ is S or D;

c. a light chain variable region CDR3 containing a sequence:

$X_1X_2X_3X_4X_5X_6X_7X_8X_9$, (SEQ ID NO: 1028)

where $X_1$ is Q, L, or H; $X_2$ is Q or K; $X_3$ is Y, A, W, or T; $X_4$ is Y, H, S, or D; $X_5$ is E, S, R, T, or N; $X_6$ is K, N, T, L, or H; $X_7$ is P; $X_8$ is Y, W, L, N, P, or R; and $X_9$ is T. In one embodiment, the light chain variable region CDR1 contains the sequence K A S K X I T (SEQ ID NO: 1056), where X is X, L, or I; or Q A S Q D I G N W L (SEQ ID NO: 1057). In another embodiment, the light chain variable region CDR2 contains the sequence S G S T L Q S (SEQ ID NO: 1058); D A T S L A D (SEQ ID NO: 1059); or D A T T L A D (SEQ ID NO: 1060). In another embodiment, the light chain variable region CDR3 contains the sequence Q Q Y Y E K P X T (SEQ ID NO: 1061) or Q Q Y Y E N P X T (SEQ ID NO: 1062) where X is Y or L.

In another series of embodiments the antibody or fragment thereof comprises a VH comprising:
a. a heavy chain variable region CDR1 containing a sequence: $SX_1AMS$ (SEQ ID NO: 1016), where $X_1$ is Y or F;
b. a heavy chain variable region CDR2 containing a sequence: AISGSG $X_1$STYYADSVKG (SEQ ID NO: 1017), where $X_1$ is S or G;
c. a heavy chain variable region CDR3 containing a sequence: $X_1X_2DX_3WSX_4X_5X_6X_7X_8TAFDL$ (SEQ ID NO: 1018), where $X_1$ is H, D or Q; $X_2$ is W, M, F, H, or R; $X_3$ is W, Y or F; $X_4$ is T, N, G, or P; $X_5$ is R, A, S, G, or Y; $X_6$ is S, P, N or T; and $X_7$ is G, S, R, or K: $X_8$ is P, M, A or L
optionally in combination with a VL comprising
a. a light chain variable region CDR1 comprising the sequence SGDALPRQYAY (SEQ ID NO: 1019)
b. a light chain variable region CDR2 comprising the sequence KDSXRPS (SEQ ID NO: 1020), where X is E or F
c. a light chain variable region CDR3 comprising the sequence QSADSSGTYXV (SEQ ID NO: 1021), where X is V or A.

In various embodiments of the above aspects, the antibody contains a heavy chain variable region CDR1, CDR2, and CDR3. In other embodiments of the above aspects, the antibody contains a light chain variable region CDR1, CDR2, and CDR3. In still other embodiments of the above aspects, the antibody contains a heavy chain variable region CDR1, CDR2, and CDR3, and a light chain variable region CDR1, CDR2, and CDR3. In particular embodiments, the antibody is a hybridoma derived antibody selected from any one or more of Antibody Nos. 35-48.

In various embodiments of the above aspects, the antigen binding fragment thereof is a single chain antibody, a single chain variable fragment (scFv), a Fab fragment, or a F(ab')2 fragment.

In another aspect, the invention provides a polynucleotide encoding the antibody or antigen binding fragment thereof of any of the above aspects.

In another aspect, the invention provides a vector containing the polynucleotide of the previous aspect.

In still another aspect, the invention provides a host cell containing the vector of the previous aspect.

In another aspect, the invention provides a method for treating neuropathic pain, the method involving administering to a patient in need thereof an antibody or antigen binding fragment thereof according to any of the above aspects. In one embodiment, the antibody or antigen binding fragment thereof is administered by intrathecal delivery.

In another aspect, the invention provides a method for the large scale production of a recombinant P2X4 polypeptide, the method involving expressing a human P2X4 protein in an SF9 cell at 27° C. for 72 hours; extracting the P2X4 protein by solubilizing in a buffer containing n-Dodecyl-beta-D-Maltoside, n-Dodecyl thio-Maltoside, CHAPS, and the Cholesteryl Hemisuccinate; then isolating the solubilized protein. In one embodiment, the SF9 cells were infected with baculovirus particles with a multiplicity of infection of 2 at a cell density of 2×10E6 cells/ml. In another embodiment, the proteins are purified using affinity and size exclusion chromatography. In another embodiment, the purified protein is maintained in a buffer containing 50 mM Tris-HCl pH 8.0, 600 mM NaCl, 10% glycerol, 0.025% n-Dodecyl-beta-D-Maltoside, 0.0125% n-Dodecyl thio-Maltoside, 0.0075% CHAPS, and 0.0015% Cholesteryl Hemisuccinate.

In another embodiment, the method generates milligram quantities of purified P2X4 human polypeptide. In another embodiment, the majority of the P2X4 protein is in the trimeric form.

In another aspect, the invention provides a recombinant human P2X4 polypeptide produced according to the method of any previous aspect. In one embodiment, at least about 65%-75% of the polypeptide is in the trimeric form.

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "P2X purinoceptor 4 (P2RX4 or P2X4) polypeptide" is meant a purinergic receptor protein or fragment thereof having at least about 85% or greater amino acid identity to the amino acid sequence provided at NCBI Accession No. Q99571 and having P2X4 biological activity. P2X4 biological activity includes $Ca^{2+}/Na^+$ conducting activity in response to ATP binding and/or P2X4 antibody binding. An exemplary human P2X4 sequence is provided below:

```
magccaalaa flfeydtpri vlirsrkvgl mnravqllil ayvigwvfvw ekgyqetdsv    61
vssvttkvkg vavtntsklg friwdvadyv ipaqeenslf vmtnviltmn qtqglcpeip  121
dattvcksda sctagsagth sngvstgrcv afngsvktce vaawcpvedd thvpqpaflk  181
aaenftllvk nniwypkfnf skrnilpnit ttylksciyd aktdpfcpif rlgkivenag  241
hsfqdmaveg gimgiqvnwd cnldraaslc lprysfrrld trdvehnvsp gynfrfakyy  301
rdlagneqrt likaygirfd iivfgkagkf diiptminig sglallgmat vlcdiivlyc  361
mkkrlyyrek kykyvedyeq glaseldq (SEQ ID NO: 1029)
```

In embodiments of the invention, a human P2X4 polypeptide has at least about 65%, 70%, 80%, 85%, 90%, 95%, or even 100% identity to NCBI Accession No. Q99571. In other embodiments, the invention provides P2X4 polypeptides comprising one or more amino acid substitutions relative to the Q99571 reference sequence, including for example: E95Q, V105M, G114D, A122V, S131N, A151P, G154R, L303P, and N306K.

An exemplary murine P2X purinoceptor 4 is provided at NCBI Accession No. Q9JJX6, which has the following sequence:

```
magccsvlgs flfeydtpri vlirsrkvgl mnrvvqllil ayvigwvfvw ekgyqetdsv    61
vssvttkakg vavtntsqlg friwdvadyv vpageenslf imtnmivtvn qtqgtcpeip  121
dktsicdsda nctlgssdth ssgigtgrcv pfnasvktce vaawcpvend agvptpaflk  181
aaenftllvk nniwypkfnf skrnilpnit tsylksciyn artdpfcpif rlgqivadag  241
hsfqemaveg gimgiqikwd cnldraashc lprysfrrld trdlehnvsp gynfrfakyy  301
rdlagneqrt ltkaygirfd iivfgkagkf diiptminvg sglallgvat vlcdvivlyc  361
mkkryyyrdk kykyvedyeq glsgemnq (SEQ ID NO: 1030)
```

An exemplary rat P2X purinoceptor 4 sequence is provided at NCBI Accession No. P51577, which has the following sequence:

```
magccsvlgs flfeydtpri vlirsrkvgl mnravqllil ayvigwvfvw ekgyqetdsv    61
vssvttkakg vavtntsqlg friwdvadyv ipaqeenslf imtnmivtvn qtqstcpeip  121
dktsicnsda dctpgsvdth ssgvatgrcv pfnesvktce vaawcpvend vgvptpaflk  181
aaenftllvk nniwypkfnf skrnilpnit tsylksciyn aqtdpfcpif rlgtivedag  241
hsfqemaveg gimgiqikwd cnldraaslc lprysfrrld trdlehnvsp gynfrfakyy  301
rdlagkeqrt ltkaygirfd iivfgkagkf diiptminvg sglallgvat vlcdvivlyc  361
mkkkyyyrdk kykyvedyeq glsgemnq (SEQ ID NO: 1031)
```

An exemplary cynomolgus monkey (e.g. macaque) P2X purinoceptor 4 sequence, which has the following sequence:

```
magccaalaa flfeydtpri vlirsrkvgl mnravqllil ayvigwvfvw ekgyqetdsv   61
vssvttkvkg vavtntsklg friwdvadyv ipaqqenslf vmtnmiltmn qtqdlcpeip  121
dvttvcksda nctagsagth sngvstgrcv pfnrsvktce vaawcpvedd thvpqpaflk  181
aaenftllvk nniwypkfnf skrnilpnit ttylksciyd aktdpfcpif rlgkivenag  241
hsfqdmaveg gimgiqvnwd cnldraaslc lprysfrrld trdvehnvsp gynfrfakyy  301
rdpagkeqrt likaygirfd iivfgkagkf diiptminig sglallgmat vlcdiivlyc  361
mkkrlyyrek kykyvedyeq glaseldp (SEQ ID NO: 1032)
```

By "P2X4 nucleic acid molecule" is meant a polynucleotide encoding a P2X4 polypeptide or fragment thereof. An exemplary human P2X4 polynucleotide sequence is provided at NCBI Accession No. NM_002560, the sequence of which follows:

```
   1 aagtgctggg atgacaggtg tgagccaccg ccccggccc ctcgcccgcc ttttgaagga
  61 gcctttcgtc ctcaagggcg aggccactcc cccccgcga gttccatgcc cctagaggg
 121 tcatcgttcc cgacggggag gtggcgccct cccccgggcc ccgggccccg accgccgtg
 181 ctgcctcctt ccgggccctc ctccgcgatg acggcgccgc cagcaggcca ggcggactgg
 241 gcggggctcc gagcggggac tgggacccag accgactagg ggactgggag cgggcggcgc
 301 ggccatggcg ggctgctgcg ccgcgctggc ggccttcctg ttcgagtacg acacgccgcg
 361 catcgtgctc atccgcagcc gcaaagtggg gctcatgaac cgcgccgtgc aactgctcat
 421 cctggcctac gtcatcgggt gggtgtttgt gtgggaaaag ggctaccagg aaactgactc
 481 cgtggtcagc tccgttacga ccaaggtcaa gggcgtggct gtgaccaaca cttctaaact
 541 tggattccgg atctgggatg tggcggatta tgtgatacca gctcaggagg aaaactccct
 601 cttcgtcatg accaacgtga tcctcaccat gaaccagaca cagggcctgt gccccgagat
 661 tccagatgcg accactgtgt gtaaatcaga tgccagctgt actgccggct ctgccggcac
 721 ccacagcaac ggagtctcaa caggcaggtg cgtagctttc aacgggtctg tcaagacgtg
 781 tgaggtggcg gcctggtgcc cggtggagga tgacacacac gtgccacaac ctgctttttt
 841 aaaggctgca gaaaacttca ctcttttggt taagaacaac atctggtatc ccaaatttaa
 901 tttcagcaag aggaatatcc ttcccaacat caccactact tacctcaagt cgtgcattta
 961 tgatgctaaa acagatccct tctgccccat attccgtctt ggcaaaatag tggagaacgc
1021 aggacacagt ttccaggaca tggccgtgga gggaggcatc atgggcatcc aggtcaactg
1081 ggactgcaac ctggacagag ccgcctccct ctgcttgccc aggtactcct ccgccgcct
1141 cgatacacgg gacgttgagc acaacgtatc tcctggctac aatttcaggt ttgccaagta
1201 ctacagagac ctggctggca acgagcagcg cacgctcatc aaggcctatg gcatccgctt
1261 cgacatcatt gtgtttggga aggcagggaa atttgacatc atccccacta tgatcaacat
1321 cggctctggc ctggcactgc taggcatggc gaccgtgctg tgtgacatca gtcctctcta
1381 ctgcatgaag aaaagactct actatcggga agaaatat aaatatgtgg aagattacga
1441 gcagggtctt gctagtgagc tggaccagtg aggcctaccc cacacctggg ctctccacag
1501 cccatcaaa gaacagagag gaggaggagg gagaaatggc caccacatca ccccagagaa
1561 atttctggaa tctgattgag tctccactcc acaagcactc agggttcccc agcagctcct
1621 gtgtgttgtg tgcaggatct gtttgcccac tcggcccagg aggtcagcag tctgttcttg
```

```
1681 gctgggtcaa ctctgctttt cccgcaacct ggggttgtcg ggggagcgct ggcccgacgc 1741 agtggcactg ctgtggcttt cagggctgga gctggctttg ctcagaagcc tcctgtctcc 1801 agctctctcc aggacaggcc cagtcctctg aggcacggcg gctctgttca agcactttat 1861 gcggcagggg aggccgcctg gctgcagtca ctagacttgt agcaggcctg ggctgcaggc 1921 ttcccccccga ccattccctg cagccatgcg gcagagctgg catttctcct cagagaagcg 1981 ctgtgctaag gtgatcgagg accagacatt aaagcgtgat tttcttaaaa aaaaaaaaa 2041 aaa (SEQ ID NO: 1033)
```

By "P2X4 biological activity" is meant ion channel conducting activity or ion channel mediated changes in cytosolic calcium levels.

By "ameliorate" is meant decrease, suppress, attenuate, diminish, arrest, or stabilize the development or progression of a disease.

The term "antibody," as used in this disclosure, refers to an immunoglobulin or a fragment or a derivative thereof, and encompasses any polypeptide comprising an antigen-binding site, regardless of whether it is produced in vitro or in vivo. The term includes, but is not limited to, polyclonal, monoclonal, monospecific, polyspecific, non-specific, humanized, single-chain, chimeric, synthetic, recombinant, hybrid, mutated, and grafted antibodies. Unless otherwise modified by the term "intact," as in "intact antibodies," for the purposes of this disclosure, the term "antibody" also includes antibody fragments such as Fab, F(ab')2, Fv, scFv, Fd, dAb, and other antibody fragments that retain antigen-binding function, i.e., the ability to bind a P2X4 polypeptide specifically. Typically, such fragments would comprise an antigen-binding domain.

The terms "antigen-binding domain," "antigen-binding fragment," and "binding fragment" refer to a part of an antibody molecule that comprises amino acids responsible for the specific binding between the antibody and the antigen. In instances, where an antigen is large, the antigen-binding domain may only bind to a part of the antigen. A portion of the antigen molecule that is responsible for specific interactions with the antigen-binding domain is referred to as "epitope" or "antigenic determinant." In particular embodiments, an antigen-binding domain comprises an antibody light chain variable region ($V_L$) and an antibody heavy chain variable region ($V_H$), however, it does not necessarily have to comprise both. For example, a so-called Fd antibody fragment consists only of a $V_H$ domain, but still retains some antigen-binding function of the intact antibody.

Binding fragments of an antibody are produced by recombinant DNA techniques, or by enzymatic or chemical cleavage of intact antibodies. Binding fragments include Fab, Fab', F(ab')2, Fv, and single-chain antibodies. An antibody other than a "bispecific" or "bifunctional" antibody is understood to have each of its binding sites identical. Digestion of antibodies with the enzyme, papain, results in two identical antigen-binding fragments, known also as "Fab" fragments, and a "Fc" fragment, having no antigen-binding activity but having the ability to crystallize Digestion of antibodies with the enzyme, pepsin, results in the a F(ab')2 fragment in which the two arms of the antibody molecule remain linked and comprise two-antigen binding sites. The F(ab')2 fragment has the ability to crosslink antigen. "Fv" when used herein refers to the minimum fragment of an antibody that retains both antigen-recognition and antigen-binding sites.

"Fab" when used herein refers to a fragment of an antibody that comprises the constant domain of the light chain and the CHI domain of the heavy chain.

The term "mAb" refers to monoclonal antibody. Antibodies of the invention comprise without limitation whole native antibodies, bispecific antibodies; chimeric antibodies; Fab, Fab', single chain V region fragments (scFv), fusion polypeptides, and unconventional antibodies.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected. In one embodiment, an antibody of the invention or fragment thereof is used to detect the presence or level of a P2X4 polypeptide.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include neuropathic pain, particularly pain associated with P2X4 channel activity or the activity of a pathway responsive to P2X4.

The term "effective amount" refers to a dosage or amount of an agent that is sufficient to reduce the activity of a P2X4 polypeptide to result in amelioration of symptoms in a patient or to achieve a desired biological outcome. Desired biological outcomes include, for example, the amelioration of chronic pain or a symptom thereof, modulation of P2X4 biological activity, or the modulation of a pathway responsive to P2X4 activity.

The term "isolated" refers to a molecule that is substantially free of other elements present in its natural environment. For instance, an isolated protein is substantially free of cellular material or other proteins from the cell or tissue source from which it is derived. The term "isolated" also refers to preparations where the isolated protein is sufficiently pure to be administered as a pharmaceutical composition, or at least 70-80% (w/w) pure, more preferably, at least 80-90% (w/w) pure, even more preferably, 90-95% pure; and, most preferably, at least 95%, 96%, 97%, 98%, 99%, or 100% (w/w) pure.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. In a particular embodiment, a fragment of a P2X4 polypeptide may contain 5, 10, 20, 30, 40, 50, 60, 70, 80, 90, 100, 200, or 300 amino acids.

By "reference" is meant a standard of comparison.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

The term "repertoire" refers to a genetically diverse collection of nucleotides derived wholly or partially from sequences that encode expressed immunoglobulins. The sequences are generated by in vivo rearrangement of, e.g., V, D, and J segments for H chains and, e.g., V and J segment for L chains. Alternatively, the sequences may be generated from a cell line by in vitro stimulation, in response to which the rearrangement occurs. Alternatively, part or all of the sequences may be obtained by combining, e.g., unrearranged V segments with D and J segments, by nucleotide synthesis, randomised mutagenesis, and other methods, e.g., as disclosed in U.S. Pat. No. 5,565,332.

By "specifically binds" is meant an agent (e.g., antibody) that recognizes and binds a molecule (e.g., polypeptide), but which does not substantially recognize and bind other molecules in a sample, for example, a biological sample. For example, two molecules that specifically bind form a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant $K_A$ is higher than $10^7$ $M^{-1}$, or more preferably higher than $10^8$ $M^{-1}$.

The strength of the binding between P2X4 and an antibody can be measured using, for example, an enzyme-linked immunoadsorption assay (ELISA), radio-immunoassay (RIA), or surface plasmon resonance-based technology (e.g., Biacore), all of which are techniques well known in the art. If necessary, non-specific binding can be reduced without substantially affecting specific binding by varying the binding conditions. The appropriate binding conditions such as concentration of antibodies, ionic strength of the solution, temperature, time allowed for binding, concentration of a blocking agent (e.g., serum albumin, milk casein, etc.), may be optimized by a skilled artisan using routine techniques.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A-1D shows an analysis of Antibody Nos. 1, 11, 29, and 33 binding to human P2X4 variants.

FIG. 2 provides the VH & VL sequences of Antibody Nos. 1-34, which were identified using phage display technology.

FIG. 3 provides a summary of P2X4 orthologue binding properties of antibodies identified using phage display selection (antibodies 1 to 34) and a summary of their functional effects measured by electrophysiology assays and reported as fraction of control current. Key: + indicates that binding was observed in FMAT assay; − indicates that no binding was observed in FMAT assay; NT indicates that the antibody was not tested in the assay.

FIG. 4 shows results of the antibodies 5, 8, 11, 18, 29, and 33 screened in electrophysiology assays. Each of these antibodies was identified as a P2X4 antagonist. Peak agonist induced inward current in response to 3 µM ATP in the presence of antibody is indicated as a fraction of control current in the absence of antibody at human or cynomolgus (cyno) P2X4.

FIG. 5 provides a summary of P2X4 orthologue binding properties of antibodies isolated from hybridomas (Antibody Nos. 35-48) and a summary of their functional effects measured by electrophysiology assays and reported as fraction of control current.

FIG. 6 provides the VH & VL sequences of Antibody Nos. 35-48.

FIG. 7 provides a summary of results of binding assays for 252 antibodies (Antibody Nos. 35-286) isolated using hybridoma technology and a summary of their functional effects measured by electrophysiology assays and reported as fraction of control current.

FIG. 8A-8F shows whole cell current traces obtained using QPatch 16X showing the agonist response (indicated temporally by the grey bar) before (black trace) and after (grey trace) addition of antibodies. Traces are superimposed for comparison. Dotted line indicates zero current. P2X4 species investigated is indicated where appropriate by (m, mouse) (hu, human). FIG. 8A, 8D, 8E, 8F show activity against huP2X4. FIGS. 8B and 8C show activity against mP2X4.

FIG. 9 shows schematically an extracellular view of predicted P2X4 trimer-Antibody No. 11 Fv complex structure. In particular, FIG. 9 illustrates the bipartite epitope-paratope interface—Antibody No. 11 VHCDRs-P2X4 protomer 1 head (major interface—large dotted circle); Antibody No. 11 VLCDRs-P2X4 protomer 2 right flipper (minor interface—small dotted circle). Three Antibody No. 11 molecules can potentially bind the same P2X4 trimer molecule. The two Fab arms of Antibody No. 11 are not likely to engage the same P2X4 trimer molecule. Antibody No. 11 is predicted to bind a P2X heteromer across the epitope formed by two P2X4 subunits.

FIG. 10 provides alignments of human, cyno, mouse and rat P2X4 sequences. The head region of the protein is indicated. Amino acids within the predicted epitope are also indicated.

FIG. 13 provides the VH & VL sequences of Antibody Nos. 208 and 316 to 321

FIG. 14 shows the effect of antibody Nos. 11, 300 and 312 on huP2X4 currents recorded on Qpatch 16X. The black trace indicates the ATP response prior to IgG addition whereas the grey trace indicates the ATP response after incubation with IgG. The dashed line indicates the zero current level and the grey bar indicates the time at which ATP was added to the cell bathing solution. Traces are overlayed for comparison. Dose response curves are plotted with normalised current values as described in Example 14 and represent mean+/−SEM, n=4.

FIG. 15 summarises $IC_{50}$ values for optimised versions of Antibody 11 at huP2X4 using either FLIPR or Qpatch 16X. Values are geometric means.

FIG. 16 summarises $IC_{50}$ values for antibodies 38, 43, 46 & 208 at murine P2X4 and/or huP2X4 expressed in HEK 293F cells obtained on Qpatch 16X.

FIG. 17 summarises the effect of antibodies 38, 43, 46 & 208 on mouse microglial P2X4 currents measured on Qpatch 16X.

FIG. 18 shows exemplary electrophysiology current traces from mouse microglia pretreated with either the control antibody NIP 228 or antibody 208 (0.33 mg/ml). The grey bar indicates the time at which ATP (30 μM) was added to the cells and the dotted line indicates the zero current level.

FIG. 19 shows example $IC_{50}$ curves obtained with two of the anti-P2X4 antibodies in the ATP stimulated calcium response assay.

FIG. 20 shows $IC_{50}$ curves (mean+/−SEM) for antibodies 46, 38 and 208 obtained from mouse microglia assayed on FLIPR. Mean $IC_{50}$ values are presented below.

FIG. 21 shows exemplar electrophysiology current traces from human monocyte derived macrophages. Time at which ATP was added to the cells is indicated by the open box. Dotted line indicates zero current.

FIG. 22 summarises the steady state inward current from human monocyte derived macrophages in response to ATP (30 μM).

Figure 8A:
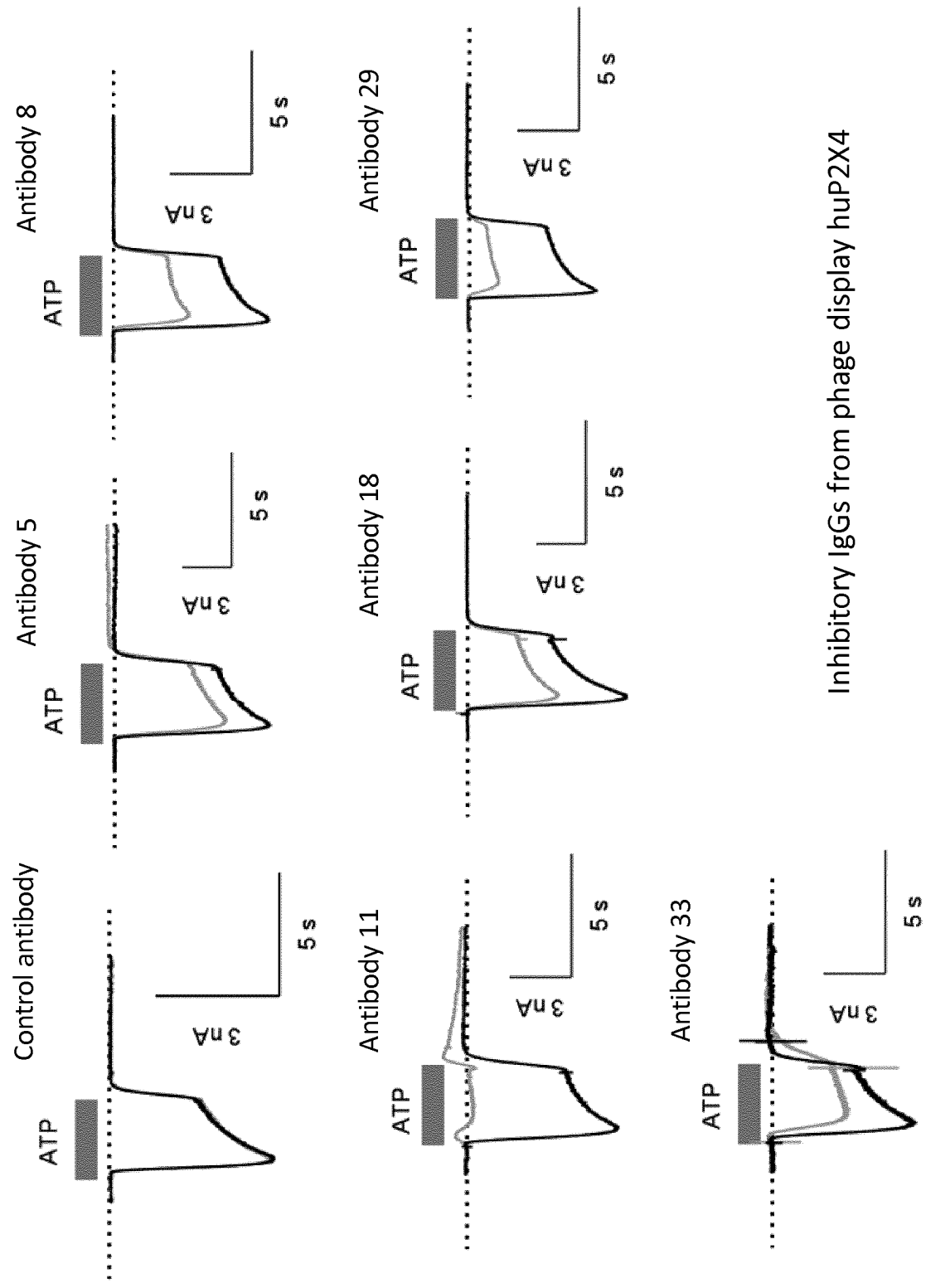
Figure 8B:
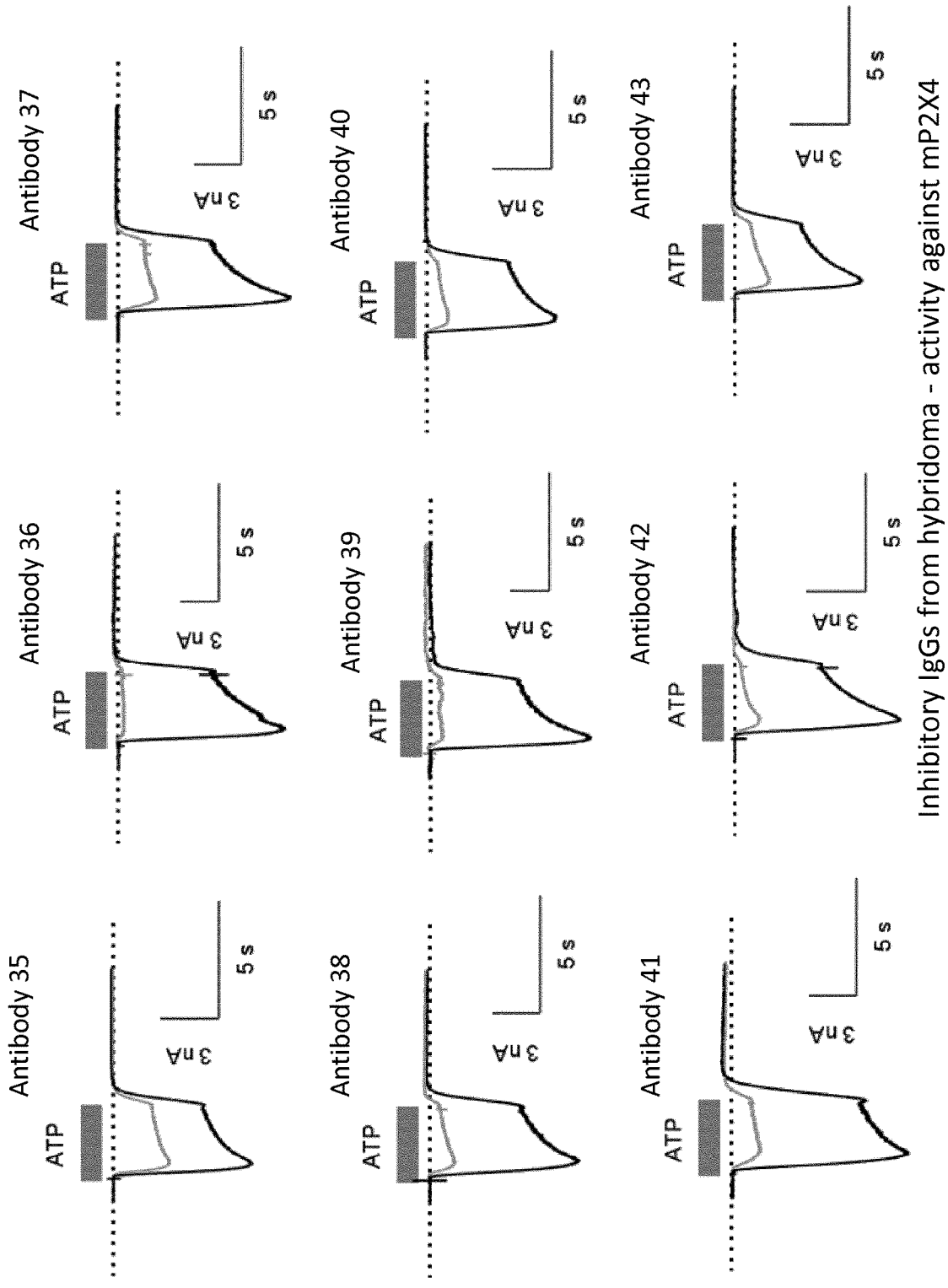
Figure 8C:
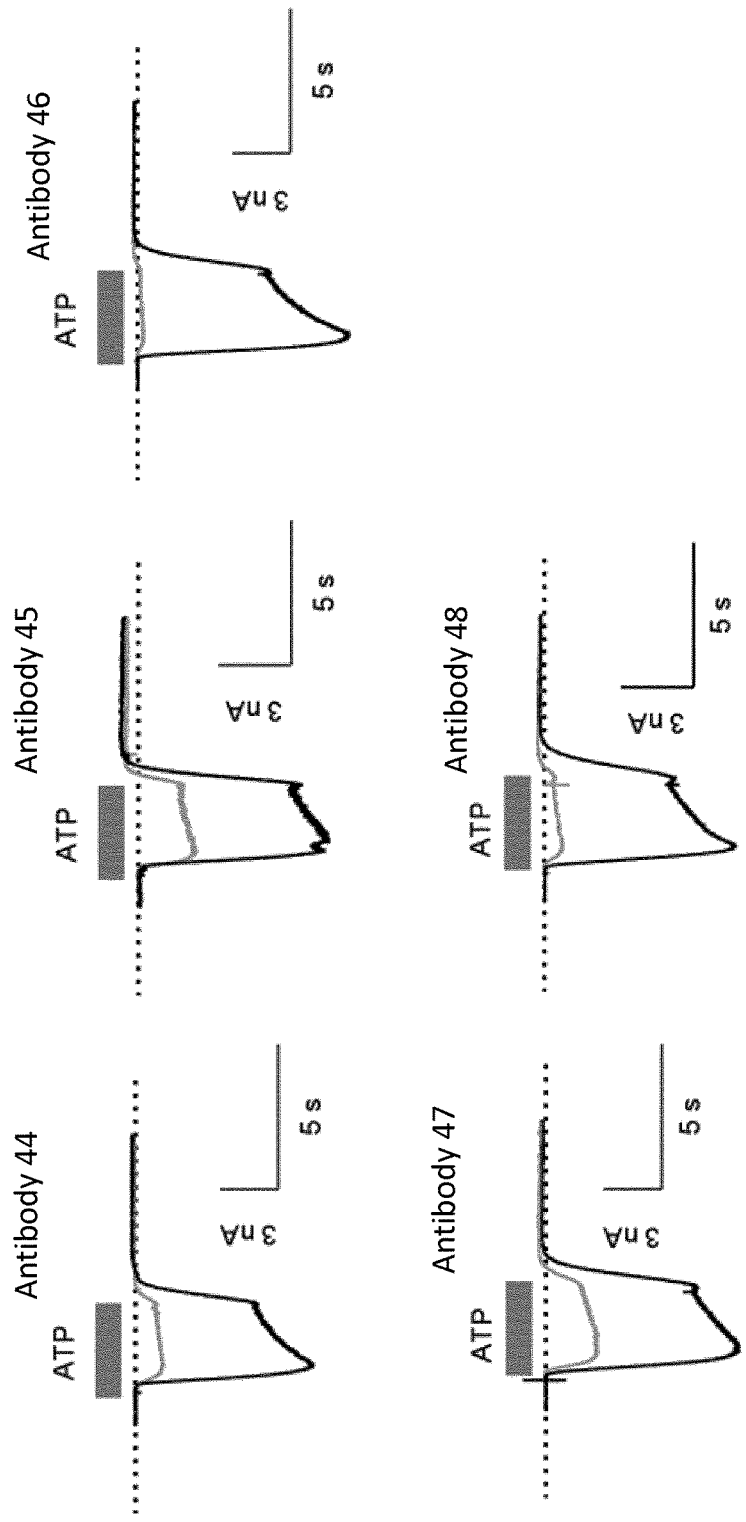

| SEQ ID | Antibody | Description |
|---|---|---|
| 1 | 1 | VH DNA |
| 2 | 1 | VH PRT |
| 3 | 1 | CDR1 PRT |
| 4 | 1 | CDR2 PRT |
| 5 | 1 | CDR3 PRT |
| 6 | 1 | FW1 PRT |
| 7 | 1 | FW2 PRT |
| 8 | 1 | FW3 PRT |
| 9 | 1 | FW4 PRT |
| 10 | 1 | VL DNA |
| 11 | 1 | VL PRT |
| 12 | 1 | CDR1 PRT |
| 13 | 1 | CDR2 PRT |
| 14 | 1 | CDR3 PRT |
| 15 | 1 | FW1 PRT |
| 16 | 1 | FW2 PRT |
| 17 | 1 | FW3 PRT |
| 18 | 1 | FW4 PRT |
| 19 | 5 | VH DNA |
| 20 | 5 | VH PRT |
| 21 | 5 | CDR1 PRT |
| 22 | 5 | CDR2 PRT |
| 23 | 5 | CDR3 PRT |
| 24 | 5 | FW1 PRT |
| 25 | 5 | FW2 PRT |
| 26 | 5 | FW3 PRT |
| 27 | 5 | FW4 PRT |
| 28 | 5 | VL DNA |
| 29 | 5 | VL PRT |
| 30 | 5 | CDR1 PRT |
| 31 | 5 | CDR2 PRT |
| 32 | 5 | CDR3 PRT |
| 33 | 5 | FW1 PRT |
| 34 | 5 | FW2 PRT |
| 35 | 5 | FW3 PRT |
| 36 | 5 | FW4 PRT |
| 37 | 8 | VH DNA |
| 38 | 8 | VH PRT |
| 39 | 8 | CDR1 PRT |
| 40 | 8 | CDR2 PRT |

-continued

| SEQ ID | Antibody | Description |
|---|---|---|
| 41 | 8 | CDR3 PRT |
| 42 | 8 | FW1 PRT |
| 43 | 8 | FW2 PRT |
| 44 | 8 | FW3 PRT |
| 45 | 8 | FW4 PRT |
| 46 | 8 | VL DNA |
| 47 | 8 | VL PRT |
| 48 | 8 | CDR1 PRT |
| 49 | 8 | CDR2 PRT |
| 50 | 8 | CDR3 PRT |
| 51 | 8 | FW1 PRT |
| 52 | 8 | FW2 PRT |
| 53 | 8 | FW3 PRT |
| 54 | 8 | FW4 PRT |
| 55 | 11 | VH DNA |
| 56 | 11 | VH PRT |
| 57 | 11 | CDR1 PRT |
| 58 | 11 | CDR2 PRT |
| 59 | 11 | CDR3 PRT |
| 60 | 11 | FW1 PRT |
| 61 | 11 | FW2 PRT |
| 62 | 11 | FW3 PRT |
| 63 | 11 | FW4 PRT |
| 64 | 11 | VL DNA |
| 65 | 11 | VL PRT |
| 66 | 11 | CDR1 PRT |
| 67 | 11 | CDR2 PRT |
| 68 | 11 | CDR3 PRT |
| 69 | 11 | FW1 PRT |
| 70 | 11 | FW2 PRT |
| 71 | 11 | FW3 PRT |
| 72 | 11 | FW4 PRT |
| 73 | 18 | VH DNA |
| 74 | 18 | VH PRT |
| 75 | 18 | CDR1 PRT |
| 76 | 18 | CDR2 PRT |
| 77 | 18 | CDR3 PRT |
| 78 | 18 | FW1 PRT |

-continued

| SEQ ID | Antibody | Description |
|---|---|---|
| 79 | 18 | FW2 PRT |
| 80 | 18 | FW3 PRT |
| 81 | 18 | FW4 PRT |
| 82 | 18 | VL DNA |
| 83 | 18 | VL PRT |
| 84 | 18 | CDR1 PRT |
| 85 | 18 | CDR2 PRT |
| 86 | 18 | CDR3 PRT |
| 87 | 18 | FW1 PRT |
| 88 | 18 | FW2 PRT |
| 89 | 18 | FW3 PRT |
| 90 | 18 | FW4 PRT |
| 91 | 29 | VH DNA |
| 92 | 29 | VH PRT |
| 93 | 29 | CDR1 PRT |
| 94 | 29 | CDR2 PRT |
| 95 | 29 | CDR3 PRT |
| 96 | 29 | FW1 PRT |
| 97 | 29 | FW2 PRT |
| 98 | 29 | FW3 PRT |
| 99 | 29 | FW4 PRT |
| 100 | 29 | VL DNA |
| 101 | 29 | VL PRT |
| 102 | 29 | CDR1 PRT |
| 103 | 29 | CDR2 PRT |
| 104 | 29 | CDR3 PRT |
| 105 | 29 | FW1 PRT |
| 106 | 29 | FW2 PRT |
| 107 | 29 | FW3 PRT |
| 108 | 29 | FW4 PRT |
| 109 | 33 | VH DNA |
| 110 | 33 | VH PRT |
| 111 | 33 | CDR1 PRT |
| 112 | 33 | CDR2 PRT |
| 113 | 33 | CDR3 PRT |
| 114 | 33 | FW1 PRT |
| 115 | 33 | FW2 PRT |
| 116 | 33 | FW3 PRT |

-continued

| SEQ ID | Antibody | Description |
|---|---|---|
| 117 | 33 | FW4 PRT |
| 118 | 33 | VL DNA |
| 119 | 33 | VL PRT |
| 120 | 33 | CDR1 PRT |
| 121 | 33 | CDR2 PRT |
| 122 | 33 | CDR3 PRT |
| 123 | 33 | FW1 PRT |
| 124 | 33 | FW2 PRT |
| 125 | 33 | FW3 PRT |
| 126 | 33 | FW4 PRT |
| 127 | 35 | VH DNA |
| 128 | 35 | VH PRT |
| 129 | 35 | CDR1 PRT |
| 130 | 35 | CDR2 PRT |
| 131 | 35 | CDR3 PRT |
| 132 | 35 | FW1 PRT |
| 133 | 35 | FW2 PRT |
| 134 | 35 | FW3 PRT |
| 135 | 35 | FW4 PRT |
| 136 | 35 | VL DNA |
| 137 | 35 | VL PRT |
| 138 | 35 | CDR1 PRT |
| 139 | 35 | CDR2 PRT |
| 140 | 35 | CDR3 PRT |
| 141 | 35 | FW1 PRT |
| 142 | 35 | FW2 PRT |
| 143 | 35 | FW3 PRT |
| 144 | 35 | FW4 PRT |
| 163 | 37 | VH DNA |
| 164 | 37 | VH PRT |
| 165 | 37 | CDR1 PRT |
| 166 | 37 | CDR2 PRT |
| 167 | 37 | CDR3 PRT |
| 168 | 37 | FW1 PRT |
| 169 | 37 | FW2 PRT |
| 170 | 37 | FW3 PRT |
| 171 | 37 | FW4 PRT |
| 172 | 37 | VL DNA |

-continued

| SEQ ID | Antibody | Description |
|---|---|---|
| 173 | 37 | VL PRT |
| 174 | 37 | CDR1 PRT |
| 175 | 37 | CDR2 PRT |
| 176 | 37 | CDR3 PRT |
| 177 | 37 | FW1 PRT |
| 178 | 37 | FW2 PRT |
| 179 | 37 | FW3 PRT |
| 180 | 37 | FW4 PRT |
| 181 | 38 | VH DNA |
| 182 | 38 | VH PRT |
| 183 | 38 | CDR1 PRT |
| 184 | 38 | CDR2 PRT |
| 185 | 38 | CDR3 PRT |
| 186 | 38 | FW1 PRT |
| 187 | 38 | FW2 PRT |
| 188 | 38 | FW3 PRT |
| 189 | 38 | FW4 PRT |
| 190 | 38 | VL DNA |
| 191 | 38 | VL PRT |
| 192 | 38 | CDR1 PRT |
| 193 | 38 | CDR2 PRT |
| 194 | 38 | CDR3 PRT |
| 195 | 38 | FW1 PRT |
| 196 | 38 | FW2 PRT |
| 197 | 38 | FW3 PRT |
| 198 | 38 | FW4 PRT |
| 217 | 40 | VH DNA |
| 218 | 40 | VH PRT |
| 219 | 40 | CDR1 PRT |
| 220 | 40 | CDR2 PRT |
| 221 | 40 | CDR3 PRT |
| 222 | 40 | FW1 PRT |
| 223 | 40 | FW2 PRT |
| 224 | 40 | FW3 PRT |
| 225 | 40 | FW4 PRT |
| 226 | 40 | VL DNA |
| 227 | 40 | VL PRT |
| 228 | 40 | CDR1 PRT |

-continued

| SEQ ID | Antibody | Description |
|---|---|---|
| 229 | 40 | CDR2 PRT |
| 230 | 40 | CDR3 PRT |
| 231 | 40 | FW1 PRT |
| 232 | 40 | FW2 PRT |
| 233 | 40 | FW3 PRT |
| 234 | 40 | FW4 PRT |
| 253 | 42 | VH DNA |
| 254 | 42 | VH PRT |
| 255 | 42 | CDR1 PRT |
| 256 | 42 | CDR2 PRT |
| 257 | 42 | CDR3 PRT |
| 258 | 42 | FW1 PRT |
| 259 | 42 | FW2 PRT |
| 260 | 42 | FW3 PRT |
| 261 | 42 | FW4 PRT |
| 262 | 42 | VL DNA |
| 263 | 42 | VL PRT |
| 264 | 42 | CDR1 PRT |
| 265 | 42 | CDR2 PRT |
| 266 | 42 | CDR3 PRT |
| 267 | 42 | FW1 PRT |
| 268 | 42 | FW2 PRT |
| 269 | 42 | FW3 PRT |
| 270 | 42 | FW4 PRT |
| 271 | 43 | VH DNA |
| 272 | 43 | VH PRT |
| 273 | 43 | CDR1 PRT |
| 274 | 43 | CDR2 PRT |
| 275 | 43 | CDR3 PRT |
| 276 | 43 | FW1 PRT |
| 277 | 43 | FW2 PRT |
| 278 | 43 | FW3 PRT |
| 279 | 43 | FW4 PRT |
| 280 | 43 | VL DNA |
| 281 | 43 | VL PRT |
| 282 | 43 | CDR1 PRT |
| 283 | 43 | CDR2 PRT |
| 284 | 43 | CDR3 PRT |

-continued

| SEQ ID | Antibody | Description |
|---|---|---|
| 285 | 43 | FW1 PRT |
| 286 | 43 | FW2 PRT |
| 287 | 43 | FW3 PRT |
| 288 | 43 | FW4 PRT |
| 289 | 44 | VH DNA |
| 290 | 44 | VH PRT |
| 291 | 44 | CDR1 PRT |
| 292 | 44 | CDR2 PRT |
| 293 | 44 | CDR3 PRT |
| 294 | 44 | FW1 PRT |
| 295 | 44 | FW2 PRT |
| 296 | 44 | FW3 PRT |
| 297 | 44 | FW4 PRT |
| 298 | 44 | VL DNA |
| 299 | 44 | VL PRT |
| 300 | 44 | CDR1 PRT |
| 301 | 44 | CDR2 PRT |
| 302 | 44 | CDR3 PRT |
| 303 | 44 | FW1 PRT |
| 304 | 44 | FW2 PRT |
| 305 | 44 | FW3 PRT |
| 306 | 44 | FW4 PRT |
| 307 | 45 | VH DNA |
| 308 | 45 | VH PRT |
| 309 | 45 | CDR1 PRT |
| 310 | 45 | CDR2 PRT |
| 311 | 45 | CDR3 PRT |
| 312 | 45 | FW1 PRT |
| 313 | 45 | FW2 PRT |
| 314 | 45 | FW3 PRT |
| 315 | 45 | FW4 PRT |
| 316 | 45 | VL DNA |
| 317 | 45 | VL PRT |
| 318 | 45 | CDR1 PRT |
| 319 | 45 | CDR2 PRT |
| 320 | 45 | CDR3 PRT |
| 321 | 45 | FW1 PRT |
| 322 | 45 | FW2 PRT |

-continued

| SEQ ID | Antibody | Description |
|---|---|---|
| 323 | 45 | FW3 PRT |
| 324 | 45 | FW4 PRT |
| 325 | 46 | VH DNA |
| 326 | 46 | VH PRT |
| 327 | 46 | CDR1 PRT |
| 328 | 46 | CDR2 PRT |
| 329 | 46 | CDR3 PRT |
| 330 | 46 | FW1 PRT |
| 331 | 46 | FW2 PRT |
| 332 | 46 | FW3 PRT |
| 333 | 46 | FW4 PRT |
| 334 | 46 | VL DNA |
| 335 | 46 | VL PRT |
| 336 | 46 | CDR1 PRT |
| 337 | 46 | CDR2 PRT |
| 338 | 46 | CDR3 PRT |
| 339 | 46 | FW1 PRT |
| 340 | 46 | FW2 PRT |
| 341 | 46 | FW3 PRT |
| 342 | 46 | FW4 PRT |
| 343 | 47 | VH DNA |
| 344 | 47 | VH PRT |
| 345 | 47 | CDR1 PRT |
| 346 | 47 | CDR2 PRT |
| 347 | 47 | CDR3 PRT |
| 348 | 47 | FW1 PRT |
| 349 | 47 | FW2 PRT |
| 350 | 47 | FW3 PRT |
| 351 | 47 | FW4 PRT |
| 352 | 47 | VL DNA |
| 353 | 47 | VL PRT |
| 354 | 47 | CDR1 PRT |
| 355 | 47 | CDR2 PRT |
| 356 | 47 | CDR3 PRT |
| 357 | 47 | FW1 PRT |
| 358 | 47 | FW2 PRT |
| 359 | 47 | FW3 PRT |
| 360 | 47 | FW4 PRT |

-continued

| SEQ ID | Antibody | Description |
|---|---|---|
| 361 | 48 | VH DNA |
| 362 | 48 | VH PRT |
| 363 | 48 | CDR1 PRT |
| 364 | 48 | CDR2 PRT |
| 365 | 48 | CDR3 PRT |
| 366 | 48 | FW1 PRT |
| 367 | 48 | FW2 PRT |
| 368 | 48 | FW3 PRT |
| 369 | 48 | FW4 PRT |
| 370 | 48 | VL DNA |
| 371 | 48 | VL PRT |
| 372 | 48 | CDR1 PRT |
| 373 | 48 | CDR2 PRT |
| 374 | 48 | CDR3 PRT |
| 375 | 48 | FW1 PRT |
| 376 | 48 | FW2 PRT |
| 377 | 48 | FW3 PRT |
| 378 | 48 | FW4 PRT |
| 379 | 287 | VH DNA |
| 380 | 287 | VH PRT |
| 381 | 287 | CDR1 PRT |
| 382 | 287 | CDR2 PRT |
| 383 | 287 | CDR3 PRT |
| 384 | 287 | FW1 PRT |
| 385 | 287 | FW2 PRT |
| 386 | 287 | FW3 PRT |
| 387 | 287 | FW4 PRT |
| 388 | 287 | VL DNA |
| 389 | 287 | VL PRT |
| 390 | 287 | CDR1 PRT |
| 391 | 287 | CDR2 PRT |
| 392 | 287 | CDR3 PRT |
| 393 | 287 | FW1 PRT |
| 394 | 287 | FW2 PRT |
| 395 | 287 | FW3 PRT |
| 396 | 287 | FW4 PRT |
| 397 | 288 | VH DNA |
| 398 | 288 | VH PRT |

-continued

| SEQ ID | Antibody | Description |
|---|---|---|
| 399 | 288 | CDR1 PRT |
| 400 | 288 | CDR2 PRT |
| 401 | 288 | CDR3 PRT |
| 402 | 288 | FW1 PRT |
| 403 | 288 | FW2 PRT |
| 404 | 288 | FW3 PRT |
| 405 | 288 | FW4 PRT |
| 406 | 288 | VL DNA |
| 407 | 288 | VL PRT |
| 408 | 288 | CDR1 PRT |
| 409 | 288 | CDR2 PRT |
| 410 | 288 | CDR3 PRT |
| 411 | 288 | FW1 PRT |
| 412 | 288 | FW2 PRT |
| 413 | 288 | FW3 PRT |
| 414 | 288 | FW4 PRT |
| 415 | 289 | VH DNA |
| 416 | 289 | VH PRT |
| 417 | 289 | CDR1 PRT |
| 418 | 289 | CDR2 PRT |
| 419 | 289 | CDR3 PRT |
| 420 | 289 | FW1 PRT |
| 421 | 289 | FW2 PRT |
| 422 | 289 | FW3 PRT |
| 423 | 289 | FW4 PRT |
| 424 | 289 | VL DNA |
| 425 | 289 | VL PRT |
| 426 | 289 | CDR1 PRT |
| 427 | 289 | CDR2 PRT |
| 428 | 289 | CDR3 PRT |
| 429 | 289 | FW1 PRT |
| 430 | 289 | FW2 PRT |
| 431 | 289 | FW3 PRT |
| 432 | 289 | FW4 PRT |
| 433 | 290 | VH DNA |
| 434 | 290 | VH PRT |
| 435 | 290 | CDR1 PRT |
| 436 | 290 | CDR2 PRT |
| 437 | 290 | CDR3 PRT |
| 438 | 290 | FW1 PRT |
| 439 | 290 | FW2 PRT |
| 440 | 290 | FW3 PRT |
| 441 | 290 | FW4 PRT |
| 442 | 290 | VL DNA |
| 443 | 290 | VL PRT |
| 444 | 290 | CDR1 PRT |
| 445 | 290 | CDR2 PRT |
| 446 | 290 | CDR3 PRT |
| 447 | 290 | FW1 PRT |
| 448 | 290 | FW2 PRT |
| 449 | 290 | FW3 PRT |
| 450 | 290 | FW4 PRT |
| 451 | 291 | VH DNA |
| 452 | 291 | VH PRT |
| 453 | 291 | CDR1 PRT |
| 454 | 291 | CDR2 PRT |
| 455 | 291 | CDR3 PRT |
| 456 | 291 | FW1 PRT |
| 457 | 291 | FW2 PRT |
| 458 | 291 | FW3 PRT |
| 459 | 291 | FW4 PRT |
| 460 | 291 | VL DNA |
| 461 | 291 | VL PRT |
| 462 | 291 | CDR1 PRT |
| 463 | 291 | CDR2 PRT |
| 464 | 291 | CDR3 PRT |
| 465 | 291 | FW1 PRT |
| 466 | 291 | FW2 PRT |
| 467 | 291 | FW3 PRT |
| 468 | 291 | FW4 PRT |
| 469 | 292 | VH DNA |
| 470 | 292 | VH PRT |
| 471 | 292 | CDR1 PRT |
| 472 | 292 | CDR2 PRT |
| 473 | 292 | CDR3 PRT |
| 474 | 292 | FW1 PRT |

-continued

| SEQ ID | Antibody | Description |
|---|---|---|
| 475 | 292 | FW2 PRT |
| 476 | 292 | FW3 PRT |
| 477 | 292 | FW4 PRT |
| 478 | 292 | VL DNA |
| 479 | 292 | VL PRT |
| 480 | 292 | CDR1 PRT |
| 481 | 292 | CDR2 PRT |
| 482 | 292 | CDR3 PRT |
| 483 | 292 | FW1 PRT |
| 484 | 292 | FW2 PRT |
| 485 | 292 | FW3 PRT |
| 486 | 292 | FW4 PRT |
| 487 | 293 | VH DNA |
| 488 | 293 | VH PRT |
| 489 | 293 | CDR1 PRT |
| 490 | 293 | CDR2 PRT |
| 491 | 293 | CDR3 PRT |
| 492 | 293 | FW1 PRT |
| 493 | 293 | FW2 PRT |
| 494 | 293 | FW3 PRT |
| 495 | 293 | FW4 PRT |
| 496 | 293 | VL DNA |
| 497 | 293 | VL PRT |
| 498 | 293 | CDR1 PRT |
| 499 | 293 | CDR2 PRT |
| 500 | 293 | CDR3 PRT |
| 501 | 293 | FW1 PRT |
| 502 | 293 | FW2 PRT |
| 503 | 293 | FW3 PRT |
| 504 | 293 | FW4 PRT |
| 505 | 294 | VH DNA |
| 506 | 294 | VH PRT |
| 507 | 294 | CDR1 PRT |
| 508 | 294 | CDR2 PRT |
| 509 | 294 | CDR3 PRT |
| 510 | 294 | FW1 PRT |
| 511 | 294 | FW2 PRT |
| 512 | 294 | FW3 PRT |

-continued

| SEQ ID | Antibody | Description |
|---|---|---|
| 513 | 294 | FW4 PRT |
| 514 | 294 | VL DNA |
| 515 | 294 | VL PRT |
| 516 | 294 | CDR1 PRT |
| 517 | 294 | CDR2 PRT |
| 518 | 294 | CDR3 PRT |
| 519 | 294 | FW1 PRT |
| 520 | 294 | FW2 PRT |
| 521 | 294 | FW3 PRT |
| 522 | 294 | FW4 PRT |
| 523 | 295 | VH DNA |
| 524 | 295 | VH PRT |
| 525 | 295 | CDR1 PRT |
| 526 | 295 | CDR2 PRT |
| 527 | 295 | CDR3 PRT |
| 528 | 295 | FW1 PRT |
| 529 | 295 | FW2 PRT |
| 530 | 295 | FW3 PRT |
| 531 | 295 | FW4 PRT |
| 532 | 295 | VL DNA |
| 533 | 295 | VL PRT |
| 534 | 295 | CDR1 PRT |
| 535 | 295 | CDR2 PRT |
| 536 | 295 | CDR3 PRT |
| 537 | 295 | FW1 PRT |
| 538 | 295 | FW2 PRT |
| 539 | 295 | FW3 PRT |
| 540 | 295 | FW4 PRT |
| 541 | 296 | VH DNA |
| 542 | 296 | VH PRT |
| 543 | 296 | CDR1 PRT |
| 544 | 296 | CDR2 PRT |
| 545 | 296 | CDR3 PRT |
| 546 | 296 | FW1 PRT |
| 547 | 296 | FW2 PRT |
| 548 | 296 | FW3 PRT |
| 549 | 296 | FW4 PRT |
| 550 | 296 | VL DNA |

-continued

| SEQ ID | Antibody | Description |
|---|---|---|
| 551 | 296 | VL PRT |
| 552 | 296 | CDR1 PRT |
| 553 | 296 | CDR2 PRT |
| 554 | 296 | CDR3 PRT |
| 555 | 296 | FW1 PRT |
| 556 | 296 | FW2 PRT |
| 557 | 296 | FW3 PRT |
| 558 | 296 | FW4 PRT |
| 559 | 297 | VH DNA |
| 560 | 297 | VH PRT |
| 561 | 297 | CDR1 PRT |
| 562 | 297 | CDR2 PRT |
| 563 | 297 | CDR3 PRT |
| 564 | 297 | FW1 PRT |
| 565 | 297 | FW2 PRT |
| 566 | 297 | FW3 PRT |
| 567 | 297 | FW4 PRT |
| 568 | 297 | VL DNA |
| 569 | 297 | VL PRT |
| 570 | 297 | CDR1 PRT |
| 571 | 297 | CDR2 PRT |
| 572 | 297 | CDR3 PRT |
| 573 | 297 | FW1 PRT |
| 574 | 297 | FW2 PRT |
| 575 | 297 | FW3 PRT |
| 576 | 297 | FW4 PRT |
| 577 | 298 | VH DNA |
| 578 | 298 | VH PRT |
| 579 | 298 | CDR1 PRT |
| 580 | 298 | CDR2 PRT |
| 581 | 298 | CDR3 PRT |
| 582 | 298 | FW1 PRT |
| 583 | 298 | FW2 PRT |
| 584 | 298 | FW3 PRT |
| 585 | 298 | FW4 PRT |
| 586 | 298 | VL DNA |
| 587 | 298 | VL PRT |
| 588 | 298 | CDR1 PRT |

-continued

| SEQ ID | Antibody | Description |
|---|---|---|
| 589 | 298 | CDR2 PRT |
| 590 | 298 | CDR3 PRT |
| 591 | 298 | FW1 PRT |
| 592 | 298 | FW2 PRT |
| 593 | 298 | FW3 PRT |
| 594 | 298 | FW4 PRT |
| 595 | 299 | VH DNA |
| 596 | 299 | VH PRT |
| 597 | 299 | CDR1 PRT |
| 598 | 299 | CDR2 PRT |
| 599 | 299 | CDR3 PRT |
| 600 | 299 | FW1 PRT |
| 601 | 299 | FW2 PRT |
| 602 | 299 | FW3 PRT |
| 603 | 299 | FW4 PRT |
| 604 | 299 | VL DNA |
| 605 | 299 | VL PRT |
| 606 | 299 | CDR1 PRT |
| 607 | 299 | CDR2 PRT |
| 608 | 299 | CDR3 PRT |
| 609 | 299 | FW1 PRT |
| 610 | 299 | FW2 PRT |
| 611 | 299 | FW3 PRT |
| 612 | 299 | FW4 PRT |
| 613 | 300 | VH DNA |
| 614 | 300 | VH PRT |
| 615 | 300 | CDR1 PRT |
| 616 | 300 | CDR2 PRT |
| 617 | 300 | CDR3 PRT |
| 618 | 300 | FW1 PRT |
| 619 | 300 | FW2 PRT |
| 620 | 300 | FW3 PRT |
| 621 | 300 | FW4 PRT |
| 622 | 300 | VL DNA |
| 623 | 300 | VL PRT |
| 624 | 300 | CDR1 PRT |
| 625 | 300 | CDR2 PRT |
| 626 | 300 | CDR3 PRT |

| SEQ ID | Antibody | Description |
|---|---|---|
| 627 | 300 | FW1 PRT |
| 628 | 300 | FW2 PRT |
| 629 | 300 | FW3 PRT |
| 630 | 300 | FW4 PRT |
| 631 | 302 | VH DNA |
| 632 | 302 | VH PRT |
| 633 | 302 | CDR1 PRT |
| 634 | 302 | CDR2 PRT |
| 635 | 302 | CDR3 PRT |
| 636 | 302 | FW1 PRT |
| 637 | 302 | FW2 PRT |
| 638 | 302 | FW3 PRT |
| 639 | 302 | FW4 PRT |
| 640 | 302 | VL DNA |
| 641 | 302 | VL PRT |
| 642 | 302 | CDR1 PRT |
| 643 | 302 | CDR2 PRT |
| 644 | 302 | CDR3 PRT |
| 645 | 302 | FW1 PRT |
| 646 | 302 | FW2 PRT |
| 647 | 302 | FW3 PRT |
| 648 | 302 | FW4 PRT |
| 649 | 303 | VH DNA |
| 650 | 303 | VH PRT |
| 651 | 303 | CDR1 PRT |
| 652 | 303 | CDR2 PRT |
| 653 | 303 | CDR3 PRT |
| 654 | 303 | FW1 PRT |
| 655 | 303 | FW2 PRT |
| 656 | 303 | FW3 PRT |
| 657 | 303 | FW4 PRT |
| 658 | 303 | VL DNA |
| 659 | 303 | VL PRT |
| 660 | 303 | CDR1 PRT |
| 661 | 303 | CDR2 PRT |
| 662 | 303 | CDR3 PRT |
| 663 | 303 | FW1 PRT |
| 664 | 303 | FW2 PRT |
| 665 | 303 | FW3 PRT |
| 666 | 303 | FW4 PRT |
| 667 | 304 | VH DNA |
| 668 | 304 | VH PRT |
| 669 | 304 | CDR1 PRT |
| 670 | 304 | CDR2 PRT |
| 671 | 304 | CDR3 PRT |
| 672 | 304 | FW1 PRT |
| 673 | 304 | FW2 PRT |
| 674 | 304 | FW3 PRT |
| 675 | 304 | FW4 PRT |
| 676 | 304 | VL DNA |
| 677 | 304 | VL PRT |
| 678 | 304 | CDR1 PRT |
| 679 | 304 | CDR2 PRT |
| 680 | 304 | CDR3 PRT |
| 681 | 304 | FW1 PRT |
| 682 | 304 | FW2 PRT |
| 683 | 304 | FW3 PRT |
| 684 | 304 | FW4 PRT |
| 685 | 305 | VH DNA |
| 686 | 305 | VH PRT |
| 687 | 305 | CDR1 PRT |
| 688 | 305 | CDR2 PRT |
| 689 | 305 | CDR3 PRT |
| 690 | 305 | FW1 PRT |
| 691 | 305 | FW2 PRT |
| 692 | 305 | FW3 PRT |
| 693 | 305 | FW4 PRT |
| 694 | 305 | VL DNA |
| 695 | 305 | VL PRT |
| 696 | 305 | CDR1 PRT |
| 697 | 305 | CDR2 PRT |
| 698 | 305 | CDR3 PRT |
| 699 | 305 | FW1 PRT |
| 700 | 305 | FW2 PRT |
| 701 | 305 | FW3 PRT |
| 702 | 305 | FW4 PRT |

-continued

| SEQ ID | Antibody | Description |
|---|---|---|
| 703 | 306 | VH DNA |
| 704 | 306 | VH PRT |
| 705 | 306 | CDR1 PRT |
| 706 | 306 | CDR2 PRT |
| 707 | 306 | CDR3 PRT |
| 708 | 306 | FW1 PRT |
| 709 | 306 | FW2 PRT |
| 710 | 306 | FW3 PRT |
| 711 | 306 | FW4 PRT |
| 712 | 306 | VL DNA |
| 713 | 306 | VL PRT |
| 714 | 306 | CDR1 PRT |
| 715 | 306 | CDR2 PRT |
| 716 | 306 | CDR3 PRT |
| 717 | 306 | FW1 PRT |
| 718 | 306 | FW2 PRT |
| 719 | 306 | FW3 PRT |
| 720 | 306 | FW4 PRT |
| 721 | 307 | VH DNA |
| 722 | 307 | VH PRT |
| 723 | 307 | CDR1 PRT |
| 724 | 307 | CDR2 PRT |
| 725 | 307 | CDR3 PRT |
| 726 | 307 | FW1 PRT |
| 727 | 307 | FW2 PRT |
| 728 | 307 | FW3 PRT |
| 729 | 307 | FW4 PRT |
| 730 | 307 | VL DNA |
| 731 | 307 | VL PRT |
| 732 | 307 | CDR1 PRT |
| 733 | 307 | CDR2 PRT |
| 734 | 307 | CDR3 PRT |
| 735 | 307 | FW1 PRT |
| 736 | 307 | FW2 PRT |
| 737 | 307 | FW3 PRT |
| 738 | 307 | FW4 PRT |
| 739 | 308 | VH DNA |
| 740 | 308 | VH PRT |

-continued

| SEQ ID | Antibody | Description |
|---|---|---|
| 741 | 308 | CDR1 PRT |
| 742 | 308 | CDR2 PRT |
| 743 | 308 | CDR3 PRT |
| 744 | 308 | FW1 PRT |
| 745 | 308 | FW2 PRT |
| 746 | 308 | FW3 PRT |
| 747 | 308 | FW4 PRT |
| 748 | 308 | VL DNA |
| 749 | 308 | VL PRT |
| 750 | 308 | CDR1 PRT |
| 751 | 308 | CDR2 PRT |
| 752 | 308 | CDR3 PRT |
| 753 | 308 | FW1 PRT |
| 754 | 308 | FW2 PRT |
| 755 | 308 | FW3 PRT |
| 756 | 308 | FW4 PRT |
| 757 | 309 | VH DNA |
| 758 | 309 | VH PRT |
| 759 | 309 | CDR1 PRT |
| 760 | 309 | CDR2 PRT |
| 761 | 309 | CDR3 PRT |
| 762 | 309 | FW1 PRT |
| 763 | 309 | FW2 PRT |
| 764 | 309 | FW3 PRT |
| 765 | 309 | FW4 PRT |
| 766 | 309 | VL DNA |
| 767 | 309 | VL PRT |
| 768 | 309 | CDR1 PRT |
| 769 | 309 | CDR2 PRT |
| 770 | 309 | CDR3 PRT |
| 771 | 309 | FW1 PRT |
| 772 | 309 | FW2 PRT |
| 773 | 309 | FW3 PRT |
| 774 | 309 | FW4 PRT |
| 775 | 310 | VH DNA |
| 776 | 310 | VH PRT |
| 777 | 310 | CDR1 PRT |
| 778 | 310 | CDR2 PRT |

-continued

| SEQ ID | Antibody | Description |
|---|---|---|
| 779 | 310 | CDR3 PRT |
| 780 | 310 | FW1 PRT |
| 781 | 310 | FW2 PRT |
| 782 | 310 | FW3 PRT |
| 783 | 310 | FW4 PRT |
| 784 | 310 | VL DNA |
| 785 | 310 | VL PRT |
| 786 | 310 | CDR1 PRT |
| 787 | 310 | CDR2 PRT |
| 788 | 310 | CDR3 PRT |
| 789 | 310 | FW1 PRT |
| 790 | 310 | FW2 PRT |
| 791 | 310 | FW3 PRT |
| 792 | 310 | FW4 PRT |
| 793 | 311 | VH DNA |
| 794 | 311 | VH PRT |
| 795 | 311 | CDR1 PRT |
| 796 | 311 | CDR2 PRT |
| 797 | 311 | CDR3 PRT |
| 798 | 311 | FW1 PRT |
| 799 | 311 | FW2 PRT |
| 800 | 311 | FW3 PRT |
| 801 | 311 | FW4 PRT |
| 802 | 311 | VL DNA |
| 803 | 311 | VL PRT |
| 804 | 311 | CDR1 PRT |
| 805 | 311 | CDR2 PRT |
| 806 | 311 | CDR3 PRT |
| 807 | 311 | FW1 PRT |
| 808 | 311 | FW2 PRT |
| 809 | 311 | FW3 PRT |
| 810 | 311 | FW4 PRT |
| 811 | 312 | VH DNA |
| 812 | 312 | VH PRT |
| 813 | 312 | CDR1 PRT |
| 814 | 312 | CDR2 PRT |
| 815 | 312 | CDR3 PRT |
| 816 | 312 | FW1 PRT |

-continued

| SEQ ID | Antibody | Description |
|---|---|---|
| 817 | 312 | FW2 PRT |
| 818 | 312 | FW3 PRT |
| 819 | 312 | FW4 PRT |
| 820 | 312 | VL DNA |
| 821 | 312 | VL PRT |
| 822 | 312 | CDR1 PRT |
| 823 | 312 | CDR2 PRT |
| 824 | 312 | CDR3 PRT |
| 825 | 312 | FW1 PRT |
| 826 | 312 | FW2 PRT |
| 827 | 312 | FW3 PRT |
| 828 | 312 | FW4 PRT |
| 829 | 313 | VH DNA |
| 830 | 313 | VH PRT |
| 831 | 313 | CDR1 PRT |
| 832 | 313 | CDR2 PRT |
| 833 | 313 | CDR3 PRT |
| 834 | 313 | FW1 PRT |
| 835 | 313 | FW2 PRT |
| 836 | 313 | FW3 PRT |
| 837 | 313 | FW4 PRT |
| 838 | 313 | VL DNA |
| 839 | 313 | VL PRT |
| 840 | 313 | CDR1 PRT |
| 841 | 313 | CDR2 PRT |
| 842 | 313 | CDR3 PRT |
| 843 | 313 | FW1 PRT |
| 844 | 313 | FW2 PRT |
| 845 | 313 | FW3 PRT |
| 846 | 313 | FW4 PRT |
| 847 | 314 | VH DNA |
| 848 | 314 | VH PRT |
| 849 | 314 | CDR1 PRT |
| 850 | 314 | CDR2 PRT |
| 851 | 314 | CDR3 PRT |
| 852 | 314 | FW1 PRT |
| 853 | 314 | FW2 PRT |
| 854 | 314 | FW3 PRT |

-continued

| SEQ ID | Antibody | Description |
|---|---|---|
| 855 | 314 | FW4 PRT |
| 856 | 314 | VL DNA |
| 857 | 314 | VL PRT |
| 858 | 314 | CDR1 PRT |
| 859 | 314 | CDR2 PRT |
| 860 | 314 | CDR3 PRT |
| 861 | 314 | FW1 PRT |
| 862 | 314 | FW2 PRT |
| 863 | 314 | FW3 PRT |
| 864 | 314 | FW4 PRT |
| 865 | 315 | VH DNA |
| 866 | 315 | VH PRT |
| 867 | 315 | CDR1 PRT |
| 868 | 315 | CDR2 PRT |
| 869 | 315 | CDR3 PRT |
| 870 | 315 | FW1 PRT |
| 871 | 315 | FW2 PRT |
| 872 | 315 | FW3 PRT |
| 873 | 315 | FW4 PRT |
| 874 | 315 | VL DNA |
| 875 | 315 | VL PRT |
| 876 | 315 | CDR1 PRT |
| 877 | 315 | CDR2 PRT |
| 878 | 315 | CDR3 PRT |
| 879 | 315 | FW1 PRT |
| 880 | 315 | FW2 PRT |
| 881 | 315 | FW3 PRT |
| 882 | 315 | FW4 PRT |
| 883 | 316 | VH DNA |
| 884 | 316 | VH PRT |
| 885 | 316 | CDR1 PRT |
| 886 | 316 | CDR2 PRT |
| 887 | 316 | CDR3 PRT |
| 888 | 316 | FW1 PRT |
| 889 | 316 | FW2 PRT |
| 890 | 316 | FW3 PRT |
| 891 | 316 | FW4 PRT |
| 892 | 316 | VL DNA |

-continued

| SEQ ID | Antibody | Description |
|---|---|---|
| 893 | 316 | VL PRT |
| 894 | 316 | CDR1 PRT |
| 895 | 316 | CDR2 PRT |
| 896 | 316 | CDR3 PRT |
| 897 | 316 | FW1 PRT |
| 898 | 316 | FW2 PRT |
| 899 | 316 | FW3 PRT |
| 900 | 316 | FW4 PRT |
| 901 | 317 | VH DNA |
| 902 | 317 | VH PRT |
| 903 | 317 | CDR1 PRT |
| 904 | 317 | CDR2 PRT |
| 905 | 317 | CDR3 PRT |
| 906 | 317 | FW1 PRT |
| 907 | 317 | FW2 PRT |
| 908 | 317 | FW3 PRT |
| 909 | 317 | FW4 PRT |
| 910 | 317 | VL DNA |
| 911 | 317 | VL PRT |
| 912 | 317 | CDR1 PRT |
| 913 | 317 | CDR2 PRT |
| 914 | 317 | CDR3 PRT |
| 915 | 317 | FW1 PRT |
| 916 | 317 | FW2 PRT |
| 917 | 317 | FW3 PRT |
| 918 | 317 | FW4 PRT |
| 919 | 318 | VH DNA |
| 920 | 318 | VH PRT |
| 921 | 318 | CDR1 PRT |
| 922 | 318 | CDR2 PRT |
| 923 | 318 | CDR3 PRT |
| 924 | 318 | FW1 PRT |
| 925 | 318 | FW2 PRT |
| 926 | 318 | FW3 PRT |
| 927 | 318 | FW4 PRT |
| 928 | 318 | VL DNA |
| 929 | 318 | VL PRT |
| 930 | 318 | CDR1 PRT |

-continued

| SEQ ID | Antibody | Description |
|---|---|---|
| 931 | 318 | CDR2 PRT |
| 932 | 318 | CDR3 PRT |
| 933 | 318 | FW1 PRT |
| 934 | 318 | FW2 PRT |
| 935 | 318 | FW3 PRT |
| 936 | 318 | FW4 PRT |
| 937 | 319 | VH DNA |
| 938 | 319 | VH PRT |
| 939 | 319 | CDR1 PRT |
| 940 | 319 | CDR2 PRT |
| 941 | 319 | CDR3 PRT |
| 942 | 319 | FW1 PRT |
| 943 | 319 | FW2 PRT |
| 944 | 319 | FW3 PRT |
| 945 | 319 | FW4 PRT |
| 946 | 319 | VL DNA |
| 947 | 319 | VL PRT |
| 948 | 319 | CDR1 PRT |
| 949 | 319 | CDR2 PRT |
| 950 | 319 | CDR3 PRT |
| 951 | 319 | FW1 PRT |
| 952 | 319 | FW2 PRT |
| 953 | 319 | FW3 PRT |
| 954 | 319 | FW4 PRT |
| 955 | 320 | VH DNA |
| 956 | 320 | VH PRT |
| 957 | 320 | CDR1 PRT |
| 958 | 320 | CDR2 PRT |
| 959 | 320 | CDR3 PRT |
| 960 | 320 | FW1 PRT |
| 961 | 320 | FW2 PRT |
| 962 | 320 | FW3 PRT |
| 963 | 320 | FW4 PRT |
| 964 | 320 | VL DNA |
| 965 | 320 | VL PRT |
| 966 | 320 | CDR1 PRT |
| 967 | 320 | CDR2 PRT |
| 968 | 320 | CDR3 PRT |

-continued

| SEQ ID | Antibody | Description |
|---|---|---|
| 969 | 320 | FW1 PRT |
| 970 | 320 | FW2 PRT |
| 971 | 320 | FW3 PRT |
| 972 | 320 | FW4 PRT |
| 973 | 321 | VH DNA |
| 974 | 321 | VH PRT |
| 975 | 321 | CDR1 PRT |
| 976 | 321 | CDR2 PRT |
| 977 | 321 | CDR3 PRT |
| 978 | 321 | FW1 PRT |
| 979 | 321 | FW2 PRT |
| 980 | 321 | FW3 PRT |
| 981 | 321 | FW4 PRT |
| 982 | 321 | VL DNA |
| 983 | 321 | VL PRT |
| 984 | 321 | CDR1 PRT |
| 985 | 321 | CDR2 PRT |
| 986 | 321 | CDR3 PRT |
| 987 | 321 | FW1 PRT |
| 988 | 321 | FW2 PRT |
| 989 | 321 | FW3 PRT |
| 990 | 321 | FW4 PRT |
| 991 | 208 | VH DNA |
| 992 | 208 | VH PRT |
| 993 | 208 | CDR1 PRT |
| 994 | 208 | CDR2 PRT |
| 995 | 208 | CDR3 PRT |
| 996 | 208 | FW1 PRT |
| 997 | 208 | FW2 PRT |
| 998 | 208 | FW3 PRT |
| 999 | 208 | FW4 PRT |
| 100 | 208 | VL DNA |
| 1001 | 208 | VL PRT |
| 1002 | 208 | CDR1 PRT |
| 1003 | 208 | CDR2 PRT |
| 1004 | 208 | CDR3 PRT |
| 1005 | 208 | FW1 PRT |
| 1006 | 208 | FW2 PRT |

-continued

| SEQ ID | Antibody | Description |
|---|---|---|
| 1007 | 208 | FW3 PRT |
| 1008 | 208 | FW4 PRT |

DETAILED DESCRIPTION OF THE INVENTION

As described below, the present invention provides antibodies that specifically bind a P2X4 polypeptide and modulate P2X4 channel activity, recombinant P2X4 polypeptides and methods for generating such polypeptides, as well as compositions and methods for generating anti-P2X4 antibodies, and methods of using P2X4 antibodies for the treatment of neuropathic pain and other indications.
Recombinant Expression of P2X4

The present invention provides purified isolated recombinant P2X4 polypeptides that form stable trimeric complexes. The invention further provides methods for the large scale production of purified and isolated human and murine P2X4 polypeptides, which is sufficient to produce milligram quantities of P2X4 protein, where the isolated and purified recombinant proteins are predominantly present as stable trimers. The total quantities of P2X4 that were produced for the selection and screening experiments described herein included 6.2 mg hP2X4 and 3.2 mg mP2X4. The production level of purified protein was 0.2 mg/L insect cell culture. As assayed by fluorescent size exclusion chromatography the protein preparation contains 50-75% trimer.

Expression and purification of human-P2X4 with a C-terminal deca Histidine tag in HEK293 cells has been described (Young et al., J. Biol. Chem. 283 (2008) 26241-26251). The purification involved solubilization using dodecylmaltoside detergent and Ni-immobilized metal affinity chromatography. A polyacrylamide gel electrophoretic purification step was required to isolate the trimeric form. Although a fully trimeric preparation of hP2X4 was claimed to have been isolated, the described yield was only 40 μg per $2.5 \times 10^8$ cells.

Another example of small scale expression and purification of trimer rat P2X channels (subtypes 2, 4 and 7) has been performed (Antonio et al., Br. J. Pharmacol. 163 (2011) 1069-1077). Rat P2X4 receptors having a C-terminal Hemaglutinin tag were expressed transiently in tsA 201 cells (a sub-clone of HEK293 cells stably expressing the SV40 large T-antigen). Receptors were solubilized in CHAPS detergent and affinity purified. Compared to expression of P2X2 and P2X7, expression of P2X4 was relatively low. The purified receptors were used in AFM imaging, which showed trimeric arrangement of the receptors and also double trimers (dimers of trimers).

In another report Sf9 insect cell system was evaluated for expression of human P2X4 and *Dictyostelium discoideum* P2XA (Valente et al., Biochim. Biophys. Acta 1808 (2011) 2859-2866). While the *D. discoideum* P2XA could be obtained in a stable, purified and detergent soluble form, the human P2X4 was reported not to be amenable to be produced in a trimeric form.

The methods present in the prior art uniformly failed to isolate substantial quantities of recombinant P2X4 polypeptides. Moreover, the prior art failed to isolate human P2X4 complexes in milligram quantities where the majority of the isolated proteins were present in trimeric form. In contrast, the methods of the invention, which are suitable for scale up, have allowed milligram scale production of purified recombinant P2X4 polypeptide. The yield of purified P2X4 obtained was 0.2 mg/L insect cell culture medium, corresponding to approximately 8 μg per $1 \times 10^8$ cells.

For the large scale production of purified P2X4, the human P2X4 and mouse P2X4 receptors were expressed in Sf9 insect cells using a baculovirus expression system. Expression and protein production are not limited to Sf9 insect cell lines, other insect cell and cell lines that support protein production include *Spodoptera frugiperda* Sf21 cells or *Trichoplusia ni* derived cell lines Tn-368 and High-Five™ BTI-TN-5B1-4. To increase protein production, P2X4 expression levels were monitored at the time of harvest, and the quality and homogeneity of the receptors was assessed using a modified size-exclusion chromatography while detecting fluorescence (FSEC) method as described by Backmark et al., (Protein Sci. 22 (2013) 1124-1132). This method is similar to the basic FSEC concept as described by Kawate and Gouaux (Structure 14 (2006) 673-681), but applied a fluorescent probe that specifically interacts with a Histidine tag on the protein. To achieve the surprising yields reported herein, cells were innoculated at a density of $1.0 \times 10e^6$/mL in SF900II medium. Cells were infected with a multiplicity of infection of 2 at a cell density of $2 \times 10e^6$ cells/ml. Protein expression was performed at 27° C. and cells were harvested 72 hours post infection. These conditions permitted an optimal quantity of the trimeric form of P2X4 to be produced. The homogeneity of protein was unexpected. While the total amount of expressed P2X4 protein increased with longer post infection times, the quality of the expressed protein as assayed by FSEC did not increase beyond 72 hours.
Anti-P2X4 Antibodies The disclosure provides anti-P2X4 antibodies that comprise novel antigen-binding fragments. In a particular embodiment, the anti-P2X4 antibody is an anti-P2X4 antibody described herein (e.g., Antibodies 1-48) or a fragment thereof.

In general, antibodies can be made, for example, using traditional hybridoma techniques (Kohler and Milstein (1975) Nature, 256: 495-499), recombinant DNA methods (U.S. Pat. No. 4,816,567), or phage display performed with antibody libraries (Clackson, T. and Lowman, H. B. Phage Display—A Practical Approach, 2004. Oxford University Press; (2) Thompson, J. et al. J Mol Biol. 256(1):77-88, 1996; (3) Osbourn, J. K. et al. Immunotechnology, 2(3):181-96, 1996). Exemplary antibodies 35-48 were obtained using hybridoma techniques as described herein. Exemplary antibodies 1-34 were obtained using phage display as described herein. For other antibody production techniques, see also Antibodies: A Laboratory Manual, eds. Harlow et al., Cold Spring Harbor Laboratory, 1988. The invention is not limited to any particular source, species of origin, or method of production.

Intact antibodies, also known as immunoglobulins, are typically tetrameric glycosylated proteins composed of two light (L) chains of approximately 25 kDa each and two heavy (H) chains of approximately 50 kDa each. Two types of light chain, designated as the λ chain and the κ chain, are found in antibodies. Depending on the amino acid sequence of the constant domain of heavy chains, immunoglobulins can be assigned to five major classes: A, D, E, G, and M, and several of these may be further divided into subclasses (isotypes), e.g., $IgG_1$, $IgG_2$, $IgG_3$, $IgG_4$, $IgA_1$, and $IgA_2$.

The subunit structures and three-dimensional configurations of different classes of immunoglobulins are well known in the art. For a review of antibody structure, see Harlow et al., supra. Briefly, each light chain is composed of an N-terminal variable domain ($V_L$) and a constant domain ($C_L$). Each heavy chain is composed of an N-terminal variable domain ($V_H$), three or four constant domains ($C_H$), and a hinge region. The $C_H$ domain most proximal to $V_H$ is designated as $C_H1$. The $V_H$ and $V_L$ domains consist of four regions of relatively conserved sequence called framework regions (FR1, FR2, FR3, and FR4), which form a scaffold for three regions of hypervariable sequence called complementarity determining regions (CDRs). The CDRs contain most of the residues responsible for specific interactions with the antigen. The three CDRs are referred to as CDR1, CDR2, and CDR3. CDR constituents on the heavy chain are referred to as H1, H2, and H3, while CDR constituents on the light chain are referred to as L1, L2, and L3, accordingly. CDR3 and, particularly H3, are the greatest source of molecular diversity within the antigen-binding domain. H3, for example, can be as short as two amino acid residues or greater than 26. In particular embodiments, a heavy chain CDR3 (H3) comprises between about 4 amino acids (see, for example, Ab No. 2) and 22 amino acids (see, for example, Ab Nos. 20 and 34).

The Fab fragment (Fragment antigen-binding) consists of the $V_H$-$C_H1$ and VL-CL domains covalently linked by a disulfide bond between the constant regions. To overcome the tendency of non-covalently linked $V_H$ and $V_L$ domains in the Fv to dissociate when co-expressed in a host cell, a so-called single chain (sc) Fv fragment (scFv) can be constructed. In a scFv, a flexible and adequately long polypeptide links either the C-terminus of the $V_H$ to the N-terminus of the $V_L$ or the C-terminus of the $V_L$ to the N-terminus of the $V_H$. Most commonly, a 15-residue $(Gly_4Ser)_3$ peptide is used as a linker, but other linkers are also known in the art.

Antibody diversity is a result of combinatorial assembly of multiple germline genes encoding variable regions and a variety of somatic events. The somatic events include recombination of variable gene segments with diversity (D) and joining (J) gene segments to make a complete $V_H$ region and the recombination of variable and joining gene segments to make a complete $V_L$ region. The recombination process itself is imprecise, resulting in the loss or addition of amino acids at the V(D)J junctions. These mechanisms of diversity occur in the developing B cell prior to antigen exposure. After antigenic stimulation, the expressed antibody genes in B cells undergo somatic mutation.

Based on the estimated number of germline gene segments, the random recombination of these segments, and random $V_H$-$V_L$ pairing, up to $1.6 \times 10^7$ different antibodies could be produced (Fundamental Immunology, 3rd ed., ed. Paul, Raven Press, New York, N.Y., 1993). When other processes that contribute to antibody diversity (such as somatic mutation) are taken into account, it is thought that upwards of $1 \times 10^{10}$ different antibodies could be potentially generated (Immunoglobulin Genes, $2^{nd}$ ed., eds. Jonio et al., Academic Press, San Diego, Calif., 1995). Because of the many processes involved in antibody diversity, it is highly unlikely that independently generated antibodies will have identical or even substantially similar amino acid sequences in the CDRs.

The disclosure provides novel CDRs derived from human immunoglobulin gene libraries. The structure for carrying a CDR will generally be an antibody heavy or light chain or a portion thereof, in which the CDR is located at a location corresponding to the CDR of naturally occurring $V_H$ and $V_L$. The structures and locations of immunoglobulin variable domains may be determined, for example, as described in Kabat et al., Sequences of Proteins of Immunological Interest, No. 91-3242, National Institutes of Health Publications, Bethesda, Md., 1991.

The amino acid sequences of anti-P2X4 antibodies 1-48, 208, and 287 to 321, including their $V_H$ and $V_L$ domains are set forth in the Figures and described herein.

Anti-P2X4 antibodies may optionally comprise antibody constant regions or parts thereof. For example, a $V_L$ domain may have attached, at its C terminus, antibody light chain constant domains including human Cκ or Cλ chains. Similarly, a specific antigen-binding domain based on a $V_H$ domain may have attached all or part of an immunoglobulin heavy chain derived from any antibody isotype, e.g., IgG, IgA, IgE, and IgM and any of the isotype subclasses, which include but are not limited to, $IgG_1$ and $IgG_4$. The DNA and amino acid sequences for the C-terminal fragment of are well known in the art (see, e.g., Kabat et al., Sequences of Proteins of Immunological Interest, No. 91-3242, National Institutes of Health Publications, Bethesda, Md., 1991).

Certain embodiments comprise a $V_H$ and/or $V_L$ domain of an Fv fragment from a P2X4 antibody. Further embodiments comprise at least one CDR of any of these $V_H$ and $V_L$ domains. Antibodies, comprising at least one of the CDR sequences set forth for Antibody Nos. 1-48 are encompassed within the scope of this invention. In one particular embodiment, an antibody of the invention comprises CDR3 of VH.

In certain embodiments, the $V_H$ and/or $V_L$ domains may be germlined, i.e., the framework regions (FRs) of these domains are mutated using conventional molecular biology techniques to match those produced by the germline cells. In other embodiments, the framework sequences remain diverged from the consensus germline sequences.

In certain embodiments, the antibodies specifically bind an epitope within the extracellular domain of human P2X4. In certain embodiments, the antibodies specifically bind an epitope within the extracellular domain of human or mouse P2X4, with an affinity of more than $10^6$ M$^{-1}$, more than $10^7$ M$^{-1}$, or more than $10^8$ M$^{-1}$.

It is contemplated that antibodies of the invention may also bind with other proteins, including, for example, recombinant proteins comprising all or a portion of the P2X4 extracellular domain.

One of ordinary skill in the art will recognize that the antibodies of this invention may be used to detect, measure, and inhibit proteins that differ somewhat from P2X4. The antibodies are expected to retain the specificity of binding so long as the target protein comprises a sequence which is at least about 60%, 70%, 80%, 90%, 95%, or more identical to any sequence of at least 100, 80, 60, 40, or 20 of contiguous amino acids of P2X4 (NCBI Ref. No. Q99571). The percent identity is determined by standard alignment algorithms such as, for example, Basic Local Alignment Tool (BLAST) described in Altshul et al. (1990) J. Mol. Biol., 215: 403-410, the algorithm of Needleman et al. (1970) J. Mol. Biol., 48: 444-453, or the algorithm of Meyers et al. (1988) Comput. Appl. Biosci., 4: 11-17.

In addition to the sequence homology analyses, epitope mapping (see, e.g., Epitope Mapping Protocols, ed. Morris, Humana Press, 1996) and secondary and tertiary structure analyses can be carried out to identify specific 3D structures assumed by the disclosed antibodies and their complexes with antigens. An example of such a 3D structure is provided for Antibody No. 11. Such methods include, but are not limited to, X-ray crystallography (Engstom (1974) Biochem. Exp. Biol., 11:7-13) and computer modeling of virtual representations of the presently disclosed antibodies (Fletterick et al. (1986) Computer Graphics and Molecular Modeling, in Current Communications in Molecular Biology, Cold Spring Harbor Laboratory, Cold Spring Harbor, N.Y.).
Derivatives This disclosure provides methods for obtaining antibodies specific for P2X4. CDRs in such antibodies are not limited to the specific sequences of $V_H$ and $V_L$ identified herein, and may include variants of these sequences that retain the ability to specifically bind P2X4. Such variants may be derived from the sequences listed herein by a skilled artisan using techniques well known in the art. For example, amino acid substitutions, deletions, or additions, can be made in the FRs and/or in the CDRs. While changes in the FRs are usually designed to improve stability and immunogenicity of the antibody, changes in the CDRs are typically designed to increase affinity of the antibody for its target. Variants of FRs also include naturally occurring immunoglobulin allotypes. Such affinity-increasing changes may be determined empirically by routine techniques that involve altering the CDR and testing the affinity of the antibody for its target. For example, conservative amino acid substitutions can be made within any one of the disclosed CDRs. Various alterations can be made according to the methods described in Antibody Engineering, $2^{nd}$ ed., Oxford University Press, ed. Borrebaeck, 1995. These include, but are not limited to, nucleotide sequences that are altered by the substitution of different codons that encode a functionally equivalent amino acid residue within the sequence, thus producing a "silent" change. For example, the nonpolar amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Substitutes for an amino acid within the sequence may be selected from other members of the class to which the amino acid belongs (see Table 1). Furthermore, any native residue in the polypeptide may also be substituted with alanine (see, e.g., MacLennan et al. (1998) Acta Physiol. Scand. Suppl. 643:55-67; Sasaki et al. (1998) Adv. Biophys. 35:1-24).

TABLE 1

| Original Residues | Exemplary Substitutions | Typical Substitutions |
| --- | --- | --- |
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4-Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala | Gly |
| Ser (S) | Thr, Ala, Cys | Thr |
| Thr (T) | Ser | Ser |
| Trp (W) | Tyr, Phe | Tyr |

TABLE 1-continued

| Original Residues | Exemplary Substitutions | Typical Substitutions |
| --- | --- | --- |
| Tyr (Y) | Trp, Phe, Thr, Ser | Phe |
| Val (V) | Ile, Met, Leu, Phe, Ala, Norleucine | Leu |

Derivatives and analogs of antibodies of the invention can be produced by various techniques well known in the art, including recombinant and synthetic methods (Maniatis (1990) Molecular Cloning, A Laboratory Manual, $2^{nd}$ ed., Cold Spring Harbor Laboratory, Cold Spring Harbor, N.Y., and Bodansky et al. (1995) The Practice of Peptide Synthesis, $2^{nd}$ ed., Spring Verlag, Berlin, Germany).

In one embodiment, a method for making a $V_H$ domain which is an amino acid sequence variant of a $V_H$ domain of the invention comprises a step of adding, deleting, substituting, or inserting one or more amino acids in the amino acid sequence of the presently disclosed $V_H$ domain, optionally combining the $V_H$ domain thus provided with one or more $V_L$ domains, and testing the $V_H$ domain or $V_H/V_L$ combination or combinations for a specific binding to P2X4 or and, optionally, testing the ability of such antigen-binding domain to modulate P2X4 activity, for example, using an electrophysiology assay described herein. The $V_L$ domain may have an amino acid sequence that is identical or is substantially identical to a polypeptide of the invention.

An analogous method can be employed in which one or more sequence variants of a $V_L$ domain disclosed herein are combined with one or more $V_H$ domains.

A further aspect of the disclosure provides a method of preparing an antigen-binding fragment that specifically binds with P2X4. The method comprises:
  (a) providing a starting repertoire of nucleic acids encoding a $V_H$ domain that either includes a CDR3 to be replaced or lacks a CDR3 encoding region;
  (b) combining the repertoire with a donor nucleic acid encoding an amino acid sequence substantially as set out herein for a $V_H$ CDR3 (i.e., H3) such that the donor nucleic acid is inserted into the CDR3 region in the repertoire, so as to provide a product repertoire of nucleic acids encoding a $V_H$ domain;
  (c) expressing the nucleic acids of the product repertoire;
  (d) selecting a binding fragment specific for P2X4; and
  (e) recovering the specific binding fragment or nucleic acid encoding it.

Again, an analogous method may be employed in which a $V_L$ CDR3 (i.e., L3) of the invention is combined with a repertoire of nucleic acids encoding a $V_L$ domain, which either include a CDR3 to be replaced or lack a CDR3 encoding region. The donor nucleic acid may be selected from nucleic acids encoding an amino acid sequence substantially as set out in Antibody Nos. 1-48.

A sequence encoding a CDR of the invention (e.g., CDR3) may be introduced into a repertoire of variable domains lacking the respective CDR (e.g., CDR3), using recombinant DNA technology, for example, using methodology described by Marks et al. (Bio/Technology (1992) 10: 779-783). In particular, consensus primers directed at or adjacent to the 5' end of the variable domain area can be used in conjunction with consensus primers to the third framework region of human $V_H$ genes to provide a repertoire of $V_H$ variable domains lacking a CDR3. The repertoire may be combined with a CDR3 of a particular antibody. Using analogous techniques, the CDR3-derived sequences may be shuffled with repertoires of $V_H$ or $V_L$ domains lacking a CDR3, and the shuffled complete $V_H$ or $V_L$ domains combined with a cognate $V_L$ or $V_H$ domain to make the P2X4-specific antibodies of the invention. The repertoire may then be displayed in a suitable host system such as the phage display system described herein or as described in WO92/01047 so that suitable antigen-binding fragments can be selected.

Analogous shuffling or combinatorial techniques are also disclosed by Stemmer (Nature (1994) 370: 389-391), who describes the technique in relation to a β-lactamase gene but observes that the approach may be used for the generation of antibodies.

In further embodiments, one may generate novel $V_H$ or $V_L$ regions carrying one or more sequences derived from the sequences disclosed herein using random mutagenesis of one or more selected $V_H$ and/or $V_L$ genes. One such technique, error-prone PCR, is described by Gram et al. (Proc. Nat. Acad. Sci. U.S.A. (1992) 89: 3576-3580).

Another method that may be used is to direct mutagenesis to CDRs of $V_H$ or $V_L$ genes. Such techniques are disclosed by Barbas et al. (Proc. Nat. Acad. Sci. U.S.A. (1994) 91: 3809-3813) and Schier et al. (J. Mol. Biol. (1996) 263: 551-567).

Similarly, one or more, or all three CDRs may be grafted into a repertoire of $V_H$ or $V_L$ domains, which are then screened for an antigen-binding fragment specific for P2X4.

A portion of an immunoglobulin variable domain will comprise at least one of the CDRs substantially as set out herein and, optionally, intervening framework regions from the scFv fragments as set out herein. The portion may include at least about 50% of either or both of FR1 and FR4, the 50% being the C-terminal 50% of FR1 and the N-terminal 50% of FR4. Additional residues at the N-terminal or C-terminal end of the substantial part of the variable domain may be those not normally associated with naturally occurring variable domain regions. For example, construction of antibodies by recombinant DNA techniques may result in the introduction of N- or C-terminal residues encoded by linkers introduced to facilitate cloning or other manipulation steps. Other manipulation steps include the introduction of linkers to join variable domains to further protein sequences including immunoglobulin heavy chain constant regions, other variable domains (for example, in the production of diabodies), or proteinaceous labels as discussed in further detail below.

Although the embodiments illustrated in the Examples comprise a "matching" pair of $V_H$ and $V_L$ domains, a skilled artisan will recognize that alternative embodiments may comprise antigen-binding fragments containing only a single CDR from either $V_L$ or $V_H$ domain. In particular embodiments, the antigen-binding fragment is CDR3 of $V_H$ (H3). Either one of the single chain specific binding domains can be used to screen for complementary domains capable of forming a two-domain specific antigen-binding fragment capable of, for example, binding to P2X4. The screening may be accomplished by phage display screening methods using the so-called hierarchical dual combinatorial approach disclosed in WO92/01047, in which an individual colony containing either an H or L chain clone is used to infect a complete library of clones encoding the other chain (L or H) and the resulting two-chain specific binding domain is selected in accordance with phage display techniques as described.

Anti-P2X4 antibodies described herein can be linked to another functional molecule, e.g., another peptide or protein (albumin, another antibody, etc.). For example, the antibodies can be linked by chemical cross-linking or by recombinant methods.

The disclosed antibodies may also be altered to have a glycosylation pattern that differs from the native pattern. For example, one or more carbohydrate moieties can be deleted and/or one or more glycosylation sites added to the original antibody. Addition of glycosylation sites to the presently disclosed antibodies may be accomplished by altering the amino acid sequence to contain glycosylation site consensus sequences known in the art. Another means of increasing the number of carbohydrate moieties on the antibodies is by chemical or enzymatic coupling of glycosides to the amino acid residues of the antibody. Such methods are described in WO 87/05330 and in Aplin et al. (1981) CRC Crit. Rev. Biochem., 22: 259-306. Removal of any carbohydrate moieties from the antibodies may be accomplished chemically or enzymatically, for example, as described by Hakimuddin et al. (1987) Arch. Biochem. Biophys., 259: 52; and Edge et al. (1981) Anal. Biochem., 118: 131 and by Thotakura et al. (1987) Meth. Enzymol., 138: 350. The antibodies may also be tagged with a detectable, or functional, label. Detectable labels include radiolabels such as $^{131}$I or $^{99}$Tc, which may also be attached to antibodies using conventional chemistry. Detectable labels also include enzyme labels such as horseradish peroxidase or alkaline phosphatase. Detectable labels further include chemical moieties such as biotin, which may be detected via binding to a specific cognate detectable moiety, e.g., labeled avidin.

Typically, an amino acid is substituted by a related amino acid having similar charge, hydrophobic, or stereochemical characteristics. Such substitutions would be within the ordinary skills of an artisan. Unlike in CDRs, more substantial changes can be made in FRs without adversely affecting the binding properties of an antibody. Changes to FRs include, but are not limited to, humanizing a non-human derived or engineering certain framework residues that are important for antigen contact or for stabilizing the binding site, e.g., changing the class or subclass of the constant region, changing specific amino acid residues which might alter the effector function such as Fc receptor binding, e.g., as described in U.S. Pat. Nos. 5,624,821 and 5,648,260 and Lund et al. (1991) J. Immun. 147: 2657-2662 and Morgan et al. (1995) Immunology 86: 319-324, or changing the species from which the constant region is derived.

One of skill in the art will appreciate that the modifications described above are not all-exhaustive, and that many other modifications would obvious to a skilled artisan in light of the teachings of the present disclosure.

Nucleic Acids, Cloning and Expression Systems

The present disclosure provides the amino acid sequence of the disclosed antibodies. Once provided with this information, one of skill in the art could readily obtain nucleic acid molecules encoding the disclosed antibodies. The nucleic acids may comprise DNA or RNA and may be wholly or partially synthetic or recombinant. Reference to a nucleotide sequence encompasses a DNA molecule with the specified sequence, and encompasses a RNA molecule with the specified sequence in which U is substituted for T, unless context requires otherwise.

The nucleic acids molecules of the invention comprise a coding sequence for a CDR, a $V_H$ domain, and/or a $V_L$ domain disclosed herein.

The present disclosure also provides constructs in the form of plasmids, vectors, phagemids, transcription or expression cassettes which comprise at least one nucleic acid molecule encoding a CDR, a $V_H$ domain, and/or a $V_L$ domain disclosed herein.

The disclosure further provides a host cell which comprises one or more constructs as above.

Also provided are nucleic acids encoding any CDR (H1, H2, H3, L1, L2, or L3), $V_H$ or $V_L$ domain, as well as methods of making of the encoded products. The method comprises expressing the encoded product from the encoding nucleic acid. Expression may be achieved by culturing under appropriate conditions recombinant host cells containing the nucleic acid. Following production by expression a $V_H$ or $V_L$ domain, or specific binding member may be isolated and/or purified using any suitable technique, then used as appropriate.

Antigen-binding fragments, $V_H$ and/or $V_L$ domains and encoding nucleic acid molecules and vectors may be isolated and/or purified from their natural environment, in substantially pure or homogeneous form, or, in the case of nucleic acid, free or substantially free of nucleic acid or genes of origin other than the sequence encoding a polypeptide with the required function.

Systems for cloning and expression of a polypeptide in a variety of different host cells are well known in the art. For cells suitable for producing antibodies, see Gene Expression Systems, Academic Press, eds. Fernandez et al., 1999. Briefly, suitable host cells include bacteria, plant cells, mammalian cells, and yeast and baculovirus systems. Mammalian cell lines available in the art for expression of a heterologous polypeptide include Chinese hamster ovary cells, HeLa cells, baby hamster kidney cells, NS0 mouse myeloma cells, and many others. A common bacterial host is E. coli. Any protein expression system compatible with the invention may be used to produce the disclosed antibodies. Suitable expression systems include transgenic animals described in Gene Expression Systems, Academic Press, eds. Fernandez et al., 1999.

Suitable vectors can be chosen or constructed, so that they contain appropriate regulatory sequences, including promoter sequences, terminator sequences, polyadenylation sequences, enhancer sequences, marker genes and other sequences as appropriate. Vectors may be plasmids or viral, e.g., phage, or phagemid, as appropriate. For further details see, for example, Sambrook et al., Molecular Cloning: A Laboratory Manual, 2nd ed., Cold Spring Harbor Laboratory Press, 1989. Many known techniques and protocols for manipulation of nucleic acid, for example, in preparation of nucleic acid constructs, mutagenesis, sequencing, introduction of DNA into cells and gene expression, and analysis of proteins, are described in detail in Current Protocols in Molecular Biology, 2nd Edition, eds. Ausubel et al., John Wiley & Sons, 1992.

A further aspect of the disclosure provides a host cell comprising a nucleic acid as disclosed here. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g., vaccinia or, for insect cells, baculovirus. For bacterial cells, suitable techniques may include calcium chloride transformation, electroporation and transfection using bacteriophage. The introduction of the nucleic acid into the cells may be followed by causing or allowing expression from the nucleic acid, e.g., by culturing host cells under conditions for expression of the gene.

Methods of Use

The disclosed anti-P2X4 antibodies are capable of modulating the electrophysiological activity of P2X4. In particular, antibodies provided herein may be used to inhibit or potentiate P2X4 channel conductance. Such antibodies can be used to treat P2X4-associated medical disorders in mammals, especially, in humans. In particular, antibodies that inhibit P2X4 activity are useful for the treatment of neuropathic pain. Antibodies that potentiate P2X4 activity are useful in other therapeutic methods, including but not limited to microglia-mediated diseases and disorders and macrophage-mediated diseases and disorders.

Antibodies of the invention can also be used for isolating P2X4 or P2X4-expressing cells.

As demonstrated in the Examples, binding of P2X4 with an anti-P2X4 antibody modulates P2X4 biological activity by potentiating or reducing passage of ions through the P2X4 channel.

The antibodies or antibody compositions of the present invention are administered in therapeutically effective amounts. Generally, a therapeutically effective amount may vary with the subject's age, condition, and sex, as well as the severity of the medical condition of the subject. The appropriate dose is chosen based on clinical indications by a treating physician.

The antibodies may be given as a bolus dose, to maximize the circulating levels of antibodies for the greatest length of time after the dose. Continuous infusion may also be used after the bolus dose.

Anti-P2X4 antibodies of the invention may be used to detect the presence of P2X4 in biological samples. Detection methods that employ antibodies are well known in the art and include, for example, ELISA, radioimmunoassay, immunoblot, Western blot, immunofluorescence, and immunoprecipitation. If desired, an anti-P2X4 antibody is modified, for example, with a ligand group (such as biotin) or a detectable marker group (such as a fluorescent group, a radioisotope or an enzyme). If desired, the antibodies of the invention may be labeled using conventional techniques. Suitable detectable labels include, for example, fluorophores, chromophores, radioactive atoms, electron-dense reagents, enzymes, and ligands having specific binding partners. Enzymes are typically detected by their activity. For example, horseradish peroxidase can be detected by its ability to convert tetramethylbenzidine (TMB) to a blue pigment, quantifiable with a spectrophotometer. For detection, suitable binding partners include, but are not limited to, biotin and avidin or streptavidin, IgG and protein A, and the numerous receptor-ligand couples known in the art. Other permutations and possibilities will be readily apparent to those of ordinary skill in the art, and are considered as equivalents within the scope of the invention.

Pharmaceutical Compositions and Methods of Administration

The invention provides pharmaceutical compositions comprising anti-P2X4 antibodies (e.g., Antibody Nos. 1-48). Such compositions are likely suitable for pharmaceutical use and administration to patients. The compositions typically comprise one or more antibodies of the present invention and a pharmaceutically acceptable excipient. The phrase "pharmaceutically acceptable excipient" includes any and all solvents, dispersion media, coatings, antibacterial agents and antifungal agents, isotonic agents, and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions. The pharmaceutical compositions may also be included in a container, pack, or dispenser together with instructions for administration.

A pharmaceutical composition of the invention is formulated to be compatible with its intended route of administration. Methods to accomplish the administration are known to those of ordinary skill in the art. The administration may, for example, be intravenous, intraperitoneal, intramuscular, intracavity, subcutaneous or transdermal. In one embodiment, neuropathic pain is treated by intrathecal administration. It may also be possible to obtain compositions which may be topically or orally administered, or which may be capable of transmission across mucous membranes.

Solutions or suspensions used for intradermal or subcutaneous application typically include one or more of the following components: a sterile diluent such as water for injection, saline solution, fixed oils, polyethylene glycols, glycerin, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. The pH can be adjusted with acids or bases, such as hydrochloric acid or sodium hydroxide. Such preparations may be enclosed in ampoules, disposable syringes or multiple dose vials made of glass or plastic.

Pharmaceutical compositions suitable for injection include sterile aqueous solutions or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars; polyalcohols such as mannitol, sorbitol, and sodium chloride in the composition. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and/or by the use of surfactants. Prolonged absorption of the injectable compositions can be brought about by including in the composition an agent which delays absorption, for example, aluminum monostearate, and gelatin.

Oral compositions generally include an inert diluent or an edible carrier. They can be enclosed in gelatin capsules or compressed into tablets. For oral administration, the antibodies can be combined with excipients and used in the form of tablets, troches, or capsules. Pharmaceutically compatible binding agents, and/or adjuvant materials can be included as part of the composition. The tablets, pills, capsules, troches, and the like can contain any of the following ingredients, or compounds of a similar nature; a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, detergents, bile salts, and fusidic acid derivatives. Transmucosal administration may be accomplished, for example, through the use of lozenges, nasal sprays, inhalers, or suppositories. For example, in case of antibodies that comprise the Fc portion, compositions may be capable of transmission across mucous membranes in intestine, mouth, or lungs (e.g., via the FcRn receptor-mediated pathway as described in U.S. Pat. No. 6,030,613). For transdermal administration, the active compounds may be formulated into ointments, salves, gels, or creams as generally known in the art. For administration by inhalation, the antibodies may be delivered in the form of an aerosol spray from pressured container or dispenser, which contains a suitable propellant, e.g., a gas such as carbon dioxide, or a nebulizer.

In certain embodiments, the presently disclosed antibodies are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions containing the presently disclosed antibodies can also be used as pharmaceutically acceptable carriers. These can be prepared according to methods known to those skilled in the art, for example, as described in U.S. Pat. No. 4,522,811.

It may be advantageous to formulate oral or parenteral compositions in a dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of the composition of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred.

The data obtained from electrophysiological experiments and animal studies can be used in formulating a range of dosage for use in humans. A dose may be formulated in animal models to achieve a circulating plasma concentration range that includes the $IC_{50}$ (i.e., the concentration of the antibody which achieves a half-maximal inhibition of symptoms). Circulating levels in plasma may be measured, for example, by high performance liquid chromatography. The effects of any particular dosage can be monitored by a suitable bioassay. The dosage lies preferably within a range of circulating concentrations with little or no toxicity. The dosage may vary depending upon the dosage form employed and the route of administration utilized.

Kits

The invention provides kits for modulating P2X4 activity. Antibodies that potentiate P2X4 activity are useful for the treatment of indications mediated by decreased P2X4 activity as described herein. Antibodies that inhibit P2X4 activity are useful for the treatment or prevention of neuropathic pain and/or microglia-mediated diseases and disorders and/or macrophage-mediated diseases and disorders. In one embodiment, the kit includes a therapeutic or prophylactic composition containing an effective amount of an anti-P2X4 antibody that modulates P2X4 activity in unit dosage form.

In some embodiments, the kit comprises a sterile container which contains a therapeutic or prophylactic cellular composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired an antibody of the invention is provided together with instructions for administering the antibody or agent to a subject having or at risk of developing neuropathic pain. The instructions will generally include information about the use of the composition for the treatment or prevention of such indications. In other embodiments, the instructions include at least one of the following: description of the therapeutic agent; dosage schedule and administration for treatment or prevention of an immune disorder or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the anti-P2X4 antibodies in assay, screening, and therapeutic methods of the invention, and are not intended to limit the scope of what the inventors regard as their invention.

EXAMPLES

Example 1: Production and Isolation of Recombinant P2X4 Proteins

Human P2X purinoceptor 4 (Q99571), a natural variant of human P2X purinoceptor 4 with an S to G mutation at position 242 (Corresponds to variant rs25644) and murine P2X purinoceptor 4 (Q9JJX6) proteins were designed with a C-terminal AVI tag (Avidity LLC) and a C-terminal Histidine tag. The constructs were cloned into pFASTBAC1 vectors (Life Technologies). Bacmids were generated in DH10Bac (Life Technologies) $E.$ $coli$ cells. Bacmids were subsequently transfected into Sf9 insect cells ($Spodoptera$ $frugiperda$ Sf9 cells from Life Technologies, cat no 11496-015) for production of recombinant baculovirus particles, which in turn were used to infect Sf9 cells for protein expression.

Expression parameters were assessed by monitoring expression level, protein quality and the homogeneity of the receptor using a modified Fluorescence-detection size-exclusion chromatography (FSEC) method described by Backmark et al., (Protein Sci. 22 (2013) 1124-1132). This method is similar to the basic FSEC concept as described by Kawate and Gouaux (Structure 14 (2006) 673-681), but applied a fluorescent probe that specifically interacts with the Histidine tag on the protein. Cells were typically innoculated at a density of 1.0×10e6/mL in SF900II medium. Cells were infected with a multiplicity of infection of 2 at a cell density of 2×10E6 cells/ml. Protein expression was performed at 27° C. and cells were harvested 72 hours post infection. Expression parameters were selected to enhance the quantity of trimer and homogeneity of protein present as trimers. As assayed by fluorescent size exclusion chromatography, the protein preparation contains 50-75% trimer. Although the total amount of receptor increased with longer post infection times, FSEC analysis indicated that protein quality declined when the expression time was increased past 72 hours.

Human P2X4 receptor and mouse P2X4 were purified as follows. Membranes were prepared from SF9 cells. Membrane proteins were extracted from the membranes by detergent solubilization, using combinations of detergents, salts, buffers and additives, including n-Dodecyl-beta-D-Maltoside CAS 69227-93-6 (0-2% (w/v)), n-Dodecyl thio-Maltoside CAS 148565-58-6 (0-1% (w/v)), (3-[(3-Cholamidopropyl)-Dimethylammonio]-1-Propane Sulfonate/N,N-Dimethyl-3-Sulfo-N-[3-[[3α,5β,7α,12α)-3,7,12-Trihydroxy-24-Oxocholan-24-yl]Amino]propyl]-1-Propanaminium Hydroxide abbreviated to CHAPS CAS 75621-03-3 (0-0.6% (w/v)), and Cholesteryl Hemisuccinate CAS 102601-49-0 (0-0.12% (w/v)). Without being bound to theory, higher concentrations of the indicated substances as well as alternative detergents support extraction of the protein from the membranes. The proteins underwent standard affinity and size exclusion chromatography purification. The purified protein was formulated in a buffer which contained 50 mM Tris-HCl pH 8.0, 600 mM NaCl, 10% (v/v) glycerol, 0.025 (w/v) % n-Dodecyl-beta-D-Maltoside CAS 69227-93-6, 0.0125% (w/v), n-Dodecyl thio-Maltoside CAS 148565-58-6, 0.0075% (w/v) (3-[(3-Cholamidopropyl)-Dimethylammonio]-1-Propane Sulfonate/N,N-Dimethyl-3-Sulfo-N-[3-[[3α,5β,7α,12α)-3,7,12-Trihydroxy-24-Oxocholan-24-yl]Amino]propyl]-1-Propanaminium Hydroxide abbreviated to CHAPS CAS 75621-03-3, and 0.0015% (w/v) Cholesteryl Hemisuccinate CAS 102601-49-0.

The purified protein was formulated under alternative conditions, including phosphate buffers and HEPES buffers 2-[4-(2-hydroxyethyl)piperazin-1-yl]ethanesulfonic acid buffers CAS 7365-45-9. The pH of the various buffers has ranged from 7.0-8.0. Salt (NaCl) has been varied between 120-600 mM. Glycerol can be excluded from the protein formulation. Various detergents have been used in protein formulation, such as lauryl maltose neopentyl glycol 2,2- didecylpropane-1,3-bis-β-D-maltopyranoside, decyl maltose neopentyl glycol 2,2-dioctylpropane-1,3-bis-β-D-maltopyranoside, octyl maltose neopentyl glycol 2,2-dihexylpropane-1,3-bis-β-D-maltopyranoside, CYMAL-5 5-Cyclohexyl-1-pentyl-β-D-maltoside CAS 250692-65-0, n-Tetradecylphosphocholine 77733-28-9, n-Decyl-β-D-Maltopyranoside CAS 82494-09-5, n-octyl-β-D-glucoside CAS 29836-26-8 and n-nonyl-β-D-glucoside CAS 69984-73-2. Formulations in other detergents are also possible. The concentration of Cholesteryl Hemisuccinate CAS 102601-49-0 can be varied and excluded from the protein formulation as well.

Example 2: Purification of Trimeric P2X4 Complexes

In vivo, P2X receptors form functional trimeric ion channels. The solubilised and purified P2X4 proteins are typically present in a range of oligomeric states, including monomers, dimers, trimers, and hexamers (i.e., dimers of trimers). This range of oligomeric states is described for example, by references (Backmark et al., Protein Sci. 22 (2013) 1124-1132; Kawate et al., Structure 14 (2006) 673-681; Kawate et al., Nature 460 (2009) 592-598; Nakazawa et al., European Journal of Pharmacology 518 (2005) 107-110; Nicke et al., Mol. Pharmacol. 63 (2003) 243-252). To obtain a stable predominantly trimeric arrangement, solubilization conditions were adjusted.

Combinations of detergents, additives, buffers and pH were varied. Optimal conditions were selected to increase the FSEC signature of the trimer while reducing larger order oligomeric arrangements and aggregates. Such undesirable forms were eluted in the void volume of the size-exclusion columns applied. Conditions tested included KPO4-HCl pH 7.4, 600 mM NaCl and 2% (w/v) n-dodecyl-beta-maltopyranoside CAS 69227-93-6. Optimal solubilization was obtained in buffers containing combinations of the detergents including n-Dodecyl-beta-D-Maltoside CAS 69227-93-6, n-Dodecyl thio-Maltoside CAS 148565-58-6, (3-[(3-Cholamidopropyl)-Dimethylammonio]-1-Propane Sulfonate/N,N-Dimethyl-3-Sulfo-N-[3-[[3α,5β,7α,12α)-3,7,12-Trihydroxy-24-Oxocholan-24-yl]Amino]propyl]-1-Propanaminium Hydroxide abbreviated to CHAPS CAS 75621-03-3, and the additive Cholesteryl Hemisuccinate CAS 102601-49-0. The purified protein was formulated in a buffer which contained 50 mM Tris-HCl pH 8.0, 600 mM NaCl, 10% (v/v) glycerol, 0.025 (w/v) % n-Dodecyl-beta-D-Maltoside CAS 69227-93-6, 0.0125% (w/v), n-Dodecyl thio-Maltoside CAS 148565-58-6, 0.0075% (w/v) (3-[(3-Cholamidopropyl)-Dimethylammonio]-1-Propane Sulfonate/N,N-Dimethyl-3-Sulfo-N-[3-[[3α,5β,7α,12α)-3,7,12-Trihydroxy-24-Oxocholan-24-yl]Amino]propyl]-1-Propanaminium Hydroxide abbreviated to CHAPS CAS 75621-03-3, and 0.0015% (w/v) Cholesteryl Hemisuccinate CAS 102601-49-0.

Example 3: Anti-P2X4 Specific Antibodies were Isolated Using Phage Display Selection Naïve human single chain Fv (scFv) phage display libraries were cloned into a phagemid vector based on the filamentous phage M13 were used for selections (Lloyd (2009) Protein Eng Des Sel 22, 159-168; Vaughan et al., Nature biotechnology 14, 309-314, 1996). Anti-P2X4 specific antibodies were isolated from the phage display libraries using a series of selection cycles on recombinant human P2X4 (hu P2X4), essentially as previously described by Vaughan et al (Vaughan et al., supra). In brief, human P2X4 in PBS (Dulbecco's PBS, pH7.4) was immobilised onto wells of a MaxiSorp® microtitre plate (Nunc) overnight at 4° C. Wells were washed with PBS then blocked for 1 hour with PBS-Marvel dried skimmed milk (3% w/v). Purified phage in PBS-Marvel (3% w/v) were added to the wells and allowed to bind coated antigen for 1 hour at room temperature. Unbound phage was removed by a series of wash cycles using PBS. Bound phage particles were eluted with trypsin for 30 minutes at 37° C., infected into E. coli TG1 bacteria and rescued for the next round of selection. Alternatively, anti-P2X4 antibodies were isolated as described above except deselection of the purified phage library against the C-terminal peptide $huP2X4_{370-388}$ (Alomone Labs # APR-002) or phenyl hydrophobic interaction chromatography (HIC) beads was performed prior to selection with the antigen.

Example 4: Generation of Rat Anti-Murine P2X4 Antibodies Using Hybridoma Technology Immunisations Purified recombinant murine P2X4 protein and murine P2X4 transfected HEK 293F cells were used to immunise Sprague Dawley rats in three groups. For group 1, rats were immunised with murine P2X4 protein; for group 2, rats were immunised with murine P2X4 transfected HEK 293F cells; and for group 3, rats were immunised by alternating murine P2X4 protein and murine P2X4 transfected HEK 293F cells.

A twenty eight day immunization protocol was used with a priming immunization on day 0, followed by four subsequent booster immunizations on days 7, 15, 22 and 24. For group 1, equal volumes of complete Freund's adjuvant and murine P2X4 protein (total protein: 100 µg) were emulsified together, and delivered to the rats subcutaneously at two sites (200 µL per site). For the subsequent three booster injections, the same amount of protein was used, emulsified in Freund's incomplete adjuvant. For group 2, murine P2X4 transfected HEK 293F cells were resuspended at 5E7 cells per mL in PBS and emulsified with equal volumes of complete Freund's adjuvant. As above, the cells were injected into rats at two sites (200 µL per site). For the subsequent three booster injections, the same number of cells was used, emulsified in Freund's incomplete adjuvant. For group 3, the priming immunization was with murine P2X4 protein as per group 1 above, followed by three booster immunizations with murine P2X4 transfected HEK 293F cells, murine P2X4 protein, and murine P2X4 transfected HEK 293F cells.

The final boosts were given intraperitoneally on day 24, group 1 and group 3 rats received murine P2X4 protein (400 µL at 50 µg/mL in Tris buffer), and group 2 rats received murine transfected HEK 293F cells (400 µL at 5E7/mL).

Tail vein bleeds were obtained from the rats before immunisation, on day 13 after the first immunization, and on day 20 after second immunisation. The IgG titres to anti-murine P2X4 were determined by a cell-based DELFIA (dissociation-enhanced lanthanide fluorescence immunoassay) assay.

Assessment of Rat Immune Response to Murine P2X4 Using a Cell-Based DELFIA

The IgG titres to murine P2X4 in sera were determined by a cell based DELFIA using both mP2X4 transfected HEK 293F and parental HEK cells. In order to reduce anti-HEK 293F cell specific antibodies in sera, before being assayed the serum samples from rats immunised with either cells alone or the alternating protein and cells strategy were incubated with non-transfected HEK 293F cells. The sera from rats immunised with protein were assayed without this pre-adsorption step.

Murine P2X4 transfected HEK 293F and parental HEK cells were plated in culture media onto black collagen coated 96 well microtitre plates at a density of 30,000 cells per well. After overnight incubation at 37° C. in a 5% $CO_2$ incubator, the culture supernatant was removed and the cells were fixed with 3.7% formaldehyde solution at 50 µL per well. All subsequent incubations were carried out at room temperature. After 5 minutes fixation, the formaldehyde solution was discarded and replaced with 200 µL of 3% marvel/PBS blocking buffer. After one hour, the blocking buffer was removed and the serum samples added in a 3-fold dilution series (50 µL per well starting from a 1:200 dilution). After incubating for one hour, the wells were washed gently three times with PBS supplemented with 0.05% (v/v) Tween 20. A biotinylated polyclonal goat anti-rat IgG Fc gamma specific secondary antibody (diluted 1:500 in marvel/PBS) was added then at 50 µL per well. Following a further one hour incubation and three gentle washes as above, Eu-N1-labeled streptavidin (Perkin Elmer) was added to the wells (diluted to 100 ng/mL in marvel/PBS, 50 µL per well). After 30 minutes incubation time, the wells were gently washed five times and DELFIA enhancement solution was added. The reaction was allowed to develop for 10 minutes, and then the plate was then read using a PerkinElmer EnVision 2103 multilabel plate reader. The TRF (time-resolved fluorescence) signal in each well was measured (excitation 340 nm, emission 615 nm).

The serum titration curves for murine P2X4 transfected HEK 293F cells and parental HEK 293F cells were plotted and the respective area under the curves (AUC) calculated. For rats immunized with murine P2X4 transfected HEK 293F cells, specific mP2X4 IgG titres were derived by subtracting the AUC values from parental HEK cells from the AUC values for the murine P2X4 transfected cells.

Monoclonal Rat IgG Isolation

Four days after the final boost, lymph nodes were aseptically harvested and cells were isolated by mechanical disruption and counted. These cells were mixed with SP2/0 myeloma cells and fused using an electrofusion apparatus. The resultant fusions were mixed with a methylcellulose-based semi-solid media and plated out into OmniTray plates. The semi-solid media comprised CloneMatrix and DMEM supplemented with 20% FCS, 10% BM Condimed H1, 1 mM sodium pyruvate and OPI media supplement, 2% hypoxanthine azaserine and FITC conjugated goat anti-rat IgG. The cells in semi-solid media were cultured for 13 days at 37° C. in a 5% $CO_2$ incubator. During this incubation period, clonal colonies are formed from a single progenitor hybridoma cell. These colonies secrete IgG that is trapped in the vicinity of the colony by the FITC conjugated anti-IgG present in the semi-solid media. The resultant immune complex formation can be observed around the cell as a fluorescent 'halo' when visualised by ClonePix FL colony picker (Molecular Devices). These haloed colonies are then picked into 96 well microtitre plates.

After 3-5 days in culture, the supernatants of the picked colonies were harvested and screened for murine P2X4 specificity by comparing binding to murine P2X4 transfected HEK 293F cells and parental HEK 293F cells by a cell-based fluorometric microvolume assay technology (FMAT) assay.

DNA Sequencing of Rat IgG

Messenger RNA (mRNA) was extracted from cells using magnetic oligo (dT) particles and converted into cDNA. PCR amplification was performed using poly-C and constant region VH/VL primers.

Rat IgG Purifications

Prior to purification, the hybridomas were tested by ELISA using a goat anti-rat IgG2a coated microtitre plate to determine which clones secreted Rat IgG2a, as this isotype is purified using a different purification matrix to rat IgG1, IgG2b and IgG2c isotypes.

Cells were propagated in 24 well plates and overgrown in serum free HL-1 medium supplemented with HyperZero and glutamine. After 10 days, the supernatants were transferred to 96 well masterblocks and rat IgG1, IgG2b and IgG2c isotypes were purified on 20 µL Phytips containing ProPlus resin (Phynexus). Rat IgG2a antibodies were purified on custom packed Phytips containing CaptureSelect IgG-Fc multiple species resin (Lift Technologies) using Perkin Elmer Minitrack. The captured rat IgGs were eluted with 75 µL of 100 mM HEPES, 140 mM NaCl pH 3.0 then neutralised with an equal volume of 200 mM HEPES pH 8.0. The purified IgGs were quantified using an absorbance reading at 280 nm in UV-Star 384 well plate.

Reformatting of Rat IgGs to Human IgG1

Rat hybridoma IgG clones were molecularly reformatted to generate chimeric constructs expressing rat VH and VL domains and human IgG1 constant domains essentially as described by Persic et al., 1997 (Gene 187, 9-18) with the following modifications. An OriP fragment was included in the expression vectors to facilitate use with CHO-transient cells and to allow episomal replication. The VH domain was cloned into a vector (pEU1.4) containing the human heavy chain constant domains and regulatory elements to express whole IgG1 heavy chain in mammalian cells. This constant region contained the triple mutations (TM) L234F/L235E/P331S resulting in an effector null human IgG1 (Oganesyan et al., (2008) Acta Crystallogr D Biol Crystallogr. 64, 700-704). Similarly, the VL domain was cloned into a vector (pEU4.4) for the expression of the human light chain (lambda) constant domains and regulatory elements to express whole IgG light chain in mammalian cells. To obtain IgGs, the heavy and light chain IgG expressing vectors were transfected into CHO-transient mammalian cells. IgGs were expressed and secreted into the medium. Harvests were filtered prior to purification, then IgG was purified using Protein A chromatography. Culture supernatants were loaded on a column of appropriate size of Ceramic Protein A (Pall 20078-036) and washed with 50 mM Tris-HCl pH 8.0, 250 mM NaCl. Bound IgG was eluted from the column using 0.1 M Sodium Citrate (pH 3.0) and neutralised by the addition of Tris-HCl (pH 9.0). The eluted material was buffer exchanged into PBS using Nap10 columns (GE Lifesciences 17-0854-02) and the concentration of IgG was determined spectrophotometrically using an extinction coefficient based on the amino acid sequence of the IgG (Pace et al., (1995) Protein Sci. 4, 2411-23). The purified IgG were analysed for purity using SDS-PAGE.

Example 5: Identification of Human P2X4 Binding Antibodies from Phage Display Selections ScFv antibodies identified from the phage display method described in Example 3 were expressed in bacteria and screened as unpurified bacterial periplasmic extracts (which contain scFv), prepared in: 0.2M HEPES buffer pH7.4, 0.5 mM EDTA and 0.5 M sucrose. Alternatively, the heavy and light chain variable regions were amplified by PCR and cloned into a vector for expression as human IgG1 antibodies in HEK293F cells.

For screening of bacterial scFv samples, 5 µl of bacterial extract was added to a 384 well assay plate (Corning 3655). Assay buffer was prepared as follows: 1X Hanks Balanced Salt Solution (HBSS) (Sigma H8264), 0.1% (v/v) BSA (PAA K05-013), 20 mM HEPES (Gibco 15630) and 1 U/ml Apyrase (Sigma A6535) and 5 µl added to the assay plate with the bacterial scFv extract. Anti-myc detection reagent (Serotec MCA2200) and anti-mouse DyLight649 (Jackson Immuno Research Labs 115-495-071) were diluted in assay buffer to 15.6 nM and 24 nM respectively in the same solution and 5 µl added to the assay plate with the scFv sample. HEK293F cells expressing human P2X4 (huP2X4) (Q99571, ENSP00000336607) were diluted to $2.6e^5$ cells/ml in assay buffer and 15 µl added to the assay plate. In parallel scFv samples were also tested for binding to HEK293F cells that did not express huP2X4.

For screening of the HEK293F expressed IgG samples, 2.5 µl of cell culture supernatant was added to the 384 well assay plate (Corning 3655). Assay buffer was prepared as described above and 7.5 µl was added to the assay plate with the IgG sample. Anti-human AlexaFluor 647 (Life Technologies A21445) was diluted in assay buffer to 6 nM and 10 µl added to the assay plate with the IgG sample. HEK293F cells expressing huP2X4 (Q99571, ENSP00000336607) were diluted to $4e^5$ cells/ml in assay buffer and 10 µl added to the assay plate. In parallel IgG samples were also tested for binding to HEK293F cells that did not express huP2X4. Assay plates set up to screen both types of samples were sealed with a Topseal plate sealer (Perkin Elmer 6005250) and incubated at room temperature for at least 4 hours before reading on the Fluorescence Microvolume Assay Technology (FMAT), a fluorescence based platform that detects fluorescence localized to bead or cells settled at the bottom of a microwell (Dietz et al., Cytometry 23:177-186 (1996), Miraglia et al., J. Biomol. Screening 4:193-204 (1999)). Data was analysed using the FMAT analysis software and events were gated based on fluorescence 0-10,000 FL1 counts, colour typically 0.15 to 0.40 and size 10-60. A minimum count of 20 events was set as a threshold before data was reported for each well. ScFv showing binding to the HEK293F huP2X4 cells, but not to the control HEK293F cells were selected for further testing if the FL1 count was above 1000 on the huP2X4 cells, IgG samples showing a specific huP2X4 binding signal of greater than 200 FL1 counts were identified as hits and characterised further.

ScFv or IgG samples which showed a specific binding signal to HEK293F huP2X4 cells as unpurified samples were subjected to DNA sequencing (Vaughan et al. supra, Nature Biotechnology 14: 309-314), (Osbourn 1996; Immunotechnology. 2, 181-196). Unique scFvs were expressed in bacteria and purified by affinity chromatography (as described by Bannister et al (2006) Biotechnology and bioengineering, 94. 931-937). Those scFv that confirmed binding to human P2X4 were generated as full IgGs and expressed and purified as described in Example 4. Purified IgG antibodies were tested for functional activity in the electrophysiology assay and for binding to cells expressing mouse and cynomologus P2X4 using the same method described for the human P2X4 cells described above except a titration of purified IgG sample was used. Results of electrophysiology assays are provided at FIGS. 3 and 4.

Example 6: Identification of Hybridoma IgGs that Bind Specifically to Murine P2X4

Supernatants generated from the immunisations were screened to identify IgGs with specific binding to mP2X4. Briefly supernatants were diluted 10 fold into assay buffer (HBSS, 0.1% (v/v) BSA, 20 mM HEPES and 1 U/ml Apyrase) and 5 µl added to the assay plate. Anti-rat detection antibody labeled with Alexa Fluor 647 (Jackson Immuno Research labs) was diluted to 6 nM and 10 µl added to the assay plate. HEK293F cells expressing mP2X4 were diluted to $2.6e^5$/ml and 15 µl added to the assay plate. IgG samples were also tested for non-specific binding in parallel by testing the samples for binding to HEK293F cells. IgGs demonstrating specific binding to mP2X4 and no binding to HEK293F cells were identified as hits and selected for antibody purification and analysis by electrophysiology. Results of the electrophysiology screen are provided in FIG. 7 together with the binding results for these samples against human and cyno P2X4 expressing cell lines using the same assay described previously Example 7: Generation of Human P2X4 Variants and Expression by Transient Transfection in HEK293F Cells To determine the epitope to which the P2X4 functional antibodies bind the following mutations were generated in human P2X4; E95Q, V105M, G114D, A122V, S131N, A151P, G154R, L303P, N306K. DNA vectors containing huP2X4 sequences with these changes were generated using standard molecular biology techniques. DNA vectors were transfected into HEK293F cells using 293-fectin (Life Technologies 12347019) following the manufacturers guidelines. Cells expressing the huP2X4 variants were incubated with Antibody Nos. 1, 11, 29, and 33 together with the anti-human AlexaFluor 647 (Life Technologies A21445) detection reagent. Binding was measured using the FMAT plate reader. Variant S131N was shown to be important for the binding of Antibody Nos. 11, 29, and 33. FIGS. 1A-1D show the results of FMAT assays characterizing binding of P2X4 antibodies to HEK293F cells expressing variants of human P2X4.

Example 8: Electrophysiological Characterization of Monoclonal Antibodies to P2X4

Methods for Phage Display Derived mAbs:—FIGS. 3 & 4

HEK 293F cells stably expressing human P2X4, mouse P2X4 or cynomolgus P2X4 were harvested at 50% confluency using accutase. Cells were then resuspended in 10 ml Freestyle 293F media supplemented with HEPES (10 mM)+ apyrase (1U/ml, ATPase/ADPase activity=1) at a density of $2-3e^6$ cells/ml. P2X4 function was assayed using the automated electrophysiology platform QPatch 16X (Sophion) in population patch configuration. Composition of QPatch extracellular buffer (QEB) was (in mM) NaCl (140), KCl (2), $MgCl_2$ (1) $CaCl_2$ (2), HEPES (10). Final composition of compound plate extracellular buffer (CPEB1) was NaCl (137.6), KCl (2.2), $MgCl_2$ (0.66), $CaCl_2$ (1.3), HEPES (6.6), $KH_2PO_4$ (0.49), $NaH_2PO_4$ (2.66). pH of extracellular buffers was adjusted to 7.4 with NaOH (1 M), osmolarity was adjusted to 300 mOsm with sucrose and the solutions were 0.2 µm filtered. Compound plate extracellular buffer was supplemented with 0.1% bovine serum albumin. The QPatch intracellular buffer contained (in mM) CsF (140), NaCl (10), EGTA (1), HEPES (10). pH of the intracellular buffer was adjusted to 7.3 with CsOH (1 M) and the solution was 0.2 µm filtered. IgGs were titrated to pH 7.4 with NaOH (1 M).

Figure 8D:
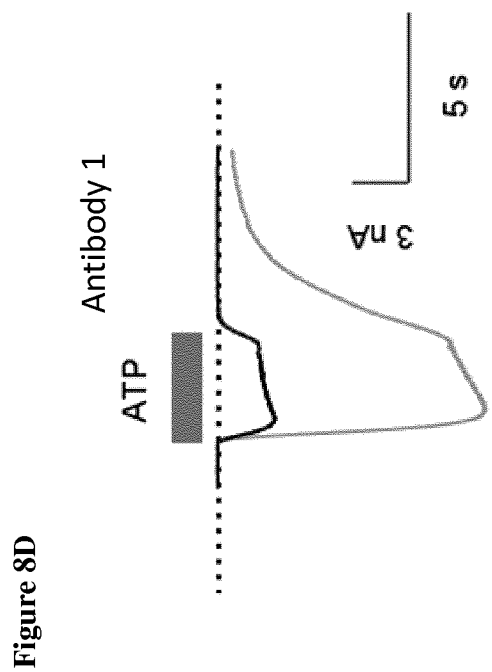
Figure 8E:
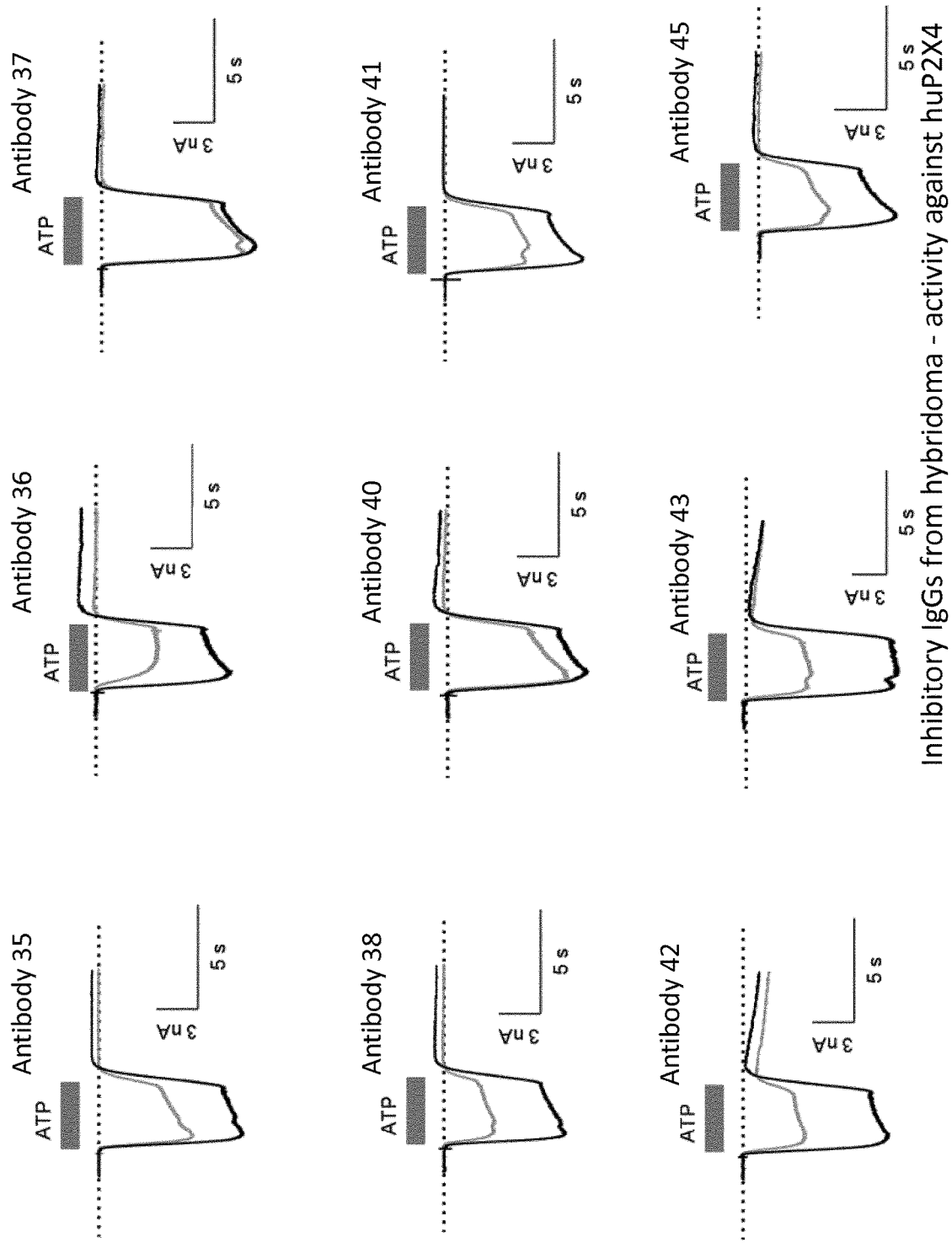
Figure 11:
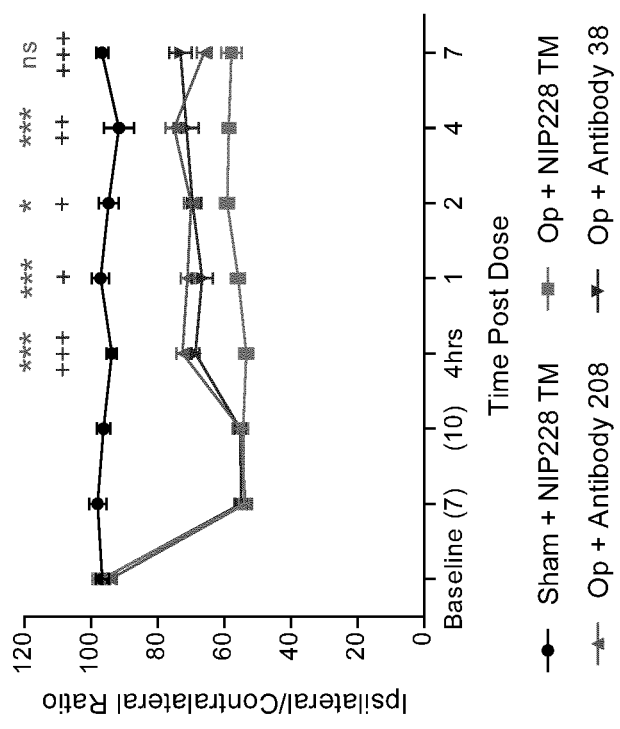
FIG. 11 shows the effect of P2X4 antibody Nos. 38 and 208 and an isotype control antibody (NIP228 TM) dosed intra-thecally (5 μg per mouse) on reversal of peripheral nerve ligation (PNL)-induced mechanical hyperalgesia as measured by the ipsilateral/contralateral ratio of paw withdrawal threshold in response to paw pressure (n=9-10 per group). Data analysed using 2 way ANOVA with time and treatment as dependant factors. Subsequent statistical significance obtained using Tukey's Post Hoc test. * P<0.05; *** P<0.001–Op+NIP228 TM vs Op+Antibody 208: +P<0.05; ++P<0.01; +++P<0.001–Op+NIP228 TM vs Op+Antibody FIG. 12 provides an alignment of the VH & VL sequences of Antibody Nos. 287 to 315, which are derived from Antibody 11.

After obtaining whole cell configuration, cells were voltage clamped at −50 mV with 70% series resistance compensation employed. The ligand agonist adenosine 5'-triphosphate disodium salt (ATP, 3 µM) in CPEB1 was applied for 3 seconds every 5 minutes for 20 minutes resulting in 4 control agonist responses. Each agonist response was washed off with CPEB1+ apyrase (1U/ml). 4 additional agonist responses were then measured every 5 minutes in the continued presence of the test IgG or an isotype control IgG (NIP 228). Exemplar traces showing the effect of inhibitory IgGs 5 mins after IgG application can be seen in FIG. 8A whereas an example of a potentiating IgG can be seen in FIG. 8D. Electrophysiology data presented in FIG. 3 and FIG. 4 were leak subtracted by subtracting the current in the absence of ligand and the magnitude of the P2X4 response measured as the peak inward current in the presence of ligand. Peak inward current in the presence of IgG+ATP after 5 minutes IgG incubation was expressed as a fraction of the $4^{th}$ control ATP response. Data were subsequently normalised to a time and concentration matched isotype control antibody response using the equation $I_{norm}=I_{IgG}*(1/I_{isotype})$ where $I_{IgG}$=fraction of control current for the test IgG and $I_{isotype}$=fraction of control current for the isotype control IgG. Six IgGs were found to significantly inhibit human P2X4 currents; Antibody Nos. 5, 8, 11, 18, 29, and 33 (FIGS. 3, 4, 8A). Inhibition of P2X4 currents was rapid, occurring at the first time point following IgG addition, whereas the isotype control IgG NIP 228 had no significant effect. IgGs were subsequently tested for function against mouse and cynomolgus P2X4 (FIGS. 3, 4) and data reported as a mean of n=3-4 experiments.

Sequences for phage display antibodies are provided in FIG. 2. Results of cross reactivity for phage display antibodies between human, cynomolgus monkey, and mouse are provided in FIG. 3. FIG. 9 provides a structural analysis of the epitope/paratope interface. FIG. 10 provides the sequence of the predicted P2X4 epitope.

Methods for Hybridoma Derived mAbs.—FIGS. 5, 7 & 8

HEK 293F cells stably expressing either mouse P2X4 (Uniprot # Q9JJX6) or human P2X4 (Uniprot # Q99571) were harvested at 50% confluency using accutase. Cells were then resuspended in 10 ml Freestyle 293F media supplemented with HEPES (10 mM)+apyrase (1U/ml, ATPase/ADPase activity=1) at a density of $2-3e^6$ cells/ml. P2X4 function was assayed using the automated electrophysiology platform QPatch 16X (Sophion) in population patch configuration. Composition of QPatch extracellular buffer (QEB) was (in mM) NaCl (140), KCl (2), $MgCl_2$ (1) $CaCl_2$ (2), HEPES (10). Final composition of compound plate extracellular buffer (CPEB2) was NaCl (115.5), KCl (1.3), $MgCl_2$ (0.66), $CaCl_2$ (1.32), HEPES (56.1). pH of extracellular buffers was adjusted to 7.4 with NaOH (1 M) and the solutions were 0.2 µm filtered. The QPatch intracellular buffer contained (in mM) CsF (140), NaCl (10), EGTA (1), HEPES (10). pH of the intracellular buffer was adjusted to 7.3 with CsOH (1 M) and the solution was 0.2 µm filtered. IgGs were titrated to pH 7.4 with NaOH (1 M). After obtaining whole cell configuration, cells were voltage clamped at −50 mV with 70% series resistance compensation employed. The ligand agonist adenosine 5'-triphosphate disodium salt (ATP) (6 µM for mouse P2X4, 3 µM for human P2X4) in QEB was applied for 3 seconds then washed off with QEB+apyrase (1U/ml). CPEB2+IgG was then incubated for 3 minutes followed by a second ATP addition. Data were leak subtracted by subtracting the current in the absence of ligand and the magnitude of the P2X4 response measured as the peak inward current in the presence of ligand. The ATP response after IgG addition was expressed as a fraction of the ATP response prior to IgG addition. The hIgG1 NIP 228 TM was used as a control antibody to determine the cutoff for defining functional antibodies. IgGs were initially screened in duplicate (FIG. 5, First screen and FIG. 7) at mP2X4 and expressed as mean of n=1-2 experiments. The control antibody NIP 228 TM had a fraction of control current of 1.08+/−0.27 (Mean+/−S.D), n=49. From these data the cutoff for defining functional inhibitory antibodies was set at <0.5 (>~2 standard deviations from the mean). Functional antibodies from the first screen were repeated with a larger sample set (n=3-4) and data reported as mean+/−SD (FIG. 5).

Results of cross reactivity for hybridoma antibodies between human and mouse are provided at FIGS. 5 and 7. Sequences for hybridoma antibodies are provided at FIGS. 6 and 13.

Example 9: In Vivo Testing of Monoclonal Antibodies to P2X4 in Seltzer Model of Neuropathic Pain 50 female C57BL/6 mice were used for the studies. All mice underwent insertion of transponders for identification purposes at least 5 days before the start of the study. Mechanical hyperalgesia was determined using an analgysemeter (Randall & Selitto 1957) (Ugo Basile). An increasing force was applied to the dorsal surface of each hind paw in turn until a withdrawal response was observed. The application of force was halted at this point and the weight in grams recorded. Data was expressed as withdrawal threshold in grams for ipsilateral and contralateral paws. Following the establishment of baseline readings mice were divided into 2 groups with approximately equal ipsilateral/contralateral ratios which underwent surgery to partially ligate the sciatic nerve or served as sham operated controls. Operated mice were anaesthetised with isoflurane. Following this approximately 1 cm of the left sciatic nerve was exposed by blunt dissection through an incision at the level of the mid thigh. A suture (9/0 Virgin Silk: Ethicon) was then passed through the dorsal third of the nerve and tied tightly. The incision was then closed using glue and the mice were allowed to recover for at least six days prior to commencement of testing. Sham operated mice underwent the same protocol but following exposure of the nerve the mice were sutured and allowed to recover.

Mice were tested for onset of hyperalgesia on days 7 and 10 post surgery. Any mice showing an ipsilateral/contralateral ratio of greater than 80% were classed as non-responders and removed from the study. Following testing on day 10 mice were further sub-divided into groups giving the final treatment groups;
  A. Group 1: Sham operated+NIP 228 TM 5 µg per mouse intra-thecal (N=10)
  B. Group 2: Nerve ligated+NIP 228 TM 5 µg per mouse intra-thecal (N=10)
  C. Group 3: Nerve ligated+Antibody No. 208 5 µg per mouse intra-thecal (N=10)
  D. Group 4: Nerve ligated+Antibody No. 38 5 µg per mouse intra-thecal (N=10)

Mice were administered NIP 228 TM (Isotype control) or test molecules on day 13 and were re-tested for changes in mechanical hyperalgesia at 4 hrs post dose and also on 1, 2, 4 and 7 days post dose. For dosing mice were anaesthetised with isoflurane. Intra-thecal administration was carried out manually into the L4-L6 area of the spinal cordNIP 228 TM and all test compounds were supplied as 1.02 mg/ml=solutions=1 µg per µl=5 µg per mouse.

Ipsilateral and contralateral readings were taken for each animal at each test time and were entered into EXCEL for calculation of ipsilateral/contralateral ratios. Summary data was transferred into PRISM for graphical and statistical analysis. Results were analysed using 2-way ANOVA. Pairwise comparisons where appropriate were made using Tukey's test.

Analysis of the results showed that partial ligation of the sciatic nerve caused a mechanical hyperalgesia which manifested as a significant reduction in the ipsilateral/contralateral ratio on day 7 and 10 when compared to sham operated controls. Following treatment with N1P228, operated mice did not show any change in the level of mechanical hyperalgesia from pre-dose levels indicating a lack of effect of the isotype control on mechanical hyperalgesia. The administration of Antibody No. 208 produced a significant reversal which was significant for up to 4 days post dose after which the response returned to baseline levels. Similar effects were seen with Antibody No. 38 (FIG. 13).

Example 10: Generation of Mouse Anti-Human P2X4 Antibodies by Hybridoma Technology Methods for Mouse Anti-Human P2X4 Antibody Generation were Carried Out in the Same Way as Described in the Previous Section of Rat Anti-Murine P2X4 Antibody Generation, Other than the Following Differences:

Immunisations

Human P2X4 (hP2X4) transfected HEK 293F and XS63 cells were used to immunise CD1 mice in three groups. In group 1, mice were immunised with hP2X4 transfected HEK 293F cells, group 2 mice were immunised with hP2X4 transfected XS63 cells, and group 3 mice were immunised by alternating hP2X4 transfected XS63 cells and hP2X4 transfected HEK 293F cells.

hP2X4 transfected cells were re-suspended at 1E8/mL and emulsified with equal volumes of complete Freund's adjuvant, and injected into mice at two sites, 100 µL per site. For the subsequent 3 injections, the same number of cells was emulsified in Freund's incomplete adjuvant and injections were performed as above. The last boost was carried out on day 24, injecting 200 µL of transfected cells at 1E8/mL intraperitoneally.

Assessment of Mouse Immune Response to hP2X4 Using a Cell-Based DELFIA

The serum IgG titres to hP2X4 were determined by a cell-based time-resolved fluorescence assays (DELFIA) using parental HEK 293F cells and hP2X4 transfected HEK 293F cells.

Monoclonal Mouse IgG Isolation

Lymphoid cells isolated from spleens and lymph nodes were fused with SP2/0 myeloma cells using an electrofusion method. The fusions were plated out into semi-solid selection media containing FITC conjugated goat anti-mouse IgG.

Cell Binding Assay for Mouse IgGs

Supernatants were initially screened for IgGs that specifically bound to hP2X4 using both the hP2X4 expressing HEK 293F and XS63 cells, and parental HEK 293F cells. The IgGs that showed specific binding to hP2X4, and no binding to parental HEK293F cells, were selected for further specificity testing on mouse P2X4 (mP2X4) HEK 293F cells. IgGs which specifically bound to hP2X4 or to both hP2X4 and mP2X4 were selected for antibody purification and functional analysis by electrophysiology.

DNA Sequencing and Purification of Mouse IgGs

Messenger RNA (mRNA) was extracted from hybridoma cells using magnetic oligo (dT) particles and reverse transcribed into cDNA. Polymerase chain reaction (PCR) amplification was performed using poly-C and constant region VH or VL primers specific to all mouse IgG subclasses.

Mouse IgGs of all subclasses (IgG1, IgG2a, IgG2b and IgG3) were purified from overgrown cell culture supernatants on ProPlus resin (Phynexus).

Functional Screening by Electrophysiology

HEK 293F cells stably expressing human P2X4 (Uniprot # Q99571) were harvested at 50% confluency using accutase. Cells were then resuspended in 10 ml Freestyle 293F media supplemented with HEPES (10 mM)+apyrase (1U/ml, ATPase/ADPase activity=1) at a density of 2-3e$^6$ cells/ml. P2X4 function was assayed using the automated electrophysiology platform QPatch 16X (Sophion) in population patch configuration. Composition of QPatch extracellular buffer (QEB) was (in mM) NaCl (140), KCl (2), MgCl$_2$ (1) CaCl$_2$ (2), HEPES (10). Final composition of compound plate extracellular buffer (CPEB2) was NaCl (115.5), KCl (1.3), MgCl$_2$ (0.66), CaCl$_2$ (1.32), HEPES (56.1). pH of extracellular buffers was adjusted to 7.4 with NaOH (1 M) and the solutions were 0.2 µm filtered. The QPatch intracellular buffer contained (in mM) CsF (140), NaCl (10), EGTA (1), HEPES (10). pH of the intracellular buffer was adjusted to 7.3 with CsOH (1 M) and the solution was 0.2 µm filtered. IgGs were titrated to pH 7.4 with NaOH (1 M). After obtaining whole cell configuration, cells were voltage clamped at −50 mV with 70% series resistance compensation employed. The ligand agonist adenosine 5'-triphosphate disodium salt (ATP, 3 µM) in QEB was applied for 3 seconds then washed off with QEB+apyrase (1U/ml). CPEB2+IgG was then incubated for 3 minutes followed by a second ATP addition. Data were leak subtracted by subtracting the current in the absence of ligand and the magnitude of the P2X4 response measured as the peak inward current in the presence of ligand. The ATP response after IgG addition was expressed as a fraction of the ATP response prior to IgG addition. The hIgG1 NIP 228 TM was used as a control antibody to determine the cutoff for defining functional antibodies. Antibody sequences are provided in FIG. 13.

Example 11: Affinity Maturation of Antibody 11

Antibody No. 11 was optimised for affinity via two approaches either; targeted or random mutagenesis followed by affinity-based phage display selections. In the targeted approach, large scFv-phage libraries derived from the lead clone were created by oligonucleotide-directed mutagenesis of the variable heavy (VH) complementarity determining regions 3 (CDR3) and light (VL) chain CDR3 using standard molecular biology techniques as described (Clackson, T. and Lowman, H. B. *Phage Display—A Practical Approach*, 2004. Oxford University Press). The libraries were subjected to affinity-based phage display selections in order to select variants with higher affinity for human P2X4. The selections were performed essentially as described previously in Example 3 with the exception of lowering the concentration of immobilised human P2X4 over four rounds of selection (10 µg/ml-1.25 µm/ml). Antibodies with improved affinity were identified in a competition assay based on Antibody 11 binding to huP2X4 expressing cells (described in Example 12). To generate further affinity improvement, CDR mutations from improved antibodies were recombined into new scFvs using standard molecular biology techniques.

Antibody 11 was also optimised using a random mutagenesis approach to identify key residues within the entire variable domain that may improve binding to human P2X4. Such a technique is described by Gram et al. [Gram et al., 1992, *Proc. Natl. Acad. Sci., USA*, 89:3576-3580], who used error-prone PCR. In some embodiments one or two amino acid substitutions are made within an entire variable domain or set of CDRs. The generated library was subjected to affinity-based selections as described for the targeted selections outlined above.

Figure 12:
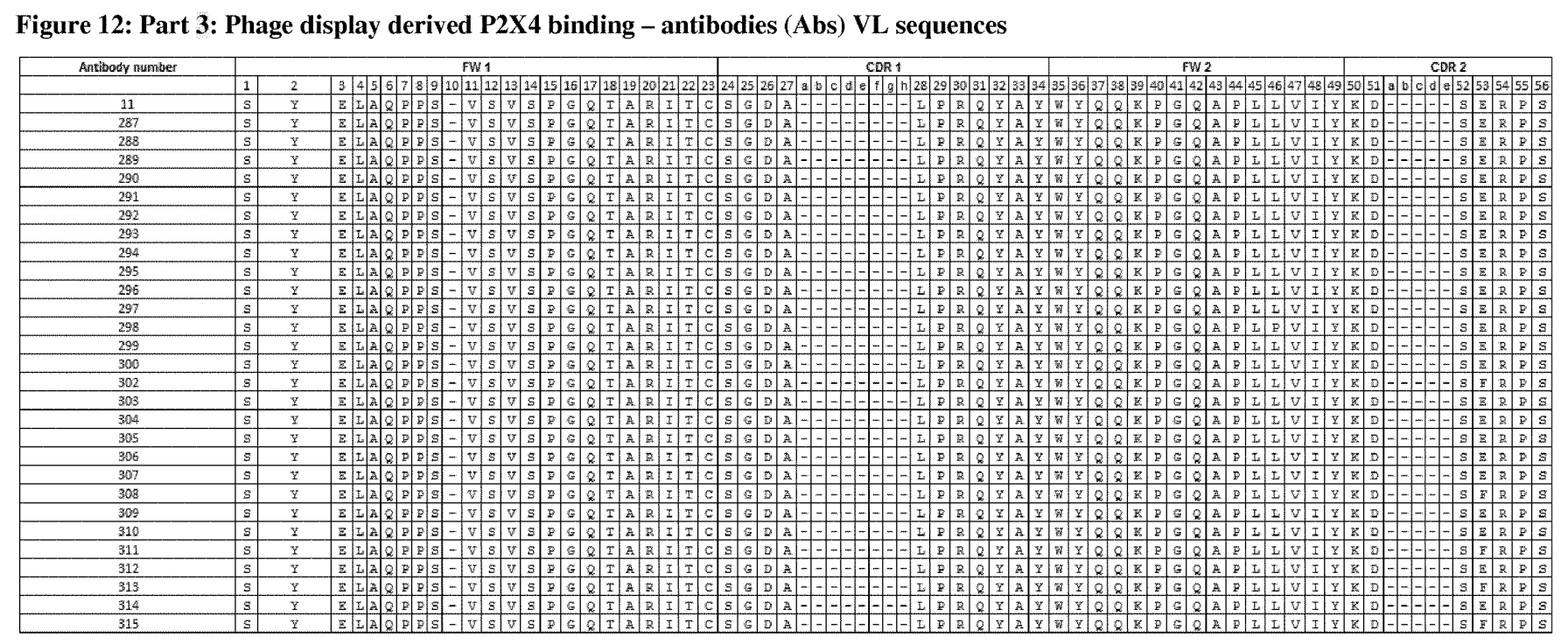

Exemplary antibodies from this selection method are disclosed herein as Antibodies 287 to 315, and an alignment of their sequences is shown in FIG. 12.

Example 12: Identification of Higher Affinity Antibodies Against Human P2X4

Phage display selection outputs described in example 11, were screened for activity in a competition assay based on Antibody 11 binding to huP2X4 expressing cells. Briefly Antibody 11 IgG was labelled with DyLight® 650 using a Lightning-Link® Rapid DyLight® 650 conjugation kit following the manufacturer's instructions (Innova Biosciences Ltd). Bacterially expressed scFv were collected into 0.2M HEPES buffer pH7.4, 0.5 mM EDTA and 0.5 M sucrose as peri plasmic extracts and added to the assay plate (Corning® 3655) together with assay buffer (HBSS, 0.1% BSA, 1U/ml apyrase, either with or without 20 mM HEPES). Antibody 11-Dylight® 650 was added to each well except the wells used to define the background binding, to a final concentration of 2 nM. HEK293F huP2X4 cells were added to each well at a final density of approximately 2000 cells per well. Plates were covered and incubated at room temperature for 2 to 3 hours before reading on a Mirrorball® plate reader (TTP Labtech, Ltd) and determining the total FL3 fluorescence per well (Median (mean intensity) fluorescence multiplied by the number of objects). Individual events were gated on size and fluorescence and a minimum object number of greater than 25 was used to determine wells with sufficient events to report a FL3 total value. % specific binding was calculated for each well using the following equation, maximal FL3 total values were defined from wells that did not receive any scFv but did receive peri plasmic sample buffer:

$$\% \text{ specific binding} = \frac{\text{sample } FL3 \text{ total} - \text{background } FL3 \text{ total}}{\text{maximal } FL3 \text{ total} - \text{background } FL3 \text{ total}} \times 100$$

Samples where the binding signal was lower than 85% specific binding were selected for sequencing and sequence unique hits were generated as purified scFv.

To confirm the inhibition of these scFv antibodies, purified scFv antibodies were diluted in assay buffer described above to generate a dilution series and the diluted samples were added to the assay plate before the addition of Antibody 11-DyLight® 650 to a final concentration of 2 nM, followed by approximately 2000 HEK293F huP2X4 cells per well. Plates were incubated at room temperature for 2 to 3 hours before being read on the Mirrorball® plate reader. Data was analysed as described above and scFv clones showing inhibition were generated as full IgG antibodies.

Example 13: Identification of Antibodies with Improved Potency Against Human P2X4 Using the Human P2X4 1321N1 Cell Line FLIPR® Assay Antibodies identified in the Antibody 11 competition assay described in example 12 were generated as purified IgG and titrated to generate a dilution series. These antibodies were diluted in assay buffer containing HBSS and 0.1% BSA and pre-incubated with 1321N1 cells expressing huP2X4 for 30 mins where the cells had previously been loaded with Fluo-4 NW calcium dye (Molecular Probes™, Life Technologies) following the manufacturer's instructions. P2X4 was activated by the addition of 104 ATP diluted in assay buffer and the resulting rise in intracellular calcium was detected by the calcium dye and measured by an increase in fluorescence using the FLIPR® Tetra plate reader (Molecular Devices, LLC). Data was calculated to determine the maximum fluorescence observed over the background fluorescence for the duration of the assay. These data were then analysed to determine % maximal response over the buffer response alone seen in wells where ATP was omitted, using the following equation:

$$\% \text{ maximal response} = \frac{\text{sample response} - \text{buffer response}}{\text{total response} - \text{buffer response}} \times 100$$

Data was analysed in Prism (GraphPad Software, Inc) to determine $IC_{50}$ values using the following equation:

Y=Bottom+(Top-Bottom)/(1+10^((Log IC50−X) *HillSlope))

To enable ranking of antibodies the top and bottom of the curves were constrained to 100 and 0 respectively. Geometric means of the $IC_{50}$ values for the antibodies tested are listed in FIG. 15 and an example of the $IC_{50}$ curves for two antibodies are shown in FIG. 19 together with an isotype control antibody

Example 14: Identification of Antibodies with Improved Potency Against Human P2X4 Using the HEK 293F huP2x4 Cell Line on the Automated Electrophysiology Platform Qpatch 16X HEK 293F cells stably expressing human P2X4, were harvested at 50% confluency using accutase. Cells were then resuspended in 10 ml Freestyle 293F media supplemented with HEPES (10 mM)+apyrase (1U/ml, ATPase/ADPase activity=1) at a density of 2-3e$^6$ cells/ml. P2X4 function was assayed using the automated electrophysiology platform QPatch 16X (Sophion) in population patch configuration. Composition of QPatch extracellular buffer (QEB) was (in mM) NaCl (140), KCl (2), MgCl$_2$ (1) CaCl$_2$ (2), HEPES (10). pH of extracellular buffers was adjusted to 7.4 with NaOH (1 M), osmolarity was adjusted to 300 mOsm with sucrose and the solutions were 0.2 µm filtered. The QPatch intracellular buffer (QIB) contained (in mM) CsF (140), NaCl (10), EGTA (1), HEPES (10). pH of the intracellular buffer was adjusted to 7.3 with CsOH (1 M) and the solution was 0.2 µm filtered. IgGs were titrated to pH 7.4 with NaOH (1 M).

For determination of the potency of optimized variants of Antibody 11, IgGs were serially diluted in QEB+0.1% bovine serum albumin and tested for function on Qpatch 16X in population patch configuration. Extracellular buffer was QEB, intracellular buffer was QIB and ATP wash buffer was QEB+apyrase (1 U/ml). In this assay, ATP (3 µM) was applied every 10 mins for 3 s with a total of 5 applications per experiment. The first two ATP additions (ATP 1 & ATP 2) were preceded by preincubation for 5 mins with QEB buffer+0.1% BSA whereas the following three ATP additions were preceded by 5 mins incubation with ascending doses of IgG. Log and half log doses of IgG were interleaved in post analysis to generate 6 point dose response curves (dose range 100-0.3 nM). Data were leak subtracted by subtracting the current in the absence of ligand and the magnitude of the P2X4 response measured as the peak inward current in the presence of ligand. The peak inward current in response to ATP was expressed as fraction of control current (ATP2) and labeled as $I/I_{basal}$. Data were fit in Prism using a log (inhibitor) vs. response—Variable slope (four parameters) equation. Y=Bottom+(Top−Bottom)/(1+10^((Log IC50−X)*HillSlope)). The top of the IgG dose response curves was defined by the response to 0.3 nM NIP 228 and constrained to this value. The bottom of the curve was constrained such that it was greater than zero. See FIG. 14-15.

Example 15

Potency determination of hybridoma derived antibodies at mouse and human P2X4. HEK 293F cells expressing P2X4 were handled as in example 8. Potency of hybridoma derived IgGs was assayed on Qpatch 16X in population patch configuration. For determination of IgG potency, IgGs were serially diluted in PBS+0.1% bovine serum albumin and tested for function on Qpatch 16X in population patch configuration. IgGs were then diluted 1:3 in QEB+0.1% BSA resulting in a final buffer composition of NaCl (137.6), KCl (2.2), MgCl$_2$ (0.66), CaCl$_2$ (1.3), HEPES (6.6), KH$_2$PO$_4$ (0.49), NaH$_2$PO$_4$ (2.66), BSA (0.1%) equivalent to CPEB1. Extracellular buffer was QEB, intracellular buffer was QIB and ATP wash buffer was QEB+apyrase (1 U/ml). In this assay, ATP (3 μM) was applied every 10 mins for 3 s with a total of 5 applications per experiment. The first two ATP additions (ATP 1 & ATP 2) were preceded by preincubation for 5 mins with CPEB1+0.1% BSA whereas the following three ATP additions were preceded by 5 mins incubation with ascending doses of IgG. Log and half log doses were interleaved in post analysis to generate 6 point dose response curves. Data were leak subtracted by subtracting the current in the absence of ligand and the magnitude of the P2X4 response measured as the peak inward current in the presence of ligand. The peak inward current in response to ATP was expressed as fraction of control current (ATP2). Data were fit in Prism using a log (inhibitor) vs. response—Variable slope (four parameters) equation. Y=Bottom+(Top−Bottom)/(1+10^((Log IC50−X)*HillSlope)). The top of the IgG dose response curves was constrained to 1 whereas the bottom of the curve was constrained such that it was greater than zero. See FIG. 16.

Example 16 Efficacy of Mouse Reactive Antibodies at Native Mouse Microglial P2X4 Culture of Mouse Microglia Primary mouse microglia were cultured from C57 neonatal pups, P2. Brains were removed from the skulls of mice and kept in media (DMEM+10% FCS+pen/strep). They were then rolled across filter paper to remove the sticky vasculature and meninges before placing in 20 ml fresh media and triturating to give a single cell suspension. Cells were then filter sterilised through a 40 μm cell strainer then centrifuged at 1200 rpm for 5 min. Cells were then resuspended in 40 ml media per flask at 4 brains per T175 flask and cultured for 1 week. After this, the media was supplemented with GM-CSF (5 ng/ml) and the cells cultured for a further week. Microglia were removed by shaking overnight in an orbital shaker incubator (no CO$_2$) with HEPES supplemented in the media (20 mM). Purified microglia were centrifuged at 1200 rpm for 5 mins and resuspended in 20 ml DMEM+10% FCS+pen/strep growth media. Cells were counted and seeded in ultra low bind T75 cell culture flasks (Corning) at 7e6 cells/flask. Microglia were then maintained in culture for 1-7 days before being used for Qpatch 16X electrophysiology assays or FLIPR calcium imaging assays.

Cell handling Qpatch:

1×T75 flask was washed twice with dPBS and cells were harvested using accutase treatment for 5-10 mins. Cells were then resuspended in 293F Freestyle media+20 mM HEPES+1U/ml accutase (10 ml) and spun down at 800 rpm for 5 mins. Cells were then resuspended in 3 ml 293F Freestyle media+20 mM HEPES+1U/ml accutase and 1 ml of cell suspension used per experiment.

Qpatch 16X was used in population patch configuration and cells voltage clamped at −70 mV. Cells were perfused with either a control antibody or test antibody for 5 minutes before ATP (30 μM) was applied. Current in the absence of ATP was subtracted from all data. Inward current in response to ATP was measured (see FIG. 15). External buffer was QEB and internal buffer was QIB. See FIGS. 17 & 18.

FLIPR:

Microglia were plated in Cell Coat Poly-D-Lysine coated 384 well plates (black, uclear) with 30 μl per well and cultured in a humidified incubator at 37° C. for 48 hours.

Media was removed and replaced with 20 ul per well of HBSS buffer+20 mM HEPES+0.1% BSA, supplemented with Screen Quest™ Fluo-8 No Wash Calcium Assay Kit (AAT Bioquest, Inc.) as per the manufacturers instructions. Cells were then incubated at 37° C. for 30 mins then returned to room temperature for 15 mins before assaying on FLIPR (Molecular devices). Ivermectin (12 μM) was made up in a further 384 well compound plate (Compound plate 1). IgGs were made up in PBS+0.1% BSA (compound plate 2). ATP (30 uM) was made up in HBSS+20 mM HEPES+0.1% BSA in a separate 384 well compound plate (Compound plate 3). Fluo-8 was excited at a wavelength of 470-495 nm and the emitted light measured at a wavelength of 515-575 nm. Camera gain was adjusted to give 1000 counts at rest with an exposure of 0.4 s. 10 ul of solution from compound plate 1 was added to the cells and the fluorescence measured. After 5 mins incubation, 10 ul of solution from compound plate 2 was added. 15 min later, ATP (5 uM final) was added and the peak end fluorescence measured between 200-300 sec post ATP addition. Fluorescence counts were normalised to the ATP response in the absence of antibody (minus background fluorescence) and plotted as % of ATP response (See FIG. 21). 10 point dose response curves for each IgG were constructed from duplicate wells and the data fit in Prism using a log (inhibitor) vs. response—Variable slope (four parameters) equation. Y=Bottom+(Top−Bottom)/(1+10^((Log IC50−X)*HillSlope)). See FIG. 20.

Example 17: Functional Effect of P2X4 Antibodies on Human Monocyte Derived Macrophages Cell Culture Human monocytes were isolated from the mononuclear fraction of peripheral blood by centrigugation on a Ficoll-Paque gradient. Cells were then purified by incubating in a T175 cell culture flask in cell culture media in the absence of serum for 1 hour. Non-adherent cells were removed and the remaining cells grown in RPMI Glutamax I media supplemented with 10% FCS (HI/GI)+1% P/S+100 ng/ml M-CSF for 7 days. Cells were fed on day 2-3 by adding an additional 10 ml of media. Macrophage were harvested by accutase treatment for 10 mins followed by cell scraping and replated in ultra-low bind T75 flasks at 6e6 cells per flask. Cells were then cultured for a further 1-10 days before being used for electrophysiological recording. On the day of experiment, cells were harvested with accutase and resuspended in 3 ml CHO ACF media+20 mM HEPES. 1 ml of cell suspension was used per experiment on Qpatch 16X in population patch configuration. Qpatch 16X assay parameters were as described for example 16. Nippon antagonist refers to 1H-naphtho[1,2-b][1,4]diazepine-2,4(3H,5H)-dione (described in Patents WO-2010/093061 and EP2397480A1 See FIGS. 21 & 22.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. An antibody or antigen binding fragment thereof that specifically binds a human P2X4 polypeptide and modulates channel activity, wherein the antibody or fragment thereof comprises a VH comprising:
   a. a heavy chain variable region CDR1 comprising the amino acid sequence: SFAMS (SEQ ID NO: 813);
   b. a heavy chain variable region CDR2 comprising the amino acid sequence: AISGSGGSTYYADSVKG (SEQ ID NO: 814);
   c. a heavy chain variable region CDR3 comprising the amino acid sequence: QFDYWSTYSGPTAFDL (SEQ ID NO: 815);
   in combination with a VL comprising:
   a. a light chain variable region CDR1 comprising the amino acid sequence SGDALPRQYAY (SEQ ID NO: 822)
   b. a light chain variable region CDR2 comprising the amino acid sequence KDSERPS (SEQ ID NO: 823)
   c. a light chain variable region CDR3 comprising the amino acid sequence QSADSSGTYVV (SEQ ID NO: 824).

2. The antibody or antigen binding fragment thereof of claim 1, wherein the antibody or fragment thereof is a P2X4 antagonist.

3. The antibody or antigen binding fragment thereof of claim 1, wherein the antibody or fragment thereof binds an epitope comprising human P2X4 amino acids 110-166 of SEQ ID NO: 1029.

4. The antibody or antigen binding fragment thereof of claim 3, wherein the antibody or fragment thereof binds an epitope comprising one or more human P2X4 amino acids selected from the group consisting of amino acids 118, 122-139, 145, 159, 180, 183, 184, 231, and 244 of SEQ ID NO: 1029.

5. A pharmaceutical composition comprising one or more antibodies or antigen binding fragments thereof according to claim 1 and a pharmaceutically acceptable excipient.

6. The antibody or antigen binding fragment thereof of claim 1, wherein the VH comprises the amino acid sequence SEQ ID NO: 812.

7. The antibody or antigen binding fragment thereof of claim 1, wherein the VL comprises the amino acid sequence SEQ ID NO: 821.

8. The antibody or antigen binding fragment thereof of claim 1, wherein the VH comprises the amino acid sequence SEQ ID NO: 812 and the VL comprises the amino acid sequence SEQ ID NO: 821.

9. A pharmaceutical composition comprising one or more antibodies or antigen binding fragments thereof according to claim 8 and a pharmaceutically acceptable excipient.

10. A method for treating neuropathic pain, the method comprising administering to a patient in need thereof an effective amount of an antibody or antigen binding fragment thereof of claim 8.

11. A method for treating neuropathic pain, the method comprising administering to a patient in need thereof an effective amount of an antibody or antigen binding fragment thereof of claim 1.

* * * * *